United States Patent
Van Berkel et al.

(10) Patent No.: US 10,017,580 B2
(45) Date of Patent: Jul. 10, 2018

(54) HUMANIZED ANTI-TN-MUC1 ANTIBODIES AND THEIR CONJUGATES

(71) Applicants: ADC THERAPEUTICS S.A., Epalinges (CH); MEDIMMUNE LIMITED, Cambridge (GB)

(72) Inventors: Patricius Henrikus Cornelis Van Berkel, Lausanne (CH); Philip Wilson Howard, Cambridge (GB); David G. Williams, Cambridge (GB)

(73) Assignees: ADC Therpeutics S.A., Epalinges (CH); Medimmune Limited, Cambridge (GB)

( * ) Notice: Subject to any disclaimer, the term of this patent is extended or adjusted under 35 U.S.C. 154(b) by 95 days.

(21) Appl. No.: 15/304,089

(22) PCT Filed: Apr. 15, 2015

(86) PCT No.: PCT/GB2015/051141
§ 371 (c)(1),
(2) Date: Oct. 14, 2016

(87) PCT Pub. No.: WO2015/159076
PCT Pub. Date: Oct. 22, 2015

(65) Prior Publication Data
US 2017/0267778 A1     Sep. 21, 2017

(30) Foreign Application Priority Data
Apr. 15, 2014   (GB) .................................. 1406767.2

(51) Int. Cl.
| | | |
|---|---|---|
| C07K 16/00 | (2006.01) | |
| C07K 16/30 | (2006.01) | |
| A61K 47/48 | (2006.01) | |
| A61K 39/00 | (2006.01) | |

(52) U.S. Cl.
CPC .... *C07K 16/3092* (2013.01); *A61K 47/48569* (2013.01); *C07K 16/30* (2013.01); *A61K 2039/505* (2013.01); *C07K 2317/24* (2013.01); *C07K 2317/52* (2013.01); *C07K 2317/54* (2013.01); *C07K 2317/55* (2013.01); *C07K 2317/56* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,923,990 A | 5/1990 | Nakano et al. |
| 5,225,539 A | 7/1993 | Winter |
| 5,530,101 A | 6/1996 | Queen et al. |
| 5,583,024 A | 12/1996 | McElroy et al. |
| 5,585,089 A | 12/1996 | Queen et al. |
| 5,621,002 A | 4/1997 | Bosslet et al. |
| 5,674,713 A | 10/1997 | McElroy et al. |
| 5,693,762 A | 12/1997 | Queen et al. |
| 5,700,670 A | 12/1997 | Yamagishi et al. |
| 5,703,080 A | 12/1997 | Nakakura et al. |
| 5,714,352 A | 2/1998 | Jakobovits |
| 5,723,323 A | 3/1998 | Kauffman et al. |
| 5,763,192 A | 6/1998 | Kauffman et al. |
| 5,766,886 A | 6/1998 | Studnicka et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,876,716 A | 3/1999 | Hansen et al. |
| 5,976,862 A | 11/1999 | Kauffman et al. |
| 6,180,370 B1 | 1/2001 | Queen et al. |
| 6,204,023 B1 | 3/2001 | Robinson et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,465,220 B1 | 10/2002 | Hassan et al. |
| 6,602,677 B1 | 8/2003 | Wood et al. |
| 6,677,435 B2 | 1/2004 | Barbas, III et al. |
| 6,759,509 B1 | 7/2004 | King et al. |
| 6,835,807 B1 | 12/2004 | Susaki et al. |
| 7,223,837 B2 | 5/2007 | De Groot et al. |
| 7,282,567 B2 | 10/2007 | Goldenberg et al. |
| 7,375,078 B2 | 5/2008 | Feng |
| 7,521,541 B2 | 4/2009 | Eigenbrot et al. |
| 7,723,485 B2 | 5/2010 | Junutula et al. |

(Continued)

FOREIGN PATENT DOCUMENTS

| | | |
|---|---|---|
| JP | 58-180487 | 10/1983 |
| WO | WO 86/05803 | 10/1986 |

(Continued)

OTHER PUBLICATIONS

Lavrsen et al. (Glycoconjugate Journal, Apr. 2013, vol. 30, No. 3, pp. 227-236) (Year: 2013).*
Amir et al., "Self-Immolative Dendrimers," Angew. Chem. Int. Ed., 2003, 42:4494-4499.
Amsberry et al., "The Lactonization of 2'-HydroxOydrocinnamic Acid Amides: A Potential Prodrug for Amines," J. Org. Chem., 1990, 55:5867.
Antonow et al., "Synthesis of DNA-Interactive Pyrrolo[2,1-c] [1,4] benzodiazepines (PBDs)," Chem. Rev., 2011, 111 (4), 2815-2864.
Arima et al., "Studies on Tomaymycin, A New Antibiotic. I Isolation and Properties of Tomaymycin," J. Antibiotics, 1972, 25, 437-444.
Axup et al., "Synthesis of site-specific antibody-drug conjugates using unnatural amino acids," Proc Natl Acad Sci USA, 2012, 109(40):16101-16106.

(Continued)

Primary Examiner — Laura B Goddard
Assistant Examiner — Meera Natarajan
(74) Attorney, Agent, or Firm — Michael Best & Friedrich LLP

(57) ABSTRACT

Humanized anti-Tn-MUC1 antibodies and conjugates thereof. Conjugates comprising pyrrolobenzodiazepines (PBDs) having a labile protecting group in the form of a linker to the antibody are described.

23 Claims, 6 Drawing Sheets

(56) References Cited

U.S. PATENT DOCUMENTS

| | | |
|---|---|---|
| 8,440,798 B2 | 5/2013 | Clausen et al. |
| 8,912,311 B2 | 12/2014 | Clausen et al. |
| 9,359,436 B2 | 6/2016 | Clausen et al. |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0052793 A1 | 3/2004 | Carter et al. |
| 2004/0121940 A1 | 6/2004 | De Groot et al. |
| 2005/0271615 A1 | 12/2005 | Shabat et al. |
| 2006/0116422 A1 | 6/2006 | De Groot et al. |

FOREIGN PATENT DOCUMENTS

| | | |
|---|---|---|
| WO | WO 1990/005370 | 5/1990 |
| WO | WO 1990/014424 | 11/1990 |
| WO | WO 1990/014430 | 11/1990 |
| WO | WO 1990/014443 | 11/1990 |
| WO | WO 1992/001047 | 1/1992 |
| WO | WO 1992/003461 | 3/1992 |
| WO | WO 1992/011272 | 7/1992 |
| WO | WO 1992/016221 | 10/1992 |
| WO | WO 1993/006213 | 4/1993 |
| WO | WO 1994/018219 | 8/1994 |
| WO | WO 1997/020032 | 6/1997 |
| WO | WO 1997/033899 | 9/1997 |
| WO | WO 1997/034911 | 9/1997 |
| WO | WO 1998/013059 | 4/1998 |
| WO | WO 1999/006834 | 2/1999 |
| WO | WO 1999/023105 | 5/1999 |
| WO | WO 1999/034824 | 7/1999 |
| WO | WO 2000/012507 | 3/2000 |
| WO | WO 2001/085215 | 11/2001 |
| WO | WO 2002/088172 | 11/2002 |
| WO | WO 2003/026577 | 4/2003 |
| WO | WO 2003/043583 | 5/2003 |
| WO | WO 2003/089574 | 10/2003 |
| WO | WO 2004/022590 | 3/2004 |
| WO | WO 2004/032828 | 4/2004 |
| WO | WO 2004/042075 | 5/2004 |
| WO | WO 2005/082023 | 9/2005 |
| WO | WO 2007/044515 | 4/2007 |
| WO | WO 2007/085930 | 8/2007 |
| WO | WO 2008/040362 | 4/2008 |
| WO | WO 2009/052249 | 4/2009 |
| WO | WO 2010/043880 | 4/2010 |
| WO | WO 2011/130598 | 10/2011 |
| WO | WO 2011/130613 | 10/2011 |
| WO | WO 2011/130615 | 10/2011 |
| WO | WO 2011/130616 | 10/2011 |

OTHER PUBLICATIONS

Berge et al., "Pharmaceutical Salts," J. Pharm. Sci., 1977, 66, 1-19.
Bose et al., "New Approaches to Pyrrolo[2,1-c][1,4] Benzodiazepines: Synthesis, DNA-Binding and Cytotoxicity of DC-81," Tetrahedron, 1992, 48, 751-758.
Burchell et al., "O-linked glycosylation in the mammary gland: changes that occur during malignancy," J. Mammary. Gland. Biol. Neoplasia., 2001, 6, 355-364.
Capellas et al., "Enzymatic condensation of cholecystokinin CCK-8 (4-6) and CCK-8 (7-8) peptide fragments in organic media," Biotechnol. Bioeng., 1997, 56(4):456-463.
Carl et al., "A Novel Connector Linkage Applicable in Prodrug Design," J. Med. Chem., 1981, 24:479-480.
Carlsson et al., "Protein Thiolation and Reversible Protein-Protein Conjugation," Biochem. J., 1978, 173:723-737.
Carter et al., "Humanization of an anti-p185$^{HER2}$ antibody for human cancer therapy," Proc. Natl. Acad. Sci. U.S.A., 1992, 89:4285.
Carter, "Potent antibody therapeutics by design," Nature Reviews Immunology, 2006, 6:343-357.
Chakravarty et al., "Plasmin-Activated Prodrugs for Cancer Chemotherapy. 2. Synthesis and Biological Activity of Peptidyl Derivatives of Doxorubicin," J. Med. Chem., 1983, 26:638-644.
Chothia et al., "Domain association in immunoglobulin molecules. The packing of variable domains," J Mol. Biol., 1985, 186(3), 651.
Chothia et al., "Canonical Structures for the Hypervariable Regions of Immunoglobulins," J. Mol. Biol., 1987, 196:901.
Clausen et al., "Monoclonal-Antibodies Directed to the Blood Group-A Associated Structure, Galactosyl-A-Specificity and Relation to the Thomsen-Friedenreich Antigen," Molecular Immunology, 1988, 25, 199-204.
Cree et al., "Methotrexate chemosensitivity by ATP luminescence in human leukemia cell lines and in breast cancer primary cultures: comparison of the TCA-100 assay with a clonogenic assay," AntiCancer Drugs, 1995, 6:398-404.
Crouch et al., "The use of ATP bioluminescence as a measure of cell proliferation and cytotoxicity," J. Immunol. Meth., 1993, 160:81-88.
De Groot et al., "Cascade-Release Dendrimers. Liberate All End Groups upon a Single Triggering Event in the Dendritic Core," Angew. Chem. Int. Ed., 2003, 42:4490-4494.
De Groot et al., "Elongated Multiple Electronic Cascade and Cyclization Spacer Systems in Activatible Anticancer Prodrugs for Enhanced Drug Release," J. Org. Chem., 2001, 66:8815-8830.
Decision of Rejection for JP 2009-530756 dated Sep. 17, 2013.
Dornan et al., "Therapeutic potential of an anti-CD79b antibody-drug conjugate anti-CD79b-vc-MMAE, for the treatment of non-Hodgkin lymphona," Blood, 2009, 114(13):2721-2729.
Doronina et al., "Enhanced Activity of Monomethylauristatin F through Monoclonal Antibody Delivery: Effects of Linker Technology on Efficacy and Toxicity," Bioconj. Chem., 2006, 17:114-124.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity," Bioconjugate Chemistry, 2002, 13, 855-869.
Dubowchik et al., "Monomethoxytrityl (MMT) as a Versatile Amino Protecting Group for Complex Prodrugs of Anticancer Compounds Sensitive Acids, Bases and Nucleophiles," Tetrahedron Letters, 1997, 38:5257-5260.
Engelmann et al., "Identification and Topology of Variant Sequences within Individual Repeat Domains of the Human Epithelial Tumor Mucin MUC1," The Journal of Biological Chemistry, 2001, vol. 276, pp. 27764-27769.
Erickson et al., "Antibody-Maytansinoid Conjugates Are Activated in Targeted Cancer Cells by Lysosomal Degradation and Linker-Dependent Intracellular Processing," Cancer Res., 2006, 66(8):4426-4433.
Fields et al., "Solid phase peptide synthesis utilizing 9-fluoroenylmethoxycarbonyl amino acids," Int. J. Peptide Protein Res., 1990, 35:161-214.
Fisch et al., "Site-specific modification of a fragment of a chimeric monoclonal antibody using reverse proteolysis," Bioconjugate Chem., 1992, 3:147-153.
Foote et al., "Antibody framework residues affecting the conformation of the hypervariable loops," J Mol. Biol., 1992, 224(2), 487.
Geiser et al., "Automation of solid-phase peptide synthesis," Macromolecular Sequencing and Synthesis, Alan R. Liss, Inc., 1988, pp. 199-218.
Getz et al., "A Comparison between the Sulfhydryl Reductants Tris(2-carboxyethyl) phosphine and Dithiothreitol for Use in Protein Biochemistry," Anal. Biochem., 1999, vol. 273:73-80.
Greene et al., "Carbamates," Protective Groups in Organic Synthesis, 1999, pp. 503-549.
Greene et al., "Protection for the Amide-NH," Protective Groups in Organic Synthesis, 1999, pp. 633-647.
Gregson et al., "Linker Length Modulates DNA Cross-Linking Reactivity and Cytotoxic Potency of C8/C8' Ether-Linked C2-exo-Unsaturated Pyrrolo [2,1-c] benzodiazepine (PBD) Dimers, J. Med. Chem., 2001, 44, 1161-1174.
Gregson et al., "Synthesis of a novel C2/C2'-exo unsaturated pyrrolobenzodiazepine cross-linking agent with remarkable DNA binding affinity and cytotoxicity," Chem. Commun., 1999, 797-798.
Hamann, "Monoclonal antibody-drug conjugates," Cancer Immunol. Immunother., 2005, 15(9):1087-1103.

(56) References Cited

OTHER PUBLICATIONS

Hamblett et al., "Effects of Drug Loading on the Antitumor Activity of a Monoclonal Antibody Drug Conjugate," Clin. Cancer Res., 2004, 10:7063-7070.
Hanish et al., "Monoclonal antibody BW835 defines a site-specific Thomsen-Friedenreich disaccharide linked to threonine within the VTSA motif of MUC1 tandem repeats," Cancer Res., 1995, 55, 4036-4040.
Hara et al., "DC 102, A New Glycosidic Pyrrolo (1,4) Benzodiazepine Antibiotic Produced by Streptomyces," J. Antibiotics, 1988, 41, 702-704.
Hay et al., "A 2-Nitroimidazole Carbamate of-5-Amino-1-(Chloromethyl)-3-[(5, 6, 7-Trimethoxynindl-1,2-Dihydro 2 Benzeind (Amino-SECO-CBI) for use wiyj adept and GEPT," Bioorg. Med. Chem. Lett., 1999, 9:2237.
Hermanson, "Heterobifunctional Cross-linkers," Bioconjugate Techniques, 1996, 234-242.
Hirohashi et al., "Blood group A cross-reacting epitope defined by monoclonal antibodies NCC-LU-35 and -81 expressed in cancer of blood group 0 or B individuals: Its identification as Tn antigen," Proc. Nati. Acad. Sci. USA, 1985, vol. 82, pp. 7039-7043.
Hochlowski et al., "Abbeymycin, A New Anthramycin-Type Antibiotic Produced by a Streptomycete," J. Antibiotics, 1987, 40, 145-148.
Hurley et al., "Covalent Binding of Antitumor Antibiotics in the Minor Groove of DNA. Mechanism of Action of CC-1065 and the Pyrrolo (1,4) benzodiazepines," Acc. Chem. Res., 1986, 19, 230-237.
International Search Report and Written Opinion for Application No. PCT/GB2015/051141 dated Jul. 22, 2015 (10 pages).
Itoh et al., "Sibanomicin, A New Pyrrolo[1,4]-Benzodiazepine Antitumor Antibiotic Produced by a Micromonospora SP," J. Antibiotics, 1988, 41, 1281-1284.
Itoh et al., "Application of Inverse Substrates to Trypsin-Catalyzed Peptide Synthesis," Bioorg. Chem., 1996, 24(1):59-68.
Jeffrey et al., "Design, Synthesis, and in Vitro Evaluation of Dipeptide-Based Antibody Minor Groove Binder Conjugates," J. Med. Chem., 2005, 48:1344-1358.
Jones et al., "Replacing the complementarity-determining regions in a human antibody with those from a mouse," Nature, 1986, 321:522.
Junutula et al., "Site-specific conjugation of a cytotoxic drug to an antibody improves the therapeutic index," Nature Biotech., 2008, 26(8):925-932.
Kabat et al., "Sequences of Proteins of Immunological Interest," 5 ed. National Technical Information Service, 1991. U.S. Dept. Health.
Kabat et al., "Sequences of Proteins of Immunological Interest," U.S. Dept. Health (1983).
King et al., "Facile synthesis of maleimide bifunctional linkers," Tetrahedron Letters, 2002, 43:1987-1990.
Kingsbury et al., "A Novel Peptide Delivery System Involving Peptidase Activated Prodrugs as Antimicrobial Agents. Synthesis and Biological Activity of Peptidyl Derivatives of 5-Fluorouracil," J. Med. Chem., 1984, 27:1447.
Kjeldsen et al., "Coexpression of Sialosyl-Tn (Neuac-Alpha-2-]6Galnac-Alpha-1-]O-Ser/Thr) and Tn (Galnac-Alpha-1-]O-Ser/Thr) Blood-Group Antigens on Tn Erythrocytes," Vox Sanguinis, 1989, 57, 81-87.
Kjeldsen et al., "Preparation and Characterization of Monoclonal-Antibodies Directed to the Tumor-Associated O-Linked Sialosyl-2-]6 Alpha-N-Acetylgalactosaminyl (Sialosyl-Tn)Epitope," Cancer Research, 1988, 48, 2214-2220.
Klee et al., "MUC1 gene-derived glycoprotein assays for monitoring breast cancer (CA 15-3, CA 27.29, BR): are they measuring the same antigen?," Arch. Pathol. Lab. Med., 2004, vol. 128, pp. 1131-1135.
Kohn, "Anthramycin," Antibiotics III, 1975, 3-11.
Konishi et al., "Chicamycin, A New Antitumor Antibiotic II. Structure Determination of Chicamycins," J. Antibiotics, 1984, 37, 200-206.

Kovtun et al., "Antibody-Drug Conjugates Designed to Eradicate Tumors with Homogeneous and Heterogeneous Expression of the Target Antigen," Cancer Res., 2006, 66(6):3214-3121.
Kreitman et al., "Immunotoxins for targeted cancer therapy," Adv. Drug Delivery Rev., 1998, 31:53.
Kumaran et al., "Conformationally Driven Protease-Catalyzed Splicing of Peptide Segments: V8 Protease-Mediated Synthesis of Fragments Derived From Thermolysin and Ribonuclease A ," Protein Sci., 1997, 6(10):2233-2241.
Kuminoto et al., "Mazethramycin, a new member of anthramycin group antibiotics," J. Antibiotics, 1980, 33, 665-667.
Lambert, "Drug-conjugated monoclonal antibodies for the treatment of cancer," Current Opin. In Pharmacol., 2005, 5:543-549.
Langley et al., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 1987, 52, 91-97.
Lavrsen et al., "Aberrantly glycosylated MUC1 is expressed on the surface of breast cancer cells and a target for antibody-dependent cell-mediated cytotoxicity," Glycoconjugate Journal, 2013, vol. 30, No. 3, pp. 227-236.
Law et al., "Lymphocyte Activation Antigen CD70 Expressed by renal Cell Carcinoma Is a Potential Therapeutic Target for Anti-CD70 Antibody-Drug Conjugates," Cancer Res., 2006, 66(4):2328-2337.
Leber et al., "A revised structure for sibiromycin," J. Am. Chem. Soc., 1988, 110, 2992-2993.
Leimgruber et al., "Isolation and characterization of anthramycin, a new antitumor antibiotic," J. Am. Chem. Soc., 1965, 87, 5791-5793.
Leimgruber et al., "The structure of anthramycin," J. Am. Chem. Soc., 1965, 87, 5793-5795.
Marcos et al., "Polypeptide GalNAc-transferases, ST6GalNAc-transferase I, and ST3Gal-transferase I Expression in Gastric Carcinoma Cell Lines," The Journal of Histochemistry & Cytochemistry, 2003, vol. 51(6): 761-771.
McDonagh, "Engineered antibody-drug conjugates with defined sites and stoichiometries of drug attachment," Protein Eng. Design & Sel., 2006, 19(7):299-307.
Morea et al., "Antibody modeling: implications for engineering and design," Methods, 2000, 20(3), 267.
Nicolaou et al., "Calicheamicin 01: A Rationally Designed Molecule with Extremely Potent and Selective DNA Cleaving Properties and Apoptosis Inducing Activity," Angew. Chem. Int. Ed. Engl., 1994, 33: 183-186.
Payne, "Progress in immunoconjugate cancer therapeutics," Cancer Cell, 2003, Cancer Cell, 2003, 3:207-212.
Presta et al., "Humanization of an antibody directed against IgE," J. Immunol., 1993, 151:2623.
Reis et al., "Characterization of a panel of monoclonal antibodies using GalNAc glycosylated peptides and recombinant MUC1," Tumor Biology, 1998, 19, 127-133.
Reis et al., "Development and characterization of an antibody directed to an alpha-N-acetyl-D-galactosamine glycosylated MUC2 peptide," Glycoconjugate Journal, 1998, 15, 51-62.
Riechmann et al., "Reshaping human antibodies for therapy," Nature, 1988, 332:323.
Rodrigues et al., "Synthesis and beta-lactamase-mediated activation of a cephalosporin-taxol prodrug," Chemistry Biology, 1995, 2:223.
Rose et al., "Effects of Deglycosylation on the Architecture of Ovine Submaxilliary Mucin Glycoprotein," The Journal of Biological Chemistry, 1984, vol. 259, No. 5, pp. 3167-3172.
Sanderson et al., "In vivo Drug-Linker Stability of an Anti-CD30 Dipeptide-Linked Auristatin Immunoconjugate," Clin. Cancer Res., 2005, 11:843-852.
Schroder et al., "Formation of the Peptide Bond," The Peptides, 1965, vol. 1, pp. 76-136.
Shamis et al., "Bioactivation of Self-Immolative Dendritic Prodrugs by Catalytic Antibody 38C2," J. Am. Chem. Soc., 2004, 126: 1726-1731.
Shimizu et al., "Prothracarcin, a novel antitumor antibiotic," J. Antibiotics, 1982, 29, 2492-2503.
Sims et al., "A Humanized CD18 Antibody Can Block Function without Cell Destruction," J. Immunol., 1993, 151:2296.

(56) References Cited

OTHER PUBLICATIONS

Sorensen et al., "Chemoenzymatically synthesized multimeric Tn/STn MUC1 glycopeptides elicit cancer-specific anti-MUC1 antibody responses and override tolerance," Glycobiology, 2006, vol. 16, No. 2, p. 96-107.
Springer, "T and Tn, General Carcinoma Auto-Antigens. Science," 1984, vol. 224, No. 4656, 1198-1206.
Storm et al., "Effect of Small Changes in Orientation on Reaction Rate," J. Amer. Chem. Soc., 1972, 94:5815.
Sun et al., "Enabling ScFvs as Multi-Drug Carriers: A Dendritic Approach," Bioorganic & Medical Chemistry Letters, 2003, 11:1761-1768.
Sun et al., "Syntheses of Dendritic Linkers Containing Chlorambucil Residues for the Preparation of Antibody-Multidrug Immunoconjugates," Bioorganic & Medical Chemistry Letters, 2002, 12:2213-2215.
Syrigos et al., "Antibody Directed Enzyme Prodrug Therapy (ADEPT): A Review of the Experimental and Clinical Considerations," Anticancer Research, 1999, 19:605-614.
Takahashi et al., "Human Fas ligand: gene structure, chromosomal location and species specificity," J. Immunol., 1994, 6:1567.
Takeuchi et al., "The epitope recognized by the unique anti-MUC1 monoclonal antibody MY.1E12 involves sialyl alpha 2-3galactosyl beta 1-3N-acetylgalactosaminide linked to a distinct threonine residue in the MUC1 tandem repeat," J. Immunol. Methods, 2002, vol. 270, 199-209.
Takeuchi et al., "Neothramycins A and B, New Antitumor Antibiotics," Antibiotics, 1976, 29, 93-96.
Tarp et al., "Identification of a novel cancer-specific immunodominant glycopeptide epitope in the MUC1 tandem repeat", Glycobiology, 2007, 17(2):197-209.
Thurnher et al., "Use of O-glycosylation-defective human lymphoid cell lines and flow cytometry to delineate the specificity of Moluccella laevis lectin and monoclonal antibody 5F4 for the Tn antigen, (GalNAc alpha 1-O-Ser/Thr)," Immunol. Lett., 1993, 36(3):239-43.
Thurston et al., "Synthesis of DNA-Interactive Pyrrolo[2,1-c][1,4]benzodiazepines," Chem. Rev. 1994, 433-465.
Thurston et al., "The molecular recognition of DNA," Chem. Brit., 1990, 26, 767-772.
Toki et al., "Protease-Mediated Fragmentation of p-Amidobenzyl Ethers: A New Strategy for the Activation of Anticancer Prodrugs," J. Org. Chem., 2002, 67:1866-1872.
Trail et al., "Monoclonal antibody drug immunoconjugates for targeted treatment of cancer," Cancer Immunol. Immunother, 2003, 52:328-337.
Tsunakawa et al., "Porothramycin, a new antibiotic of the anthramycin group: Production, isolation, structure and biological activity," J. Antibiotics, 1988, 41, 1366-1373.
Verhoeyen et al., "Reshaping Human Antibodies: Grafting an Antilysozyme Activity," Science, 1988, 239:1534.
Von Mensdorff-Pouilly et al., "Reactivity of natural and induced human antibodies to MUC1 mucin with MUC1 peptides and N-acetylgalactosamine (GalNAc) peptides," International Journal of Cancer, 2000, 86, 702-712.
Werlen et al., "Site-specific conjugation of an enzyme and an antibody fragment," Bioconjugate Chem., 1994, 5:411-417.
Wu et al., "Arming antibodies: prospects and challenges for immunoconjugates," Nature Biotech. 2006, 23(9):1137-1145.
Xie et al., "In vivo behaviour of antibody- drug conjugates for the targeted treatment of cancer," Expert. Opin. Biol. Ther., 2006, 6(3):281-291.
Yamamoto et al., "A novel monoclonal antibody specific for sialylated MUC1 mucin," Jpn. J.Cancer Res., 1996, 87, 488-496.

* cited by examiner

HUMANIZED ANTI-TN-MUC1 ANTIBODIES AND THEIR CONJUGATES

SEQUENCE LISTING

The sequence listing is filed with the application in electronic and paper formats and is incorporated by reference herein. The sequence listing text file ASFILED_SequenceListing.txt, document number 20953088, was created on May 3, 2017, and is 80,958 bytes in size.

The present disclosure relates to humanized anti-Tn-MUC1 antibodies and conjugates thereof. Conjugates comprising pyrrolobenzodiazepines (PBDs) having a labile protecting group in the form of a linker to the antibody are described.

BACKGROUND

Anti-Tn-MUC1 Antibodies

The human mucin MUC1 is a polymorphic transmembrane glycoprotein expressed on the apical surfaces of simple and glandular epithelia. MUC1 is highly overexpressed and aberrantly O-glycosylated in adenocarcinomas. The extracellular domain of the mucin contains variable number of tandem repeats (25-125) of 20 amino acid residues with five potential sites for O-glycosylation. O-glycans are incompletely processed in cancer cells resulting in the expression of the pancarcinoma carbohydrate antigens Tn (GalNAcα1-O-Ser/Thr), STn (NeuAcα2-6GalNAcα1-O-Ser/Thr), and T (Galβ1-3GalNAcα1-O-Ser/Thr). MUC1 expressed by breast carcinoma cells carries the short cancer-associated Tn, STn, and T antigens as well as the mono- and disialyl core 1 structure (ST, NeuAcα2-3Galβ1-3[NeuAcα2-6]+/−GalNAcα1-O-Ser/Thr) found widely in normal cells. In contrast, MUC1 expressed in normal breast epithelial cells generally carry branched core 2 O-glycans (Galβ1-3[GlcNAcβ1-6]GalNAcα1-O-Ser/Thr) with lactosamine extensions. The cell membrane bound mucin MUC1 has long been considered a prime target for immunotherapeutic intervention. The existence of anti-MUC1 antibodies and circulating immune complexes containing MUC1 in breast cancer patients that correlates with improved prognosis, clearly supports MUC1 as a target. However, until recently, stimulation of an effective cellular or humoral immune response to cancer-associated forms of MUC1 in patients or transgenic animals expressing the human MUC1 gene (using defined immunogens as opposed to cell based therapies) had not been achieved.

More recent research has demonstrated that immunization with long Tn- or 5Tn-MUC1 tandem repeat glycopeptides can override tolerance in humanized MUC1 transgenic Balb/c mice (Sorensen et al. 2006, and example 1 of WO2008/040362). The humoral immune response induced with the glycopeptide vaccines was highly specific for the Tn/STn-MUC1 glycoforms and MUC1 expressed by human cancer cells. This research was developed, with the same group demonstrating that immunization with an immunogenic glycopeptide comprising a GSTA motif O-glycosylated at least at the T-residue or at the S-residue induces a cancer specific immune response toward MUC1 (WO2008/040362). Examples of antibodies produced using this technique include the mouse monoclonal antibodies "5E5" (secreted by the hybridoma deposited at the European Collection of Cell Cultures (ECACC) on 20 Sep. 19, 2006 under accession number STHM1 06092102) and "2D9" (secreted by the hybridoma deposited at the European Collection of Cell Cultures (ECACC) on Sep. 19, 2006 under accession number STHM2 06092101). The human/mouse mouse version of mouse monoclonal antibody "5E5" (secreted by the hybridoma deposited at the European Collection of Cell Cultures (ECACC) on 20 Sep. 19, 2006 under accession number STHM1 06092102) is herein described as "mouse 5E5".

Pyrrolobenzodiazepines

Some pyrrolobenzodiazepines (PBDs) have the ability to recognise and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994); Antonow, D. and Thurston, D. E., *Chem. Rev.* 2011 111 (4), 2815-2864). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102) (Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

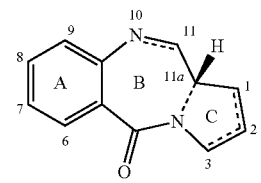

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

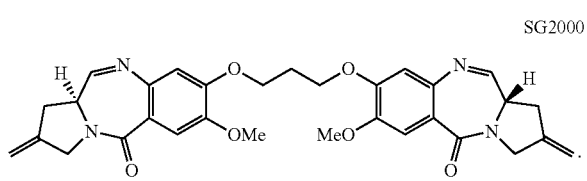

WO 2007/085930 describes the preparation of dimer PBD compounds having linker groups for connection to a cell binding agent, such as an antibody. The linker is present in the bridge linking the monomer PBD units of the dimer.

A particularly advantageous pyrrolobenzodiazepine compound is described by Gregson et al. (*Chem. Commun.* 1999, 797-798) as compound 1, and by Gregson et al. (*J. Med. Chem.* 2001, 44, 1161-1174) as compound 4a. This compound, also known as SG2000, is shown below:

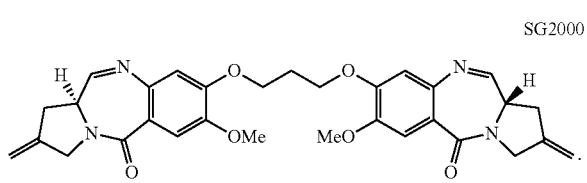

WO 2007/085930 describes the preparation of dimer PBD compounds having linker groups for connection to a cell binding agent, such as an antibody. The linker is present in the bridge linking the monomer PBD units of the dimer.

WO 2011/130613 and WO 2011/130616 describe dimer PBD compounds having linker groups for connection to a cell binding agent, such as an antibody. The linker in these compounds is attached to the PBD core via the C2 position, and are generally cleaved by action of an enzyme on the linker group. In WO 2011/130598, the linker in these compounds is attached to one of the available N10 positions on the PBD core, and are generally cleaved by action of an enzyme on the linker group.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) *Expert. Opin. Biol. Ther.* 6(3):281-291; Kovtun et al (2006) *Cancer Res.* 66(6): 3214-3121; Law et al (2006) *Cancer Res.* 66(4):2328-2337; Wu et al (2005) *Nature Biotech.* 23(9):1137-1145; Lambert J. (2005) *Current Opin. in Pharmacol.* 5:543-549; Hamann P. (2005) *Expert Opin. Ther. Patents* 15(9):1087-1103; Payne, G. (2003) *Cancer Cell* 3:207-212; Trail et al (2003) *Cancer Immunol. Immunother.* 52:328-337; Syrigos and Epenetos (1999) *Anticancer Research* 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Dornan et al (2009) *Blood* 114(13):2721-2729; U.S. Pat. No. 7,521,541; U.S. Pat. No. 7,723,485; WO2009/052249; McDonagh (2006) Protein Eng. Design & Sel. 19(7): 299-307; Doronina et al (2006) Bioconj. Chem. 17:114-124; Erickson et al (2006) *Cancer Res.* 66(8):1-8; Sanderson et al (2005) *Clin. Cancer Res.* 11:843-852; Jeffrey et al (2005) *J. Med. Chem.* 48:1344-1358; Hamblett et al (2004) *Clin. Cancer Res.* 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

The present inventors have developed humanised antibodies based on the 'mouse 5E5' antibody, along with antibody-drug conjugates comprising the humanised 5E5 antibodies and PBD drug-moieties.

DETAILED DISCLOSURE

The present disclosure provides humanized anti-Tn-MUC1 antibodies based on the 'mouse 5E5' antibody and conjugates thereof. Examples of antibody conjugates encompassed by the disclosure include conjugates of a drug, reporter, organic moiety, and/or binding moiety. Particularly preferred are antibody-drug conjugates comprising pyrrolobenzodiazepines (PBDs) having a labile C2 or N10 protecting group in the form of a linker to the humanized anti-Tn-MUC1 antibody.

Starting from the sequence of the 'mouse 5E5' heavy chain variable region (SEQ ID NO:1) and the 'mouse 5E5' light chain variable region (SEQ ID NO:30) the present inventors have generated a number of humanised heavy chain variable regions (SEQ ID NOs:2-29) and humanised light chain variable regions (SEQ ID NOs:31-34) with a view to creating antibodies that have lower immunogenicity in a human individual than the 'mouse 5E5' antibody whilst retaining antigen-binding potency. Surprisingly, these humanised antibodies have also been found to have other advantageous properties, such as improved affinity for the Tn-MUC1 antigen, increased melting temperature ($T_m$), and/or increased levels of expression (for example, by cultured mammalian cells).

Accordingly, in one aspect the present disclosure comprises an isolated humanized antibody that binds to Tn-MUC1, wherein the isolated humanized antibody comprises;
a heavy chain variable region having the amino acid sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, or 29;
a light chain variable region having the amino acid sequence of SEQ ID NO: 30, 31, 32, 33, or 34; and,
optionally, comprises a constant region derived from one or more human antibodies.

In some embodiments the isolated humanized antibody that binds to Tn-MUC1 comprises; a heavy chain variable region having the amino acid sequence of SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, or 29; a light chain variable region having the amino acid sequence of SEQ ID NO: 31, 32, 33, or 34; and, optionally, comprises a constant region derived from one or more human antibodies.

In some embodiments, the humanized antibody does not comprise a heavy chain variable region having the amino acid sequence of SEQ ID NO: 1 and a light chain variable region having the amino acid sequence of SEQ ID NO: 30.

In some embodiments the isolated humanized antibody that binds to Tn-MUC1 comprises:

(i) a heavy chain variable region having the amino acid sequence of SEQ ID NO: 2 and a light chain variable region having the amino acid sequence of SEQ ID NO: 30;

(ii) a heavy chain variable region having the amino acid sequence of SEQ ID NO: 3 and a light chain variable region having the amino acid sequence of SEQ ID NO: 30;

(iii) a heavy chain variable region having the amino acid sequence of SEQ ID NO: 4 and a light chain variable region having the amino acid sequence of SEQ ID NO: 30;

(iv) a heavy chain variable region having the amino acid sequence of SEQ ID NO: 5 and a light chain variable region having the amino acid sequence of SEQ ID NO: 30;

(v) a heavy chain variable region having the amino acid sequence of SEQ ID NO: 6 and a light chain variable region having the amino acid sequence of SEQ ID NO: 30;

(vi) a heavy chain variable region having the amino acid sequence of SEQ ID NO: 7 and a light chain variable region having the amino acid sequence of SEQ ID NO: 30;

(vii) a heavy chain variable region having the amino acid sequence of SEQ ID NO: 8 and a light chain variable region having the amino acid sequence of SEQ ID NO: 30;

(viii) a heavy chain variable region having the amino acid sequence of SEQ ID NO: 9 and a light chain variable region having the amino acid sequence of SEQ ID NO: 30;

(ix) a heavy chain variable region having the amino acid sequence of SEQ ID NO: 10 and a light chain variable region having the amino acid sequence of SEQ ID NO: 30;

(x) a heavy chain variable region having the amino acid sequence of SEQ ID NO: 11 and a light chain variable region having the amino acid sequence of SEQ ID NO: 30;

(xi) a heavy chain variable region having the amino acid sequence of SEQ ID NO: 12 and a light chain variable region having the amino acid sequence of SEQ ID NO: 30;

(xii) a heavy chain variable region having the amino acid sequence of SEQ ID NO: 13 and a light chain variable region having the amino acid sequence of SEQ ID NO: 30;

(xiii) a heavy chain variable region having the amino acid sequence of SEQ ID NO: 14 and a light chain variable region having the amino acid sequence of SEQ ID NO: 30;

(xiv) a heavy chain variable region having the amino acid sequence of SEQ ID NO: 15 and a light chain variable region having the amino acid sequence of SEQ ID NO: 30;

(xv) a heavy chain variable region having the amino acid sequence of SEQ ID NO: 16 and a light chain variable region having the amino acid sequence of SEQ ID NO: 30;

(xvi) a heavy chain variable region having the amino acid sequence of SEQ ID NO: 17 and a light chain variable region having the amino acid sequence of SEQ ID NO: 30;

(xvii) a heavy chain variable region having the amino acid sequence of SEQ ID NO: 18 and a light chain variable region having the amino acid sequence of SEQ ID NO: 30;

(xviii) a heavy chain variable region having the amino acid sequence of SEQ ID NO: 19 and a light chain variable region having the amino acid sequence of SEQ ID NO: 30;

(xix) a heavy chain variable region having the amino acid sequence of SEQ ID NO: 20 and a light chain variable region having the amino acid sequence of SEQ ID NO: 30;

(xx) a heavy chain variable region having the amino acid sequence of SEQ ID NO: 21 and a light chain variable region having the amino acid sequence of SEQ ID NO: 30;

(xxi) a heavy chain variable region having the amino acid sequence of SEQ ID NO: 22 and a light chain variable region having the amino acid sequence of SEQ ID NO: 30;

(xxii) a heavy chain variable region having the amino acid sequence of SEQ ID NO: 23 and a light chain variable region having the amino acid sequence of SEQ ID NO: 30;

(xxiii) a heavy chain variable region having the amino acid sequence of SEQ ID NO: 24 and a light chain variable region having the amino acid sequence of SEQ ID NO: 30;

(xxiv) a heavy chain variable region having the amino acid sequence of SEQ ID NO: 25 and a light chain variable region having the amino acid sequence of SEQ ID NO: 30;

(xxv) a heavy chain variable region having the amino acid sequence of SEQ ID NO: 26 and a light chain variable region having the amino acid sequence of SEQ ID NO: 30;

(xxvi) a heavy chain variable region having the amino acid sequence of SEQ ID NO: 27 and a light chain variable region having the amino acid sequence of SEQ ID NO: 30;

(xxvii) a heavy chain variable region having the amino acid sequence of SEQ ID NO: 28 and a light chain variable region having the amino acid sequence of SEQ ID NO: 30;

(xxviii) a heavy chain variable region having the amino acid sequence of SEQ ID NO: 29 and a light chain variable region having the amino acid sequence of SEQ ID NO: 30;

(xxix) a heavy chain variable region having the amino acid sequence of SEQ ID NO: 1 and a light chain variable region having the amino acid sequence of SEQ ID NO: 31;

(xxx) a heavy chain variable region having the amino acid sequence of SEQ ID NO: 2 and a light chain variable region having the amino acid sequence of SEQ ID NO: 31;

(xxxi) a heavy chain variable region having the amino acid sequence of SEQ ID NO: 3 and a light chain variable region having the amino acid sequence of SEQ ID NO: 31;

(xxxii) a heavy chain variable region having the amino acid sequence of SEQ ID NO: 4 and a light chain variable region having the amino acid sequence of SEQ ID NO: 31;

(xxxiii) a heavy chain variable region having the amino acid sequence of SEQ ID NO: 5 and a light chain variable region having the amino acid sequence of SEQ ID NO: 31;

(xxxiv) a heavy chain variable region having the amino acid sequence of SEQ ID NO: 6 and a light chain variable region having the amino acid sequence of SEQ ID NO: 31;

(xxxv) a heavy chain variable region having the amino acid sequence of SEQ ID NO: 7 and a light chain variable region having the amino acid sequence of SEQ ID NO: 31;

(xxxvi) a heavy chain variable region having the amino acid sequence of SEQ ID NO: 8 and a light chain variable region having the amino acid sequence of SEQ ID NO: 31;

(xxxvii) a heavy chain variable region having the amino acid sequence of SEQ ID NO: 9 and a light chain variable region having the amino acid sequence of SEQ ID NO: 31;

(xxxviii) a heavy chain variable region having the amino acid sequence of SEQ ID NO: 10 and a light chain variable region having the amino acid sequence of SEQ ID NO: 31;

(xxxix) a heavy chain variable region having the amino acid sequence of SEQ ID NO: 11 and a light chain variable region having the amino acid sequence of SEQ ID NO: 31;

(xl) a heavy chain variable region having the amino acid sequence of SEQ ID NO: 12 and a light chain variable region having the amino acid sequence of SEQ ID NO: 31;

(xli) a heavy chain variable region having the amino acid sequence of SEQ ID NO: 13 and a light chain variable region having the amino acid sequence of SEQ ID NO: 31;

(xlii) a heavy chain variable region having the amino acid sequence of SEQ ID NO: 14 and a light chain variable region having the amino acid sequence of SEQ ID NO: 31;

(xliii) a heavy chain variable region having the amino acid sequence of SEQ ID NO: 15 and a light chain variable region having the amino acid sequence of SEQ ID NO: 31;

(xliv) a heavy chain variable region having the amino acid sequence of SEQ ID NO: 16 and a light chain variable region having the amino acid sequence of SEQ ID NO: 31;

(xlv) a heavy chain variable region having the amino acid sequence of SEQ ID NO: 17 and a light chain variable region having the amino acid sequence of SEQ ID NO: 31;

(xlvi) a heavy chain variable region having the amino acid sequence of SEQ ID NO: 18 and a light chain variable region having the amino acid sequence of SEQ ID NO: 31;

(xlvii) a heavy chain variable region having the amino acid sequence of SEQ ID NO: 19 and a light chain variable region having the amino acid sequence of SEQ ID NO: 31;

(xlviii) a heavy chain variable region having the amino acid sequence of SEQ ID NO: 20 and a light chain variable region having the amino acid sequence of SEQ ID NO: 31;

(xlix) a heavy chain variable region having the amino acid sequence of SEQ ID NO: 21 and a light chain variable region having the amino acid sequence of SEQ ID NO: 31;

(l) a heavy chain variable region having the amino acid sequence of SEQ ID NO: 22 and a light chain variable region having the amino acid sequence of SEQ ID NO: 31;

(li) a heavy chain variable region having the amino acid sequence of SEQ ID NO: 23 and a light chain variable region having the amino acid sequence of SEQ ID NO: 31;

(lii) a heavy chain variable region having the amino acid sequence of SEQ ID NO: 24 and a light chain variable region having the amino acid sequence of SEQ ID NO: 31;

(liii) a heavy chain variable region having the amino acid sequence of SEQ ID NO: 25 and a light chain variable region having the amino acid sequence of SEQ ID NO: 31;

(liv) a heavy chain variable region having the amino acid sequence of SEQ ID NO: 26 and a light chain variable region having the amino acid sequence of SEQ ID NO: 31;

(lv) a heavy chain variable region having the amino acid sequence of SEQ ID NO: 27 and a light chain variable region having the amino acid sequence of SEQ ID NO: 31;

(lvi) a heavy chain variable region having the amino acid sequence of SEQ ID NO: 28 and a light chain variable region having the amino acid sequence of SEQ ID NO: 31;

(lvii) a heavy chain variable region having the amino acid sequence of SEQ ID NO: 29 and a light chain variable region having the amino acid sequence of SEQ ID NO: 31;

(lviii) a heavy chain variable region having the amino acid sequence of SEQ ID NO: 1 and a light chain variable region having the amino acid sequence of SEQ ID NO: 32;

(lix) a heavy chain variable region having the amino acid sequence of SEQ ID NO: 2 and a light chain variable region having the amino acid sequence of SEQ ID NO: 32;

(lx) a heavy chain variable region having the amino acid sequence of SEQ ID NO: 3 and a light chain variable region having the amino acid sequence of SEQ ID NO: 32;

(lxi) a heavy chain variable region having the amino acid sequence of SEQ ID NO: 4 and a light chain variable region having the amino acid sequence of SEQ ID NO: 32;

(lxii) a heavy chain variable region having the amino acid sequence of SEQ ID NO: 5 and a light chain variable region having the amino acid sequence of SEQ ID NO: 32;

(lxiii) a heavy chain variable region having the amino acid sequence of SEQ ID NO: 6 and a light chain variable region having the amino acid sequence of SEQ ID NO: 32;

(lxiv) a heavy chain variable region having the amino acid sequence of SEQ ID NO: 7 and a light chain variable region having the amino acid sequence of SEQ ID NO: 32;

(lxv) a heavy chain variable region having the amino acid sequence of SEQ ID NO: 8 and a light chain variable region having the amino acid sequence of SEQ ID NO: 32;

(lxvi) a heavy chain variable region having the amino acid sequence of SEQ ID NO: 9 and a light chain variable region having the amino acid sequence of SEQ ID NO: 32;

(lxvii) a heavy chain variable region having the amino acid sequence of SEQ ID NO: 10 and a light chain variable region having the amino acid sequence of SEQ ID NO: 32;

(lxviii) a heavy chain variable region having the amino acid sequence of SEQ ID NO: 11 and a light chain variable region having the amino acid sequence of SEQ ID NO: 32;

(lxix) a heavy chain variable region having the amino acid sequence of SEQ ID NO: 12 and a light chain variable region having the amino acid sequence of SEQ ID NO: 32;

(lxx) a heavy chain variable region having the amino acid sequence of SEQ ID NO: 13 and a light chain variable region having the amino acid sequence of SEQ ID NO: 32;

(lxxi) a heavy chain variable region having the amino acid sequence of SEQ ID NO: 14 and a light chain variable region having the amino acid sequence of SEQ ID NO: 32;

(lxxii) a heavy chain variable region having the amino acid sequence of SEQ ID NO: 15 and a light chain variable region having the amino acid sequence of SEQ ID NO: 32;

(lxxiii) a heavy chain variable region having the amino acid sequence of SEQ ID NO: 16 and a light chain variable region having the amino acid sequence of SEQ ID NO: 32;

(lxxiv) a heavy chain variable region having the amino acid sequence of SEQ ID NO: 17 and a light chain variable region having the amino acid sequence of SEQ ID NO: 32;

(lxxv) a heavy chain variable region having the amino acid sequence of SEQ ID NO: 18 and a light chain variable region having the amino acid sequence of SEQ ID NO: 32;

(lxxvi) a heavy chain variable region having the amino acid sequence of SEQ ID NO: 19 and a light chain variable region having the amino acid sequence of SEQ ID NO: 32;

(lxxvii) a heavy chain variable region having the amino acid sequence of SEQ ID NO: 20 and a light chain variable region having the amino acid sequence of SEQ ID NO: 32;

(lxxviii) a heavy chain variable region having the amino acid sequence of SEQ ID NO: 21 and a light chain variable region having the amino acid sequence of SEQ ID NO: 32;

(lxxix) a heavy chain variable region having the amino acid sequence of SEQ ID NO: 22 and a light chain variable region having the amino acid sequence of SEQ ID NO: 32;

(lxxx) a heavy chain variable region having the amino acid sequence of SEQ ID NO: 23 and a light chain variable region having the amino acid sequence of SEQ ID NO: 32;

(lxxxi) a heavy chain variable region having the amino acid sequence of SEQ ID NO: 24 and a light chain variable region having the amino acid sequence of SEQ ID NO: 32;

(lxxxii) a heavy chain variable region having the amino acid sequence of SEQ ID NO: 25 and a light chain variable region having the amino acid sequence of SEQ ID NO: 32;

(lxxxiii) a heavy chain variable region having the amino acid sequence of SEQ ID NO: 26 and a light chain variable region having the amino acid sequence of SEQ ID NO: 32;

(lxxxiv) a heavy chain variable region having the amino acid sequence of SEQ ID NO: 27 and a light chain variable region having the amino acid sequence of SEQ ID NO: 32;

(lxxxv) a heavy chain variable region having the amino acid sequence of SEQ ID NO: 28 and a light chain variable region having the amino acid sequence of SEQ ID NO: 32;

(lxxxvi) a heavy chain variable region having the amino acid sequence of SEQ ID NO: 29 and a light chain variable region having the amino acid sequence of SEQ ID NO: 32;

(lxxxvii) a heavy chain variable region having the amino acid sequence of SEQ ID NO: 1 and a light chain variable region having the amino acid sequence of SEQ ID NO: 33;

(lxxxviii) a heavy chain variable region having the amino acid sequence of SEQ ID NO: 2 and a light chain variable region having the amino acid sequence of SEQ ID NO: 33;

(lxxxix) a heavy chain variable region having the amino acid sequence of SEQ ID NO: 3 and a light chain variable region having the amino acid sequence of SEQ ID NO: 33;

(xc) a heavy chain variable region having the amino acid sequence of SEQ ID NO: 4 and a light chain variable region having the amino acid sequence of SEQ ID NO: 33;

(xci) a heavy chain variable region having the amino acid sequence of SEQ ID NO: 5 and a light chain variable region having the amino acid sequence of SEQ ID NO: 33;

(xcii) a heavy chain variable region having the amino acid sequence of SEQ ID NO: 6 and a light chain variable region having the amino acid sequence of SEQ ID NO: 33;

(xciii) a heavy chain variable region having the amino acid sequence of SEQ ID NO: 7 and a light chain variable region having the amino acid sequence of SEQ ID NO: 33;

(xciv) a heavy chain variable region having the amino acid sequence of SEQ ID NO: 8 and a light chain variable region having the amino acid sequence of SEQ ID NO: 33;

(xcv) a heavy chain variable region having the amino acid sequence of SEQ ID NO: 9 and a light chain variable region having the amino acid sequence of SEQ ID NO: 33;

(xcvi) a heavy chain variable region having the amino acid sequence of SEQ ID NO: 10 and a light chain variable region having the amino acid sequence of SEQ ID NO: 33;

(xcvii) a heavy chain variable region having the amino acid sequence of SEQ ID NO: 11 and a light chain variable region having the amino acid sequence of SEQ ID NO: 33;

(xciii) a heavy chain variable region having the amino acid sequence of SEQ ID NO: 12 and a light chain variable region having the amino acid sequence of SEQ ID NO: 33;

(xciv) a heavy chain variable region having the amino acid sequence of SEQ ID NO: 13 and a light chain variable region having the amino acid sequence of SEQ ID NO: 33;

(xcv) a heavy chain variable region having the amino acid sequence of SEQ ID NO: 14 and a light chain variable region having the amino acid sequence of SEQ ID NO: 33;

(xcvi) a heavy chain variable region having the amino acid sequence of SEQ ID NO: 15 and a light chain variable region having the amino acid sequence of SEQ ID NO: 33;

(xcvii) a heavy chain variable region having the amino acid sequence of SEQ ID NO: 16 and a light chain variable region having the amino acid sequence of SEQ ID NO: 33;

(xcviii) a heavy chain variable region having the amino acid sequence of SEQ ID NO: 17 and a light chain variable region having the amino acid sequence of SEQ ID NO: 33;

(xciv) a heavy chain variable region having the amino acid sequence of SEQ ID NO: 18 and a light chain variable region having the amino acid sequence of SEQ ID NO: 33;

(xcv) a heavy chain variable region having the amino acid sequence of SEQ ID NO: 19 and a light chain variable region having the amino acid sequence of SEQ ID NO: 33;

(xcvi) a heavy chain variable region having the amino acid sequence of SEQ ID NO: 20 and a light chain variable region having the amino acid sequence of SEQ ID NO: 33;

(xcvii) a heavy chain variable region having the amino acid sequence of SEQ ID NO: 21 and a light chain variable region having the amino acid sequence of SEQ ID NO: 33;

(xcviii) a heavy chain variable region having the amino acid sequence of SEQ ID NO: 22 and a light chain variable region having the amino acid sequence of SEQ ID NO: 33;

(xcix) a heavy chain variable region having the amino acid sequence of SEQ ID NO: 23 and a light chain variable region having the amino acid sequence of SEQ ID NO: 33;

(c) a heavy chain variable region having the amino acid sequence of SEQ ID NO: 24 and a light chain variable region having the amino acid sequence of SEQ ID NO: 33;

(ci) a heavy chain variable region having the amino acid sequence of SEQ ID NO: 25 and a light chain variable region having the amino acid sequence of SEQ ID NO: 33;

(cii) a heavy chain variable region having the amino acid sequence of SEQ ID NO: 26 and a light chain variable region having the amino acid sequence of SEQ ID NO: 33;

(ciii) a heavy chain variable region having the amino acid sequence of SEQ ID NO: 27 and a light chain variable region having the amino acid sequence of SEQ ID NO: 33;

(civ) a heavy chain variable region having the amino acid sequence of SEQ ID NO: 28 and a light chain variable region having the amino acid sequence of SEQ ID NO: 33;

(cv) a heavy chain variable region having the amino acid sequence of SEQ ID NO: 29 and a light chain variable region having the amino acid sequence of SEQ ID NO: 33;

(cvi) a heavy chain variable region having the amino acid sequence of SEQ ID NO: 1 and a light chain variable region having the amino acid sequence of SEQ ID NO: 34;

(cvii) a heavy chain variable region having the amino acid sequence of SEQ ID NO: 2 and a light chain variable region having the amino acid sequence of SEQ ID NO: 34;

(cviii) a heavy chain variable region having the amino acid sequence of SEQ ID NO: 3 and a light chain variable region having the amino acid sequence of SEQ ID NO: 34;

(cix) a heavy chain variable region having the amino acid sequence of SEQ ID NO: 4 and a light chain variable region having the amino acid sequence of SEQ ID NO: 34;

(cx) a heavy chain variable region having the amino acid sequence of SEQ ID NO: 5 and a light chain variable region having the amino acid sequence of SEQ ID NO: 34;

(cxi) a heavy chain variable region having the amino acid sequence of SEQ ID NO: 6 and a light chain variable region having the amino acid sequence of SEQ ID NO: 34;

(cxii) a heavy chain variable region having the amino acid sequence of SEQ ID NO: 7 and a light chain variable region having the amino acid sequence of SEQ ID NO: 34;

(cxiii) a heavy chain variable region having the amino acid sequence of SEQ ID NO: 8 and a light chain variable region having the amino acid sequence of SEQ ID NO: 34;

(cxiv) a heavy chain variable region having the amino acid sequence of SEQ ID NO: 9 and a light chain variable region having the amino acid sequence of SEQ ID NO: 34;

(cxv) a heavy chain variable region having the amino acid sequence of SEQ ID NO: 10 and a light chain variable region having the amino acid sequence of SEQ ID NO: 34;

(cxvi) a heavy chain variable region having the amino acid sequence of SEQ ID NO: 11 and a light chain variable region having the amino acid sequence of SEQ ID NO: 34;

(cxvii) a heavy chain variable region having the amino acid sequence of SEQ ID NO: 12 and a light chain variable region having the amino acid sequence of SEQ ID NO: 34;

(cxviii) a heavy chain variable region having the amino acid sequence of SEQ ID NO: 13 and a light chain variable region having the amino acid sequence of SEQ ID NO: 34;

(cxix) a heavy chain variable region having the amino acid sequence of SEQ ID NO: 14 and a light chain variable region having the amino acid sequence of SEQ ID NO: 34;

(cxx) a heavy chain variable region having the amino acid sequence of SEQ ID NO: 15 and a light chain variable region having the amino acid sequence of SEQ ID NO: 34;

(cxxi) a heavy chain variable region having the amino acid sequence of SEQ ID NO: 16 and a light chain variable region having the amino acid sequence of SEQ ID NO: 34;

(cxxii) a heavy chain variable region having the amino acid sequence of SEQ ID NO: 17 and a light chain variable region having the amino acid sequence of SEQ ID NO: 34;
(cxxiii) a heavy chain variable region having the amino acid sequence of SEQ ID NO: 18 and a light chain variable region having the amino acid sequence of SEQ ID NO: 34;
(cxxiv) a heavy chain variable region having the amino acid sequence of SEQ ID NO: 19 and a light chain variable region having the amino acid sequence of SEQ ID NO: 34;
(cxxv) a heavy chain variable region having the amino acid sequence of SEQ ID NO: 20 and a light chain variable region having the amino acid sequence of SEQ ID NO: 34;
(cxxvi) a heavy chain variable region having the amino acid sequence of SEQ ID NO: 21 and a light chain variable region having the amino acid sequence of SEQ ID NO: 34;
(cxxvii) a heavy chain variable region having the amino acid sequence of SEQ ID NO: 22 and a light chain variable region having the amino acid sequence of SEQ ID NO: 34;
(cxxviii) a heavy chain variable region having the amino acid sequence of SEQ ID NO: 23 and a light chain variable region having the amino acid sequence of SEQ ID NO: 34;
(cxxix) a heavy chain variable region having the amino acid sequence of SEQ ID NO: 24 and a light chain variable region having the amino acid sequence of SEQ ID NO: 34;
(cxxx) a heavy chain variable region having the amino acid sequence of SEQ ID NO: 25 and a light chain variable region having the amino acid sequence of SEQ ID NO: 34;
(cxxxi) a heavy chain variable region having the amino acid sequence of SEQ ID NO: 26 and a light chain variable region having the amino acid sequence of SEQ ID NO: 34;
(cxxxii) a heavy chain variable region having the amino acid sequence of SEQ ID NO: 27 and a light chain variable region having the amino acid sequence of SEQ ID NO: 34;
(cxxxiii) a heavy chain variable region having the amino acid sequence of SEQ ID NO: 28 and a light chain variable region having the amino acid sequence of SEQ ID NO: 34; or
(cxxxiv) a heavy chain variable region having the amino acid sequence of SEQ ID NO: 29 and a light chain variable region having the amino acid sequence of SEQ ID NO: 34.

The sequences of the antibody heavy chain variable regions and/or the light chain variable regions disclosed herein may be modified by, for example, insertions, substitutions and/or deletions to the extent that the humanized antibody maintains the ability to bind to human-Tn-MUC1. The skilled person can ascertain the maintenance of this activity by performing the functional assays described herein, or known in the art. Accordingly, in some embodiments the heavy chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion. In some embodiments the light chain variable region comprises no more than 20 insertions, substitutions and/or deletions, such as no more than 15, no more than 10, no more than 9, no more than 8, no more than 7, no more than 6, no more than 5, no more than 4, no more than 3, no more than 2, or no more than 1 insertion, substitution and/or deletion. In some embodiments the humanized antibodies of the disclosure include antibodies comprising $V_H$ and $V_L$ domains with amino acid sequences that are identical to the sequences described herein.

Antibody Affinity

In some embodiments the humanized antibody binds Tn-MUC1 with a dissociation constant ($K_D$) of at least $10^{-6}$ M, such as at least $5\times10^{-7}$ M, at least $10^{-7}$ M, at least $5\times10^{-8}$ M, at least $10^{-9}$ M, such as at least $5\times10^{-10}$ M, at least $10^{-10}$ M, at least $5\times10^{-11}$ M, at least $10^{-11}$ M, at least $5\times10^{-12}$ M, at least $10^{-12}$ M, at least $5\times10^{-13}$ M, at least $10^{-13}$ M, at least $5\times10^{-14}$ M, at least $10^{-14}$ M, at least $5\times10^{-15}$ M, or at least $10^{-15}$ M. In one embodiment the humanized antibody competitively inhibits the in vivo and/or in vitro binding to Tn-MUC1 of an antibody comprising a heavy chain variable region having the amino acid sequence of SEQ ID NO: 1 and a light chain variable region having the amino acid sequence of SEQ ID NO: 30. In one embodiment the humanized antibody competitively inhibits the in vivo and/or in vitro binding to Tn-MUC1 of the 'mouse 5E5' antibody. In some embodiments an equimolar dose of the humanised antibody competitively inhibits at least 20% of the binding by the 'mouse 5E5' antibody, such as at least 30%, at least 40%, at least 50%, at least 60%, at least 70%, at least 80%, or at least 90% of the binding. Percentage binding may be measured by, for example, a competitive ELISA assay where % inhibition of binding is calculated as [(1-absorbance of test sample)/(absorbance of negative control)].

In some embodiments, the humanised antibody binds Tn-MUC1 on ELISA with an $EC_{50}$ of no more than 70 ng/ml, such as no more than 65 ng/ml, no more than 60 ng/ml, no more than 55 ng/ml, no more than 50 ng/ml, no more than 45 ng/ml, no more than 40 ng/ml, no more than 35 ng/ml, no more than 30 ng/ml, no more than 25 ng/ml, no more than 20 ng/ml, no more than 15 ng/ml, no more than 10 ng/ml, or no more than 5 ng/ml.

In some embodiments the humanised antibody binds to cells expressing Tn-MUC1 e.g. ZR-75-1 cells with an $EC_{50}$ of no more than 70 ng/ml, such as no more than 65 ng/ml, no more than 60 ng/ml, no more than 55 ng/ml, no more than 50 ng/ml, no more than 45 ng/ml, no more than 40 ng/ml, no more than 35 ng/ml, no more than 30 ng/ml, no more than 25 ng/ml, no more than 20 ng/ml, no more than 15 ng/ml, no more than 10 ng/ml, or no more than 5 ng/ml.

Antibody Expression

In some embodiments the humanized antibody of the disclosure expresses at a level of at least 10 µg/ml in a static HEK293T transient transfection system, for example, at least 15 µg/ml, at least 20 µg/ml, at least 25 µg/ml, at least 30 µg/ml. In some embodiments the humanized antibody expresses at a level of at least 20 µg/ml in a shaken HEK293T transient transfection system, for example, at least 25 µg/ml, at least 30 µg/ml, at least 35 µg/ml, at least 40 µg/ml, at least 45 µg/ml, at least 50 µg/ml, at least 55 µg/ml, or at least 60 µg/ml. In some embodiments the transient transfection is performed as set out in Protocol 2 or Protocol 7 described herein, optionally with IgG quantification as set out in Protocol 3 described herein In one embodiment the humanized antibody of the disclosure expresses at a level higher than an antibody or antibody fragment comprising a heavy chain variable region having the amino acid sequence of SEQ ID NO: 1 and a light chain variable region having the amino acid sequence of SEQ ID NO: 30. In one embodiment the humanized antibody expresses at a level higher than the 'mouse 5E5' antibody, for example an expression level that is at least 20% higher than that of mouse 5E5, such as at least 40% higher, at least 60% higher, at least 80% higher, at least 100% higher, at least 150% higher, or at least 200% higher than that of mouse 5E5. The expression levels of the antibodies are compared under conditions which are identical (other than for the identity of the antibodies). In some embodiments the antibodies are expressed as set out in Protocol 2 described herein, optionally with IgG quantification as set out in Protocol 3 described herein Antibody Thermal Stability In some embodiments the humanized antibody of the disclosure has a melting temperature ($T_m$) of at least 60° C., such as at least 62° C., at least 64° C., at least 66° C., at least 68° C., at least 70° C., at least 72° C., at least 74° C., at least 76° C., at least 78° C., or at least 80° C. In some embodiments the melting temperature is measured according to protocol 5 defined herein. In one embodiment the humanized antibody has a melting temperature ($T_m$) higher than an otherwise identical antibody or antibody fragment comprising a heavy chain variable region having the amino acid sequence of SEQ ID NO: 1 and a light chain variable region having the amino acid sequence of SEQ ID NO: 30. In one embodiment the humanized antibody has a melting temperature ($T_m$) higher than the 'mouse 5E5' antibody, for example a $T_m$ that is at least 1° C. higher than that of mouse 5E5, such as at least 2° C. higher, at least 3° C. higher, at least 4° C. higher, at least 5° C. higher, at least 8° C. higher, or at least 10° C. higher than that of mouse 5E5.

Antibody Immunogenicity

Preferably the humanized antibody of the disclosure has reduced immunogenicity in a human subject as compared to a non-humanized antibody of the same specificity (for example, a mouse antibody precursor prior to humanization. In one embodiment the humanized antibody has immunogenicity in a human subject lower than an otherwise identical antibody or antibody fragment comprising a heavy chain variable region having the amino acid sequence of SEQ ID NO: 1 and a light chain variable region having the amino acid sequence of SEQ ID NO: 30. In one embodiment the humanized antibody has immunogenicity in a human subject lower than the 'mouse 5E5' antibody.

Low or reduced immunogenicity can be characterized by the ability to treat patients for extended periods with measurable alleviation of symptoms and low and/or acceptable toxicity. Low or acceptable immunogenicity and/or high affinity, as well as other suitable properties, can contribute to the therapeutic results achieved. "Reduced immunogenicity" is defined herein as raising significant HAHA, HACA or HAMA responses in less 90%, such as less than 80%, less than 70%, less than 60%, less than 50%, less than 40%, less than 30%, less than 20%, less than 10% of the proportion of patients who show a significant HAHA, HACA or HAMA response when treated with the mouse 5E5 antibody.

Effective Dose

In some embodiments an antibody-drug conjugate comprising the humanized antibody has an $EC_{50}$ of less than 35 ng/ml, such as less than 30 ng/ml, less than 25 ng/ml, less than 20 ng/ml, or less than 15 ng/ml. In some embodiments the $EC_{50}$ of the antibody-drug conjugate is at least 2 ng/ml lower than an otherwise identical conjugate comprising an antibody comprising a heavy chain variable region having the amino acid sequence of SEQ ID NO: 1 and a light chain variable region having the amino acid sequence of SEQ ID NO: 30, for example at least 5 ng/ml lower, at least 10 ng/ml lower, at least 15 ng/ml lower, at least 20 ng/ml lower, at least 25 ng/ml lower, or at least 30 ng/ml lower. In some embodiments the $EC_{50}$ of the antibody-drug conjugate is at least 2 ng/ml lower than an otherwise identical conjugate comprising the 'mouse 5E5' antibody, for example at least 5 ng/ml lower, at least 10 ng/ml lower, at least 15 ng/ml lower, at least 20 ng/ml lower, at least 25 ng/ml lower, or at least 30 ng/ml lower.

PBD Antibody-Drug Conjugates

Non-Site-Specific Conjugates

One aspect of the present disclosure comprises a conjugate of formula $L\text{-}(D^L)_p$, where $D^L$ is of formula I or II:

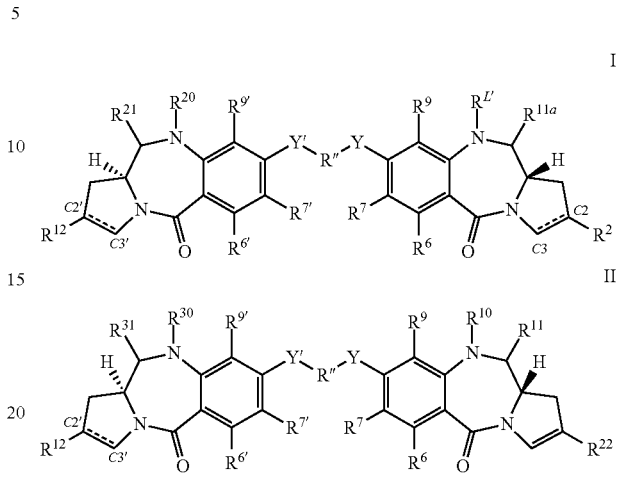

wherein:

L is an isolated humanized antibody that binds to Tn-MUC1 (Ab) as defined above; when there is a double bond present between C2' and C3', $R^{12}$ is selected from the group consisting of:

(ia) $C_{5\text{-}10}$ aryl group, optionally substituted by one or more substituents selected from the group comprising: halo, nitro, cyano, ether, carboxy, ester, $C_{1\text{-}7}$ alkyl, $C_{3\text{-}7}$ heterocyclyl and bis-oxy-$C_{1\text{-}3}$ alkylene;

(ib) $C_{1\text{-}5}$ saturated aliphatic alkyl;

(ic) $C_{3\text{-}6}$ saturated cycloalkyl;

(id)

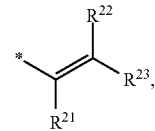

wherein each of $R^{21}$, $R^{22}$ and $R^{23}$ are independently selected from H, $C_{1\text{-}3}$ saturated alkyl, $C_{2\text{-}3}$ alkenyl, $C_{2\text{-}3}$ alkynyl and cyclopropyl, where the total number of carbon atoms in the $R^{12}$ group is no more than 5;

(ie)

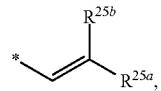

wherein one of $R^{25a}$ and $R^{25b}$ is H and the other is selected from: phenyl, which phenyl is optionally substituted by a group selected from halo, methyl, methoxy; pyridyl; and thiophenyl; and (if)

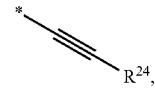

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

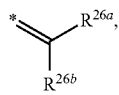

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, NH$_2$, NHR, NRR', nitro, Me$_3$Sn and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, NH$_2$, NHR, NHRR', nitro, Me$_3$Sn and halo; R" is a $C_{3-12}$ alkylene group, which chain may be interrupted by one or more heteroatoms, e.g. O, S, NR$^{N2}$ (where R$^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, OR$^A$, where R$^A$ is $C_{1-4}$ alkyl, and SO$_z$M, where z is 2 or 3 and M is a monovalent pharmaceutically acceptable cation;

$R^{20}$ and $R^{21}$ either together form a double bond between the nitrogen and carbon atoms to which they are bound; or;

$R^{20}$ is selected from H and R$^C$, where R$^C$ is a capping group;

$R^{21}$ is selected from OH, OR$^A$ and SO$_z$M;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

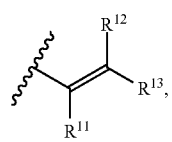

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

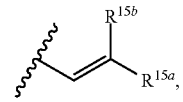

wherein one of $R^{15a}$ and $R^{15b}$ is H and the other is selected from: phenyl, which phenyl is optionally substituted by a group selected from halo, methyl, methoxy; pyridyl; and thiophenyl; and (if)

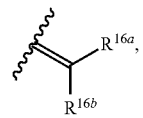

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

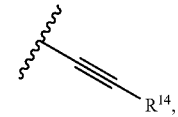

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

IIIa

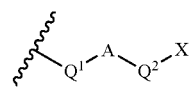

where A is a $C_{5-7}$ aryl group, and either (i) $Q^1$ is a single bond, and $Q^2$ is selected from a single bond and —Z—(CH$_2$)$_n$—, where Z is selected from a single bond, O, S and NH and n is from 1 to 3; or (ii) $Q^1$ is —CH=CH—, and $Q^2$ is a single bond;

(b)

IIIb

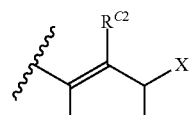

where;
$R^{C1}$, $R^{C2}$ and $R^{C3}$ are independently selected from H and unsubstituted $C_{1-2}$ alkyl;

(c)

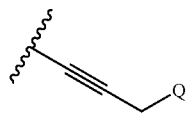

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

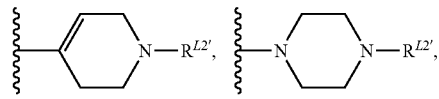

$NR^N R^{L2'}$, wherein $R^N$ is selected from the group comprising H and $C_{1-4}$ alkyl;
$R^{L2'}$ is a linker for connection to the antibody (Ab);
$R^{10}$ and $R^{11}$ either together form a double bond between the nitrogen and carbon atoms to which they are bound or;
$R^{10}$ is H and $R^{11}$ is selected from OH, $OR^A$ and $SO_zM$;
$R^{30}$ and $R^{31}$ either together form a double bond between the nitrogen and carbon atoms to which they are bound or;
$R^{30}$ is H and $R^{31}$ is selected from OH, $OR^A$ and $SO_zM$.

Site-specific Conjugates

Accordingly, in one aspect the disclosure provides a conjugate of formula L-(DL)p, where DL is of formula I or II:

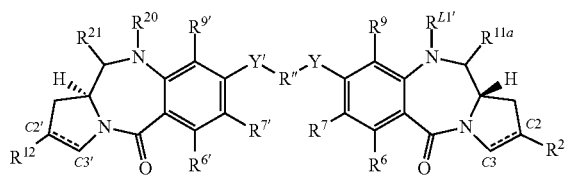

I

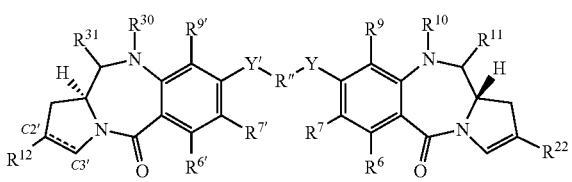

II wherein:
L is an isolated humanized antibody (Ab) that binds to Tn-MUC1 as defined above, and further comprises an antibody heavy chain constant region, or a portion of an antibody heavy chain constant region (such as an Fc region or a CH3 domain);
when there is a double bond present between C2' and C3', $R^{12}$ is selected from the group consisting of:
(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{13}$ alkylene;
(ib) $C_{1-5}$ saturated aliphatic alkyl;
(ic) $C_{3-6}$ saturated cycloalkyl;

(id)

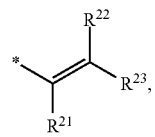

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

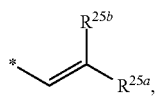

wherein one of $R^{25a}$ and $R^{25b}$ is H and the other is selected from: phenyl, which phenyl is optionally substituted by a group selected from halo, methyl, methoxy; pyridyl; and thiophenyl; and (if)

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;
when there is a single bond present between C2' and C3', $R^{12}$ is

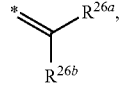

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo; R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) C1-s saturated aliphatic alkyl;

(ic) $C_{3-6}$ saturated cycloalkyl;

(id)

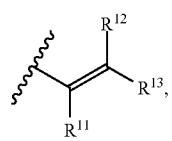

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

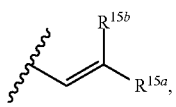

wherein one of $R^{15a}$ and $R^{15b}$ is H and the other is selected from: phenyl, which phenyl is optionally substituted by a group selected from halo, methyl, methoxy; pyridyl; and thiophenyl; and (if)

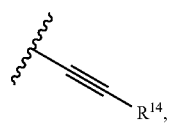

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

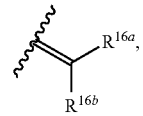

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

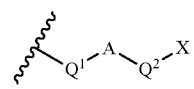

IIIa where A is a $C_{5-7}$ aryl group, and either (i) $Q^1$ is a single bond, and $Q^2$ is selected from a single bond and —Z—$(CH_2)_n$—, where Z is selected from a single bond, O, S and NH and n is from 1 to 3; or (ii) $Q^1$ is —CH=CH—, and $Q^2$ is a single bond;

(b)

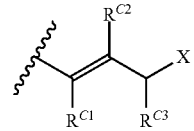

IIIb where;

$R^{C1}$, $R^{C2}$ and $R^{C3}$ are independently selected from H and unsubstituted $C_{1-2}$ alkyl;

(c)

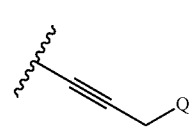

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

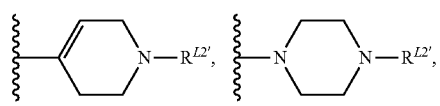

$NR^NR^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^4$ and $SO_zM$;

$R^{30}$ and $R^{31}$ either together form a double bond between the nitrogen and carbon atoms to which they are bound or;

$R^{30}$ is H and $R^{31}$ is selected from OH, $OR^4$ and $SO_zM$.

[Formula I and II]

wherein the conjugation of the drug moiety to the antibody is at amino acid residue 442, as numbered according to the numbering system of the EU index as set forth in Kabat et al. (1991, NIH Publication 91-3242, National Technical Information Service, Springfield, Va., hereinafter "Kabat"; the "EU index as set forth in Kabat" refers to the residue numbering of the human IgG 1 EU antibody as described in Kabat et al. supra.)

In preferred embodiments the antibody heavy chain constant region, or portion thereof, comprises an amino acid substitution at position 442 to introduce an amino acid residue particularly useful for conjugation, such as cysteine. Other amino acids useful for conjugation include lysine, tyrosine, histidine, selenocysteine, selenomethionine, and some non-natural amino acids (for example, a non-natural amino acid comprising a thiol suitable for conjugation).

In some embodiments the antibody heavy chain constant region, or portion thereof, comprises a $C_H3$ domain having a sequence selected from the group consisting of SEQ ID NOs. 160, 161, 162, 163, 164 and 165, the sequence optionally comprising an amino acid substitution at position 442 to introduce an amino acid residue particularly useful for conjugation, such as cysteine. That is, in some preferred embodiments the antibody heavy chain constant region, or portion thereof, comprises a CH3 domain having a sequence selected from the group consisting of SEQ ID NOs. 166, 167, 168, 169, 170 or 171. In some embodiments, the antibody heavy chain region consists of, or consists essentially of any one of these CH3 domains. The sequence of the $C_H3$ domains disclosed herein may be modified by, for example, insertions, substitutions and/or deletions. In some embodiments the $C_H3$ domain sequences disclosed herein comprises no more than 1 amino acid substitution, deletion or insertion, for example no more 2, 3, 4, 5, 6, 7, 8, 9, 10, 11, 12, 13, 14, 15, 16, 17, 18, 19, or no more than 20 amino acid substitutions, deletions or insertions.

In some embodiments the antibody heavy chain constant region, or portion thereof, comprises a Fc domain having a sequence selected from the group consisting of SEQ ID NOs. 180, 181, 182, 183, 184 and 185, the sequence optionally comprising an amino acid substitution at position 442 to introduce an amino acid residue particularly useful for conjugation, such as cysteine. That is, in some preferred embodiments the antibody heavy chain constant region, or portion thereof, comprises a Fc domain having a sequence selected from the group consisting of SEQ ID NOs. 186, 187, 188, 189, 190 or 191. In some embodiments, the antibody heavy chain domain consists of, or consists essentially of any one of these Fc regions. The sequence of the Fc domains disclosed herein may be modified by, for example, insertions, substitutions and/or deletions. In some embodiments the Fc domain sequences disclosed herein comprises no more than 1 amino acid substitution, deletion or insertion, for example no more 2, 3, 4, 5, 6, 7, 8, 9, 10, 11, 12, 13, 14, 15, 16, 17, 18, 19, or no more than 20 amino acid substitutions, deletions or insertions.

In some embodiments the antibody or antibody heavy chain constant region is selected from an IgA1, IgA2, IgD, IgE, IgM or IgG isotype. Preferably the antibody heavy chain constant region is an IgG isotype. In some embodiments the antibody heavy chain constant region is selected from an IgG1, IgG2, IgG3, or an IgG4 subclass.

In particularly preferred embodiments the antibody is an intact IgG antibody. That is an antibody comprising two light chains, each having a variable and constant domain, and two heavy chains, each having one variable domain and three constant domains.

Therapeutic Index

In some embodiments the site-specific conjugates described herein have an improved therapeutic index as compared to an otherwise identical non site-specific conjugate. In some embodiments the therapeutic index for a site specific conjugate descried herein is at least 2% higher than an otherwise identical non site-specific conjugate. That is, if the non site-specific conjugate has a therapeutic index of 100:1, the site specific conjugate has a therapeutic index of at least 102:1. In some embodiments the therapeutic index for a site specific conjugate descried herein is at least 5% higher than an otherwise identical non site-specific conjugate, for example at least 5% higher, at least 7% higher, at least 10% higher, at least 12% higher, at least 15% higher, at least 20% higher, at least 25% higher, at least 30% higher, at least 40% higher, at least 50% higher, at least 70% higher, at least 100% higher, at least 150% higher, or at least 200% higher than an otherwise identical non site-specific conjugate.

Conjugate Stability

In some embodiments the site-specific conjugates described herein have an improved stability as compared to an otherwise identical non site-specific conjugate.

Conjugate stability can be assessed by using hydrophobic interaction chromatograph (HIC) to monitor the drug to antibody (DAR) ratio of a conjugate over the course of an assay. Over the course of time, instability of the bonds between the antibody and drug units will result in a peoportion of the bonds breaking and the gradual decrease in the average DAR of a sample of conjugates. The more stable a given conjugate is, the slower the rate and/or extent of decrease in DAR will be. An excess of N-acetyl cystiene can be added to the assay medium in order to promote instability and so improve assay sensitivity.

Accordingly, in some embodiments the DAR of the site-specific conjugates described herein decreases by no more than 0.5 after a 40 hour incubation with a 50× molar excess of N-acetyl cysteine at 37° C., for example no more than 0.4, no more, than 0.3, no more than 0.2, or no more than 0.1. In some embodiments the DAR of the site-specific conjugates described herein decreases by no more than 0.5 after a 24 hour incubation with a 50× molar excess of N-acetyl cysteine at 37° C., for example no more than 0.4, no more, than 0.3, no more than 0.2, or no more than 0.1. In some embodiments the stability assay is performed in a 25 mM Tris, 1.5 mM EDTA pH 8 buffer and, optionally, the DAR measured by HIC.

Some Embodiments

Listed below are some specifically contemplated embodiments.

A conjugate as described herein wherein the antibody comprises a VH domain having the sequence SEQ ID NO. 9, a VL domain having the sequence SEQ ID NO. 31, and a $C_H3$ domain having the sequence SEQ ID NO. 166.

A conjugate as described herein wherein the antibody comprises a VH domain having the sequence SEQ ID NO.

9, a VL domain having the sequence SEQ ID NO. 31, and a $C_H3$ domain having the sequence SEQ ID NO. 167.

A conjugate as described herein wherein the antibody comprises a VH domain having the sequence SEQ ID NO. 9, a VL domain having the sequence SEQ ID NO. 31, and a $C_H3$ domain having the sequence SEQ ID NO. 168.

A conjugate as described herein wherein the antibody comprises a VH domain having the sequence SEQ ID NO. 9, a VL domain having the sequence SEQ ID NO. 31, and a $C_H3$ domain having the sequence SEQ ID NO. 169.

A conjugate as described herein wherein the antibody comprises a VH domain having the sequence SEQ ID NO. 9, a VL domain having the sequence SEQ ID NO. 31, and a $C_H3$ domain having the sequence SEQ ID NO. 170.

A conjugate as described herein wherein the antibody comprises a VH domain having the sequence SEQ ID NO. 9, a VL domain having the sequence SEQ ID NO. 31, and a $C_H3$ domain having the sequence SEQ ID NO. 171.

A conjugate as described herein wherein the antibody comprises a VH domain having the sequence SEQ ID NO. 9, a VL domain having the sequence SEQ ID NO. 31, and a Fc region having the sequence SEQ ID NO. 186.

A conjugate as described herein wherein the antibody comprises a VH domain having the sequence SEQ ID NO. 9, a VL domain having the sequence SEQ ID NO. 31, and a Fc region having the sequence SEQ ID NO. 187.

A conjugate as described herein wherein the antibody comprises a VH domain having the sequence SEQ ID NO. 9, a VL domain having the sequence SEQ ID NO. 31, and a Fc region having the sequence SEQ ID NO. 188.

A conjugate as described herein wherein the antibody comprises a VH domain having the sequence SEQ ID NO. 9, a VL domain having the sequence SEQ ID NO. 31, and a Fc region having the sequence SEQ ID NO. 189.

A conjugate as described herein wherein the antibody comprises a VH domain having the sequence SEQ ID NO. 9, a VL domain having the sequence SEQ ID NO. 31, and a Fc region having the sequence SEQ ID NO. 190.

A conjugate as described herein wherein the antibody comprises a VH domain having the sequence SEQ ID NO. 9, a VL domain having the sequence SEQ ID NO. 31, and a Fc region having the sequence SEQ ID NO. 191.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 166.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 167.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 168.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 169.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 170.

A conjugate as described herein wherein the antibody comprises a VH domain having the sequence SEQ ID NO. 9, a VL domain having the sequence SEQ ID NO. 33, and a $C_H3$ domain having the sequence SEQ ID NO. 171.

A conjugate as described herein wherein the antibody comprises a VH domain having the sequence SEQ ID NO. 9, a VL domain having the sequence SEQ ID NO. 33, and a Fc region having the sequence SEQ ID NO. 186.

A conjugate as described herein wherein the antibody comprises a VH domain having the sequence SEQ ID NO. 9, a VL domain having the sequence SEQ ID NO. 33, and a Fc region having the sequence SEQ ID NO. 187.

A conjugate as described herein wherein the antibody comprises a VH domain having the sequence SEQ ID NO. 9, a VL domain having the sequence SEQ ID NO. 33, and a Fc region having the sequence SEQ ID NO. 188.

A conjugate as described herein wherein the antibody comprises a VH domain having the sequence SEQ ID NO. 9, a VL domain having the sequence SEQ ID NO. 33, and a Fc region having the sequence SEQ ID NO. 189.

A conjugate as described herein wherein the antibody comprises a VH domain having the sequence SEQ ID NO. 9, a VL domain having the sequence SEQ ID NO. 33, and a Fc region having the sequence SEQ ID NO. 190.

A conjugate as described herein wherein the antibody comprises a VH domain having the sequence SEQ ID NO. 9, a VL domain having the sequence SEQ ID NO. 33, and a Fc region having the sequence SEQ ID NO. 191.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 166.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 167.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 168.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 169.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 170.

A conjugate as described herein wherein the antibody comprises a VH domain having the sequence SEQ ID NO. 19, a VL domain having the sequence SEQ ID NO. 31, and a $C_H3$ domain having the sequence SEQ ID NO. 171.

A conjugate as described herein wherein the antibody comprises a VH domain having the sequence SEQ ID NO. 19, a VL domain having the sequence SEQ ID NO. 31, and a Fc region having the sequence SEQ ID NO. 186.

A conjugate as described herein wherein the antibody comprises a VH domain having the sequence SEQ ID NO. 19, a VL domain having the sequence SEQ ID NO. 31, and a Fc region having the sequence SEQ ID NO. 187.

A conjugate as described herein wherein the antibody comprises a VH domain having the sequence SEQ ID NO. 19, a VL domain having the sequence SEQ ID NO. 31, and a Fc region having the sequence SEQ ID NO. 188.

A conjugate as described herein wherein the antibody comprises a VH domain having the sequence SEQ ID NO. 19, a VL domain having the sequence SEQ ID NO. 31, and a Fc region having the sequence SEQ ID NO. 189.

A conjugate as described herein wherein the antibody comprises a VH domain having the sequence SEQ ID NO.

19, a VL domain having the sequence SEQ ID NO. 31, and a Fc region having the sequence SEQ ID NO. 190.

A conjugate as described herein wherein the antibody comprises a VH domain having the sequence SEQ ID NO. 19, a VL domain having the sequence SEQ ID NO. 31, and a Fc region having the sequence SEQ ID NO. 191.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 166.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 167.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 168.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 169.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 170.

A conjugate as described herein wherein the antibody comprises a VH domain having the sequence SEQ ID NO. 28, a VL domain having the sequence SEQ ID NO. 31, and a $C_H3$ domain having the sequence SEQ ID NO. 171.

A conjugate as described herein wherein the antibody comprises a VH domain having the sequence SEQ ID NO. 28, a VL domain having the sequence SEQ ID NO. 31, and a Fc region having the sequence SEQ ID NO. 186.

A conjugate as described herein wherein the antibody comprises a VH domain having the sequence SEQ ID NO. 28, a VL domain having the sequence SEQ ID NO. 31, and a Fc region having the sequence SEQ ID NO. 187.

A conjugate as described herein wherein the antibody comprises a VH domain having the sequence SEQ ID NO. 28, a VL domain having the sequence SEQ ID NO. 31, and a Fc region having the sequence SEQ ID NO. 188.

A conjugate as described herein wherein the antibody comprises a VH domain having the sequence SEQ ID NO. 28, a VL domain having the sequence SEQ ID NO. 31, and a Fc region having the sequence SEQ ID NO. 189.

A conjugate as described herein wherein the antibody comprises a VH domain having the sequence SEQ ID NO. 28, a VL domain having the sequence SEQ ID NO. 31, and a Fc region having the sequence SEQ ID NO. 190.

A conjugate as described herein wherein the antibody comprises a VH domain having the sequence SEQ ID NO. 28, a VL domain having the sequence SEQ ID NO. 31, and a Fc region having the sequence SEQ ID NO. 191.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 166.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 167.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 168.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 169.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 170.

A conjugate as described herein wherein the antibody comprises a VH domain having the sequence SEQ ID NO. 19, a VL domain having the sequence SEQ ID NO. 33, and a $C_H3$ domain having the sequence SEQ ID NO. 171.

A conjugate as described herein wherein the antibody comprises a VH domain having the sequence SEQ ID NO. 19, a VL domain having the sequence SEQ ID NO. 33, and a Fc region having the sequence SEQ ID NO. 186.

A conjugate as described herein wherein the antibody comprises a VH domain having the sequence SEQ ID NO. 19, a VL domain having the sequence SEQ ID NO. 33, and a Fc region having the sequence SEQ ID NO. 187.

A conjugate as described herein wherein the antibody comprises a VH domain having the sequence SEQ ID NO. 19, a VL domain having the sequence SEQ ID NO. 33, and a Fc region having the sequence SEQ ID NO. 188.

A conjugate as described herein wherein the antibody comprises a VH domain having the sequence SEQ ID NO. 19, a VL domain having the sequence SEQ ID NO. 33, and a Fc region having the sequence SEQ ID NO. 189.

A conjugate as described herein wherein the antibody comprises a VH domain having the sequence SEQ ID NO. 19, a VL domain having the sequence SEQ ID NO. 33, and a Fc region having the sequence SEQ ID NO. 190.

A conjugate as described herein wherein the antibody comprises a VH domain having the sequence SEQ ID NO. 19, a VL domain having the sequence SEQ ID NO. 33, and a Fc region having the sequence SEQ ID NO. 191.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 166.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 167.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 168.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 169.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 170.

A conjugate as described herein wherein the antibody comprises a VH domain having the sequence SEQ ID NO. 28, a VL domain having the sequence SEQ ID NO. 33, and a $C_H3$ domain having the sequence SEQ ID NO. 171.

A conjugate as described herein wherein the antibody comprises a VH domain having the sequence SEQ ID NO. 28, a VL domain having the sequence SEQ ID NO. 33, and a Fc region having the sequence SEQ ID NO. 186.

A conjugate as described herein wherein the antibody comprises a VH domain having the sequence SEQ ID NO.

28, a VL domain having the sequence SEQ ID NO. 33, and a Fc region having the sequence SEQ ID NO. 187.

A conjugate as described herein wherein the antibody comprises a VH domain having the sequence SEQ ID NO. 28, a VL domain having the sequence SEQ ID NO. 33, and a Fc region having the sequence SEQ ID NO. 188.

A conjugate as described herein wherein the antibody comprises a VH domain having the sequence SEQ ID NO. 28, a VL domain having the sequence SEQ ID NO. 33, and a Fc region having the sequence SEQ ID NO. 189.

A conjugate as described herein wherein the antibody comprises a VH domain having the sequence SEQ ID NO. 28, a VL domain having the sequence SEQ ID NO. 33, and a Fc region having the sequence SEQ ID NO. 190.

A conjugate as described herein wherein the antibody comprises a VH domain having the sequence SEQ ID NO. 28, a VL domain having the sequence SEQ ID NO. 33, and a Fc region having the sequence SEQ ID NO. 191.

Non-Site-Specific & Site-Specific Conjugates

In some embodiments, it may be preferred that the conjugate is selected from a conjugate of formula ConjA, ConjB, ConjC, ConjD, ConjE, ConjF, ConjG and ConjH:

ConjA

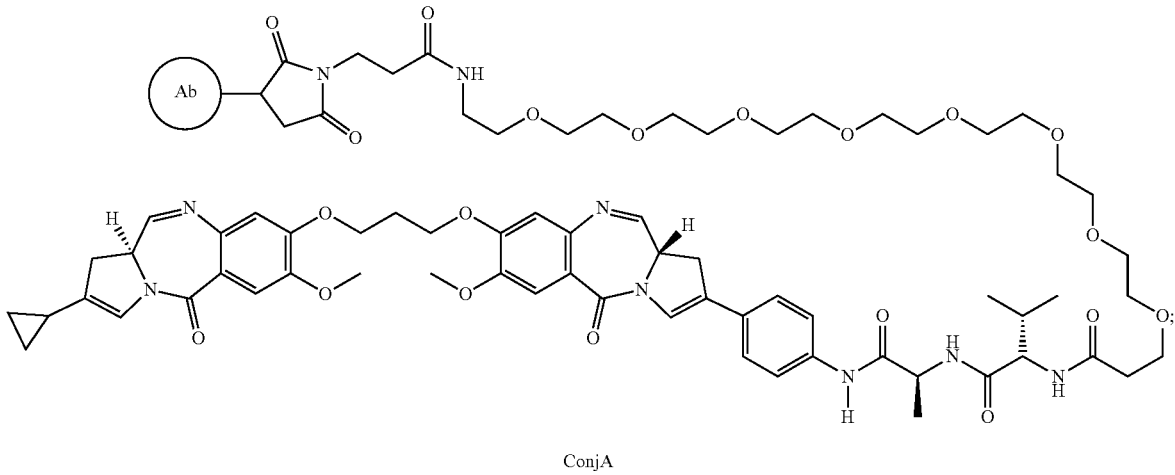

ConjA

ConjB

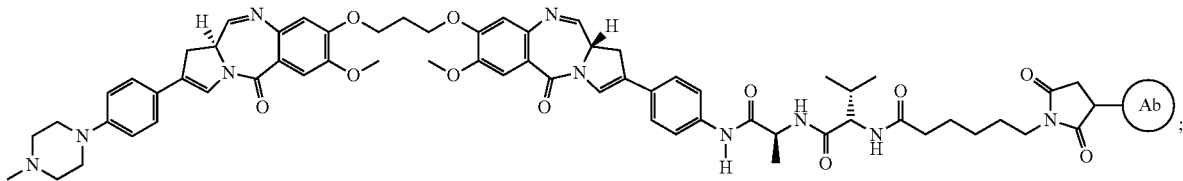

ConjB

ConjC:

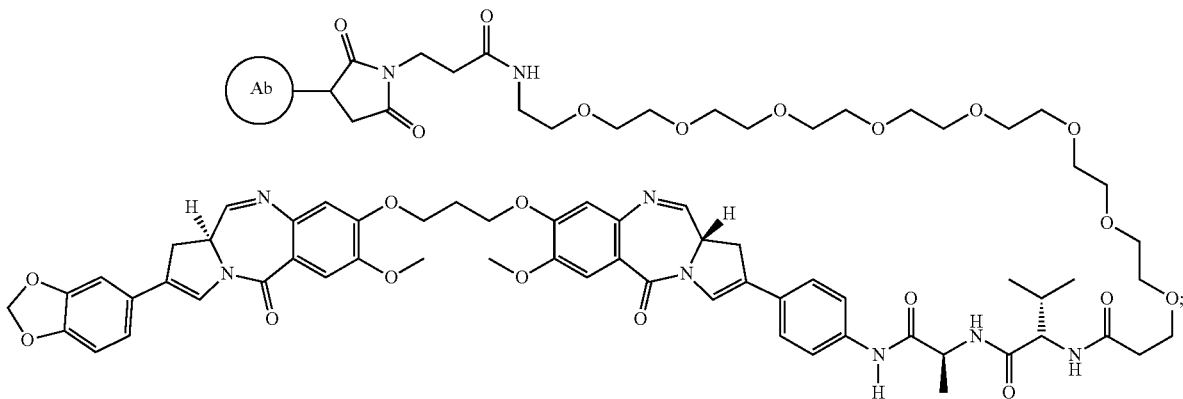

ConjC

-continued
ConjD:
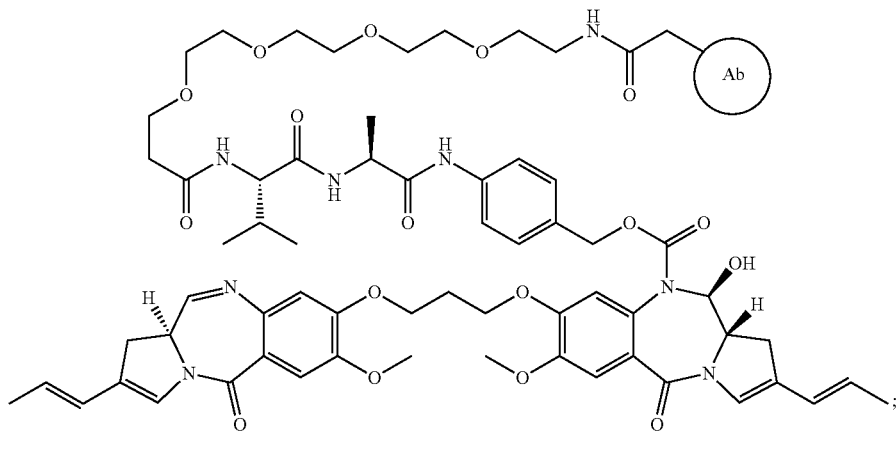
ConjD
ConjE:
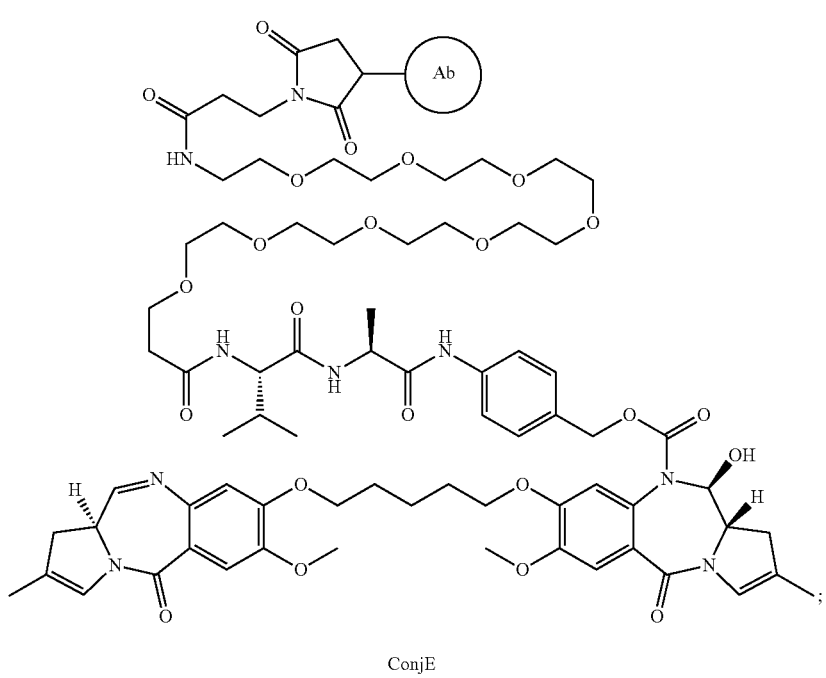
ConjE
ConjF:
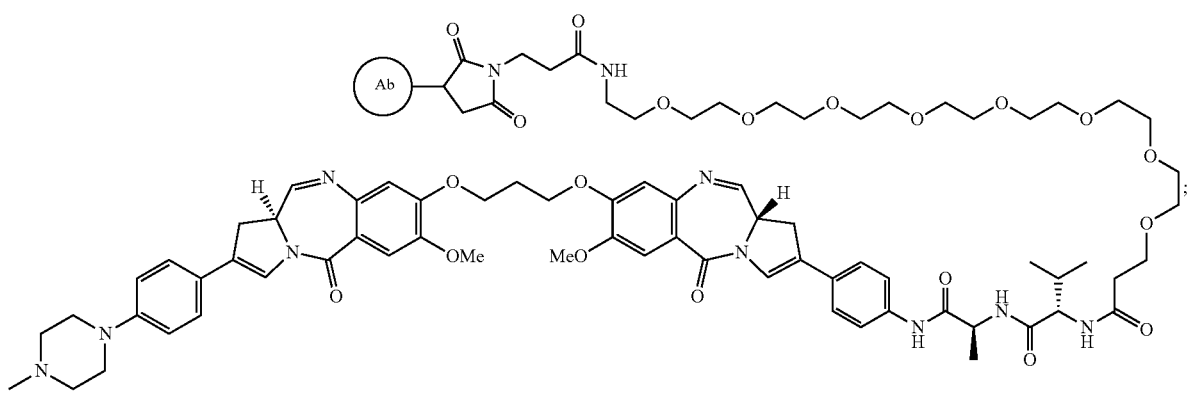
ConjF ConjG:

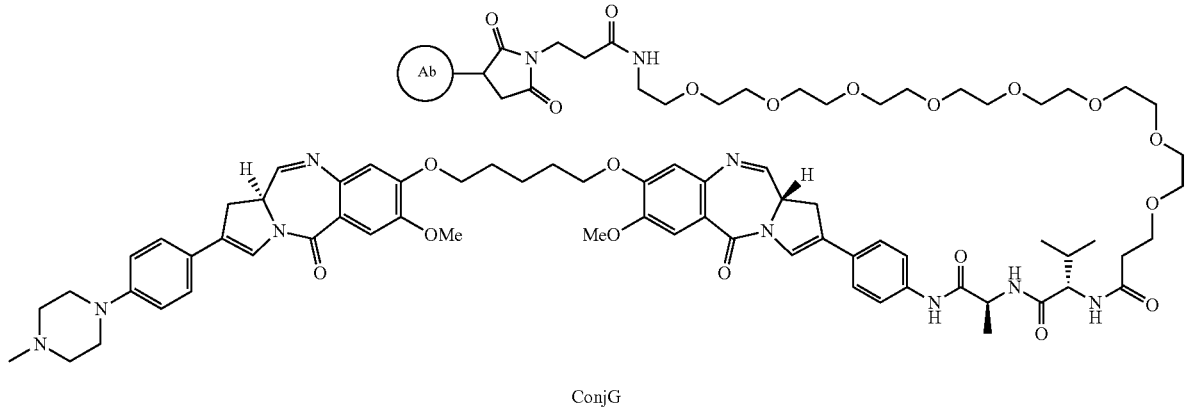

ConjG

ConjH:

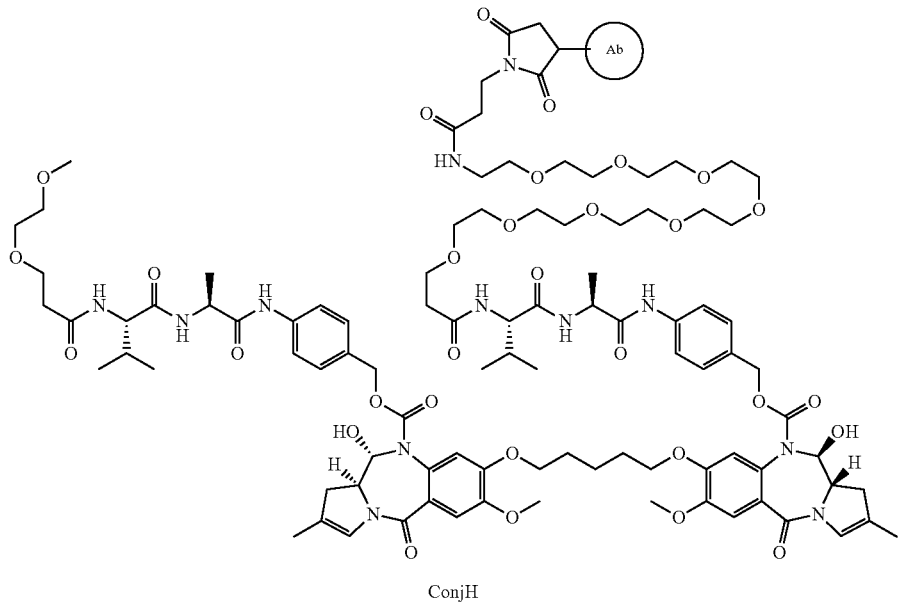

ConjH

The link to the moiety shown is via a free S (active thiol) on the cell binding agent.

The subscript p in the formula I is an integer of from 1 to 20. Accordingly, the Conjugates comprise an antibody (Ab) as defined above covalently linked to at least one Drug unit by a Linker unit. The Ligand unit, described more fully below, is a targeting agent that binds to a target moiety. Accordingly, the present disclosure also provides methods for the treatment of, for example, various cancers and autoimmune disease. The drug loading is represented by p, the number of drug molecules per antibody. Drug loading may range from 1 to 20 Drug units ($D^L$) per antibody. For compositions, p represents the average drug loading of the Conjugates in the composition, and p ranges from 1 to 20.

A further aspect of the disclosure provides a method of making a conjugate according to the first aspect of the disclosure comprising conjugating a compound of formula $I^L$ or $II^L$:

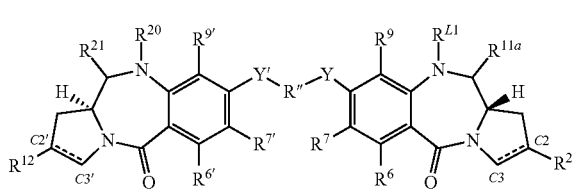

$I^L$

$II^L$ to the antibody (Ab) as defined above, wherein:

$R^{L1}$ is a linker suitable for conjugation to the antibody (Ab);

R$^{22L}$ is of formula IIIa$^L$, formula IIIb$^L$ or formula IIIc$^L$:

(a)

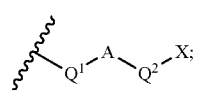
IIIa (b)

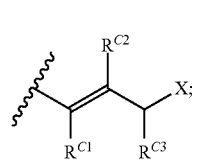
IIIb (c)

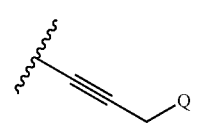
IIIc where Q$^L$ is selected from O—R$^{L2}$, S—R$^{L2}$ and NR$^N$—R$^{L2}$, and R$^N$ is selected from H, methyl and ethyl X$^L$ is selected from the group comprising: O—R$^{L2}$, S—R$^{L2}$, CO$_2$—R$^{L2}$, CO—R$^{L2}$, N=C=O—R$^{L2}$, NHNH—R$^{L2}$, CONHNH—R$^{L2}$,

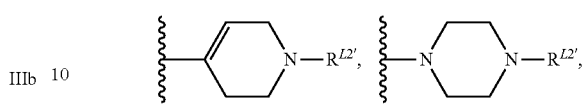

NR$^N$R$^L$, wherein R$^N$ is selected from the group comprising H and C$_{1-4}$ alkyl;

R$^{L2}$ is a linker suitable for conjugation to the antibody (Ab);

and all the remaining groups are as defined in the first aspect.

Thus it may be preferred in the further aspect, that the disclosure provides a method of making a conjugate selected from the group consisting of ConjA, ConjB, ConjC, ConjD, ConjE, ConjF, ConjG and ConjH comprising conjugating a compound which is selected respectively from A:

A:

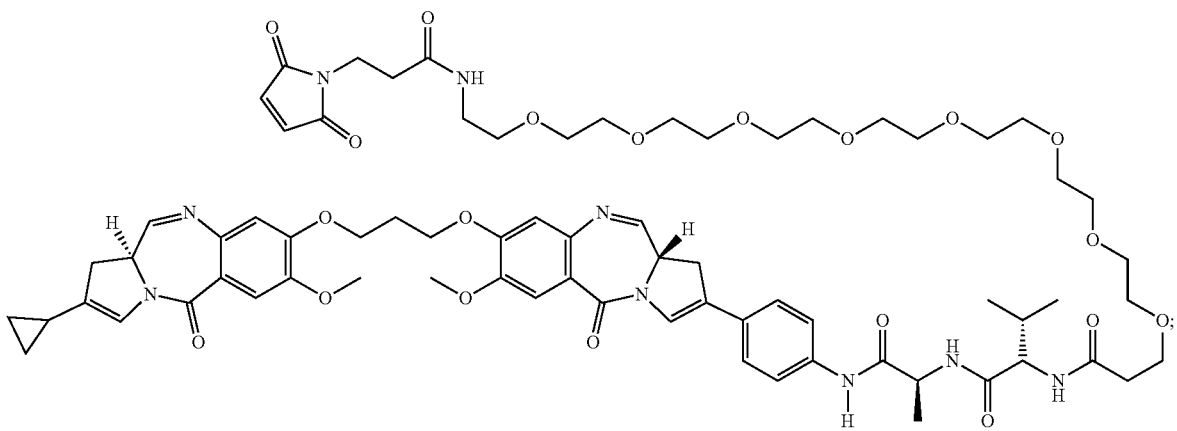

A

B:

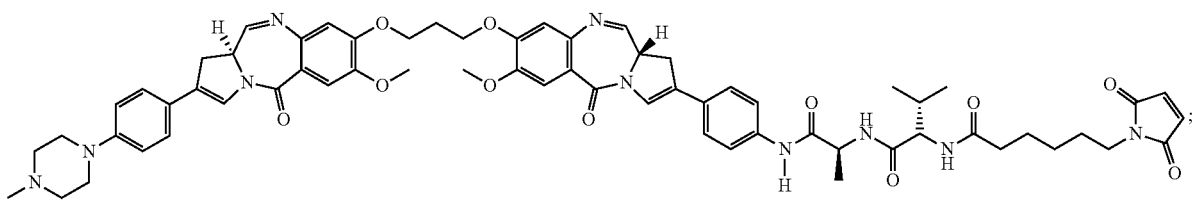

B

C:
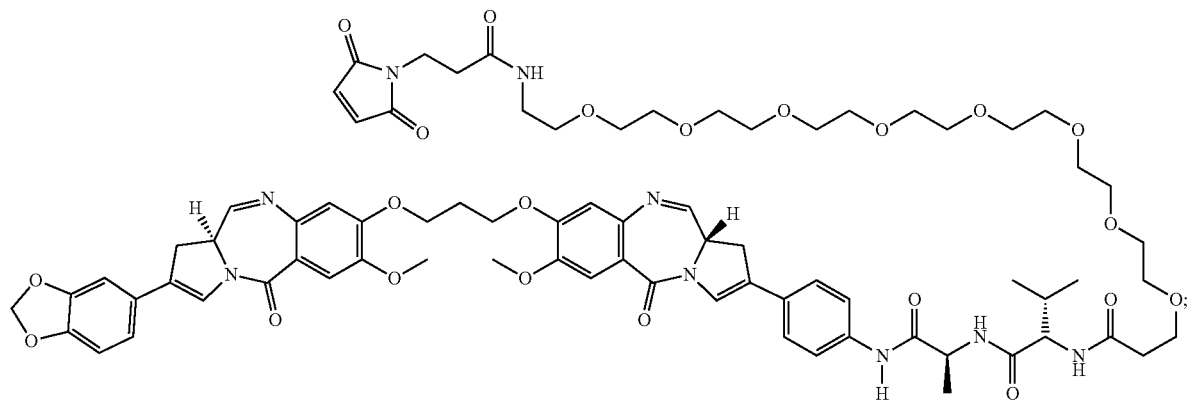
C
D:
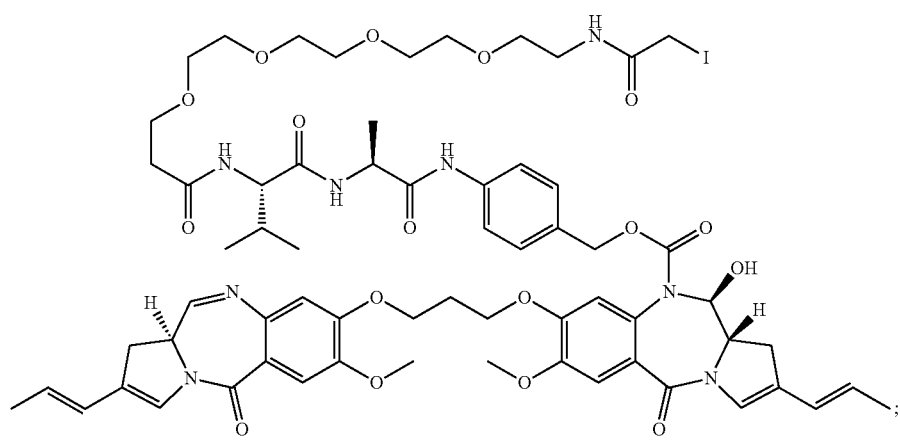
D
E:
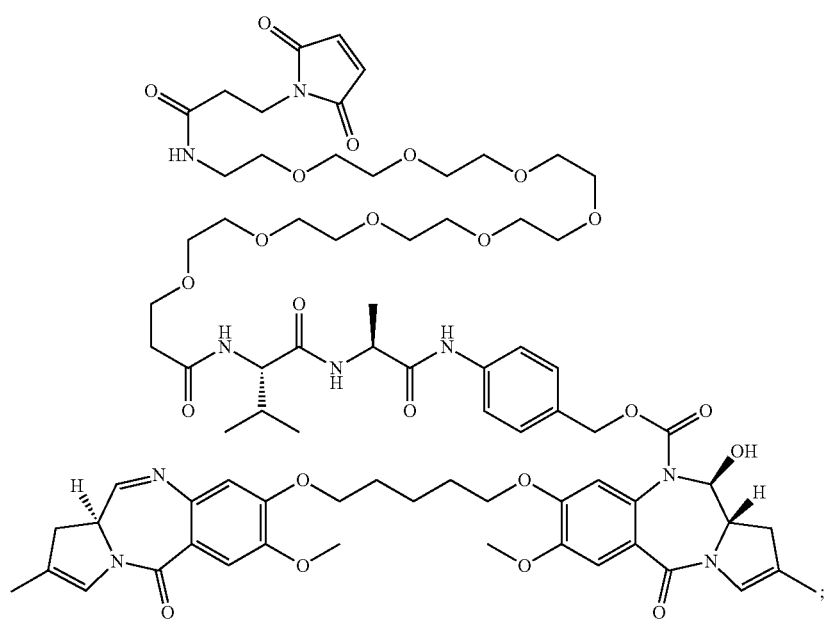
E

F:
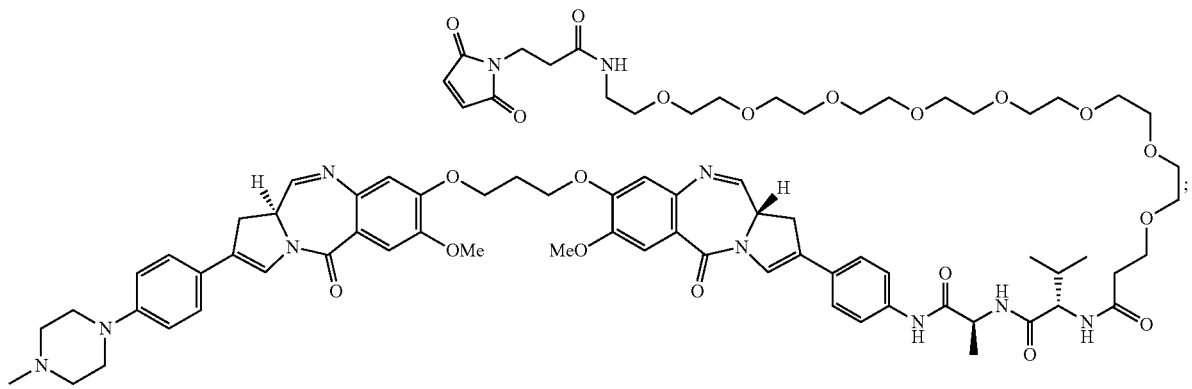
G:
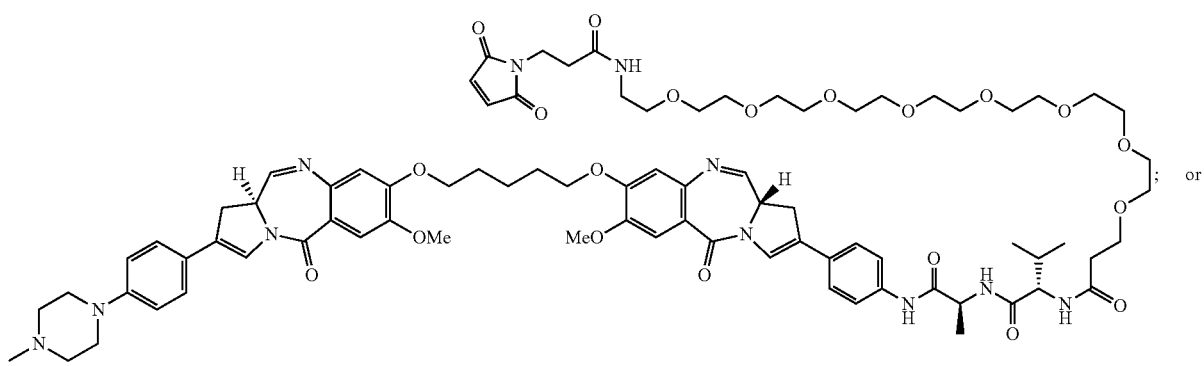
H:
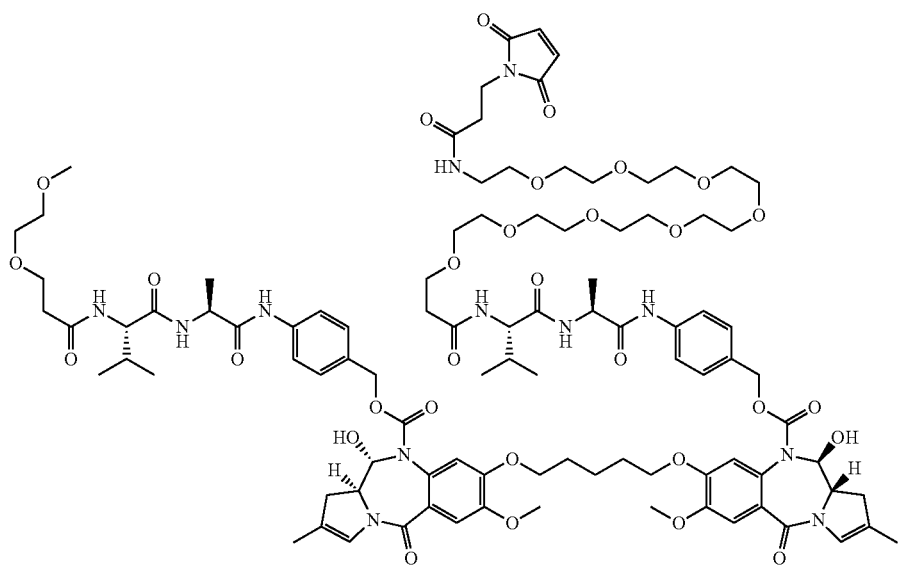
with an antibody (Ab) as defined above.

WO 2011/130615 discloses compound 26:

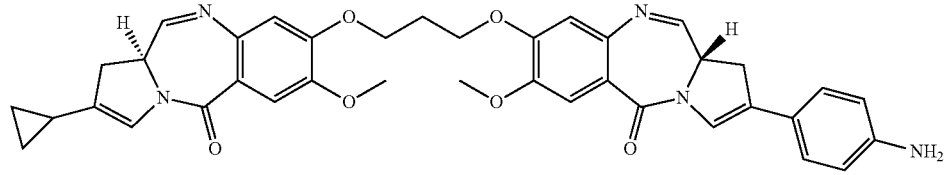

26 which is the parent compound of A. Compound A comprises this PBD with a linker for attachment to a cell binding agent. The cell binding agent provides a number of ethylene glycol moieties to provide solubility which is useful in the synthesis of conjugates.

WO 2010/043380 and WO 2011/130613 disclose compound 30:

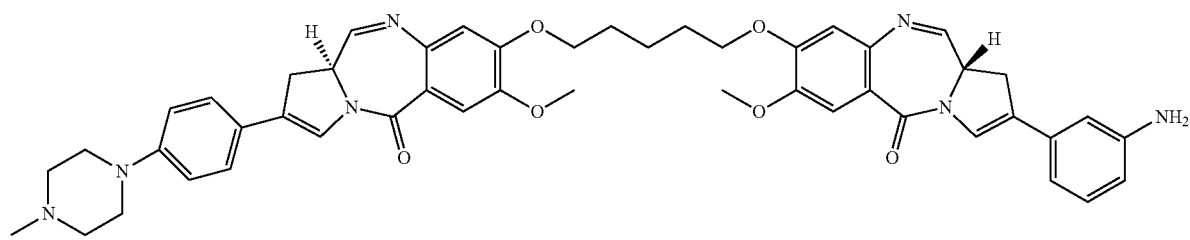

30

WO 2011/130613 also discloses compound 51:

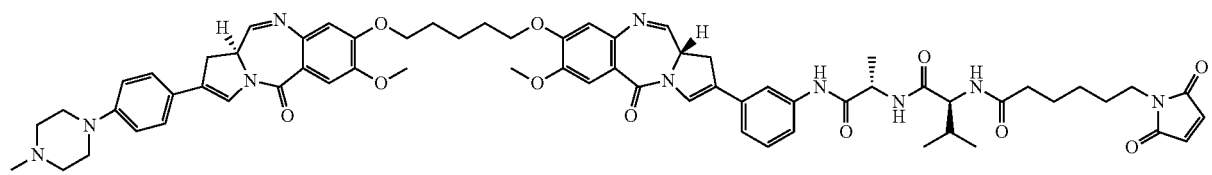

30

Compounds B and F differ from compound 30 by only having a $(CH_2)_3$ tether between the PBD moieties, instead of a $(CH_2)_5$ tether, which reduces the lipophilicity of the released PBD dimer. The linking group in compounds B, F and G is attached to the C2-phenyl group in the para rather than meta position.

WO 2011/130613 discloses compound 93:

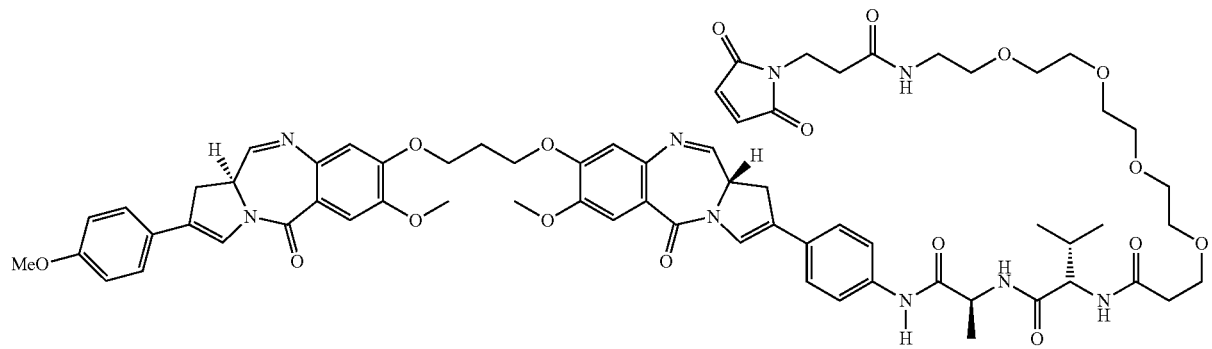

93

Compound C differs from this in two respects. The cell binding agent provides an increased number of ethylene glycol moieties to provide solubility which is useful in the synthesis of conjugates, and the phenyl substituent provide two rather than one oxygen atom, which also aids solubility. Compound C's structure may also mean it binds more strongly in the minor groove.

WO 2011/130598 discloses compound 80:

Compound H has a cleavable protecting group on the second imine group which avoids cross-reactions during its synthesis and in the final product avoids the formation of carbinolamine and carbinolamine methyl ethers. This protection also avoids the presence of an reactive imine group in the molecule.

Compounds A, B, C, D, E, F, G and H have two sp$^2$ centres in each C-ring, which may allow for stronger binding

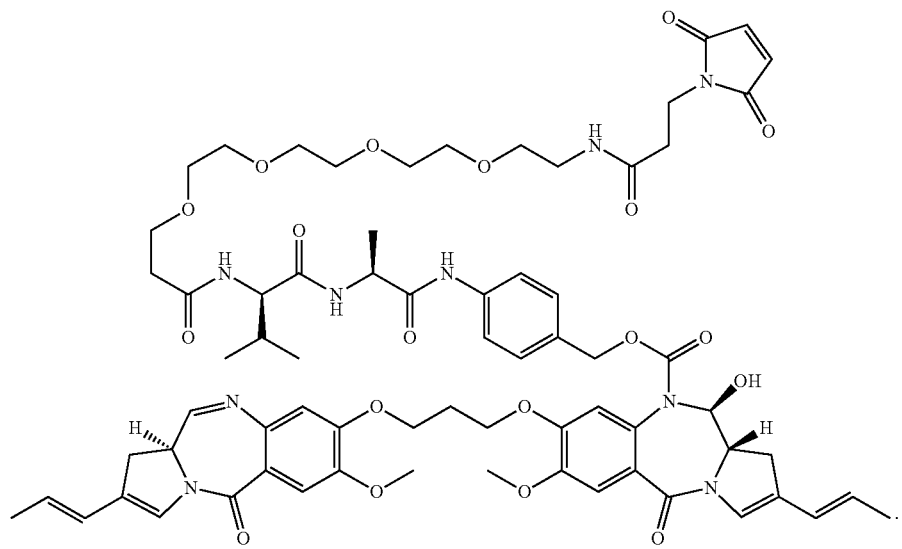

80

Compound D differs from this by comprising an iodoacetamide group for linking to the cell binding agent. This group may offer advantages over compound 80 with regards to its stability when bound to a cell binding agent (see below). The malemide group in compound 80 can undergo a retro-Michael reaction, becoming unconjugated from the cell binding agent, and thus vulnerable to scavenging by other thiol containing biological molecules, such as albumin and glutathione. Such unconjugation cannot occur with compound A. Also, the iodoacetamide group may avoid other unwanted side reactions.

Compounds E and H differ from previously disclosed PBD dimers with a drug linker having a C2-3 endo-double bond, by having a smaller, less lipophilic C2 substituent, e.g. 4F-phenyl, propylene. As such, the conjugates of compound B (see below) are less likely to aggregate once synthesised. Such aggregation of conjugates can be measured by Size exclusion chromatography (SEC).

in the minor groove of DNA, than for compounds with only one sp$^2$ centre in each C-ring.

The drug linkers disclosed in WO 2010/043880, WO 2011/130613, WO 2011/130598 and WO 2011/130616 may be used in the present disclosure, and are incorporated herein by reference. The drug linkers described herein may be synthesised as described in these disclosures.

DETAILED DESCRIPTION

The present disclosure is suitable for use in providing a PBD compound to a preferred site in a subject. The conjugate may allow the release of an active PBD compound that does not retain any part of the linker. In such as case there is no stub present that could affect the reactivity of the PBD compound.

ConjA would release the compound RelA:

RelA

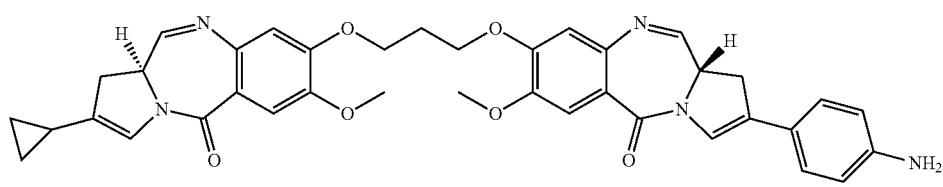

ConjB and ConjF would release the compound RelB:

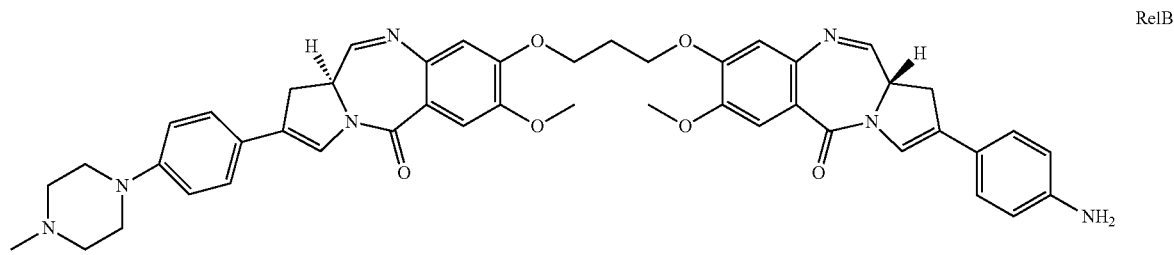 [SMILES: COc1cc2c(cc1OCCCOc1cc3c(cc1OC)C(=O)N1C=C(c4ccc(N5CCN(C)CC5)cc4)C[C@H]1C=N3)N=C[C@@H]1CC(c3ccc(N)cc3)=CN1C2=O]

ConjC would release the compound RelC:

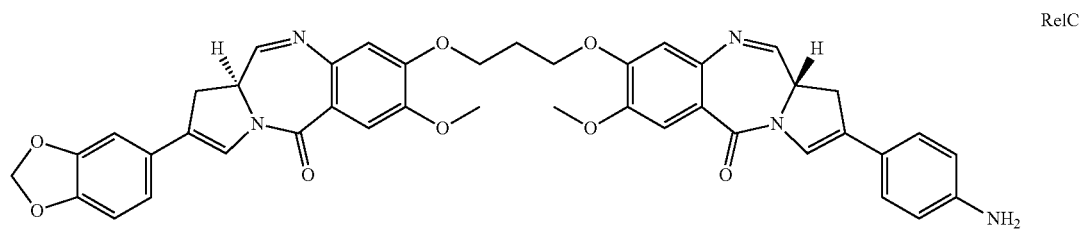 [SMILES: COc1cc2c(cc1OCCCOc1cc3c(cc1OC)C(=O)N1C=C(c4ccc5c(c4)OCO5)C[C@H]1C=N3)N=C[C@@H]1CC(c3ccc(N)cc3)=CN1C2=O]

ConjD would release the compound RelD:

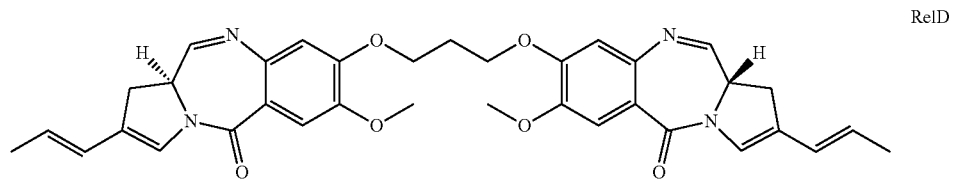 [SMILES: C/C=C/C1=CN2C(=O)c3cc(OC)c(OCCCOc4cc5c(cc4OC)C(=O)N4C=C(/C=C/C)C[C@H]4C=N5)cc3N=C[C@@H]2C1]

ConjE and ConjH would release the compound RelE:

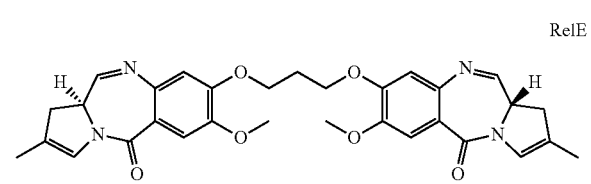

and ConjG would release the compound RelG:

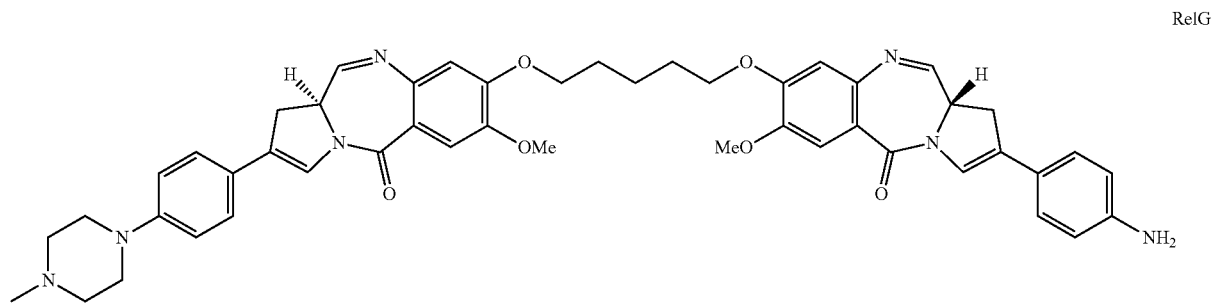 [SMILES: COc1cc2c(cc1OCCCCCOc1cc3c(cc1OC)C(=O)N1C=C(c4ccc(N5CCN(C)CC5)cc4)C[C@H]1C=N3)N=C[C@@H]1CC(c3ccc(N)cc3)=CN1C2=O]

The specified link between the PBD dimer and the antibody, in the present disclosure is preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow specific intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Delivery of the compounds of formulae RelA, RelB, RelC, RelD, RelE or RelG is achieved at the desired activation site of the conjugates of formulae ConjA, ConjB, ConjC, ConjD, ConjE, ConhF, ConjG or ConjH by the action of an enzyme, such as cathepsin, on the linking group, and in particular on the valine-alanine dipeptide moiety.

The disclosure also provided the means produce the antibodies of the disclosure.

Accordingly, in another aspect the disclosure provides nucleic acid molecules encoding the humanised antibodies, along with nucleic acid molecules complementary nucleic acid molecules encoding the humanised antibodies.

In another aspect the disclosure provides a vector, such as an expression vector, comprising a nucleic acid of the disclosure.

In another aspect, the disclosure provides host cells transfected with a vector of the disclosure. The host cells may be prokaryotic or eukaryotic. For example, the cells may be bacterial, fungal, insect, or mammalian (such as mouse, primate or human).

In another aspect the disclosure provides a method of making the antibodies by culturing the host cells of the disclosure.

The disclosure provides methods relating to the identification of subjects particularly suitable for treatment with the drug-conjugates of the disclosure. Also provided are methods for determining the optimum timing and dosage of administration of the drug-conjugates of the disclosure to a subject. In some embodiments the subject has a proliferative disease, such as cancer. In some embodiments the subject has an autoimmune disease. Preferably, administration of the treatment inhibits or reduces one or more aspects of the disease, for example reduces tumour volume, or reduces the level of one or more biomarkers of tumour progression, such as MUC1, Tn-MUC1, CA 27.29 (also known as BR 27.29) and CA 15-3 (see Klee G G and Schreiber W E, Arch. Pathol. Lab. Med vol 128, page 1131-1136 (2004)). In some embodiments the level of the biomarker is reduced to no more than 90% of the level immediately before treatment, such as no more than 80%, no more than 70%, no more than 60%, no more than 50%, no more than 40%, no more than 30%, no more than 20%, no more than 10%, or no more than 5% of the level immediately before treatment. In some embodiment "MUC1" has the sequence as disclosed in UniProtKB entry P15941 (Entry no. 160, sequence 3, 19 Mar. 2014). In some embodiments CA15-3 comprises at least one repeat of the sequence APDTRPAPGSTAPPAH-GVTS.

In one aspect the disclosure provides a method of selecting a subject for treatment with the drug-conjugate or pharmaceutical composition of the disclosure, the method comprising assessing the level of one or more biomarkers associated with disease pathology, wherein subjects having the one or more biomarker, or subjects having a level of the one or more biomarkers which exceeds a threshold level, are selected for treatment. In some embodiments the biomarker is Tn-MUC1, CA 27.29, or CA 15-3. In some embodiments the threshold is at least 10% higher than the upper boundary of the normal clinical range, such as at least 20% higher, at least 30% higher, at least 40% higher, at least 50% higher, at least 100% higher, or at least 200% higher.

In another aspect the disclosure provides a method of timing the administration of treatment of a subject with the drug-conjugate or pharmaceutical composition of the disclosure, the method comprising assessing the level of one or more biomarkers associated with disease pathology, wherein the treatment is administered when the subject has the one or more biomarker, or the subject has a level of one or more biomarkers which exceeds a threshold level. In some embodiments the biomarker is Tn-MUC1, CA 2729, or CA 15-3. In some embodiments the threshold is at least 10% higher than the upper boundary of the normal clinical range, such as at least 20% higher, at least 30% higher, at least 40% higher, at least 50% higher, at least 100% higher, or at least 200% higher.

In another aspect the disclosure provides a method of determining the optimum dosage of the drug-conjugate or pharmaceutical composition of the disclosure for administration to a subject, the method comprising assessing the level of one or more biomarkers associated with disease pathology, wherein subjects having the one or more biomarker, or subjects having a level of the one or more biomarkers which exceeds the threshold level, are selected for a particular dosage level. In some embodiments the biomarker is Tn-MUC1, CA 27.29, or CA 15-3. In some embodiments the threshold is at least 10% higher than the upper boundary of the normal clinical range, such as at least 20% higher, at least 30% higher, at least 40% higher, at least 50% higher, at least 100% higher, or at least 200% higher.

In some embodiments the level of one or more biomarkers is assessed in a sample of blood, urine, other body fluid, or tissue. Level of one or more biomarkers samples can be assessed by immunoassay, proteomic assay, nucleic acid hybridization or amplification assays, immunohistochemistry, or in situ hybridization assays.

Definitions

Antibody

The term "antibody" is intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian Tn-MUC1. For example, antibody fragments capable of binding to Tn-MUC1 or portions thereof, including, but not limited to monoclonal antibodies (including full-length monoclonal antibodies), polyclonal antibodies, multispecific antibodies formed from at least two different epitope binding fragments (e.g., bispecific antibodies), human antibodies, humanized antibodies, camelised antibodies, chimeric antibodies, single-chain Fvs (scFv), chimeric T-cell antigen receptors, single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the disclosure), intrabodies, and epitope-binding fragments of any of the above. In particular, antibodies include immunoglobulin molecules and immunologically active fragments of immunoglobulin molecules, i.e., molecules that contain at least one antigen binding site. Antibodies may be derived from any mammal, including, but not limited to, humans, monkeys, pigs, horses, rabbits, dogs, cats, mice, etc., or other animals such as birds (e.g. chickens).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

Humanized

As used herein "humanized" antibodies include any combination of the herein described Anti-Tn-MUC1 antibodies. Humanized antibodies include those wherein the CDR's are derived from one or more of the Anti-Tn-MUC1 antibodies described herein and at least a portion, or the remainder of the antibody is derived from one or more human antibodies. Thus, the human part of the antibody may include the framework, $C_L$, $C_H$ domains (e.g., $C_{H1}$, $C_{H2}$, $C_{H3}$), hinge, ($V_L$, $V_H$)) regions which are substantially non-immunogenic in humans. The regions of the antibody that are derived from human antibodies need not have 100% identity with human antibodies and may have, for example, at least 90% identity with a human antibody, such as at least 91%, at least 92%, at least 93%, at least 94%, at least 95%, at least 96%, at least 97%, at least 98%, at least 99%, or at least 100%. In a preferred embodiment, as many of the human amino acid residues as possible are retained, but critical human residues may be modified as necessary to support the antigen binding site formed by the CDRs and recapitulate the antigen binding potency of the original mouse antibody. Such changes or variations optionally and preferably retain or reduce the immunogenicity in humans or other primate species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

For example, in some embodiments the humanised antibody of the disclosure are produced by a method comprising he step of grafting the CDRs of the mouse 5E5 antibody into human FW regions such as AB066839, AY392978.1 and AF455547.1. In some embodiments the method of producing the humanised antibodies of the invention further comprises the step of back-mutating mismatches at vernier and 5 Å CDR envelope residues. In other embodiments the method of producing the humanised antibodies of the invention further comprises the step of back-mutating mismatched vernier residues only.

Methods for engineering or humanizing non-human or human antibodies can be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH05/kuby05.htm; www.library.thinkquest.org/12429/Immune/Antibody.html; www.hhmi.org/grants/lectures/1996/vlab/; www.path.cam.ac.uk/.about.mrc7/mikeimages.html; www.antibodyresource.com/; mcb.harvard.edu/BioLinks/Immunology.html. www.immunologylink.com/; pathbox. wustl.edu/.about.hcenter/index.html; www.biotech. ufl.edu/. about.hcl/; www.pebio.com/pa/340913/340913.html; www.nal. usda.gov/awic/pubs/antibody/; www.m.ehime-u. ac.jp/.about.yasuhito/Elisa.html; www.biodesign.com/ table.asp; www.icnet.uk/axp/facs/davies/links.html; www. biotech.ufl.edu/.about.fccl/protocol.html; www. isacnet.org/sites_geo.html; aximtl.imt. uni-marburg.de/. about.rek/AEPStart.html; baserv.uci.kun.nl/.about.jraats/ linksl.html; www.recab.uni-hd.de/immuno.bme.nwvu.edu/; www.mrc-cpe.cam.ac.uk/imt-doc/public/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh.ch/.about.honegger/AHOseminar/ Slide01.html; www.cryst.bbk.ac.uk/.about.ubcg07s/; www.nimr.mrc.ac.uk/CC/ccaewg/ccaewg.htm; www.path. cam.ac.uk/.about.mrc7/humanisation/TAHHP.html; www.ibt.unam.mx/vir/structure/stat_aim.html; www.biosci. missouri.edu/smithgp/index.html; www.cryst.bioc.cam.ac. uk/.about.fmolina/Web-pages/Pept/spottech.html; www.jer- ini.de/fr_products.htm; www.patents.ibm.con/ibm.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental sequences. Three-dimensional immunoglobulin models are commonly available and are familiar to those skilled in the art. Computer programs are available which generate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering the antibody can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The human constant region of the humanized antibody can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the humanized antibody comprises an IgG1 heavy chain and a IgG1 K light chain. The isolated humanized antibodies described herein comprise antibody amino acid sequences disclosed herein encoded by any suitable polynucleotide.

Modifications

The sequences of the antibody heavy chain variable regions and/or the light chain variable regions disclosed herein may be modified by substitution, insertion or deletion. Preferably, such modified humanized antibodies bind Tn MUC1 with an EC50 of less than 35 ng/ml, such as less than 30 ng/ml, less than 25 ng/ml, less than 20 ng/ml, or less than 15 ng/ml, and/or substantially neutralize at least one activity of at the Tn-MUC1 protein. In one embodiment the modified humanized antibody competitively inhibits the in vivo and/or in vitro binding to Tn-MUC1 of an antibody comprising a heavy chain variable region having the amino acid sequence of SEQ ID NO: 1 and a light chain variable region having the amino acid sequence of SEQ ID NO: 30. In one embodiment the modified humanized antibody competitively inhibits the in vivo and/or in vitro binding to Tn-MUC1 of the 'mouse 5E5' antibody. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Preferred conservative substitutions are those wherein one amino acid is substituted for another within the groups of amino acids indicated herein below:

Amino acids having polar side chains (Asp, Glu, Lys, Arg, His, Asn, Gin, Ser, Thr, Tyr, and Cys)

Amino acids having non-polar side chains (Gly, Ala, Val, Leu, Ile, Phe, Trp, Pro, and Met)

Amino acids having aliphatic side chains (Gly, Ala Val, Leu, Ile)

Amino acids having cyclic side chains (Phe, Tyr, Trp, His, Pro)

Amino acids having aromatic side chains (Phe, Tyr, Trp)

Amino acids having acidic side chains (Asp, Glu)

Amino acids having basic side chains (Lys, Arg, His)

Amino acids having amide side chains (Asn, Gin)

Amino acids having hydroxy side chains (Ser, Thr)

Amino acids having sulphur-containing side chains (Cys, Met),

Neutral, weakly hydrophobic amino acids (Pro, Ala, Gly, Ser, Thr)

Hydrophilic, acidic amino acids (Gin, Asn, Glu, Asp), and Hydrophobic amino acids (Leu, Ile, Val)

Particular preferred conservative amino acids substitution groups are: Val-Leu-Ile, Phe-Tyr, Lys-Arg, Ala-Val, and Asn-Gln.

Constant Regions

Human genes which encode the constant (C) regions of the humanized antibodies, fragments and regions can be derived from a human fetal liver library, by known methods. Human C region genes can be derived from any human cell including those which express and produce human immunoglobulins. The human $C_H$ region can be derived from any of the known classes or isotypes of human H chains, including γ, μ, α, δ, ε, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the $C_H$ region is derived from gamma 1 (IgG1).

The human CL region can be derived from either human L chain isotype, kappa or lambda.

In some embodiments the antibody or fragment comprises an Fc region with an effector function. In some embodiments the antibody comprises an Fc region without an effector function.

Genes encoding human immunoglobulin C regions are obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof. Chimeric antibody fragments, such as F(ab')2, F(ab') and F(ab), can be prepared by designing a chimeric H chain gene which is appropriately truncated. For example, a chimeric gene encoding an H chain portion of an F(ab')2 fragment would include DNA sequences encoding the CH1 domain and hinge region of the H chain, followed by a translational stop codon to yield the truncated molecule.

Antibody Production

Humanized antibodies, fragments and regions can be produced by cloning DNA segments encoding the H and L chain antigen-binding regions of the anti-Tn-MUC1 antibody, and joining these DNA segments to DNA segments including CH and CL regions, respectively, to produce full length immunoglobulin-encoding genes.

For full-length antibody molecules, the immunoglobulin cDNAs can be obtained from mRNA of hybridoma cell lines. Antibody heavy and light chains are cloned in a mammalian expression vector system. Assembly is documented with DNA sequence analysis. The antibody construct can be expressed in human or other mammalian host cell lines. The construct can be validated by transient transfection assays and immunoassay of the expressed antibody. Stable cell lines with the highest productivity can be isolated and screened using rapid assay methods.

Functional Moieties

The humanised antibody of the disclosure may be conjugated to a functional moiety. The conjugation may be via, for example, chemical coupling, genetic fusion, non-covalent association or otherwise. In preferred embodiments the antibody and functional moiety are conjugated via covalent attachment. Conjugation between the antibody and functional moiety may be direct or indirect (for example, through linker sequences). In some embodiments the antibody molecule is engineered to provide a functional group capable of reacting with the functional moiety, or alternatively the antibody molecule is provided with a linker group that is capable of reacting with the functional moiety. One example of indirect linkage is then the functional moiety is a radionucleotide chelated by a macrocyclic chelators such as 1,4,7,10-tetraazacyclododecane-N,N',N",N"'tetraacetic acid (DOTA) which can be attached to the antibody via a linker molecule.

An example use of non-covalent association between the humanised antibody of the disclosure and the functional moiety is a so-called 'pre-targeting' format. In this format, a subject is first administered a binding molecule comprising (1) a first portion that specifically binds a target antigen (such as TnMUC1), and (2) a second portion that specifically binds a functional moiety. The functional moiety is then subsequently administered to the subject, where it is bound by the in-situ bispecific antibody and, therefore, co-localised with the target antigen. Typically, the first portion of the binding molecule is an antibody or antibody fragment as described herein. The second portion of the binding molecule may also be an antibody or antibody fragment which specifically binds the functional moiety; alternatively, the second portion of the binding molecule may be a non-antibody binding member such as those described herein, for example, biotin or (strep)avidin. This pre-targeting' format finds particular use in radiotherapy, where the second portion of the binding molecule binds a functional moiety comprising a radionucleotide, such as a radionucleotide-chelator complex, a radionucleotide-biotin conjugate or radionucleotide-(strep)avidin conjugate.

Examples of functional moieties include an amino acid, a peptide, a protein, a polysaccharide, a nucleoside, a nucleotide, an oligonucleotide, a nucleic acid, a drug, a hormone, a lipid, a lipid assembly, a synthetic polymer, a polymeric microparticle, a biological cell, a virus, a reporter (such as a fluorophore, a chromophore, or a dye), a toxin, a hapten, an enzyme, a binding member (such as an antibody, an antibody fragment, or an affinity tag), a radioisotope or radioisotope-chelator complex, solid matrixes, semisolid matrixes and combinations thereof, or an organic moiety. In preferred embodiments the functional moiety is a PBD drug moiety.

Examples of a drug include a cytotoxic agent, a chemotherapeutic agent, a peptide, a peptidomimetic, a protein scaffold, DNA, RNA, siRNA, microRNA, and a peptidonucleic acid. In preferred embodiments the functional moiety is a PBD drug moiety. In other embodiments the humanised antibody is conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, cholera toxin, or diphtheria toxin; a protein such as tumor necrosis factor, a-interferon, P-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J Immunol., 6: 1567), and VEGf (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-I"), interleukin-2 ("IL-2"), interleukin-4 ("IL-4"), interleukin-6 ("IL-6"), interleukin-7 ("IL-7"), interleukin-9 ("IL-9"), interleukin-15 ("IL-15"), interleukin-12 ("IL-12"), granulocyte macrophage colony stimulating factor ("GMCSF"), and granulocyte colony stimulating factor ("G-CSF")), or a growth factor (e.g., growth hormone ("GH")). The drug may also be a pro-drug for conversion to active drug at a target site in a patient. Alternatively, any of the antibodies disclosed herein can be incorporated into a prodrug system. Such prodrug systems are well known in the art and include ADEPT systems in which an antibody disclosed herein is conjugated or conjugatable or fused to an agent capable of converting a prodrug to a cytotoxic moiety is an enzyme for use in antibody directed enzyme prodrug therapy.

Examples of a reporter include a fluorophore, a chromophore, a radionuclide, and an enzyme. Such antibody-reporter conjugates can be useful for monitoring or prognosing the development or progression of a disorder (such as, but not limited to cancer) as part of a clinical testing procedure, such as determining the efficacy of a particular therapy. Such diagnosis and detection can accomplished by fusing or conjugating the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, bioluminescent materials, such as but not limited to, luciferase, luciferin, and aequorin; radioactive materials (naked or in complex with a suitable chelator), such as but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($3^5$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

Examples of a binding member include an antibody or antibody fragment, biotin and/or streptavidin, or an affinity tag. Affinity tags can be introduced into the antibodies disclosed herein to enable them to be manipulated or detected in one or more subsequent steps. A wide range of affinity tags are known in the art suitable affinity tags include members of specific binding pairs, antibodies and antigens, biotin which binds to streptavidin and avidin, polyhistidine (e.g. hexa-His or tri-His tags) or amino di- or tri-carboxylates which bind to metal ions such as Ni2+ or Co2+, Flag or Glu epitopes which bind to anti-Flag antibodies, S-tags which bind to streptavidin, calmodulin binding peptide which binds to calmodulin in the presence of Ca2+; ribonuclease S which binds to aporibonuclease S; and c-Myc which recognises anti-c-Myc antibody. Examples of other affinity tags that can be used will be apparent to those skilled in the art. Antibodies including these affinity tags can be easily purified and manipulated.

A toxin, cytotoxin or cytotoxic agent includes any agent that is detrimental to cells. Examples of toxins include radioisotopes (naked or in compex with a suitable chelator) such as $^{131}$I, a ribosome inactivating protein such as pseudomonas exotoxin (PE38 fragment), plant or bacterial toxins such as ricin, the α-chain of ricin, saporin, pokeweed antiviral protein, diphtheria toxin, or *Pseudomonas* exotoxin A (Kreitman and Pastan (1998) Adv. Drug Delivery Rev. 31:53.). Other toxins and cytotoxins include, e.g., a cytostatic or cytocidal agent, or a radioactive metal ion, e.g., alpha-emitters. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homo logs thereof, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Chemical toxins can also be taken from the group chosen from duocarmycin (U.S. Pat. Nos. 5,703,080; 4,923, 990), methotrexate, doxorubicin, melphalan, chlorambucil, ARA-C, vindesine, mitomycin C, cisplatinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, In one embodiment, the cytotoxic agent is chosen from an enediyne, a lexitropsin, a duocarmycin, a taxane, a puromycin, a dolastatin, a maytansinoid, and a vinca alkaloid. In other embodiments, the cytotoxic agent is paclitaxel, docetaxel, CC-I 065, SN-3 8, topotecan, morpholino-doxorubicin, rhizoxin, cyanomorpholino-doxorubicin, dolastatin-10, echinomycin, combretastatin, calicheamicin, maytansine, DM-I, an auristatin or other dolastatin derivatives, such as auristatin E or auristatin F, AEB, AEVB, AEFP, MMAE (monomethylauristatin E), MMAF (monomethylauristatin F), eleutherobin or netropsin. In certain embodiments, the cytoxic agent is Maytansine or Maytansinoids, and derivatives thereof, wherein an antibodies (full length or fragments) of the disclosure are conjugated to one or more maytansinoid molecules. Maytansinoids are mitotic inhibitors which act by inhibiting tubulin polymerization. In other embodiments the toxin is a small molecule or protein toxins, such as, but not limited to abrin, brucine, cicutoxin, diphtheria toxin, batrachotoxin, botulism toxin, shiga toxin, endotoxin, *Pseudomonas* exotoxin, *Pseudomonas* endotoxin, tetanus toxin, pertussis toxin, anthrax toxin, cholera toxin, falcarinol, fumonisin BI, fumonisin B2, aflatoxin, maurotoxin, agitoxin, charybdotoxin, margatoxin, slotoxin, scyllatoxin, hefutoxin, calciseptine, taicatoxin, calcicludine, geldanamycin, gelonin, lotaustralin, ocratoxin A, patulin, ricin, strychnine, trichothecene, zearlenone, and tetradotoxin. Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, P APII, and PAP-S), *Momordica charantia* inhibitor, curcin, crotin, *Sapaonaria officinalis* inhibitor, gelonin, mitogellin, restrictocin, phenomycin, enomycin and the tricothecenes.

The humanized antibody may be modified by conjugation to an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms. In certain embodiments, the cytotoxic or cytostatic agent is a dolastatin. In more specific embodiments, the dolastatin is of the auristatin class. In a specific embodiment of the disclosure, the cytotoxic or cytostatic agent is MMAE. In another specific embodiment of the disclosure, the cytotoxic or cytostatic agent is AEFP. In another specific embodiment of the disclosure, the cytotoxic or cytostatic agent is MMAF.

The humanized antibody and antigen-binding fragments can comprise one or more organic moieties that are covalently bonded, directly or indirectly, to the antibody. Each organic moiety that is bonded to an antibody or antigen-binding fragment described herein can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the present disclosure. Hydrophilic polymers suitable for modifying antibodies described herein can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody described herein has a molecular weight of about 800 to about 150,000 Daltons as a separate molecular entity. For example PEG5000 and PEG20,000, wherein the numerical component of the name is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

The addition of organic moieties to antibodies may be done to modify the antibody properties, and in particular their pharmacological properties. An example is the conjugation of antibody molecules to poly(alkylene glycol) molecules, in particular polyethylene glycol (PEG) molecules, that may be used to enhance the half-life or other pharmacological properties of polypeptide therapeutics. PEGylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation PEGylation works by increasing the molecular weight of the therapeutic polypeptide by conjugating the polypeptide to one or more PEG polymer molecules. This is particularly applicable to types of antibody molecules that are fragments of complete antibodies, such as Fab fragments.

Fatty acids and fatty acid esters suitable for modifying antibodies described herein can be saturated or can contain one or more units of unsaturation. Fatty acids that are suitable for modifying antibodies described herein include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-δ 9-octadecanoate (C18, oleate), all cis-δ 5,8,11,14-eicosatetraenoate (C20, arachidonate), octanedioic acid, tetradecanedioic acid, octadecanedioic acid, docosanedioic acid, and similar fatty acids. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent C1-C12 group wherein one or more carbon atoms can be replaced by a heteroatom such as oxygen, nitrogen or sulfur. Suitable linker moieties include, for example, tetraethylene glycol, —(CH2)3-, —NH—(CH2)6-NH—, —(CH2)2-NH— and —CH2-O—CH2-CH2-O—CH2-CH2-O—CH—NH—.

Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies can be produced by reacting a human antibody or antigen-binding fragment with a modifying agent. For example, the organic moieties can be bonded to the antibody in a non-site-specific manner by employing an amine-reactive modifying agent, for example, an NHS ester of PEG. Modified human antibodies or antigen-binding fragments can also be prepared by reducing disulfide bonds (e.g., inter-chain disulfide bonds) of an antibody or antigen-binding fragment. The reduced antibody or antigen-binding fragment can then be reacted with a thiol-reactive modifying agent to produce the modified antibody described herein. Modified human antibodies and antigen-binding fragments comprising an organic moiety that is bonded to specific sites of an antibody described herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as $Na^+$ and $K^+$. Examples of pharmaceutically acceptable divalent inorganic cations include, but are not limited to, alkaline earth cations such as $Ca^{2+}$ and $Mg^{2+}$. Examples of pharmaceutically acceptable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) (C5), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, —CH═$CH_2$), 1-propenyl (—CH═CH—$CH_3$), 2-propenyl (allyl, —CH—CH═$CH_2$), isopropenyl (1-methylvinyl, —C($CH_3$)═$CH_2$), butenyl ($C_4$), pentenyl (C5), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —$CH_2$—C≡CH).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and saturated polycyclic hydrocarbon compounds:

norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine (C6);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. The term "$C_{5-7}$ aryl", as used herein, pertains to a monovalent moiety obtained by removing a hydrogen atom from an aromatic ring atom of an aromatic compound, which moiety has from 5 to 7 ring atoms and the term "$C_{5-10}$ aryl", as used herein, pertains to a monovalent moiety obtained by removing a hydrogen atom from an aromatic ring atom of an aromatic compound, which moiety has from 5 to 10 ring atoms. Preferably, each ring has from 5 to 7 ring atoms.

In this context, the prefixes (e.g. $C_{3-20}$, $C_{5-7}$, $C_{5-6}$, $C_{5-10}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene (Cis), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($C_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($C_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($C_2$), phenoxathiin ($C_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group.

Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$aryl group, preferably hydrogen or a $C_{1-7}$ alkyl group.

Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

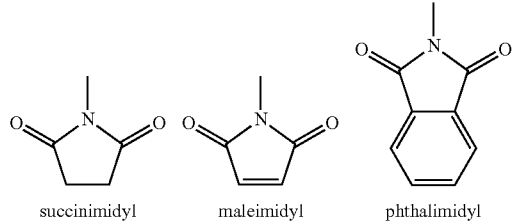

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

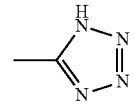

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{5-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^{22}$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^{22}$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Alkylene $C_{3-12}$ alkylene: The term "$C_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the subclasses alkenylene, alkynylene, cycloalkylene, etc., discussed below.

Examples of linear saturated $C_{3-12}$ alkylene groups include, but are not limited to, —(CH$_2$)$_n$— where n is an integer from 3 to 12, for example, —CH$_2$CH$_2$CH$_2$-(propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated $C_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{3-12}$ alkylene groups ($C_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH$_2$—CH=CH—, —CH=CH—CH$_2$—CH$_2$—CH=CH—, —CH=CH—CH$_2$—CH$_2$—CH=CH—, and —CH$_2$—C≡C—CH$_2$—.

Examples of branched partially unsaturated $C_{3-12}$ alkylene groups ($C_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated $C_{3-12}$ alkylene groups ($C_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated $C_{3-12}$ alkylene groups ($C_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Carbamate nitrogen protecting group: the term "carbamate nitrogen protecting group" pertains to a moiety which masks the nitrogen in the imine bond, and these are well known in the art. These groups have the following structure:

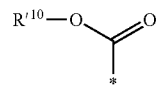

wherein $R'^{10}$ is R as defined above. A large number of suitable groups are described on pages 503 to 549 of Greene, T. W. and Wuts, G. M., Protective Groups in Organic Synthesis, 3$^{rd}$ Edition, John Wiley & Sons, Inc., 1999, which is incorporated herein by reference.

Hemi-aminal nitrogen protecting group: the term "hemi-aminal nitrogen protecting group" pertains to a group having the following structure:

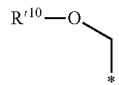

wherein $R'^{10}$ is R as defined above. A large number of suitable groups are described on pages 633 to 647 as amide protecting groups of Greene, T. W. and Wuts, G. M., Protective Groups in Organic Synthesis, 3$^{rd}$ Edition, John Wiley & Sons, Inc., 1999, which is incorporated herein by reference.

The groups Carbamate nitrogen protecting group and Hemi-aminal nitrogen protecting group may be jointly termed a "nitrogen protecting group for synthesis".

Conjugates

The present disclosure provides a conjugate comprising a PBD compound connected to the antibody via a Linker Unit.

In one embodiment, the conjugate comprises the antibody connected to a spacer connecting group, the spacer connected to a trigger, the trigger connected to a self-immolative linker, and the self-immolative linker connected to the N10 position of the PBD compound. Such a conjugate is illustrated below:

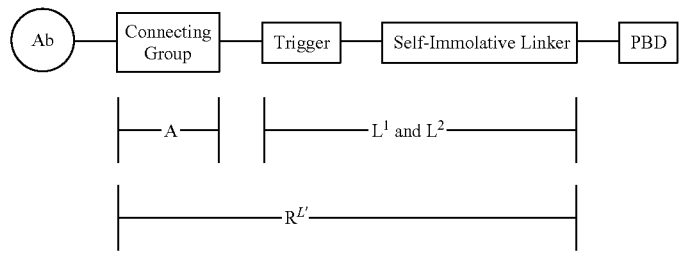

where Ab is the antibody as defined above and PBD is a pyrrolobenzodiazepine compound (D), as described herein. The illustration shows the portions that correspond to $R^{L'}$, A, $L^1$ and $L^2$ in certain embodiments of the disclosure. $R^{L'}$ may be either $R^{L1'}$ or $R^{L2'}$. D is $D^L$ with $R^{L1'}$ or $R^{L2'}$ removed.

The present disclosure is suitable for use in providing a PBD compound to a preferred site in a subject. In the preferred embodiments, the conjugate allows the release of an active PBD compound that does not retain any part of the linker. There is no stub present that could affect the reactivity of the PBD compound.

The linker attaches the antibody to the PBD drug moiety D through covalent bond(s). The linker is a bifunctional or multifunctional moiety which can be used to link one or more drug moiety (D) and an antibody unit (Ab) to form antibody-drug conjugates (ADC). The linker ($R^L$) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety and to the antibody. A cysteine thiol, or an amine, e.g. N-terminus or amino acid side chain such as lysine, of the antibody (Ab) can form a bond with a functional group of a linker or spacer reagent, PBD drug moiety (D) or drug-linker reagent ($D^L$, $D-R^L$), where $R^L$ can be $R^{L1}$ or $R^{L2}$.

The linkers of the ADC preferably prevent aggregation of ADC molecules and keep the ADC freely soluble in aqueous media and in a monomeric state.

The linkers of the ADC are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the PBD drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

In another embodiment, the linker may be substituted with groups which modulate aggregation, solubility or reactivity. For example, a sulfonate substituent may increase water solubility of the reagent and facilitate the coupling reaction of the linker reagent with the antibody or the drug moiety, or facilitate the coupling reaction of Ab-L with $D^L$, or $D^L$-L with Ab, depending on the synthetic route employed to prepare the ADC.

In one embodiment, L-$R^{L'}$ is a group:

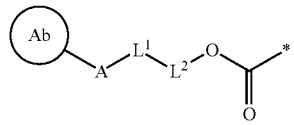

where the asterisk indicates the point of attachment to the Drug Unit (D), Ab is the antibody (L), $L^1$ is a linker, A is a connecting group connecting $L^1$ to the antibody, $L^2$ is a covalent bond or together with —OC(=O)— forms a self-immolative linker, and $L^1$ or $L^2$ is a cleavable linker.

$L^1$ is preferably the cleavable linker, and may be referred to as a trigger for activation of the linker for cleavage.

The nature of $L^1$ and $L^2$, where present, can vary widely. These groups are chosen on the basis of their cleavage characteristics, which may be dictated by the conditions at the site to which the conjugate is delivered. Those linkers that are cleaved by the action of enzymes are preferred, although linkers that are cleavable by changes in pH (e.g. acid or base labile), temperature or upon irradiation (e.g. photolabile) may also be used. Linkers that are cleavable under reducing or oxidising conditions may also find use in the present disclosure.

$L^1$ may comprise a contiguous sequence of amino acids. The amino acid sequence may be the target substrate for enzymatic cleavage, thereby allowing release of L-$R^{L'}$ from the N10 position.

In one embodiment, $L^1$ is cleavable by the action of an enzyme. In one embodiment, the enzyme is an esterase or a peptidase.

In one embodiment, $L^2$ is present and together with —C(=O)O— forms a self-immolative linker. In one embodiment, $L^2$ is a substrate for enzymatic activity, thereby allowing release of L-$R^{L'}$ from the N10 position.

In one embodiment, where $L^1$ is cleavable by the action of an enzyme and $L^2$ is present, the enzyme cleaves the bond between $L^1$ and $L^2$.

$L^1$ and $L^2$, where present, may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

An amino group of $L^1$ that connects to $L^2$ may be the N-terminus of an amino acid or may be derived from an amino group of an amino acid side chain, for example a lysine amino acid side chain.

A carboxyl group of $L^1$ that connects to $L^2$ may be the C-terminus of an amino acid or may be derived from a carboxyl group of an amino acid side chain, for example a glutamic acid amino acid side chain.

A hydroxyl group of $L^1$ that connects to $L^2$ may be derived from a hydroxyl group of an amino acid side chain, for example a serine amino acid side chain.

The term "amino acid side chain" includes those groups found in: (i) naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; (ii) minor amino acids such as ornithine and citrulline; (iii) unnatural amino acids, beta-amino acids, synthetic analogs and derivatives of naturally occurring amino acids; and (iv) all enantiomers, diastereomers, isomerically enriched, isotopically labelled (e.g. $^2H$, $^3H$, $^{14}C$ $^{15}N$), protected forms, and racemic mixtures thereof.

In one embodiment, —C(=O)O— and $L^2$ together form the group:

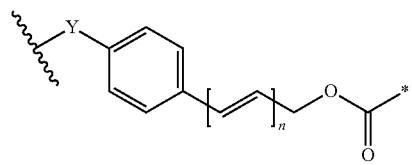

where the asterisk indicates the point of attachment to the N10 position, the wavy line indicates the point of attachment to the linker $L^1$, Y is —N(H)—, —O—, —C(=O)N(H)— or —C(=O)O—, and n is 0 to 3. The phenylene ring is optionally substituted with one, two or three substituents as described herein. In one embodiment, the phenylene group is optionally substituted with halo, $NO_2$, R or OR.

In one embodiment, Y is NH.

In one embodiment, n is 0 or 1. Preferably, n is 0.

Where Y is NH and n is 0, the self-immolative linker may be referred to as a p-aminobenzylcarbonyl linker (PABC).

The self-immolative linker will allow for release of the protected compound when a remote site is activated, proceeding along the lines shown below (for n=O):

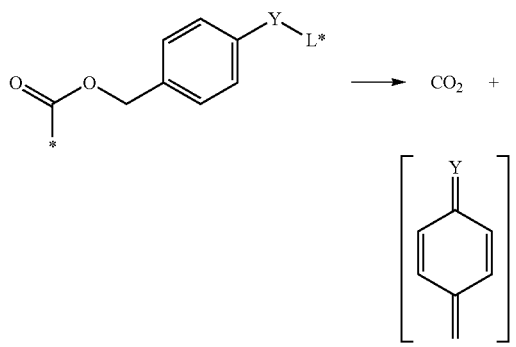

where L* is the activated form of the remaining portion of the linker. These groups have the advantage of separating the site of activation from the compound being protected. As described above, the phenylene group may be optionally substituted.

In one embodiment described herein, the group L* is a linker $L^1$ as described herein, which may include a dipeptide group.

In another embodiment, —C(=O)O— and $L^2$ together form a group selected from:

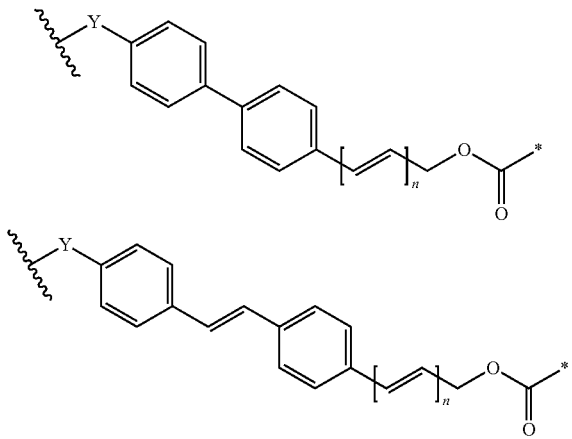

where the asterisk, the wavy line, Y, and n are as defined above. Each phenylene ring is optionally substituted with one, two or three substituents as described herein. In one embodiment, the phenylene ring having the Y substituent is optionally substituted and the phenylene ring not having the Y substituent is unsubstituted. In one embodiment, the phenylene ring having the Y substituent is unsubstituted and the phenylene ring not having the Y substituent is optionally substituted.

In another embodiment, —C(=O)O— and $L^2$ together form a group selected from:

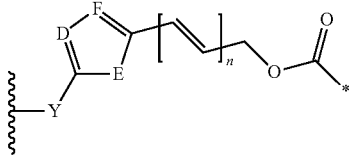

where the asterisk, the wavy line, Y, and n are as defined above, E is O, S or NR, D is N, CH, or CR, and F is N, CH, or CR.

In one embodiment, D is N.
In one embodiment, D is CH.
In one embodiment, E is O or S.
In one embodiment, F is CH.

In a preferred embodiment, the linker is a cathepsin labile linker.

In one embodiment, $L^1$ comprises a dipeptide The dipeptide may be represented as —NH—$X_1$—$X_2$—CO—, where —NH— and —CO— represent the N- and C-terminals of the amino acid groups $X_1$ and $X_2$ respectively. The amino acids in the dipeptide may be any combination of natural amino acids. Where the linker is a cathepsin labile linker, the dipeptide may be the site of action for cathepsin-mediated cleavage.

Additionally, for those amino acids groups having carboxyl or amino side chain functionality, for example Glu and Lys respectively, CO and NH may represent that side chain functionality.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Cit-
where Cit is citrulline.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-.

Most preferably, the group —$X_1$—$X_2$— in dipeptide, —NH—X, —$X_2$—CO—, is -Phe-Lys- or -Val-Ala-.

Other dipeptide combinations may be used, including those described by Dubowchik et al., *Bioconjugate Chemistry*, 2002, 13, 855-869, which is incorporated herein by reference.

In one embodiment, the amino acid side chain is derivatised, where appropriate. For example, an amino group or carboxy group of an amino acid side chain may be derivatised. In one embodiment, an amino group $NH_2$ of a side chain amino acid, such as lysine, is a derivatised form selected from the group consisting of NHR and NRR'.

In one embodiment, a carboxy group COOH of a side chain amino acid, such as aspartic acid, is a derivatised form selected from the group consisting of COOR, CONH$_2$, CONHR and CONRR'.

In one embodiment, the amino acid side chain is chemically protected, where appropriate. The side chain protecting group may be a group as discussed below in relation to the group R$^L$. The present inventors have established that protected amino acid sequences are cleavable by enzymes. For example, it has been established that a dipeptide sequence comprising a Boc side chain-protected Lys residue is cleavable by cathepsin.

Protecting groups for the side chains of amino acids are well known in the art and are described in the Novabiochem Catalog. Additional protecting group strategies are set out in Protective Groups in Organic Synthesis, Greene and Wuts.

Possible side chain protecting groups are shown below for those amino acids having reactive side chain functionality:

Arg: Z, Mtr, Tos;
Asn: Trt, Xan;
Asp: Bzl, t-Bu;
Cys: Acm, Bzl, Bzl-OMe, Bzl-Me, Trt;
Glu: Bzl, t-Bu;
Gln: Trt, Xan;
His: Boc, Dnp, Tos, Trt;
Lys: Boc, Z—Cl, Fmoc, Z, Alloc;
Ser: Bzl, TBDMS, TBDPS;
Thr: Bz;
Trp: Boc;
Tyr: Bzl, Z, Z—Br.

In one embodiment, the side chain protection is selected to be orthogonal to a group provided as, or as part of, a capping group, where present. Thus, the removal of the side chain protecting group does not remove the capping group, or any protecting group functionality that is part of the capping group.

In other embodiments of the disclosure, the amino acids selected are those having no reactive side chain functionality. For example, the amino acids may be selected from: Ala, Gly, Ile, Leu, Met, Phe, Pro, and Val.

In one embodiment, the dipeptide is used in combination with a self-immolative linker. The self-immolative linker may be connected to —X$_2$—.

Where a self-immolative linker is present, —X$_2$— is connected directly to the self-immolative linker. Preferably the group —X$_2$—CO— is connected to Y, where Y is NH, thereby forming the group —X$_2$—CO—NH—.

—NH—X$_1$— is connected directly to A. A may comprise the functionality —CO— thereby to form an amide link with —X$_1$—.

In one embodiment, L$^1$ and L$^2$ together with —OC(=O)— comprise the group NH—X$_1$—X$_2$—CO-PABC-. The PABC group is connected directly to the N10 position. Preferably, the self-immolative linker and the dipeptide together form the group —NH-Phe-Lys-CO—NH-PABC- which is illustrated below:

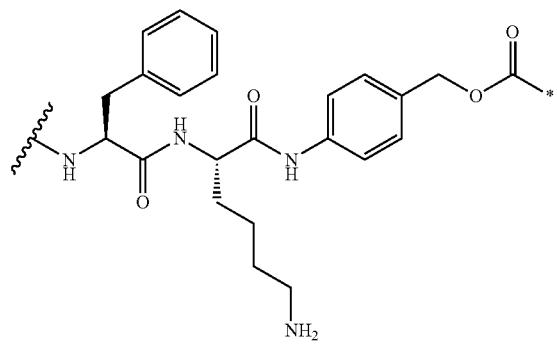 [SMILES: *N[C@@H](Cc1ccccc1)C(=O)N[C@@H](CCCCN)C(=O)Nc1ccc(COC(*)=O)cc1]

where the asterisk indicates the point of attachment to the N10 position, and the wavy line indicates the point of attachment to the remaining portion of the linker L$^1$ or the point of attachment to A. Preferably, the wavy line indicates the point of attachment to A. The side chain of the Lys amino acid may be protected, for example, with Boc, Fmoc, or Alloc, as described above.

Alternatively, the self-immolative linker and the dipeptide together form the group —NH-Val-Ala-CO—NH-PABC-, which is illustrated below:

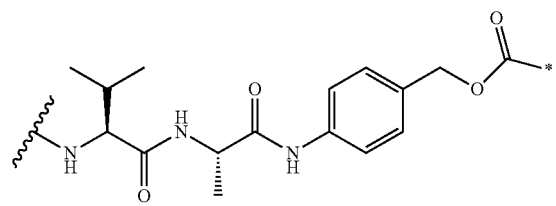 [SMILES: *N[C@H](C(=O)N[C@@H](C)C(=O)Nc1ccc(COC(*)=O)cc1)C(C)C]

where the asterisk and the wavy line are as defined above.

Alternatively, the self-immolative linker and the dipeptide together form the group —NH-Val-Cit-CO—NH-PABC-, which is illustrated below:

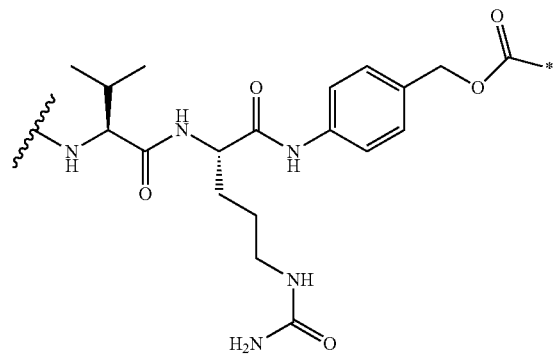 [SMILES: *N[C@H](C(=O)N[C@@H](CCCNC(N)=O)C(=O)Nc1ccc(COC(*)=O)cc1)C(C)C]

where the asterisk and the wavy line are as defined above.

In one embodiment, A is a covalent bond. Thus, L$^1$ and the antibody are directly connected. For example, where L$^1$ comprises a contiguous amino acid sequence, the N-terminus of the sequence may connect directly to the antibody.

Thus, where A is a covalent bond, the connection between the antibody and L$^1$ may be selected from:

—C(=O)NH—,
—C(=O)O—,
—NHC(=O)—,

—OC(=O)—,
—OC(=O)O—,
—NHC(=O)O—,
—OC(=O)NH—,
—NHC(=O)NH—,
—C(=O)NHC(=O)—,
—S—,
—S—S—,
—CH₂C(=O)—, and
=N—NH—.

An amino group of L¹ that connects to the antibody may be the N-terminus of an amino acid or may be derived from an amino group of an amino acid side chain, for example a lysine amino acid side chain.

An carboxyl group of L¹ that connects to the antibody may be the C-terminus of an amino acid or may be derived from a carboxyl group of an amino acid side chain, for example a glutamic acid amino acid side chain.

A hydroxyl group of L¹ that connects to the antibody may be derived from a hydroxyl group of an amino acid side chain, for example a serine amino acid side chain.

A thiol group of L¹ that connects to the antibody may be derived from a thiol group of an amino acid side chain, for example a serine amino acid side chain.

The comments above in relation to the amino, carboxyl, hydroxyl and thiol groups of L¹ also apply to the antibody.

In one embodiment, L² together with —OC(=O)— represents:

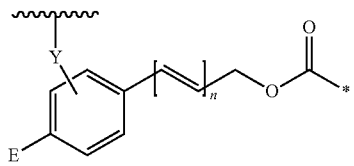

where the asterisk indicates the point of attachment to the N10 position, the wavy line indicates the point of attachment to L¹, n is 0 to 3, Y is a covalent bond or a functional group, and E is an activatable group, for example by enzymatic action or light, thereby to generate a self-immolative unit. The phenylene ring is optionally further substituted with one, two or three substituents as described herein. In one embodiment, the phenylene group is optionally further substituted with halo, NO₂, R or OR. Preferably n is 0 or 1, most preferably 0.

E is selected such that the group is susceptible to activation, e.g. by light or by the action of an enzyme. E may be —NO₂ or glucoronic acid. The former may be susceptible to the action of a nitroreductase, the latter to the action of a β-glucoronidase.

In this embodiment, the self-immolative linker will allow for release of the protected compound when E is activated, proceeding along the lines shown below (for n=0):

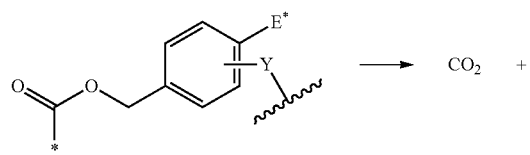

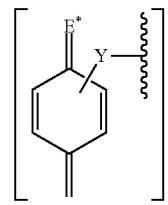

where the asterisk indicates the point of attachment to the N10 position, E* is the activated form of E, and Y is as described above. These groups have the advantage of separating the site of activation from the compound being protected. As described above, the phenylene group may be optionally further substituted.

The group Y may be a covalent bond to L¹.

The group Y may be a functional group selected from:
—C(=O)—
—NH—
—O—
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—, and
—S—.

Where L¹ is a dipeptide, it is preferred that Y is —NH— or —C(=O)—, thereby to form an amide bond between L¹ and Y. In this embodiment, the dipeptide sequence need not be a substrate for an enzymatic activity.

In another embodiment, A is a spacer group. Thus, L¹ and the antibody are indirectly connected.

L¹ and A may be connected by a bond selected from:
—C(=O)NH—,
—C(=O)O—,
—NHC(=O)—,
—OC(=O)—,
—OC(=O)O—,
—NHC(=O)O—,
—OC(=O)NH—, and
—NHC(=O)NH—.

In one embodiment, the group A is:

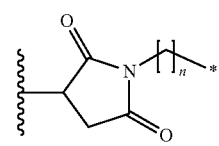

where the asterisk indicates the point of attachment to L¹, the wavy line indicates the point of attachment to the antibody, and n is 0 to 6. In one embodiment, n is 5.

In one embodiment, the group A is:

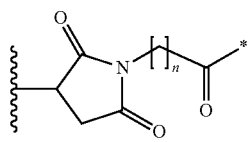

where the asterisk indicates the point of attachment to $L^1$, the wavy line indicates the point of attachment to the antibody, and n is 0 to 6. In one embodiment, n is 5.
In one embodiment, the group A is:

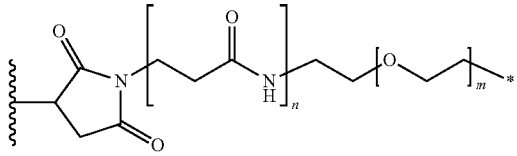

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.
In one embodiment, the group A is:

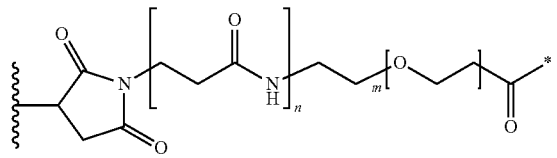

where the asterisk indicates the point of attachment to $L^1$, the wavy line indicates the point of attachment to the antibody, n is 0 or 1, and m is 0 to 30. In a preferred embodiment, n is 1 and m is 0 to 10, 1 to 8, preferably 4 to 8, and most preferably 4 or 8. In another embodiment, m is 10 to 30, and preferably 20 to 30. Alternatively, m is 0 to 50. In this embodiment, m is preferably 10-40 and n is 1.

In one embodiment, the connection between the antibody and A is through a thiol residue of the antibody and a maleimide group of A.

In one embodiment, the connection between the antibody and A is:

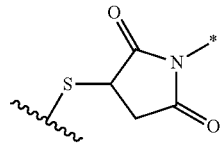 [SMILES: *SC1CC(=O)N(*)C1=O]

where the asterisk indicates the point of attachment to the remaining portion of A and the wavy line indicates the point of attachment to the remaining portion of the antibody. In this embodiment, the S atom is typically derived from the antibody.

In each of the embodiments above, an alternative functionality may be used in place of the maleimide-derived group shown below:

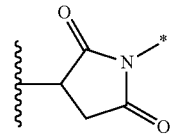 [SMILES: *C1CC(=O)N(*)C1=O]

where the wavy line indicates the point of attachment to the antibody as before, and the asterisk indicates the bond to the remaining portion of the A group.

In one embodiment, the maleimide-derived group is replaced with the group:

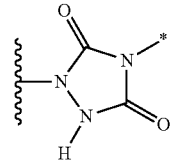

where the wavy line indicates point of attachment to the antibody, and the asterisk indicates the bond to the remaining portion of the A group.

In one embodiment, the maleimide-derived group is replaced with a group, which optionally together with the antibody, is selected from:
—C(=O)NH—,
—C(=O)O—,
—NHC(=O)—,
—OC(=O)—,
—OC(=O)O—,
—NHC(=O)O—,
—OC(=O)NH—,
—NHC(=O)NH—,
—NHC(=O)NH,
—C(=O)NHC(=O)—,
—S—,
—S—S—,
—CH$_2$C(=O)—
—C(=O)CH$_2$—,
=N—NH—, and
—NH—N=.

In one embodiment, the maleimide-derived group is replaced with a group, which optionally together with the antibody, is selected from:

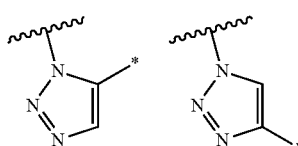

where the wavy line indicates either the point of attachment to the antibody or the bond to the remaining portion of the A group, and the asterisk indicates the other of the point of attachment to the antibody or the bond to the remaining portion of the A group.
Other groups suitable for connecting $L^1$ to the antibody are described in WO 2005/082023.

In one embodiment, the Connecting Group A is present, the Trigger $L^1$ is present and Self-Immolative Linker $L^2$ is absent. Thus, $L^1$ and the Drug unit are directly connected via a bond. Equivalently in this embodiment, $L^2$ is a bond. This may be particularly relevant when DL is of Formula II.

$L^1$ and D may be connected by a bond selected from:
—C(=O)N<,
—C(=O)O—,
—NHC(=O)—,
—OC(=O)—,
—OC(=O)O—,
—NHC(=O)O—,
—OC(=O)N<, and
—NHC(=O)N<,
where N< or O— are part of D.

In one embodiment, $L^1$ and D are preferably connected by a bond selected from:
—C(=O)N<, and
—NHC(=O)—.

In one embodiment, $L^1$ comprises a dipeptide and one end of the dipeptide is linked to D. As described above, the amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-, and
-Trp-Cit-;
where Cit is citrulline. In such a dipeptide, —NH— is the amino group of $X_1$, and CO is the carbonyl group of $X_2$.

Preferably, the group —$X_1$—$X_2$— in dipeptide, —NH—$X_1$—$X_2$—CO—, is selected from:
-Phe-Lys-,
-Val-Ala-,
-Val-Lys-,
-Ala-Lys-, and
-Val-Cit-.

Most preferably, the group —$X_1$—$X_2$— in dipeptide, —NH—$X_1$—$X_2$—CO—, is -Phe-Lys- or -Val-Ala-.

Other dipeptide combinations of interest include:
-Gly-Gly-,
-Pro-Pro-, and
-Val-Glu-.

Other dipeptide combinations may be used, including those described above.

In one embodiment, $L^1$-D is:

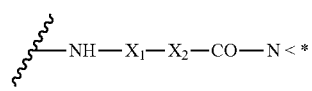

where —NH—$X_1$—$X_2$—CO is the dipeptide, —N< is part of the Drug unit, the asterisk indicates the points of attachment to the remainder of the Drug unit, and the wavy line indicates the point of attachment to the remaining portion of $L^1$ or the point of attachment to A. Preferably, the wavy line indicates the point of attachment to A.

In one embodiment, the dipeptide is valine-alanine and $L^1$-D is:

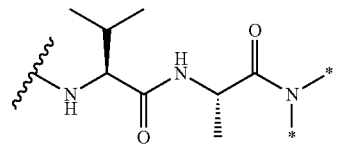 [SMILES: *N[C@H](C(=O)N[C@@H](C)C(=O)N(*)*)C(C)C]

where the asterisks, —N< and the wavy line are as defined above.

In one embodiment, the dipeptide is phenylalanine-lysine and $L^1$-D is:

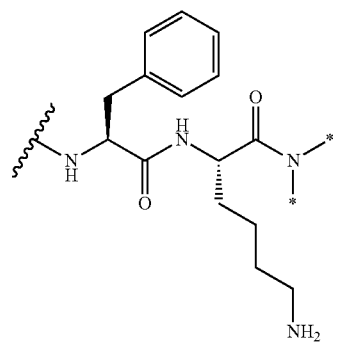 [SMILES: *N[C@@H](Cc1ccccc1)C(=O)N[C@@H](CCCCN)C(=O)N(*)*]

where the asterisks, —N< and the wavy line are as defined above.

In one embodiment, the dipeptide is valine-citrulline.

In one embodiment, the groups A-$L^1$ are:

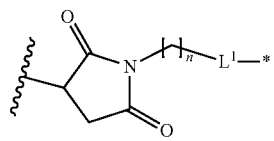

where the asterisk indicates the point of attachment to $L^2$ or D, the wavy line indicates the point of attachment to the Ligand unit, and n is 0 to 6. In one embodiment, n is 5.

In one embodiment, the groups A-$L^1$ are:

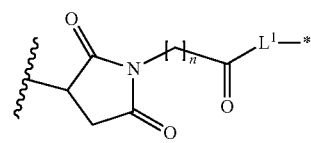

where the asterisk indicates the point of attachment to $L^2$ or D, the wavy line indicates the point of attachment to the Ligand unit, and n is 0 to 6. In one embodiment, n is 5.

In one embodiment, the groups A-L¹ are:

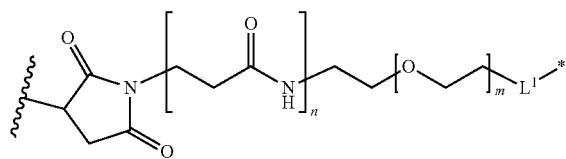

where the asterisk indicates the point of attachment to L² or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L¹ are:

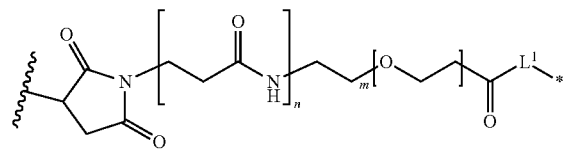

where the asterisk indicates the point of attachment to L² or D, the wavy line indicates the point of attachment to the Ligand unit, n is 0 or 1, and m is 0 to 30. In a preferred embodiment, n is 1 and m is 0 to 10, 1 to 7, preferably 3 to 7, most preferably 3 or 7.

In one embodiment, the groups A-L¹ are:

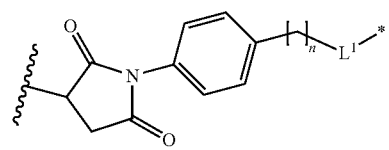

where the asterisk indicates the point of attachment to L² or D, the wavy line indicates the point of attachment to the Ligand unit, and n is 0 to 6. In one embodiment, n is 5.

In one embodiment, the groups A-L¹ are:

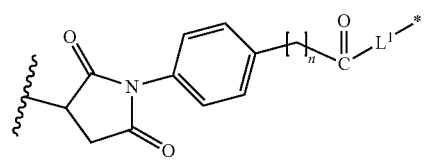

where the asterisk indicates the point of attachment to L² or D, the wavy line indicates the point of attachment to the Ligand unit, and n is 0 to 6. In one embodiment, n is 5.

In one embodiment, the groups A-L¹ are:

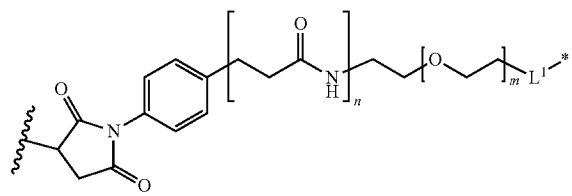

where the asterisk indicates the point of attachment to L² or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L¹ is:

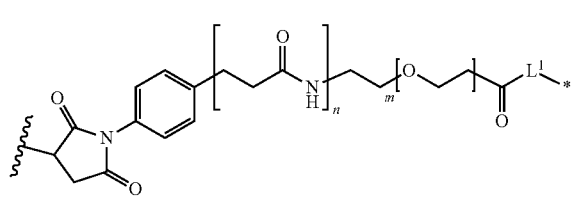

where the asterisk indicates the point of attachment to L² or D, the wavy line indicates the point of attachment to the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups A-L¹ are:

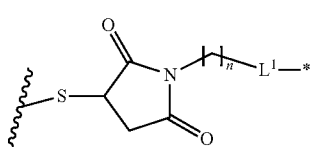

where the asterisk indicates the point of attachment to L² or D, S is a sulfur group of the Ligand unit, the wavy line indicates the point of attachment to the rest of the Ligand unit, and n is 0 to 6. In one embodiment, n is 5.

In one embodiment, the group A-L¹ are:

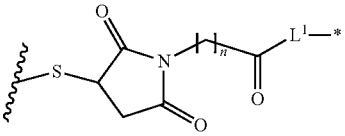

where the asterisk indicates the point of attachment to L² or D, S is a sulfur group of the Ligand unit, the wavy line indicates the point of attachment to the remainder of the Ligand unit, and n is 0 to 6. In one embodiment, n is 5.

In one embodiment, the groups $A^1$-$L^1$ are:

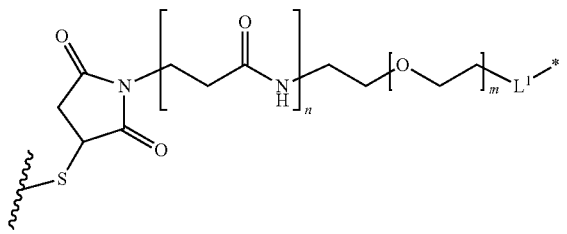

where the asterisk indicates the point of attachment to $L^2$ or D, S is a sulfur group of the Ligand unit, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

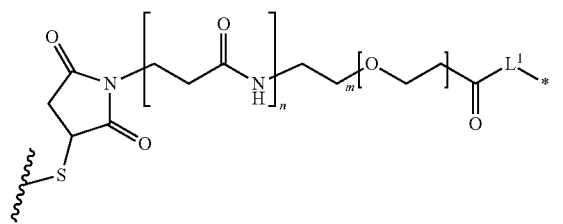

where the asterisk indicates the point of attachment to $L^2$ or D, the wavy line indicates the point of attachment to the Ligand unit, n is 0 or 1, and m is 0 to 30. In a preferred embodiment, n is 1 and m is 0 to 10, 1 to 7, preferably 4 to 8, most preferably 4 or 8.

In one embodiment, the groups $A^1$-$L^1$ are:

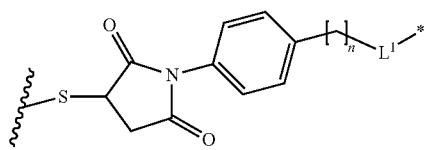

where the asterisk indicates the point of attachment to $L^2$ or D, the wavy line indicates the point of attachment to the remainder of the Ligand unit, and n is 0 to 6. In one embodiment, n is 5.

In one embodiment, the groups $A^1$-$L^1$ are:

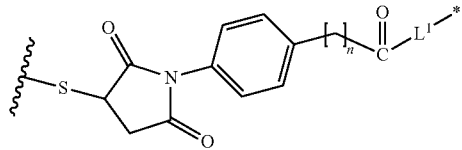

where the asterisk indicates the point of attachment to $L^2$ or D, the wavy line indicates the point of attachment to the remainder of the Ligand unit, and n is 0 to 6. In one embodiment, n is 5.

In one embodiment, the groups $A^1$-$L^1$ are:

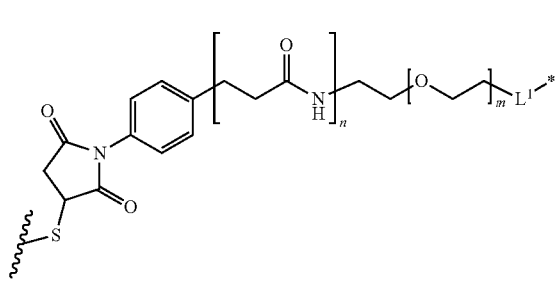

where the asterisk indicates the point of attachment to $L^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

In one embodiment, the groups $A^1$-$L^1$ are:

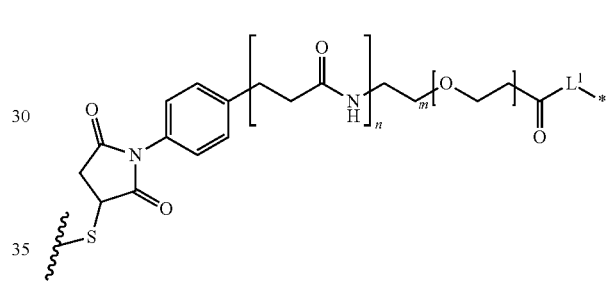

where the asterisk indicates the point of attachment to $L^2$ or D, the wavy line indicates the point of attachment to the remainder of the Ligand unit, n is 0 or 1, and m is 0 to 30. In a preferred embodiment, n is 1 and m is 0 to 10, 1 to 8, preferably 4 to 8, most preferably 4 or 8.

The group $R^{L'}$ is derivable from the group $R^L$. The group $R^L$ may be converted to a group $R^{L'}$ by connection of an antibody to a functional group of $R^L$. Other steps may be taken to convert $R^L$ to $R^{L'}$. These steps may include the removal of protecting groups, where present, or the installation of an appropriate functional group.

$R^L$

Linkers can include protease-cleavable peptidic moieties comprising one or more amino acid units. Peptide linker reagents may be prepared by solid phase or liquid phase synthesis methods (E. Schröder and K. Lübke, *The Peptides*, volume 1, pp 76-136 (1965) Academic Press) that are well known in the field of peptide chemistry, including t-BOC chemistry (Geiser et al "Automation of solid-phase peptide synthesis" in *Macromolecular Sequencing and Synthesis*, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

Exemplary amino acid linkers include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Amino acid side chains include those occurring naturally, as well as minor amino acids and non-naturally occurring amino acid analogs, such as citrulline. Amino acid side chains include hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, as well as the following structures:

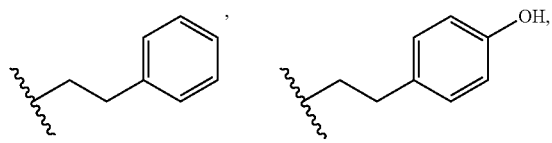

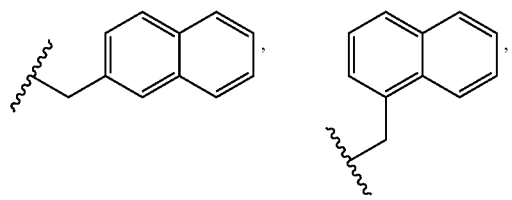

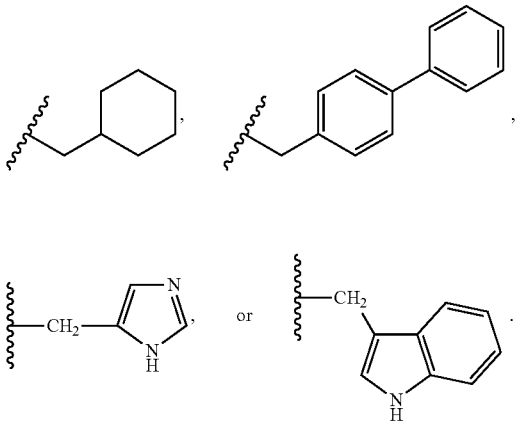

When the amino acid side chains include other than hydrogen (glycine), the carbon atom to which the amino acid side chain is attached is chiral. Each carbon atom to which the amino acid side chain is attached is independently in the (S) or (R) configuration, or a racemic mixture. Drug-linker reagents may thus be enantiomerically pure, racemic, or diastereomeric.

In exemplary embodiments, amino acid side chains are selected from those of natural and non-natural amino acids, including alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, norleucine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit).

An exemplary valine-citrulline (val-cit or vc) dipeptide linker reagent useful for constructing a linker-PBD drug moiety intermediate for conjugation to an antibody, having a para-aminobenzylcarbamoyl (PAB) self-immolative spacer has the structure:

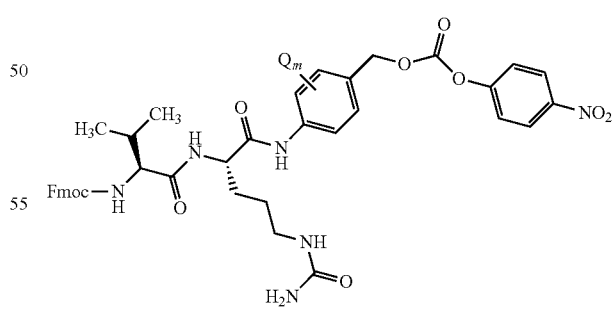

where Q is C$_1$-C$_8$ alkyl, —O—(C$_1$-C$_8$ alkyl), -halogen, —NO$_2$ or —CN; and m is an integer ranging from 0-4.

An exemplary phe-lys(Mtr) dipeptide linker reagent having a p-aminobenzyl group can be prepared according to Dubowchik, et al. (1997) Tetrahedron Letters, 38:5257-60, and has the structure:

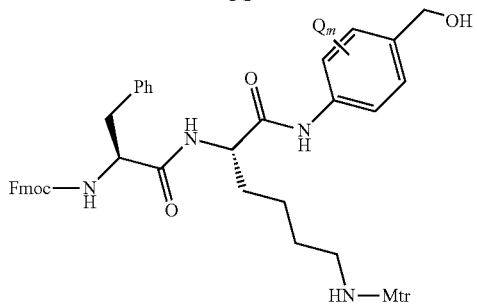

where Mtr is mono-4-methoxytrityl, Q is $C_1$-$C_8$ alkyl, —O—($C_1$-$C_8$ alkyl), -halogen, —$NO_2$ or —CN; and m is an integer ranging from 0-4.

The "self-immolative linker" PAB (para-aminobenzyloxycarbonyl), attaches the drug moiety to the antibody in the antibody drug conjugate (Carl et al (1981) J. Med. Chem. 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. No. 6,218,519; U.S. Pat. No. 6,835,807; U.S. Pat. No. 6,268,488; US20040018194; WO98/13059; US20040052793; U.S. Pat. No. 6,677,435; U.S. Pat. No. 5,621,002; US20040121940; WO2004/032828). Other examples of self-immolative spacers besides PAB include, but are not limited to: (i) aromatic compounds that are electronically similar to the PAB group such as 2-aminoimidazol-5-methanol derivatives (Hay et al. (1999) Bioorg. Med. Chem. Lett. 9:2237), thiazoles (U.S. Pat. No. 7,375,078), multiple, elongated PAB units (de Groot et al (2001) J. Org. Chem. 66:8815-8830); and ortho or para-aminobenzylacetals; and (ii) homologated styryl PAB analogs (U.S. Pat. No. 7,223,837). Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacers useful in ADC.

In one embodiment, a valine-citrulline dipeptide PAB analog reagent has a 2,6 dimethyl phenyl group and has the structure:

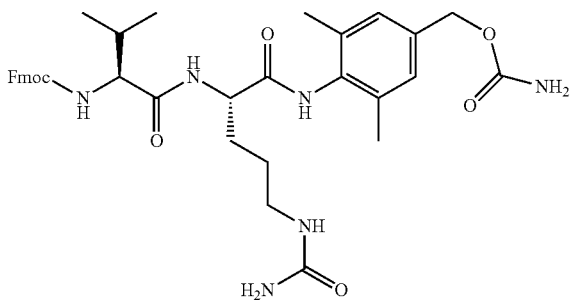

Linker reagents useful for the antibody drug conjugates of the disclosure include, but are not limited to: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and bis-maleimide reagents: DTME, BMB, BMDB, BMH, BMOE, 1,8-bis-maleimidodiethyleneglycol (BM(PEO)$_2$), and 1,11-bis-maleimidotriethyleneglycol (BM(PEO)$_3$), which are commercially available from Pierce Biotechnology, Inc., ThermoScientific, Rockford, Ill., and other reagent suppliers. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, PBD drug moiety, or linker intermediate include iodoacetamide, bromoacetamide, vinyl pyridine, disulfide, pyridyl disulfide, isocyanate, and isothiocyanate.

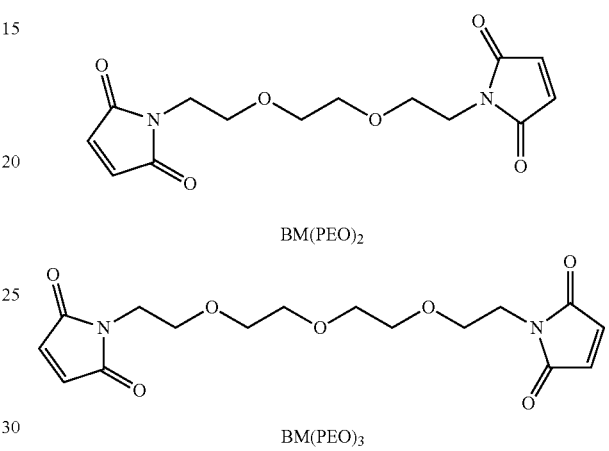

Other embodiments of linker reagents are: N-succinimidyl-4-(2-pyridylthio)pentanoate (SPP), N-succinimidyl-3-(2-pyridyldithio) propionate (SPDP, Carlsson et al (1978) Biochem. J. 173:723-737), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic or branched linker.

One exemplary embodiment of a dendritic type linker has the structure:

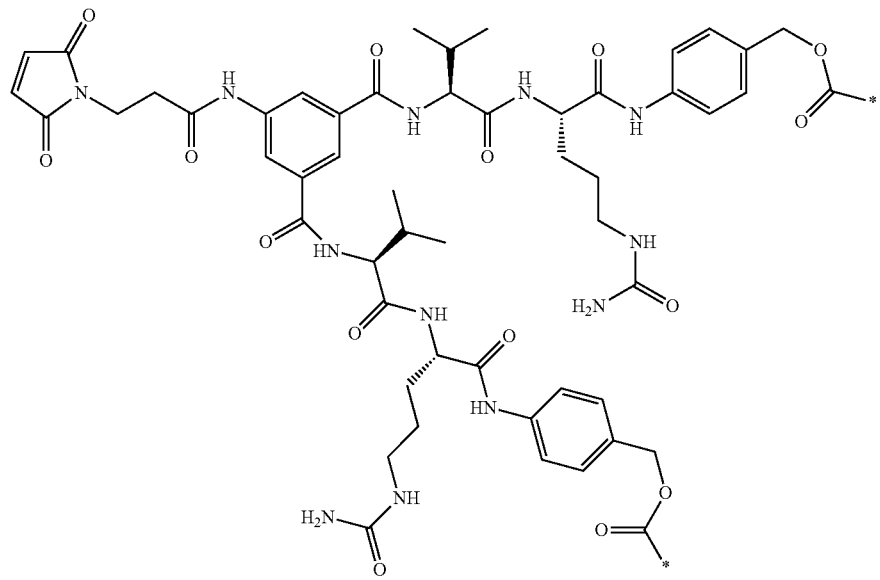 [SMILES: *C(=O)OCc1ccc(NC(=O)[C@H](CCCNC(N)=O)NC(=O)[C@@H](NC(=O)c2cc(NC(=O)CCN3C(=O)C=CC3=O)cc(C(=O)N[C@H](C(=O)N[C@@H](CCCNC(N)=O)C(=O)Nc3ccc(COC(*)=O)cc3)C(C)C)c2)C(C)C)cc1]

where the asterisk indicate the point of attachment to the N10 position of a PBD moiety.

$R^C$, Capping Group

The conjugate of the first aspect of the disclosure may have a capping group $R^C$ at the N10 position.

The group $R^C$ is removable from the N10 position of the PBD moiety to leave an N10-C11 imine bond, a carbinolamine, a substituted carbinolamine, where $QR^{11}$ is $OSO_3M$, a bisulfite adduct, a thiocarbinolamine, a substituted thiocarbinolamine, or a substituted carbinalamine.

In one embodiment, $R^C$, may be a protecting group that is removable to leave an N10-C11 imine bond, a carbinolamine, a substituted cabinolamine, or, where $QR^{11}$ is $OSO_3M$, a bisulfite adduct. In one embodiment, $R^C$ is a protecting group that is removable to leave an N10-C11 imine bond.

The group $R^C$ is intended to be removable under the same conditions as those required for the removal of the group $R^{10}$, for example to yield an N10-C11 imine bond, a carbinolamine and so on. The capping group acts as a protecting group for the intended functionality at the N10 position. The capping group is intended not to be reactive towards an antibody. For example, $R^C$ is not the same as $R^L$.

Compounds having a capping group may be used as intermediates in the synthesis of dimers having an imine monomer. Alternatively, compounds having a capping group may be used as conjugates, where the capping group is removed at the target location to yield an imine, a carbinolamine, a substituted cabinolamine and so on. Thus, in this embodiment, the capping group may be referred to as a therapeutically removable nitrogen protecting group, as defined in the inventors' earlier application WO 00/12507.

In one embodiment, the group $R^C$ is removable under the conditions that cleave the linker $R^L$ of the group $R^{10}$. Thus, in one embodiment, the capping group is cleavable by the action of an enzyme.

In an alternative embodiment, the capping group is removable prior to the connection of the linker $R^L$ to the antibody. In this embodiment, the capping group is removable under conditions that do not cleave the linker $R^L$.

Where a compound includes a functional group $G^1$ to form a connection to the antibody, the capping group is removable prior to the addition or unmasking of $G^1$.

The capping group may be used as part of a protecting group strategy to ensure that only one of the monomer units in a dimer is connected to an antibody.

The capping group may be used as a mask for a N10-C11 imine bond. The capping group may be removed at such time as the imine functionality is required in the compound. The capping group is also a mask for a carbinolamine, a substituted cabinolamine, and a bisulfite adduct, as described above.

$R^C$ may be an N10 protecting group, such as those groups described in the inventors' earlier application, WO 00/12507. In one embodiment, $R^C$ is a therapeutically removable nitrogen protecting group, as defined in the inventors' earlier application, WO 00/12507.

In one embodiment, $R^C$ is a carbamate protecting group.

In one embodiment, the carbamate protecting group is selected from:

Alloc, Fmoc, Boc, Troc, Teoc, Psec, Cbz and PNZ.

Optionally, the carbamate protecting group is further selected from Moc.

In one embodiment, $R^C$ is a linker group $R^L$ lacking the functional group for connection to the antibody.

This application is particularly concerned with those $R^C$ groups which are carbamates.

In one embodiment, $R^C$ is a group:

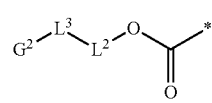

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

Where $L^3$ and $L^2$ are both covalent bonds, $G^2$ and OC(=O) together form a carbamate protecting group as defined above.

$L^1$ is as defined above in relation to $R^{10}$
$L^2$ is as defined above in relation to $R^{10}$ Various terminating groups are described below, including those based on well known protecting groups.

In one embodiment $L^3$ is a cleavable linker $L^1$, and $L^2$, together with OC(=O), forms a self-immolative linker. In this embodiment, $G^2$ is Ac (acetyl) or Moc, or a carbamate protecting group selected from:

Alloc, Fmoc, Boc, Troc, Teoc, Psec, Cbz and PNZ.

Optionally, the carbamate protecting group is further selected from Moc.

In another embodiment, $G^2$ is an acyl group —C(=O)$G^3$, where $G^3$ is selected from alkyl (including cycloalkyl, alkenyl and alkynyl), heteroalkyl, heterocyclyl and aryl (including heteroaryl and carboaryl). These groups may be optionally substituted. The acyl group together with an amino group of $L^3$ or $L^2$, where appropriate, may form an amide bond. The acyl group together with a hydroxy group of $L^3$ or $L^2$, where appropriate, may form an ester bond.

In one embodiment, $G^3$ is heteroalkyl. The heteroalkyl group may comprise polyethylene glycol. The heteroalkyl group may have a heteroatom, such as O or N, adjacent to the acyl group, thereby forming a carbamate or carbonate group, where appropriate, with a heteroatom present in the group $L^3$ or $L^2$, where appropriate.

In one embodiment, $G^3$ is selected from $NH_2$, NHR and NRR'. Preferably, $G^3$ is NRR'.

In one embodiment $G^2$ is the group:

where the asterisk indicates the point of attachment to $L^3$, n is 0 to 6 and $G^4$ is selected from OH, OR, SH, SR, COOR, $CONH_2$, CONHR, CONRR', $NH_2$, NHR, NRR', $NO_2$, and halo. The groups OH, SH, $NH_2$ and NHR are protected. In one embodiment, n is 1 to 6, and preferably n is 5. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Most preferably $G^4$ is OMe.

In one embodiment, the group $G^2$ is:

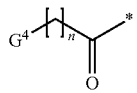

where the asterisk indicates the point of attachment to $L^3$, and n and $G^4$ are as defined above.

In one embodiment, the group $G^2$ is:

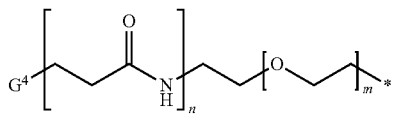

where the asterisk indicates the point of attachment to $L^3$, n is 0 or 1, m is 0 to 50, and $G^4$ is selected from OH, OR, SH, SR, COOR, $CONH_2$, CONHR, CONRR', $NH_2$, NHR, NRR', $NO_2$, and halo. In a preferred embodiment, n is 1 and m is 0 to 10, 1 to 2, preferably 4 to 8, and most preferably 4 or 8. In another embodiment, n is 1 and m is 10 to 50, preferably 20 to 40. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

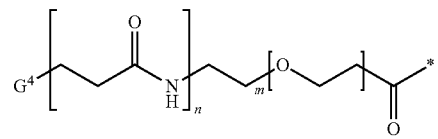

where the asterisk indicates the point of attachment to $L^3$, and n, m and $G^4$ are as defined above.

In one embodiment, the group $G^2$ is:

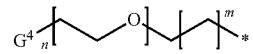

where n is 1-20, m is 0-6, and $G^4$ is selected from OH, OR, SH, SR, COOR, $CONH_2$, CONHR, CONRR', $NH_2$, NHR, NRR', $NO_2$, and halo. In one embodiment, n is 1-10. In another embodiment, n is 10 to 50, preferably 20 to 40. In one embodiment, n is 1. In one embodiment, m is 1. The groups OH, SH, $NH_2$ and NHR are protected. In one embodiment, $G^4$ is OR, SR, COOR, $CONH_2$, CONHR, CONRR', and NRR'. In one embodiment, $G^4$ is OR, SR, and NRR'. Preferably $G^4$ is selected from OR and NRR', most preferably $G^4$ is OR. Preferably $G^4$ is OMe.

In one embodiment, the group $G^2$ is:

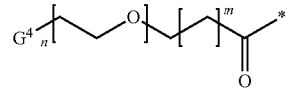

where the asterisk indicates the point of attachment to $L^3$, and n, m and $G^4$ are as defined above.

In each of the embodiments above $G^4$ may be OH, SH, $NH_2$ and NHR. These groups are preferably protected.

In one embodiment, OH is protected with Bzl, TBDMS, or TBDPS.

In one embodiment, SH is protected with Acm, Bzl, Bzl-OMe, Bzl-Me, or Trt.

In one embodiment, $NH_2$ or NHR are protected with Boc, Moc, Z—Cl, Fmoc, Z, or Alloc.

In one embodiment, the group $G^2$ is present in combination with a group $L^3$, which group is a dipeptide.

The capping group is not intended for connection to the antibody. Thus, the other monomer present in the dimer serves as the point of connection to the antibody via a linker.

Accordingly, it is preferred that the functionality present in the capping group is not available for reaction with an antibody. Thus, reactive functional groups such as OH, SH, NH$_2$, COOH are preferably avoided. However, such functionality may be present in the capping group if protected, as described above.

EMBODIMENTS

Embodiments of the present disclosure include ConjA wherein the antibody is as defined above.

Embodiments of the present disclosure include ConjB wherein the antibody is as defined above.

Embodiments of the present disclosure include ConjC wherein the antibody is as defined above.

Embodiments of the present disclosure include ConjD wherein the antibody is as defined above.

Embodiments of the present disclosure include ConjE wherein the antibody is as defined above.

Embodiments of the present disclosure include ConjF wherein the antibody is as defined above.

Embodiments of the present disclosure include ConjG wherein the antibody is as defined above.

Embodiments of the present disclosure include ConjH wherein the antibody is as defined above.

Drug Loading

The drug loading is the average number of PBD drugs per antibody, e.g. antibody. Where the compounds of the disclosure are bound to native cysteines, drug loading may range from 1 to 8 drugs ($D^L$) per antibody, i.e. where 1, 2, 3, 4, 5, 6, 7, and 8 drug moieties are covalently attached to the antibody. Compositions of conjugates include collections of antibodies, conjugated with a range of drugs, from 1 to 8. Where the compounds of the disclosure are bound to lysines, drug loading may range from 1 to 80 drugs ($D^L$) per antibody, although an upper limit of 40, 20, 10 or 8 may be preferred. Compositions of conjugates include collections of antibodies, conjugated with a range of drugs, from 1 to 80, 1 to 40, 1 to 20, 1 to 10 or 1 to 8.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates.

For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading, e.g. p >5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. No. 7,521,541; U.S. Pat. No. 7,723,485; WO2009/052249). The engineered cysteine thiols may react with linker reagents or the drug-linker reagents of the present disclosure which have thiol-reactive, electrophilic groups such as maleimide or alpha-halo amides to form ADC with cysteine engineered antibodies and the PBD drug moieties. The location of the drug moiety can thus be designed, controlled, and known. The drug loading can be controlled since the engineered cysteine thiol groups typically react with thiol-reactive linker reagents or drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Alternatively, site-specific conjugation can be achieved by engineering antibodies to contain unnatural amino acids in their heavy and/or light chains as described by Axup et al. ((2012), Proc Natl Acad Sci USA. 109(40):16101-16116). The unnatural amino acids provide the additional advantage that orthogonal chemistry can be designed to attach the linker reagent and drug.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug moieties may be attached, via the linker, at different sites on the antibody.

Thus the antibody-drug conjugate compositions of the disclosure include mixtures of antibody-drug conjugate compounds where the antibody has one or more PBD drug moieties and where the drug moieties may be attached to the antibody at various amino acid residues.

In one embodiment, the average number of dimer pyrrolobenzodiazepine groups per antibody is in the range 1 to 20. In some embodiments the range is selected from 1 to 8, 2 to 8, 2 to 6, 2 to 4, and 4 to 8.

In some embodiments, there is one dimer pyrrolobenzodiazepine group per antibody.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as N$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

The disclosure includes compounds where a solvent adds across the imine bond of the PBD moiety, which is illustrated below where the solvent is water or an alcohol (R$^A$OH, where R$^A$ is C$_{1-4}$ alkyl):

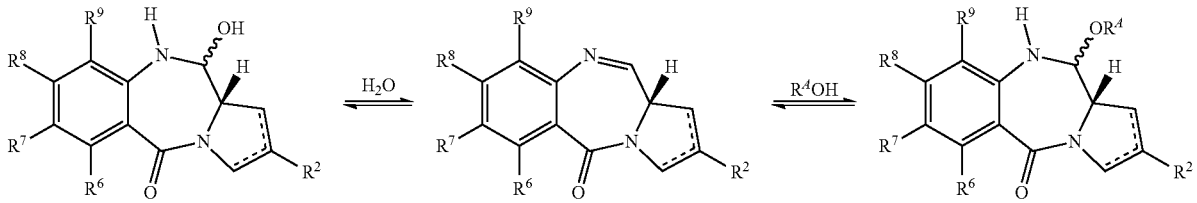

These forms can be called the carbinolamine and carbinolamine ether forms of the PBD (as described in the section relating to R$^{10}$ above). The balance of these equilibria depend on the conditions in which the compounds are found, as well as the nature of the moiety itself.

These particular compounds may be isolated in solid form, for example, by lyophilisation.

Isomers

Certain compounds of the disclosure may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the disclosure may contain asymmetric or chiral centers, and therefore exist in different stereoisomeric forms. It is intended that all stereoisomeric forms of the compounds of the disclosure, including but not limited to, diastereomers, enantiomers and atropisomers, as well as mixtures thereof such as racemic mixtures, form part of the present disclosure. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

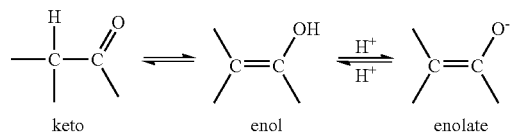

keto     enol     enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the disclosure include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this disclosure any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Biological Activity

In Vitro Cell Proliferation Assays

Generally, the cytotoxic or cytostatic activity of an antibody-drug conjugate (ADC) is measured by: exposing mammalian cells having receptor proteins to the antibody of the ADC in a cell culture medium; culturing the cells for a period from about 6 hours to about 5 to 7 days; and measuring cell viability. Cell-based in vitro assays are used to measure viability (proliferation), cytotoxicity, and induction of apoptosis (caspase activation) of an ADC of the disclosure.

The in vitro potency of antibody-drug conjugates can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) *J. Immunol. Meth.* 160:81-88; U.S. Pat. No. 6,602,677). The CellTiter-Glo® Assay is conducted in 96 well format, making it amenable to automated high-throughput screening (HTS) (Cree et al (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

The in vitro potency of antibody-drug conjugates can also be measured by a cytotoxicity assay. Cultured adherent cells are washed with PBS, detached with trypsin, diluted in complete medium, containing 10% FCS, centrifuged, resuspended in fresh medium and counted with a haemocytometer. Suspension cultures are counted directly. Monodisperse cell suspensions suitable for counting may require agitation of the suspension by repeated aspiration to break up cell clumps.

The cell suspension is diluted to the desired seeding density and dispensed (100 µl per well) into black 96 well plates. Plates of adherent cell lines are incubated overnight to allow adherence. Suspension cell cultures can be used on the day of seeding.

A stock solution (1 ml) of ADC (20 µg/ml) is made in the appropriate cell culture medium.

Serial 10-fold dilutions of stock ADC are made in 15 ml centrifuge tubes by serially transferring 100 µl to 900 µl of cell culture medium.

Four replicate wells of each ADC dilution (100 µl) are dispensed in 96-well black plates, previously plated with cell suspension (100 µl), resulting in a final volume of 200 µl. Control wells receive cell culture medium (100 µl).

If the doubling time of the cell line is greater than 30 hours, ADC incubation is for 5 days, otherwise a four day incubation is done.

At the end of the incubation period, cell viability is assessed with the Alamar blue assay.

AlamarBlue (Invitrogen) is dispensed over the whole plate (20 µl per well) and incubated for 4 hours. Alamar blue fluorescence is measured at excitation 570 nm, emission 585 nm on the Varioskan flash plate reader. Percentage cell survival is calculated from the mean fluorescence in the ADC treated wells compared to the mean fluorescence in the control wells.

Use

The conjugates of the disclosure may be used to provide a PBD compound at a target location.

The target location is preferably a proliferative cell population. The antibody is an antibody for an antigen present on a proliferative cell population.

In one embodiment the antigen is absent or present at a reduced level in a non-proliferative cell population compared to the amount of antigen present in the proliferative cell population, for example a tumour cell population.

At the target location the linker may be cleaved so as to release a compound RelA, RelB, RelC, RelD, RelE or RelG. Thus, the conjugate may be used to selectively provide a compound RelA, RelB, RelC, RelD, RelE or RelG to the target location.

The linker may be cleaved by an enzyme present at the target location.

The target location may be in vitro, in vivo or ex vivo.

The antibody-drug conjugate (ADC) compounds of the disclosure include those with utility for anticancer activity. In particular, the compounds include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. a lower efficacious dose, may be achieved.

Thus, in one aspect, the present disclosure provides a conjugate compound as described herein for use in therapy.

In a further aspect there is also provides a conjugate compound as described herein for use in the treatment of a proliferative disease. A second aspect of the present disclosure provides the use of a conjugate compound in the manufacture of a medicament for treating a proliferative disease.

One of ordinary skill in the art is readily able to determine whether or not a candidate conjugate treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of particular interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

It is contemplated that the antibody-drug conjugates (ADC) of the present disclosure may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Methods of Treatment

The conjugates of the present disclosure may be used in a method of therapy. Also provided is a method of treatment, comprising administering to a subject in need of treatment a therapeutically-effective amount of a conjugate compound of the disclosure. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound of the disclosure may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1l (*Angew Chem. Intl. Ed. Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rlL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™ OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Also included in the definition of "chemotherapeutic agent" are agents which modulate specific molecules or classes of molecule that are of particular importance in cancer pathology. Examples of specific molecules of interest are vEGF and EGFR (HER1, HER2, and/or HER3). An examples of a class of molecules of interest are the immune checkpoint modulators such as the anti PDL-1 or CTLA4 immune modulators. Examples of such suitable agents include antibodies, nucleic acids (e.g. ribozymes, siRNAs), and small molecules. In some embodiments the agents inhibit the expression and/or activity of the specific molecules. In some embodiments the agents activate the expression and/or activity of the specific molecules.

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Formulations

While it is possible for the conjugate compound to be used (e.g., administered) alone, it is often preferable to present it as a composition or formulation.

In one embodiment, the composition is a pharmaceutical composition (e.g., formulation, preparation, medicament) comprising a conjugate compound, as described herein, and a pharmaceutically acceptable carrier, diluent, or excipient.

In one embodiment, the composition is a pharmaceutical composition comprising at least one conjugate compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 20th edition, pub. Lippincott, Williams & Wilkins, 2000; and *Handbook of Pharmaceutical Excipients*, 2nd edition, 1994.

Another aspect of the present disclosure pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring Dosage It will be appreciated by one of skill in the art that appropriate dosages of the conjugate compound, and compositions comprising the conjugate compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the conjugate compound is administered to a human patient according to the following dosage regime: about 50 or about 75 mg, 3 or 4 times daily.

In one embodiment, the conjugate compound is administered to a human patient according to the following dosage regime: about 100 or about 125 mg, 2 times daily.

The dosage amounts described above may apply to the conjugate (including the PBD moiety and the linker to the antibody) or to the effective amount of PBD compound provided, for example the amount of compound that is releasable after cleavage of the linker.

For the prevention or treatment of disease, the appropriate dosage of an ADC of the disclosure will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of an ADC. Other dosage regimens may be useful. The progress of this therapy is easily monitored by conventional techniques and assays.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Preparation of Drug Conjugates

Antibody drug conjugates may be prepared by several routes, employing organic chemistry reactions, conditions, and reagents known to those skilled in the art, including reaction of a nucleophilic group of an antibody with a drug-linker reagent. This method may be employed to prepare the antibody-drug conjugates of the disclosure.

Nucleophilic groups on antibodies include, but are not limited to side chain thiol groups, e.g. cysteine. Thiol groups are nucleophilic and capable of reacting to form covalent bonds with electrophilic groups on linker moieties such as those of the present disclosure. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

FURTHER PREFERENCES

The following preferences may apply to all aspects of the disclosure as described above, or may relate to a single aspect. The preferences may be combined together in any combination.

In some embodiments, $R^{6'}$, $R^{7'}$, $R^{9'}$, and Y' are preferably the same as $R^6$, $R^7$, $R^9$, and Y respectively.

Dimer Link

Y and Y' are preferably O.

R" is preferably a $C_{3-7}$ alkylene group with no substituents. More preferably R" is a $C_3$, $C_5$ or $C_7$ alkylene. Most preferably, R" is a $C_3$ or $C_5$ alkylene.

$R^6$ to $R^9$ $R^9$ is preferably H.

$R^6$ is preferably selected from H, OH, OR, SH, $NH_2$, nitro and halo, and is more preferably H or halo, and most preferably is H.

$R^7$ is preferably selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{5-10}$ aryl groups. R may be more preferably a $C_{1-4}$ alkyl group, which may or may not be substituted. A substituent of interest is a $C_{5-6}$ aryl group (e.g. phenyl). Particularly preferred substituents at the 7-positions are OMe and $OCH_2Ph$. Other substituents of particular interest are dimethylamino (i.e. $-NMe_2$); $-(OC_2H_4)_qOMe$, where q is from 0 to 2; nitrogen-containing CO heterocyclyls, including morpholino, piperidinyl and N-methyl-piperazinyl.

These preferences apply to $R^{9'}$, $R^{6'}$ and $R^{7'}$ respectively.

$R^{12}$

When there is a double bond present between C2' and C3', $R^{12}$ is selected from:

(a) $C_{5-10}$ aryl group, optionally substituted by one or more substituents selected from the group comprising: halo, nitro, cyano, ether, $C_{1-7}$ alkyl, $C_{3-7}$ heterocyclyl and bis-oxy-$C_{1-3}$ alkylene;

(b) $C_{1-5}$ saturated aliphatic alkyl;

(c) $C_{3-6}$ saturated cycloalkyl;

(d)

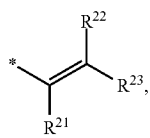

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(e)

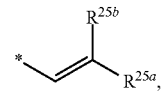

wherein one of $R^{25a}$ and $R^{25b}$ is H and the other is selected from: phenyl, which phenyl is optionally substituted by a group selected from halo methyl, methoxy; pyridyl; and thiophenyl; and (f)

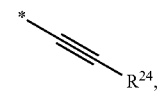

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl.

When $R^{12}$ is a $C_{5-10}$ aryl group, it may be a $C_{5-7}$ aryl group. A $C_{5-7}$ aryl group may be a phenyl group or a $C_{5-7}$ heteroaryl group, for example furanyl, thiophenyl and pyridyl. In some embodiments, $R^{12}$ is preferably phenyl. In other embodiments, $R^{12}$ is preferably thiophenyl, for example, thiophen-2-yl and thiophen-3-yl.

When $R^{12}$ is a $C_{5-10}$ aryl group, it may be a $C_{8-10}$ aryl, for example a quinolinyl or isoquinolinyl group. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. Of these quinolin-3-yl and quinolin-6-yl may be preferred. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. Of these isoquinolin-3-yl and isoquinolin-6-yl may be preferred.

When $R^{12}$ is a $C_{5-10}$ aryl group, it may bear any number of substituent groups. It preferably bears from 1 to 3 substituent groups, with 1 and 2 being more preferred, and singly substituted groups being most preferred. The substituents may be any position.

Where $R^{12}$ is $C_{5-7}$ aryl group, a single substituent is preferably on a ring atom that is not adjacent the bond to the remainder of the compound, i.e. it is preferably β or γ to the bond to the remainder of the compound. Therefore, where the $C_{5-7}$ aryl group is phenyl, the substituent is preferably in the meta- or para-positions, and more preferably is in the para-position.

Where $R^{12}$ is a $C_{8-10}$ aryl group, for example quinolinyl or isoquinolinyl, it may bear any number of substituents at any position of the quinoline or isoquinoline rings. In some embodiments, it bears one, two or three substituents, and these may be on either the proximal and distal rings or both (if more than one substituent).

$R^{12}$ Substituents, when $R^{12}$ is a $C_{5-10}$ Aryl Group

If a substituent on $R^{12}$ when $R^{12}$ is a $C_{5-10}$ aryl group is halo, it is preferably F or Cl, more preferably Cl.

If a substituent on $R^{12}$ when $R^{12}$ is a $C_{5-10}$ aryl group is ether, it may in some embodiments be an alkoxy group, for example, a $C_{1-7}$ alkoxy group (e.g. methoxy, ethoxy) or it may in some embodiments be a $C_{5-7}$ aryloxy group (e.g. phenoxy, pyridyloxy, furanyloxy). The alkoxy group may itself be further substituted, for example by an amino group (e.g. dimethylamino).

If a substituent on $R^{12}$ when $R^{12}$ is a $C_{5-10}$ aryl group is $C_{1-7}$ alkyl, it may preferably be a $C_{1-4}$ alkyl group (e.g. methyl, ethyl, propryl, butyl).

If a substituent on $R^{12}$ when $R^{12}$ is a $C_{5-10}$ aryl group is $C_{3-7}$ heterocyclyl, it may in some embodiments be $C_6$ nitrogen containing heterocyclyl group, e.g. morpholino, thiomorpholino, piperidinyl, piperazinyl. These groups may be bound to the rest of the PBD moiety via the nitrogen atom. These groups may be further substituted, for example, by $C_{1-4}$ alkyl groups.

If the $C_6$ nitrogen containing heterocyclyl group is piperazinyl, the said further substituent may be on the second nitrogen ring atom.

If a substituent on $R^{12}$ when $R^{12}$ is a $C_{5-10}$ aryl group is bis-oxy-$C_{1-3}$ alkylene, this is preferably bis-oxy-methylene or bis-oxy-ethylene.

If a substituent on $R^{12}$ when $R^{12}$ is a $C_{5-10}$ aryl group is ester, this is preferably methyl ester or ethyl ester.

Particularly preferred substituents when $R^{12}$ is a $C_{5-10}$ aryl group include methoxy, ethoxy, fluoro, chloro, cyano, bis-oxy-methylene, methyl-piperazinyl, morpholino and methyl-thiophenyl. Other particularly preferred substituent for $R^{12}$ are dimethylaminopropyloxy and carboxy.

Particularly preferred substituted $R^{12}$ groups when $R^{12}$ is a $C_{5-10}$ aryl group include, but are not limited to, 4-methoxy-phenyl, 3-methoxyphenyl, 4-ethoxy-phenyl, 3-ethoxy-phenyl, 4-fluoro-phenyl, 4-chloro-phenyl, 3,4-bisoxymethylene-phenyl, 4-methylthiophenyl, 4-cyanophenyl, 4-phenoxyphenyl, quinolin-3-yl and quinolin-6-yl, isoquinolin-3-yl and isoquinolin-6-yl, 2-thienyl, 2-furanyl, methoxynaphthyl, and naphthyl. Another possible substituted $R^{12}$ group is 4-nitrophenyl. $R^{12}$ groups of particular interest include 4-(4-methylpiperazin-1-yl)phenyl and 3,4-bisoxymethylene-phenyl.

When $R^{12}$ is $C_{1-5}$ saturated aliphatic alkyl, it may be methyl, ethyl, propyl, butyl or pentyl. In some embodiments, it may be methyl, ethyl or propyl (n-pentyl or isopropyl). In some of these embodiments, it may be methyl. In other embodiments, it may be butyl or pentyl, which may be linear or branched.

When $R^{12}$ is $C_{3-6}$ saturated cycloalkyl, it may be cyclopropyl, cyclobutyl, cyclopentyl or cyclohexyl. In some embodiments, it may be cyclopropyl.

When $R^{12}$ is

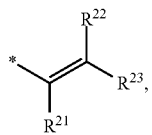

each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5. In some embodiments, the total number of carbon atoms in the $R^{12}$ group is no more than 4 or no more than 3.

In some embodiments, one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

In other embodiments, two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

In some embodiments, the groups that are not H are selected from methyl and ethyl. In some of these embodiments, the groups that re not H are methyl.

In some embodiments, $R^{21}$ is H.
In some embodiments, $R^{22}$ is H.
In some embodiments, $R^{23}$ is H.
In some embodiments, $R^{21}$ and $R^{22}$ are H.
In some embodiments, $R^{21}$ and $R^{23}$ are H.
In some embodiments, $R^{22}$ and $R^{23}$ are H.

An $R^{12}$ group of particular interest is:

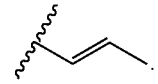 [SMILES: */C=C/C]

When $R^{12}$ is

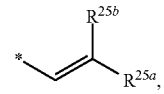

one of $R^{25a}$ and $R^{25b}$ is H and the other is selected from: phenyl, which phenyl is optionally substituted by a group selected from halo, methyl, methoxy; pyridyl; and thiophenyl. In some embodiments, the group which is not H is optionally substituted phenyl. If the phenyl optional substituent is halo, it is preferably fluoro. In some embodiment, the phenyl group is unsubstituted.

When $R^{12}$ is

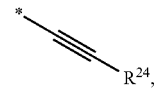

$R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo methyl, methoxy; pyridyl; and thiophenyl. If the phenyl optional substituent is halo, it is preferably fluoro. In some embodiment, the phenyl group is unsubstituted.

In some embodiments, $R^{24}$ is selected from H, methyl, ethyl, ethenyl and ethynyl. In some of these embodiments, $R^{24}$ is selected from H and methyl.

When there is a single bond present between C2' and C3', $R^{12}$ is

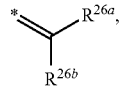

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester.

In some embodiments, it is preferred that $R^{26a}$ and $R^{26b}$ are both H.

In other embodiments, it is preferred that $R^{26a}$ and $R^{26b}$ are both methyl.

In further embodiments, it is preferred that one of $R^{26a}$ and $R^{26b}$ is H, and the other is selected from $C_{1-4}$ saturated alkyl, $C_{2-3}$ alkenyl, which alkyl and alkenyl groups are optionally substituted. In these further embodiment, it may be further preferred that the group which is not H is selected from methyl and ethyl.

$R^2$

The above preferences for $R^{12}$ apply equally to $R^2$.

$R^{22}$

In some embodiments, $R^{22}$ is of formula IIa.

A in $R^{22}$ when it is of formula IIa may be phenyl group or a $C_{5-7}$ heteroaryl group, for example furanyl, thiophenyl and pyridyl. In some embodiments, A is preferably phenyl.

$Q^2$-X may be on any of the available ring atoms of the $C_{5-7}$ aryl group, but is preferably on a ring atom that is not adjacent the bond to the remainder of the compound, i.e. it is preferably β or γ to the bond to the remainder of the compound. Therefore, where the $C_{5-7}$ aryl group (A) is phenyl, the substituent ($Q^2$-X) is preferably in the meta- or para-positions, and more preferably is in the para-position.

In some embodiments, $Q^1$ is a single bond. In these embodiments, $Q^2$ is selected from a single bond and —Z—$(CH_2)_n$—, where Z is selected from a single bond, O, S and NH and is from 1 to 3. In some of these embodiments, $Q^2$ is a single bond. In other embodiments, $Q^2$ is —Z—$(CH_2)_n$—. In these embodiments, Z may be O or S and n may be 1 or n may be 2. In other of these embodiments, Z may be a single bond and n may be 1.

In other embodiments, $Q^1$ is —CH=CH—.

In other embodiments, $R^{22}$ is of formula IIb. In these embodiments, $R^{C1}$, $R^{C2}$ and $R^{C3}$ are independently selected from H and unsubstituted $C_{1-2}$ alkyl. In some preferred embodiments, $R^{C1}$, $R^{C2}$ and $R^{C3}$ are all H. In other embodiments, $R^{C1}$, $R^{C2}$ and $R^{C3}$ are all methyl. In certain embodiments, $R^{C1}$, $R^{C2}$ and $R^{C3}$ are independently selected from H and methyl.

X is a group selected from the list comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

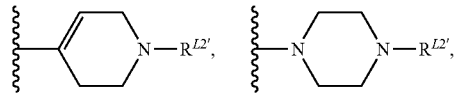

$NR^N R^{L2'}$, wherein $R^N$ is selected from the group comprising H and $C_{1-4}$ alkyl. X may preferably be: OH, SH, $CO_2$H, —N=C=O or $NHR^N$, and may more preferably be: O—$R^{L2'}$, S—$R^{L2'}$, $CO_2$—$R^{L2'}$, —NH—C(=O)—$R^{L2'}$ or NH—$R^{L2'}$. Particularly preferred groups include: O—$R^{L2'}$, S—$R^{L2'}$ and NH—$R^{L2'}$, with NH—$R^{L2'}$ being the most preferred group.

In some embodiments $R^{22}$ is of formula IIc. In these embodiments, it is preferred that Q is $NR^N$—$R^{L2'}$. In other embodiments, Q is O—$R^{L2'}$. In further embodiments, Q is S—$R^{L2'}$. $R^N$ is preferably selected from H and methyl. In some embodiment, $R^N$ is H. In other embodiments, $R^N$ is methyl.

In some embodiments, $R^{22}$ may be -A-$CH_2$—X and -A-X. In these embodiments, X may be O—$R^{L2'}$, S—$R^{L2'}$, $CO_2$—$R^{L2'}$, CO—$R^{L2'}$ and NH—$R^{L2'}$. In particularly preferred embodiments, X may be NH—$R^{L2'}$.

$R^{10}$, $R^{11}$

In some embodiments, $R^{10}$ and $R^{11}$ together form a double bond between the nitrogen and carbon atoms to which they are bound.

In some embodiments, $R^{11}$ is OH.

In some embodiments, $R^{11}$ is OMe.

In some embodiments, $R^{11}$ is $SO_zM$, where z is 2 or 3 and M is a monovalent pharmaceutically acceptable cation.

$R^{11a}$

In some embodiments, $R^{11a}$ is OH.

In some embodiments, $R^{11a}$ is OMe.

In some embodiments, $R^{11a}$ is $SO_zM$, where z is 2 or 3 and M is a monovalent pharmaceutically acceptable cation.

$R^{20}$, $R^{21}$

In some embodiments, $R^{20}$ and $R^{21}$ together form a double bond between the nitrogen and carbon atoms to which they are bound.

In some embodiments $R^{20}$ is H.

In some embodiments, $R^{20}$ is $R^C$.

In some embodiments, $R^{21}$ is OH.

In some embodiments, $R^{21}$ is OMe.

In some embodiments, $R^{21}$ is $SO_zM$, where z is 2 or 3 and M is a monovalent pharmaceutically acceptable cation.

$R^{30}$, $R^{31}$

In some embodiments, $R^{30}$ and $R^{31}$ together form a double bond between the nitrogen and carbon atoms to which they are bound.

In some embodiments, $R^{31}$ is OH.

In some embodiments, $R^{31}$ is OMe.

In some embodiments, $R^{31}$ is $SO_zM$, where z is 2 or 3 and M is a monovalent pharmaceutically acceptable cation.

M and z

It is preferred that M is a monovalent pharmaceutically acceptable cation, and is more preferably $N^+$.

z is preferably 3.

Preferred conjugates of the first aspect of the present disclosure may have a $D^L$ of formula Ia:

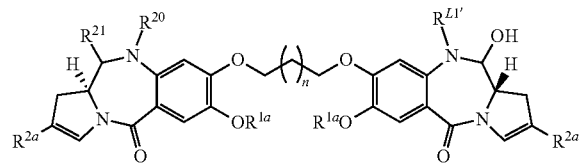

Ia where $R^{L1'}$, $R^{20}$ and $R^{21}$ are as defined above;

n is 1 or 3;

$R^{1a}$ is methyl or phenyl; and $R^{2a}$ is selected from:

(a)

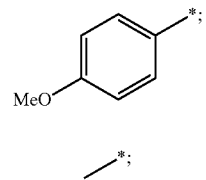

(b)

/*;

(c) 

(d) 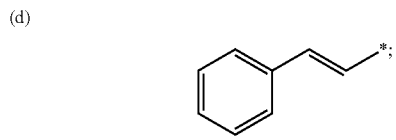

(e) 

(f) 

(g) 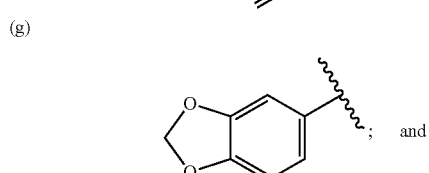 and (h) 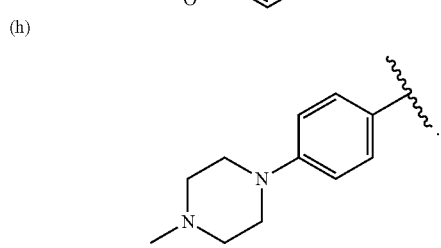

Preferred conjugates of the first aspect of the present disclosure may have a $D^L$ of formula Ib:

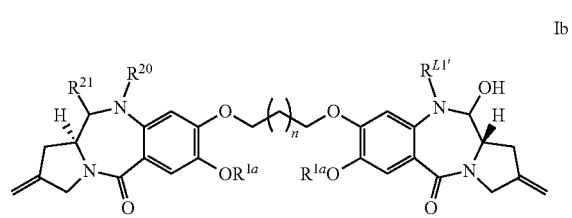

where
$R^{L1'}$, $R^{20}$ and $R^{21}$ are as defined above;
n is 1 or 3; and
$R^{1a}$ is methyl or phenyl.

Preferred conjugates of the first aspect of the present disclosure may have a $D^L$ of formula Ic:

where $R^{L2'}$, $R^{10}$, $R^{11}$, $R^{30}$ and $R^{31}$ are as defined above
n is 1 or 3;
$R^{12a}$ is selected from:

(a) 

(b) 

(c) 

(d) 

(e) 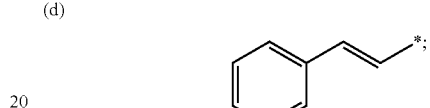

(f) 

(g)  and (h) 

the amino group is at either the meta or para positions of the phenyl group.

Preferred conjugates of the first aspect of the present disclosure may have a $D^L$ of formula Id:

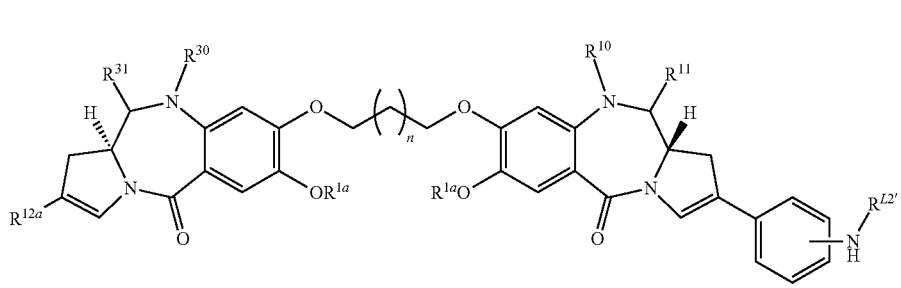

Id
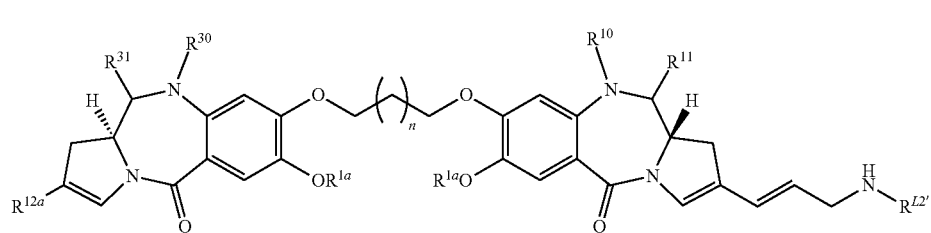
where $R^{L2'}$, $R^{10}$, $R^{11}$, $R^{30}$ and $R^{31}$ are as defined above
n is 1 or 3;
$R^{1a}$ is methyl or phenyl;
$R^{12a}$ is selected from:
(a)
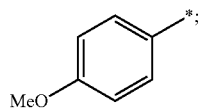
(b)
-continued
(h)
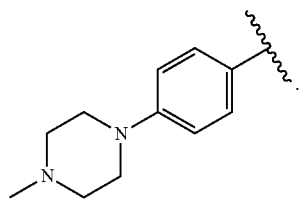
Preferred conjugates of the first aspect of the present disclosure may have a $D^L$ of formula Ie:
Ie
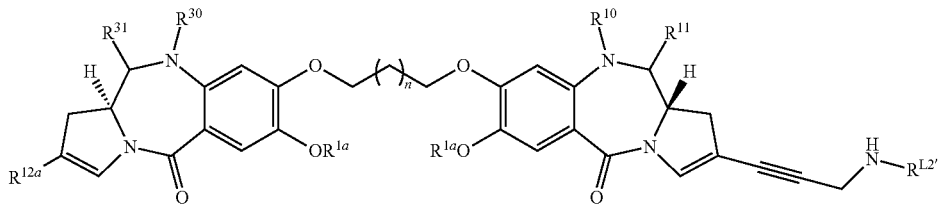
where $R^{L2'}$, $R^{10}$, $R^{11}$, $R^{30}$ and $R^{31}$ are as defined above
n is 1 or 3;
$R^{1a}$ is methyl or phenyl;
$R^{12a}$ is selected from:
(a)
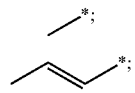
(b)
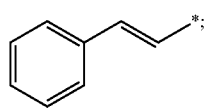
(c)
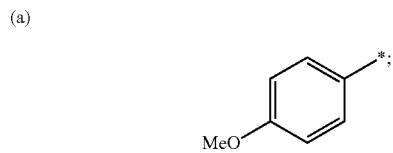
(c)
(d)
(e)
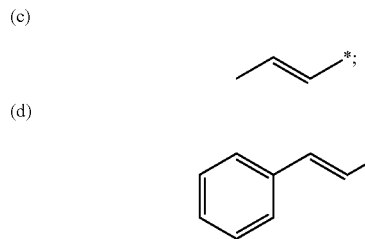
(f)
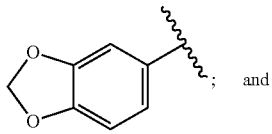
(g)
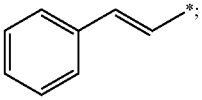
and (e)

(f)

(g)

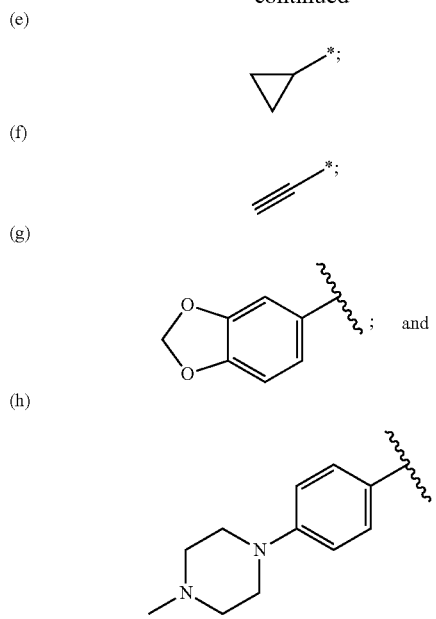

and (h)

MATERIALS AND METHODS

Figure 1:
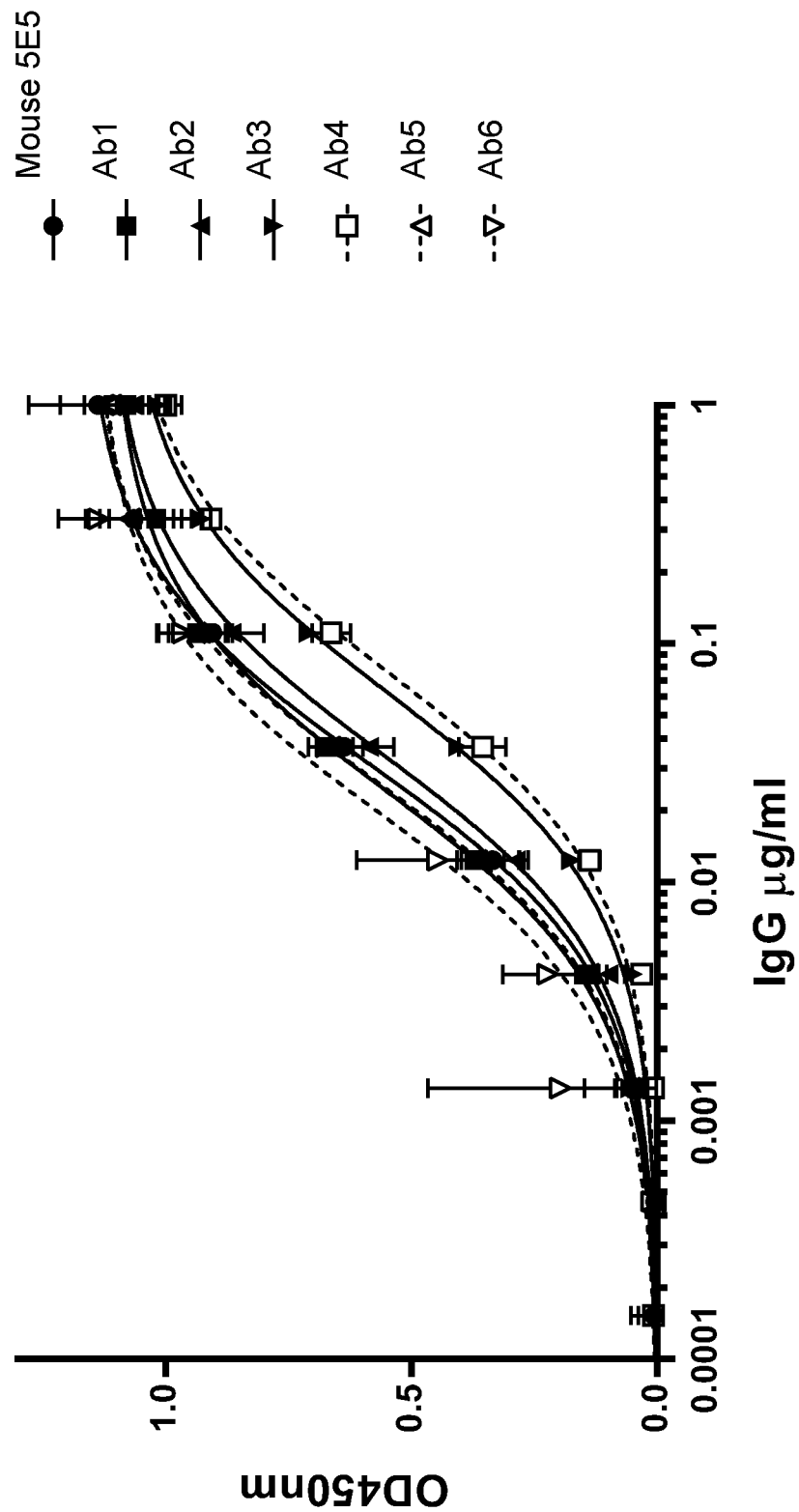
FIG. 1: Tn-MUC1 binding of final humanised versions Ab1, Ab2, Ab3, Ab4, Ab5, and Ab6.

Protocol 1: Subcloning from GeneArt Vector into Expression Vectors
Materials
  Restriction enzymes (New England Biolabs): AgeI (#R0552); BsiWI (#R0553); EcoRI: (#R0101); NheI: (#R0131)
  QIAprep Spin Miniprep Kit (Qiagen#27104 or 27105)
  QIAquick Gel Extraction (Qiagen#28704)
  Antarctic Phosphatase (NEB#M0289S)
  pFUSE2-CLIg-hk vector (Invivogen #pfuse2-hclk)
  pFUSE-CHIg-hG1 (Invivogen #pfuse-hchg1)
  Zeocin 100 mg/ml (Invivogen #ant-zn-1)
  Blasticidin 10 mg/ml (Invivogen #ant-bl-1)
  5-alpha Competent E. coli (High Efficiency) (New England Biolabs #C29871)
  LigaFast™ Rapid DNA Ligation System (Promega #M8221)
  Agarose-LE0020 (Life Technologies #AM9040)
  TAE buffer
  Fushk-fwd; CTT TGC CTG ACC CTG CTT GC
  FushG1-bak; TCA CCG GTT CGG GGA AGT AG
  Fushk-bak: TCA GCA GGC ACA CAA CAG AGG
  Pfuse3'bak: TTC CAT ACC ACA TTT GTA GAG GT Method
1) 5 μg of each GeneArt construct and each pfuse vector were restriction-digested in 10 μl:
   a) Light chain construct and vector pFUSE2-CHIg-hk were digested with AgeI+BsiW1 in NEB buffer 1, incubating 1 hr at 37 C followed by 1 hr at 55 C.
   b) Heavy chain construct and vector pFUSE-CHIg-hG1 were digested with ECoRI+NheI in NEB buffer 1, incubating 1 hr at 37 C.
2) Digested heavy and light chain vectors were dephosphorylated using Antarctic Phosphatase:
   a) Add 1/10 volume of 10× Antarctic Phosphatase Reaction Buffer.
   b) Add 1 μl of Antarctic Phosphatase (NEB, 5,000 units/ml) and mix.
   c) Incubate for 15 minutes at 37° C.
   d) Heat inactivate for 5 minutes at 65° C.
3) Cut vectors were purified by electrophoresis in agarose gel (1.5% w/v in TAE buffer)
4) Cut inserts were purified in agarose gel (1.0% w/v in TAE buffer).
5) Gel fragments containing DNA were solubilised and the DNA extracted using the QIAquick Gel Extraction kit following manufacturer's instructions.
6) Cut insert and complementary cut vector were ligated with T4 DNA Ligase for 1 hr at room temperature, following the manufacturer's instructions and using a 1:2 molar ratio of vector:insert DNA.
7) Competent E. coli were transformed with the ligation mix according to the manufacturer's instructions: 42 C heat shock; add SOC 1 nl and shake 1 hr 37 C, then and spread on warmed selection LB agar plates:
   a) For heavy chain constructs, Zeocin 25 μg/ml
   b) For light chain constructs, Blasticidin 100 μg/ml
8) Plates were incubated overnight at 37 C, then colonies (3) were picked from each plate and inoculated into 3 ml LB containing Zeocin 25 μg/ml or Blasticidin 50 μg/ml, and shaken overnight
9) DNA plasmids were isolated from each culture using the QIAprep Spin Miniprep Kit following the manufacturer's instructions
10) Heavy or light chain construct plasmids (10 μl) were restriction digested as before, and electrophoresed on agarose gel (1.5% w/v in TAE buffer).
11) Those plasmids producing an approx 450 bp fragment were validated by DNA sequencing using primers Fushk-fwd (for VH and VL); FushG1-bak (for VH); Fushk-bak (for VL)

Protocol 2. Transient Transfection of HEK293T Cells with Expression Constructs
Materials
  Cells: HEK293T cells
  Culture medium: DMEM high glucose 4.5 g/L (PAA) with 10% v/v FCS, penicillin and streptomycin
  Fugene HD transfection reagent (Promega # E2311)
  Opti-MEM (Life Technologies #11058-021) or
  FreeStyle 293 Expression Medium (Life Technologies #12338-018)
Method
  Grow HEK293T cells in a T75 or T175 flask in a CO$_2$-gassed cell culture incubator. Split cultures 1:3 every 2 days or 1:4 to 1:5 every 3-4 days. The cells adhere weakly to the flasks and only a light trypsinisation is necessary to detach cells during passaging.
  The day before transfection:
  1. Trypsinise the cells, wash 1× in DMEM/10% FCS and count the cells.

2. Seed cells in a 6 well plate in 2 ml per well containing $2\times10^5$ cells.

Next day, check cells are at least 80% confluent and replace the medium (2 ml/well).

1. 1.2 µg of total DNA (0.6 ug of each high and light chain DNA) is needed for each transfection and better results are obtained if the DNA concentration is at or above 90 ng/µl.
2. Add 0.6 ug of VH and 0.6 ug VK expression plasmid DNAs into of Fugene HD (4.5 µl) and OptiMEM/ Freestyle medium, in a total volume of 60 ul, avoiding touching the sides of the tube with the Fugene HD.
3. Mix and leave at RT for 15 minutes.
4. Add Fugene mixture drop-wise around the well of HEK293T cells.
5. Return the 6-well plate to the $CO_2$-gassed cell culture incubator for 4 days.
6. Harvest each conditioned medium, centrifuge, and store at 4° C.

Protocol 3: IgG Quantitation by ELISA
Materials
   Nunc-Immuno Plate MaxiSorp (Life Technologies, 43945A)
   Goat Anti-Human IgG(Fc)-AffiniPure: Stratech Scientific, 109-005-098-JIR; 1 mg: 1.3 mg/ml;
   Human IgG1/kappa antibody (Sigma, 1-3889-1 mg: 1 mg/ml)
   Goat anti-human kappa light chain peroxidase conjugate (Sigma, A-7164-1 ml)
   1-Step Turbo TMB-ELISA, 250 mL (Thermo Scientific: #34022)
   Acid stop=0.6M HCL
   Sample enzyme conjugate (SEC) buffer Tween 20 (0.02% v/v), BSA 0.2% (w/v) in PBS
   Washing buffer: 1×PBS, Tween 20 (0.1% v/v)
Method
1. Coat each well of a 96-well immunoplate with 100 µl aliquots of goat anti-human IgG antibody, (0.4 µg/ml in PBS: dilute stock ×3000),
2. Incubate overnight at 4° C. (Plates may be stored for 1 month at this stage).
3. Wash coated plate 3× with PBS
4. Block the anti-Ig-coated plate: add 200 ul BSA (3% in PBS):
5. Incubate 37 C 1 hr
6. Prepare 1 ug/ml solution of the human IgG1/kappa antibody in SEC buffer (×1000 diln)
7. Into a polypropylene (low binding) plate, dispense 200 µl SEC buffer into all wells excepting cols 1 & 7—dispense 300 ul SEC buffer.
8. Into this polypropylene plate, pipette 50 µl/well of IgG std (1 ug/ml) and 2 ul/well of unknowns into rows A-H, cols 1 & 7
9. Serially transfer 100 µl across plate to achieve serial ×3 dilutions.
10. Transfer 100 ul from each well of polypropylene plate to the corresponding well of the blocked anti-IgG-coated plate.
11. Incubate at 37° C. for 1 hr.
12. Wash plate 3× with washing buffer.
13. Add 100 µl/well of goat anti-human kappa chain HRP conjugate (×1000 in SEC buffer).
14. Incubate at 37° C. for 1 hr.
15. Wash plate 3× with washing buffer
16. Wash plate 2× with PBS
17. Add 100 µl of TMB Turbo substrate to each well,
18. Incubate at room temp, 30 min.
19. Stop reaction by adding 100 µl of acid stop to each well.
20. Read the optical density at 450 nm (colour stable overnight at 4 C if you cannot read immediately).
21. Std curve plot in Excel: fit using polynomial to calculate unknowns Protocol 4: Tn-MUC1 Binding ELISA
Materials
   16TR-MUC1-Tn (Tn-MUC1) was from Guys Hospital and stored in aliquots at −20 C.
   Goat anti-human kappa light chain peroxidase conjugate (Sigma, A-7164-1 ml)
   Nunc-Immuno Plate MaxiSorp (Life Technologies, 43945A)
   Plate washer: Biotek LS405
   3% BSA: BSA 3% w/v in PBS
   PBS Tween: Tween 20 0.05% v/v in PBS
   PBS/Tween/BSA: BSA 0.5% w/v in PBS/Tween
   1-Step Turbo TMB-ELISA (Thermo Scientific #3402)
Protocol
1. Dispense 50 µl/well of 16TR-MUC1-Tn (2 ug/ml in PBS)
2. Cover with adhesive plate sealer and incubate at 4 C overnight.
3. Block: Dispense 50 µl/well of 3% BSA and incubate for 1 hr 37 C,
4. Wash plate with PBS/Tween 3×
5. Serially 3-fold dilute 5E5 antibodies (2 ml HEK293T culture supernatants) on non-binding polypropylene plate in PBS/Tween/BSA: serially transfer 50 ul onto 100 ul.
6. Transfer 50 ul from antibody dilution plate onto washed, blocked Tn-MUC1-coated plate
7. Incubate 37 C 1 hr
8. Wash plate with PBS/Tween 3×
9. Dispense anti-human IgG-HRP conjugate, diluted 1:1000 in PBS/Tween/BSA
10. Incubate 37 C 1 hr
11. Wash plate with PBS/Tween 3
12. Wash plate with PBS 3×
13. Dispense 100 ul/well 1-Step Turbo TMB-ELISA substrate solution
14. Incubate 30 min at room temperature (or less if reaction is rapid)
15. Dispense 100 ul/well 0.6M HCl to stop the substrate reaction
16. Measure optical density at 450 nm Protocol 5: Thermal Denaturation Assay
Materials
   Purified antibody or unpurified HEK293T transient transfection conditioned medium containing antibody
   PBS
   0.5 ml PCR tubes
   PCR machine
   Antigen-binding ELISA protocol and materials
   Antigen-coated ELISA plate
Method
1. Dispense 0.2 ml of recombinant antibody at or near EC50 i.e. 0.05 ug/ml diluted in HEK293F medium) in 8×PCR tubes
2. Take each tube individually and run in its individual 2-step PCR cycle (Table 1 below)—use a PCR machine with the unheated lid option selected
3. Hold at 4 C until the ELISA assay, to be run on the same day.
4. Apply each sample to 2 wells of a (BSA−) blocked antigen-coated ELISA plate at 50 ul/well 5. Run the antigen-binding ELISA
6. Plot OD$_{450}$ nm vs temperature of heating
7. Compare the 50% inactivation temperature of each antibody

| PCR heating programs: | | |
|---|---|---|
| Tube number | 10 minutes at | Hold at |
| 1 | 4 | 4 |
| 2 | 50 | 4 |
| 3 | 55 | 4 |
| 4 | 60 | 4 |
| 5 | 65 | 4 |
| 6 | 70 | 4 |
| 7 | 75 | 4 |
| 8 | 80 | 4 |

Protocol 6: ZR-75-1 Cell Binding Assay by Flow Cytometry
Materials
  Wash solution: PBS 0.1% (w/v) sodium azide
  Binding buffer: PBS, 10% normal goat serum, 0.1% (w/v) sodium azide)
  96 well U-well microplate
Protocol Exponentially growing cells are suspended by incubation with cell dissociation buffer enzyme-free, Hanks-based (Gibco 13150-016) following the manufacturer's instructions. A cell count/viability is done on a dilution of 10 ul cells+Trypan Blue, 10 ul, with a haemocytomer. The suspension is centrifuged and the cell pellet re-suspended in binding buffer at 3×10^6 per ml. If significant levels of aggregates are present in the cell count, the suspension is filtered to remove aggregates. The cell suspension is dispensed (50 ul/well) in 96 well U-bottom plates and cooled on ice for 10 minutes. Primary antibody (50 ul/well) diluted in binding buffer (typically 1 ug per ml or less) is added to each well and incubated at 4° C. for 1 hour. The microplate is centrifuged 5 min at 300-400 g at 4° C., flicked to remove the supernatant and then the cell pellet re-suspended in 200 uL of wash buffer (PBS, 0.1% sodium azide). Centrifugation and re-suspension are done 4 times in all. After the last centrifugation, cells are re-suspended in 50 uL of binding buffer containing the biotin labelled conjugate 1:250 (kept at −20 C: Biotin-SP-AffiniPure F(ab')2 Fragment Goat antihuman IgG (H+L); Jackson 109-066-088). Cells are incubated for 1 hour at 4 C, then washed 4 times as before. Cells are resuspended in 50 ul of binding buffer containing Streptavidin, Alexa Fluor® 488 conjugate (Life Technologies s11223) diluted 1:250 and Fixable Viability Dye eFluor® 780 (eBioscience 65-0865) diluted 1:2000, The cells are incubated at 4° C. for 1 hour and then washed 3 times, as above. Cells are then re-suspended in PBS if reading immediately or fixed in 100 ul of paraformaldehyde (2% (w/v) in PBS) and analysed with by flow cytometer (Accuri C6), gating on live cells which have a lower Fixable Viability Dye MFI compared to dead cells.

Protocol 7: HEK293F Shake Culture

FreeStyle™ 293-F cells were cultured according to the Life Technologies protocol (in 400 ml to 10^6 cells/ml. FreeStyle™ 293 Expression Medium (40 ml) was added to a 50 ml tube followed by 133 g of VH plasmid DNA and 160 g of VH plasmid DNA together with DNA plasmids to enhance expression such as pAdvantage, p21, SV40LT and p27. The total DNA added was 467 µg. The solution was mixed twice by inversion and 800 µl of a 1 mg/ml linear PEI solution was added dropwise. The transfection solution was vortexed briefly and incubated at room temperature for 10 minutes. The transfection solution was then added dropwise directly to the cell culture whilst swirling the flask gently. The culture was then returned to shaken incubation conditions. Antibiotic was added after 8 hours. Medium was harvested after about 14 days.

General Experimental Methods

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS (b=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, $F_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS Conditions:
Method 1 (Default Method, Used Unless Stated Otherwise)

The HPLC (Waters Alliance 2695) was run using a mobile phase of water (A) (formic acid 0.1%) and acetonitrile (B) (formic acid 0.1%). Gradient: initial composition 5% B held over 1.0 min, then increase from 5% B to 95% B over a 3 min period. The composition was held for 0.1 min at 95% B, then returned to 5% B in 0.03 minutes and hold there for 0.87 min. Total gradient run time equals 5 minutes.

Method 2

The HPLC (Waters Alliance 2695) was run using a mobile phase of water (A) (formic acid 0.1%) and acetonitrile (B) (formic acid 0.1%). Gradient: initial composition 5% B held over 1.0 minute, then increase from 5% B to 95% B over a 2.5 minute period. The composition was held for 0.5 minutes at 95% B, then returned to 5% B in 0.1 minutes and hold there for 0.9 min. Total gradient run time equals 5 minutes.

For Both Methods

Flow rate 3.0 mL/min, 400 µL was split via a zero dead volume tee piece which passes into the mass spectrometer. Wavelength detection range: 220 to 400 nm. Function type: diode array (535 scans). Column: Phenomenex Onyx Monolithic C18 50×4.60 mm.

The reverse phase flash purification conditions were as follows: The Flash purification system (Varian 971-Fp) was run using a mobile phase of water (A) and acetonitrile (B). Gradient: initial composition 5% B over 20 C.V. (Column Volume) then 5% B to 70% B within 60 C.V. The composition was held for 15 C.V. at 95% B, and then returned to 5% B in 5 C.V. and held at 5% B for 10 C.V. Total gradient run time equals 120 C.V. Flow rate 6.0 mL/min. Wavelength detection range: 254 nm. Column: Agilent AX1372-1 SF10-5.5gC8.

Preparative HPLC: Reverse-phase ultra-high-performance liquid chromatography (UPLC) was carried out on Phenomenex Gemini NX 5μ C-18 columns of the following dimensions: 150×4.6 mm for analysis, and 150×21.20 mm for preparative work. All UPLC experiments were performed with gradient conditions. Eluents used were solvent A ($H_2O$ with 0.1% Formic acid) and solvent B ($CH_3CN$ with 0.1% Formic acid). Flow rates used were 1.0 ml/min for analytical, and 20.0 ml/min for preparative HPLC. Detection was at 254 and 280 nm.

Synthesis of Intermediate 12

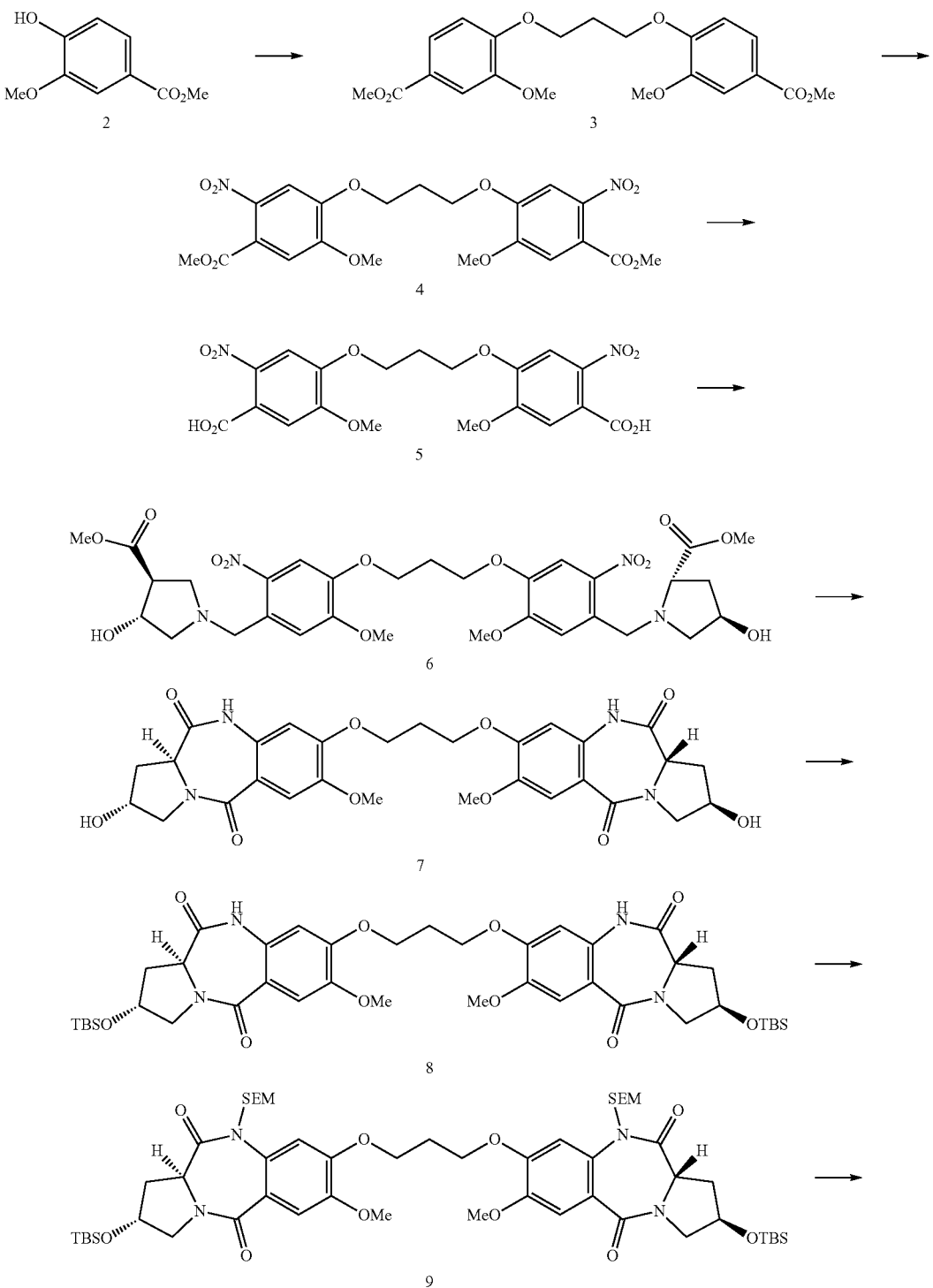

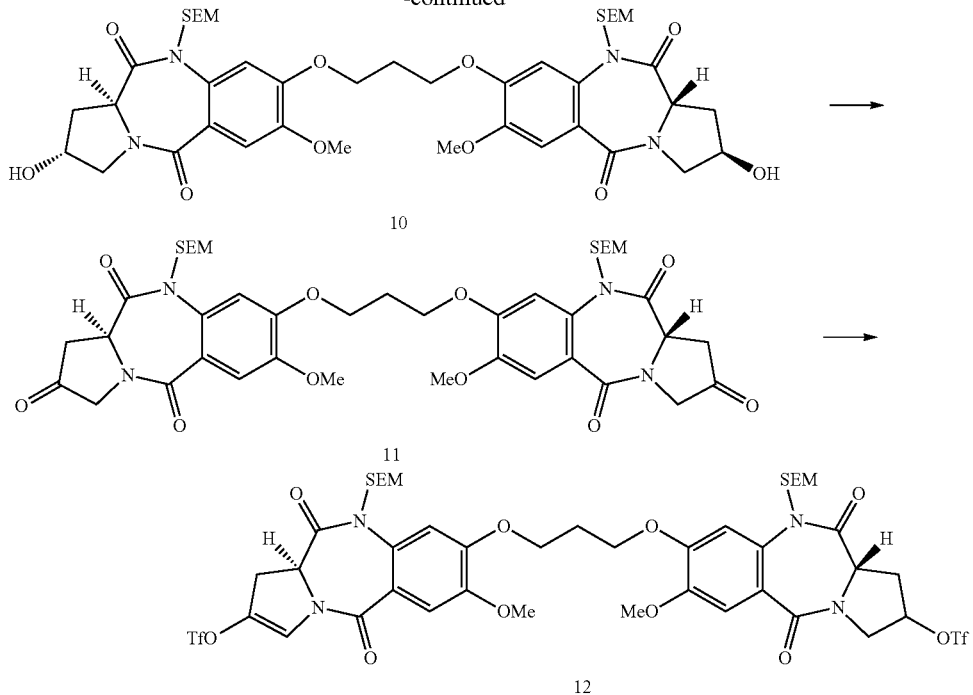

10

11

12

(a) 1',3'-Bis[2-methoxy-4-(methoxycarbonyl)phenoxy]propane (3)

Diisopropyl azodicarboxylate (71.3 mL, 73.2 g, 362 mmol) was added drop-wise over a period of 60 min to an overhead stirred solution of methyl vanillate 2 (60.0 g, 329 mmol) and $Ph_3P$ (129.4 g, 494 mmol) in anhydrous THF (800 mL) at 0-5° C. (ice/acetone) under a nitrogen atmosphere. The reaction mixture was allowed to stir at 0-5° C. for an additional 1 hour after which time a solution of 1,3-propanediol (11.4 mL, 12.0 g, 158 mmol) in THF (12 mL) was added drop-wise over a period of 20 min. The reaction mixture was allowed to warm to room temperature and stirred for 5 days. The resulting white precipitate 3 was collected by vacuum filtration, washed with THF and dried in a vacuum desiccator to constant weight. Yield=54.7 g (84% based on 1,3-propanediol). Purity satisfactory by LC/MS (3.20 min (ES+) m/z (relative intensity) 427 ([M+Na]$^+$., 10); $^1$H NMR (400 MHz, $CDCl_3$) δ 7.64 (dd, 2H, J=1.8, 8.3 Hz), 7.54 (d, 2H, J=1.8 Hz), 6.93 (d, 2H, J=8.5 Hz), 4.30 (t, 4H, J=6.1 Hz), 3.90 (s, 6H), 3.89 (s, 6H), 2.40 (p, 2H, J=6.0 Hz).

(b) 1',3'-Bis[2-methoxy-4-(methoxycarbonyl)-5-nitrophenoxy]propane (4)

Solid $Cu(NO_3)_2 \cdot 3H_2O$ (81.5 g, 337.5 mmol) was added slowly to an overhead stirred slurry of the bis-ester 3 (54.7 g, 135 mmol) in acetic anhydride (650 mL) at 0-5° C. (ice/acetone). The reaction mixture was allowed to stir for 1 hour at 0-5° C. and then allowed to warm to room temperature. A mild exotherm (ca. 40-50° C.), accompanied by thickening of the mixture and evolution of $NO_2$ was observed at this stage. Additional acetic anhydride (300 mL) was added and the reaction mixture was allowed to stir for 16 hours at room temperature. The reaction mixture was poured on to ice (~1.5 L), stirred and allowed to return to room temperature. The resulting yellow precipitate was collected by vacuum filtration and dried in a desiccator to afford the desired bis-nitro compound 4 as a yellow solid. Yield=66.7 g (100%). Purity satisfactory by LC/MS (3.25 min (ES+) m/z (relative intensity) 517 ([M+Na]$^+$., 40); $^1$H NMR (400 MHz, $CDCl_3$) δ 7.49 (s, 2H), 7.06 (s, 2H), 4.32 (t, 4H, J=6.0 Hz), 3.95 (s, 6H), 3.90 (s, 6H), 2.45-2.40 (m, 2H).

(c) 1',3'-Bis(4-carboxy-2-methoxy-5-nitrophenoxy)propane (5)

A slurry of the methyl ester 4 (66.7 g, 135 mmol) in THF (700 mL) was treated with 1N NaOH (700 mL) and the reaction mixture was allowed to stir vigorously at room temperature. After 4 days stirring, the slurry became a dark coloured solution which was subjected to rotary evaporation under reduced pressure to remove THF. The resulting aqueous residue was acidified to pH 1 with concentrated HCl and the colourless precipitate 5 was collected and dried thoroughly in a vacuum oven (50° C.). Yield=54.5 g (87%). Purity satisfactory by LC/MS (2.65 min (ES+) m/z (relative intensity) 489 ([M+Na]$^+$., 30)); $^1$H NMR (400 MHz, DMSO-$d_6$) δ 7.62 (s, 2H), 7.30 (s, 2H), 4.29 (t, 4H, J=6.0 Hz), 3.85 (s, 6H), 2.30-2.26 (m, 2H).

(d) 1,1'-[[(Propane-1,3-diyl)dioxy]bis[(5-methoxy-2-nitro-1,4-phenylene)carbonyl]]bis[(2S,4R)-methyl-4-hydroxypyrrolidine-2-carboxylate] (6)

Oxalyl chloride (24.5 mL, 35.6 g, 281 mmol) was added to a stirred suspension of the nitrobenzoic acid 5 (43 g, 92.3 mmol) and DMF (6 mL) in anhydrous DCM (600 mL). Following initial effervescence the reaction suspension became a solution and the mixture was allowed to stir at room temperature for 16 hours. Conversion to the acid chloride was confirmed by treating a sample of the reaction mixture with MeOH and the resulting bis-methyl ester was observed by LC/MS. The majority of solvent was removed by evaporation under reduced pressure; the resulting concentrated solution was re-dissolved in a minimum amount of dry DCM and triturated with diethyl ether. The resulting yellow precipitate was collected by filtration, washed with cold diethyl ether and dried for 1 hour in a vacuum oven at 40° C. The solid acid chloride was added portionwise over a period of 25 min to a stirred suspension of (2S,4R)-methyl-4-hydroxypyrrolidine-2-carboxylate hydrochloride (38.1 g, 210 mmol) and TEA (64.5 mL, g, 463 mmol) in DCM (400 mL) at −40° C. (dry ice/$CH_3CN$). Immediately, the reaction was complete as judged by LC/MS (2.47 min (ES+) m/z (relative intensity) 721 ([M+H]$^+$., 100). The mixture was diluted with DCM (200 mL) and washed with 1N HCl (300 mL), saturated $NaHCO_3$ (300 mL), brine (400 mL), dried ($MgSO_4$), filtered and the solvent evaporated in vacuo to give the pure product 6 as an orange solid (66.7 g, 100%). [α]$^{22}_D$=−46.1° (c=0.47, $CHCl_3$); $^1$H NMR (400 MHz, $CDCl_3$) (rotamers) δ 7.63 (s, 2H), 6.82 (s, 2H), 4.79-4.72 (m, 2H), 4.49-4.28 (m, 6H), 3.96 (s, 6H), 3.79 (s, 6H), 3.46-3.38 (m, 2H), 3.02 (d, 2H, J=11.1 Hz), 2.48-2.30 (m, 4H), 2.29-2.04 (m, 4H); $^{13}$C NMR (100 MHz, $CDCl_3$) (rotamers) δ 172.4, 166.7, 154.6, 148.4, 137.2, 127.0, 109.7, 108.2, 69.7, 65.1, 57.4, 57.0, 56.7, 52.4, 37.8, 29.0; IR (ATR, $CHCl_3$) 3410 (br), 3010, 2953, 1741, 1622, 1577, 1519, 1455, 1429, 1334, 1274, 1211, 1177, 1072, 1050, 1008, 871 cm$^{-1}$; MS (ES$^+$) m/z (relative intensity) 721 ([M+H]$^+$., 47), 388 (80); HRMS [M+H]$^+$. theoretical $C_{31}H_{36}N_4O_{16}$ m/z 721.2199, found (ES$^+$) m/z 721.2227.

(e) 1,1'-[[(Propane-1,3-diyl)dioxy]bis(11aS,2R)-2-(hydroxy)-7-methoxy-1,2,3,10,11,11a-hexahydro-5H-pyrrolo[2,1-c][1,4]-benzodiazepin-5,11-dione] (7)

Method A:
A solution of the nitro-ester 6 (44 g, 61.1 mmol) in MeOH (2.8 L) was added to freshly purchased Raney® nickel (~50 g of a ~50% slurry in $H_2O$) and anti-bumping granules in a 5 L 3-neck round bottomed flask. The mixture was heated at reflux and then treated dropwise with a solution of hydrazine hydrate (21.6 mL, 22.2 g, 693 mmol) in MeOH (200 mL) at which point vigorous effervescence was observed. When the addition was complete (~45 min) additional Raney® nickel was added carefully until effervescence had ceased and the initial yellow colour of the reaction mixture was discharged. The mixture was heated at reflux for a further 5 min at which point the reaction was deemed complete by TLC (90:10 v/v $CHCl_3$/MeOH) and LC/MS (2.12 min (ES+) m/z (relative intensity) 597 ([M+H]$^+$., 100)). The reaction mixture was filtered hot immediately through a sinter funnel containing celite with vacuum suction. The filtrate was reduced in volume by evaporation in vacuo at which point a colourless precipitate formed which was collected by filtration and dried in a vacuum desiccator to provide 7 (31 g, 85%). [α]$^{27}_D$=+404° (C=0.10, DMF); $^1$H NMR (400 MHz, DMSO-$d_6$) δ 10.2 (s, 2H, NH), 7.26 (s, 2H), 6.73 (s, 2H), 5.11 (d, 2H, J=3.98 Hz, OH), 4.32-4.27 (m, 2H), 4.19-4.07 (m, 6H), 3.78 (s, 6H), 3.62 (dd, 2H, J=12.1, 3.60 Hz), 3.43 (dd, 2H, J=12.0, 4.72 Hz), 2.67-2.57 (m, 2H), 2.26 (p, 2H, J=5.90 Hz), 1.99-1.89 (m, 2H); $^{13}$C NMR (100 MHz, DMSO-$d_6$) δ 169.1, 164.0, 149.9, 144.5, 129.8, 117.1, 111.3, 104.5, 54.8, 54.4, 53.1, 33.5, 27.5; IR (ATR, neat) 3438, 1680, 1654, 1610, 1605, 1516, 1490, 1434, 1379, 1263, 1234, 1216, 1177, 1156, 1115, 1089, 1038, 1018, 952, 870 cm$^{-1}$; MS (ES$^+$) m/z (relative intensity) 619 ([M+Na]$^+$., 10), 597 ([M+H]$^+$., 52), 445 (12), 326 (11); HRMS [M+H]$^+$. theoretical $C_{29}H_{32}N_4O_{10}$ m/z 597.2191, found (ES$^+$) m/z 597.2205.

Method B:
A suspension of 10% Pd/C (7.5 g, 10% w/w) in DMF (40 mL) was added to a solution of the nitro-ester 6 (75 g, 104 mmol) in DMF (360 mL). The suspension was hydrogenated in a Parr hydrogenation apparatus over 8 hours. Progress of the reaction was monitored by LC/MS after the hydrogen uptake had stopped. Solid Pd/C was removed by filtration and the filtrate was concentrated by rotary evaporation under vacuum (below 10 mbar) at 40° C. to afford a dark oil containing traces of DMF and residual charcoal. The residue was digested in EtOH (500 mL) at 40° C. on a water bath (rotary evaporator bath) and the resulting suspension was filtered through celite and washed with ethanol (500 mL) to give a clear filtrate. Hydrazine hydrate (10 mL, 321 mmol) was added to the solution and the reaction mixture was heated at reflux. After 20 minutes the formation of a white precipitate was observed and reflux was allowed to continue for a further 30 minutes. The mixture was allowed to cool down to room temperature and the precipitate was retrieved by filtration, washed with diethyl ether (2:1 volume of precipitate) and dried in a vacuum desiccator to provide 7 (50 g, 81%). Analytical data for method B: Identical to those obtained for Method A (optical rotation, $^1$H NMR, LC/MS and TLC).

(f) 1,1'-[[(Propane-1,3-diyl)dioxy]bis(11aS,2R)-2-(tert-butyldimethylsilyloxy)-7-methoxy-1,2,3,10,11,11a-hexahydro-5H-pyrrolo[2,1-c][1,4]-benzodiazepin-5,11-dione] (8)

TBSCl (27.6 g, 182.9 mmol) and imidazole (29.9 g, 438.8 mmol) were added to a cloudy solution of the tetralactam 7 (21.8 g, 36.6 mmol) in anhydrous DMF (400 mL) at 0° C. (ice/acetone). The mixture was allowed to stir under a nitrogen atmosphere for 3 hours after which time the reaction was deemed complete as judged by LC/MS (3.90 min (ES+) m/z (relative intensity) 825 ([M+H]$^+$., 100). The reaction mixture was poured onto ice (~1.75 L) and allowed to warm to room temperature with stirring. The resulting white precipitate was collected by vacuum filtration, washed with $H_2O$, diethyl ether and dried in the vacuum desicator to provide pure 8 (30.1 g, 99%). [α]$^{23}_D$=+234° (c=0.41, $CHCl_3$); $^1$H NMR (400 MHz, $CDCl_3$) δ 8.65 (s, 2H, NH), 7.44 (s, 2H), 6.54 (s, 2H), 4.50 (p, 2H, J=5.38 Hz), 4.21-4.10 (m, 6H), 3.87 (s, 6H), 3.73-3.63 (m, 4H), 2.85-2.79 (m, 2H), 2.36-2.29 (m, 2H), 2.07-1.99 (m, 2H), 0.86 (s, 18H), 0.08 (s, 12H); $^{13}$C NMR (100 MHz, $CDCl_3$) δ 170.4, 165.7, 151.4, 146.6, 129.7, 118.9, 112.8, 105.3, 69.2, 65.4, 56.3, 55.7, 54.2, 35.2, 28.7, 25.7, 18.0, −4.82 and −4.86; IR (ATR, $CHCl_3$) 3235, 2955, 2926, 2855, 1698, 1695, 1603, 1518, 1491, 1446, 1380, 1356, 1251, 1220, 1120, 1099, 1033 cm$^{-1}$; MS (ES$^+$) m/z (relative intensity) 825 ([M+H]$^+$., 62), 721 (14), 440 (38); HRMS [M+H]$^+$. theoretical $C_{41}H_{60}N_4O_{10}Si_2$ m/z 825.3921, found (ES$^+$) m/z 825.3948.

(g) 1,1'-[[(Propane-1, 3-diyl)dioxy]bis(11aS,2R)-2-(tert-butyldimethylsilyloxy)-7-methoxy-10-((2-(trimethylsilyl)ethoxy)methyl)-1,2,3,10,11,11a-hexahydro-5H-pyrrolo[2,1-c][1,4]-benzodiazepin-5,11-dione] (9)

A solution of n-BuLi (68.3 mL of a 1.6 M solution in hexane, 109 mmol) was added dropwise to a stirred suspension of the tetralactam 8 (30.08 g, 36.4 mmol) in anhydrous THF (600 mL) at −30° C. (dry ice/ethylene glycol) under a nitrogen atmosphere. The reaction mixture was allowed to stir at this temperature for 1 hour (now a reddish orange colour) at which point a solution of SEMCl (19.3 mL, 18.2 g, 109 mmol) in anhydrous THF (120 mL) was added dropwise. The reaction mixture was allowed to slowly warm to room temperature and was stirred for 16 hours under a nitrogen atmosphere. The reaction was deemed complete as judged by TLC (EtOAc) and LC/MS (4.77 min (ES+) m/z (relative intensity) 1085 ([M+H]$^+$., 100). The THF was removed by evaporation in vacuo and the resulting residue dissolved in EtOAc (750 mL), washed with $H_2O$ (250 mL), brine (250 mL), dried ($MgSO_4$) filtered and evaporated in vacuo to provide the crude N10-SEM-protected tetralactam 9 as an oil (max$^m$39.5 g, 100%). Product carried through to next step without purification. $[\alpha]^{23}_D$=+163° (c=0.41, $CHCl_3$); $^1H$ NMR (400 MHz, $CDCl_3$) δ 7.33 (s, 2H), 7.22 (s, 2H), 5.47 (d, 2H, J=9.98 Hz), 4.68 (d, 2H, J=9.99 Hz), 4.57 (p, 2H, J=5.77 Hz), 4.29-4.19 (m, 6H), 3.89 (s, 6H), 3.79-3.51 (m, 8H), 2.87-2.81 (m, 2H), 2.41 (p, 2H, J=5.81 Hz), 2.03-1.90 (m, 2H), 1.02-0.81 (m, 22H), 0.09 (s, 12H), 0.01 (s, 18H); $^{13}C$ NMR (100 MHz, $CDCl_3$) δ 170.0, 165.7, 151.2, 147.5, 133.8, 121.8, 111.6, 106.9, 78.1, 69.6, 67.1, 65.5, 56.6, 56.3, 53.7, 35.6, 30.0, 25.8, 18.4, 18.1, −1.24, −4.73; IR (ATR, $CHCl_3$) 2951, 1685, 1640, 1606, 1517, 1462, 1433, 1360, 1247, 1127, 1065 cm$^{-1}$; MS (ES$^+$) m/z (relative intensity) 1113 ([M+Na]$^+$., 48), 1085 ([M+H]$^+$., 100), 1009 (5), 813 (6); HRMS [M+H]$^+$. theoretical $C_{53}H_{88}N_4O_{12}Si_4$ m/z 1085.5548, found (ES$^+$) m/z 1085.5542.

(h) 1,1'-[[(Propane-1,3-diyl)dioxy]bis(11aS,2R)-2-hydroxy-7-methoxy-10-((2-(trimethylsilyl)ethoxy) methyl)-1,2,3,10,11,11a-hexahydro-5H-pyrrolo[2,1-c][1,4]-benzodiazepin-5,11-dione] (10)

A solution of TBAF (150 mL of a 1.0 M solution in THF, 150 mmol) was added to a stirred solution of the crude bis-silyl ether 9 [84.0 g (max$^m$ 56.8 g), 52.4 mmol] in THF (800 mL) at room temperature. After stirring for 1 hour, analysis of the reaction mixture by TLC (95:5 v/v $CHCl_3$/MeOH) revealed completion of reaction. The THF was removed by evaporation under reduced pressure at room temperature and the resulting residue dissolved in EtOAc (500 mL) and washed with $NH_4Cl$ (300 mL). The combined organic layers were washed with brine (60 mL), dried ($MgSO_4$), filtered and evaporated under reduced pressure to provide the crude product. Purification by flash chromatography (gradient elution: 100% $CHCl_3$ to 96:4 v/v $CHCl_3$/MeOH) gave the pure tetralactam 10 as a white foam (36.0 g, 79%). LC/MS 3.33 min (ES$^+$) m/z (relative intensity) 879 ([M+Na]$^+$., 100), 857 ([M+H]$^+$., 40); $[\alpha]^{23}_D$=+202° (c=0.34, $CHCl_3$); $^1H$ NMR (400 MHz, $CDCl_3$) δ 7.28 (s, 2H), 7.20 (s, 2H), 5.44 (d, 2H, J=10.0 Hz), 4.72 (d, 2H, J=10.0 Hz), 4.61-4.58 (m, 2H), 4.25 (t, 4H, J=5.83 Hz), 4.20-4.16 (m, 2H), 3.91-3.85 (m, 8H), 3.77-3.54 (m, 6H), 3.01 (br s, 2H, OH), 2.96-2.90 (m, 2H), 2.38 (p, 2H, J=5.77 Hz), 2.11-2.05 (m, 2H), 1.00-0.91 (m, 4H), 0.00 (s, 18H); $^{13}C$ NMR (100 MHz, $CDCl_3$) δ 169.5, 165.9, 151.3, 147.4, 133.7, 121.5, 111.6, 106.9, 79.4, 69.3, 67.2, 65.2, 56.5, 56.2, 54.1, 35.2, 29.1, 18.4, −1.23; IR (ATR, $CHCl_3$) 2956, 1684, 1625, 1604, 1518, 1464, 1434, 1361, 1238, 1058, 1021 cm$^{-1}$; MS (ES$^+$) m/z (relative intensity) 885 ([M+29]$^+$., 70), 857 ([M+H]$^+$., 100), 711 (8), 448 (17); HRMS [M+H]$^+$. theoretical $C_{41}H_{60}N_4O_{12}Si_2$ m/z 857.3819, found (ES$^+$) m/z 857.3826.

(i) 1,1'-[[(Propane-1,3-diyl)dioxy]bis(11aS)-7-methoxy-2-oxo-10-((2-(trimethylsilyl)ethoxy) methyl)-1,2,3,10,11,11a-hexahydro-5H-pyrrolo[2,1-c][1,4]-benzodiazepin-5,11-dione] (11)

Diol 10 (25.6 g, 30 mmol, 1 eq.), NaOAc (6.9 g, 84 mmol, 2.8 eq.) and TEMPO (188 mg, 1.2 mmol, 0.04 eq.) were dissolved in DCM (326 mL) under Ar. This was cooled to −8° C. (internal temperature) and TCCA (9.7 g, 42 mmol, 1.4 eq.) was added portionwise over 15 minutes. TLC (EtOAc) and LC/MS [3.60 min. (ES+) m/z (relative intensity) 854.21 ([M+H]$^+$., 40), (ES−) m/z (relative intensity) 887.07 ([M−H+Cl]$^-$., 10)] after 30 minutes indicated that reaction was complete. Cold DCM (200 mL) was added and the mixture was filtered through a pad of Celite before washing with a solution of saturated sodium hydrogen carbonate/sodium thiosulfate (1:1 v/v; 200 mL×2). The organic layer was dried with $MgSO_4$, filtered and the solvent removed in vacuo to yield a yellow/orange sponge (25.4 g, 99%). LC/MS [3.60 min. (ES+) m/z (relative intensity) 854.21 ([M+H]$^+$., 40); $[\alpha]^{20}_D$=+291° (C=0.26, $CHCl_3$); $^1H$ NMR (400 MHz, $CDCl_3$) δ 7.32 (s, 2H), 7.25 (s, 2H), 5.50 (d, 2H, J=10.1 Hz), 4.75 (d, 2H, J=10.1 Hz), 4.60 (dd, 2H, J=9.85, 3.07 Hz), 4.31-4.18 (m, 6H), 3.89-3.84 (m, 8H), 3.78-3.62 (m, 4H), 3.55 (dd, 2H, J=19.2, 2.85 Hz), 2.76 (dd, 2H, J=19.2, 9.90 Hz), 2.42 (p, 2H, J=5.77 Hz), 0.98-0.91 (m, 4H), 0.00 (s, 18H); $^{13}C$ NMR (100 MHz, $CDCl_3$) δ 206.8, 168.8, 165.9, 151.8, 148.0, 133.9, 120.9, 111.6, 107.2, 78.2, 67.3, 65.6, 56.3, 54.9, 52.4, 37.4, 29.0, 18.4, −1.24; IR (ATR, $CHCl_3$) 2957, 1763, 1685, 1644, 1606, 1516, 1457, 1434, 1360, 1247, 1209, 1098, 1066, 1023 cm$^{-1}$; MS (ES$^+$) m/z (relative intensity) 881 ([M+29]$^+$., 38), 853 ([M+H]$^+$., 100), 707 (8), 542 (12); HRMS [M+H]$^+$. theoretical $C_{41}H_{56}N_4O_{12}Si_2$ m/z 853.3506, found (ES$^+$) m/z 853.3502.

(j) 1,1'-[[(Propane-1,3-diyl)dioxy]bis(11aS)-7-methoxy-2-[[(trifluoromethyl)sulfonyl]oxy]-10-((2-(trimethylsilyl)ethoxy)methyl)-1, 10,11,11a-tetrahydro-5H-pyrrolo[2,1-c][1,4]-benzodiazepin-5,11-dione] (12)

Anhydrous 2,6-lutidine (5.15 mL, 4.74 g, 44.2 mmol) was injected in one portion to a vigorously stirred solution of bis-ketone 11 (6.08 g, 7.1 mmol) in dry DCM (180 mL) at −45° C. (dry ice/acetonitrile) under a nitrogen atmosphere. Anhydrous triflic anhydride, taken from a freshly opened ampoule (7.2 mL, 12.08 g, 42.8 mmol), was injected rapidly dropwise, while maintaining the temperature at −40° C. or below. The reaction mixture was allowed to stir at −45° C. for 1 hour at which point TLC (50/50 v/v n-hexane/EtOAc) revealed the complete consumption of starting material. The cold reaction mixture was immediately diluted with DCM (200 mL) and, with vigorous shaking, washed with water (1×100 mL), 5% citric acid solution (1×200 mL) saturated $NaHCO_3$ (200 mL), brine (100 mL) and dried ($MgSO_4$). Filtration and evaporation of the solvent under reduced pressure afforded the crude product which was purified by flash column chromatography (gradient elution: 90:10 v/v n-hexane/EtOAc to 70:30 v/v n-hexane/EtOAc) to afford bis-enol triflate 12 as a yellow foam (5.5 g, 70%). LC/MS 4.32 min (ES+) m/z (relative intensity) 1139 ([M+Na]$^+$., 20); $[\alpha]^{24D}$=+271° (C=0.18, $CHCl_3$); $^1H$ NMR (400 MHz, $CDCl_3$) δ 7.33 (s, 2H), 7.26 (s, 2H), 7.14 (t, 2H, J=1.97 Hz), 5.51 (d, 2H, J=10.1 Hz), 4.76 (d, 2H, J=10.1 Hz), 4.62 (dd, 2H, J=11.0, 3.69 Hz), 4.32-4.23 (m, 4H), 3.94-3.90 (m, 8H), 3.81-3.64 (m, 4H), 3.16 (ddd, 2H, J=16.3, 11.0, 2.36 Hz), 2.43 (p, 2H, J=5.85 Hz), 1.23-0.92 (m, 4H), 0.02 (s, 18H);

$^{13}$C NMR (100 MHz, CDCl$_3$) δ 167.1, 162.7, 151.9, 148.0, 138.4, 133.6, 120.2, 118.8, 111.9, 107.4, 78.6, 67.5, 65.6, 56.7, 56.3, 30.8, 29.0, 18.4, −1.25; IR (ATR, CHCl$_3$) 2958, 1690, 1646, 1605, 1517, 1456, 1428, 1360, 1327, 1207, 1136, 1096, 1060, 1022, 938, 913 cm$^{-1}$; MS (ES$^+$) m/z (relative intensity) 1144 ([M+28]$^+$., 100), 1117 ([M+H]$^+$., 48), 1041 (40), 578 (8); HRMS [M+H]$^+$. theoretical C$_{43}$H$_{54}$N$_4$O$_{16}$Si$_2$S$_2$F$_6$ m/z 1117.2491, found (ES$^+$) m/z 1117.2465.
Example 1
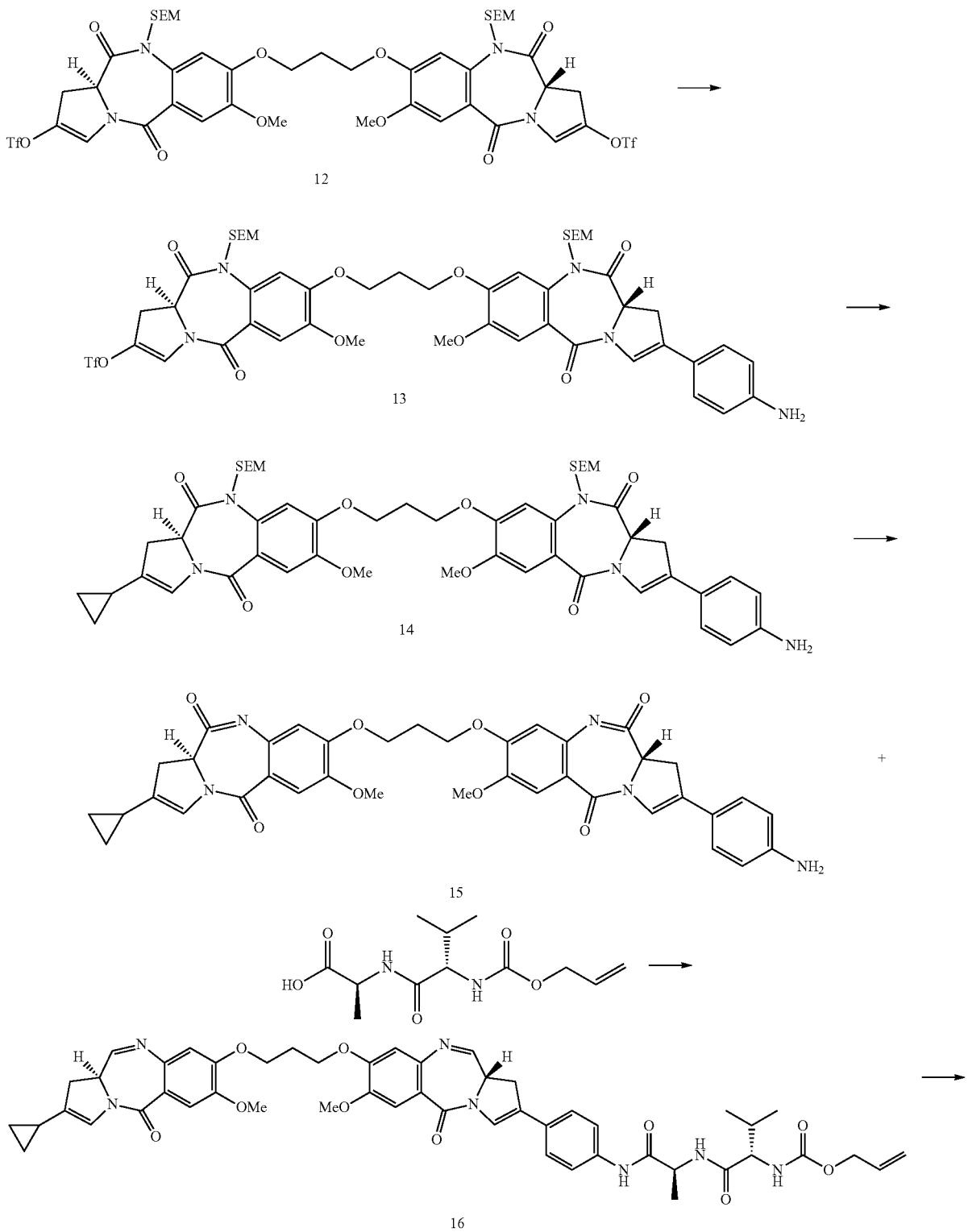

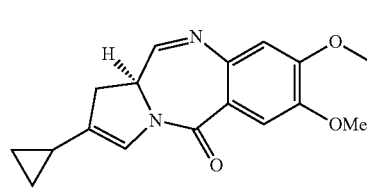
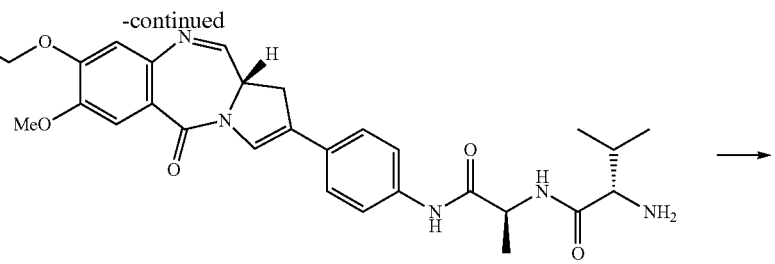

-continued

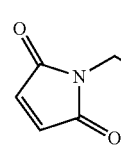

17

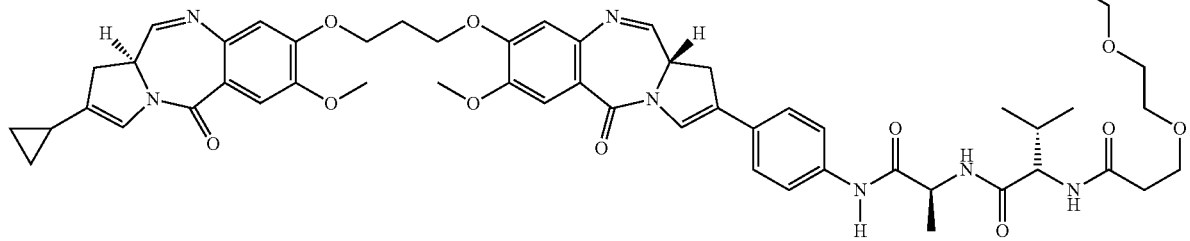

18

(a) (S)-8-(3-(((S)-2-(4-aminophenyl)-7-methoxy-5,11-dioxo-10-((2-(trimethyl)ethoxy)methyl)-5,10,11,11a-tetrahydro-1H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (13)

Pd(PPh$_3$)$_4$ (116.9 mg, 0.101 mmol) was added to a stirred mixture of the bis-enol triflate 12 (5.65 g, 5.06 mmol), 4-Aminophenylboronic acid pinacol ester (1 g, 4.56 mmol), Na$_2$CO$_3$ (2.46 g, 23.2 mmol), MeOH (37 mL), toluene (74 mL) and water (37 mL). The reaction mixture was allowed to stir at 30° C. under a nitrogen atmosphere for 24 hours after which time all the boronic ester has consumed. The reaction mixture was then evaporated to dryness before the residue was taken up in EtOAc (150 mL) and washed with H$_2$O (2×100 mL), brine (150 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 13 as a yellowish foam (2.4 g, 45%). LC/MS 4.02 min (ES+) m/z (relative intensity) 1060.21 ([M+H]$^+$., 100); $^1$H-NMR: (CDCl$_3$, 400 MHz) δ 7.40 (s, 1H), 7.33 (s, 1H), 7.27 (bs, 3H), 7.24 (d, 2H, J=8.5 Hz), 7.15 (t, 1H, J=2.0 Hz), 6.66 (d, 2H, J=8.5 Hz), 5.52 (d, 2H, J=10.0 Hz), 4.77 (d, 1H, J=10.0 Hz), 4.76 (d, 1H, J=10.0 Hz), 4.62 (dd, 1H, J=3.7, 11.0 Hz), 4.58 (dd, 1H, J=3.4, 10.6 Hz), 4.29 (t, 4H, J=5.6 Hz), 4.00-3.85 (m, 8H), 3.80-3.60 (m, 4H), 3.16 (ddd, 1H, J=2.4, 11.0, 16.3 Hz), 3.11 (ddd, 1H, J=2.2, 10.5, 16.1 Hz), 2.43 (p, 2H, J=5.9 Hz), 1.1-0.9 (m, 4H), 0.2 (s, 18H). $^{13}$C-NMR: (CDCl$_3$, 100 MHz) δ 169.8, 168.3, 164.0, 162.7, 153.3, 152.6, 149.28, 149.0, 147.6, 139.6, 134.8, 134.5, 127.9, 127.5, 125.1, 123.21, 121.5, 120.5, 120.1, 116.4, 113.2, 108.7, 79.8, 79.6, 68.7, 68.5, 67.0, 66.8, 58.8, 58.0, 57.6, 32.8, 32.0, 30.3, 19.7, 0.25.

(b) (S)-2-(4-Aminophenyl)-8-(3-(((S)-2-cyclopropyl-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-10-((2-(trimethylsilyl)ethoxy)methyl)-1H-benzo[e]pyrrolo[1,2-a][1,4]diazepine-5,11(10H,11aH)-dione (14)

Triphenylarsine (0.24 g, 0.8 mmol), silver (I) oxide (1.02 g, 4.4 mmol), cyclopropylboronic acid (0.47 g, 5.5 mmol) and starting material 13 (1.15 g, 1.1 mmol) were dissolved in dioxane (30 mL) under an argon atmosphere. Potassium phosphate tribasic (2.8 g, 13.2 mmol) was ground-up with a pestle and mortar and quickly added to the reaction mixture. The reaction mixture was evacuated and flushed with argon 3 times and heated to 71° C. Palladium (11)bis (benzonitrile chloride) (84 mg, 0.22 mmol) was added and the reaction vessel was evacuated and flushed with argon 3 times. After 10 minutes a small sample was taken for analysis by TLC (80:20 v/v ethyl acetate/hexane) and LC/MS. After 30 minutes the reaction had gone to completion (LC/MS analysis indicated complete consumption of starting material) and the reaction was filtered through celite and the filter pad washed with ethyl acetate (400 mL). The filtrate was washed with water (2×200 mL) and brine (2×200 mL). The organic layer was dried with MgSO$_4$, filtered and the solvent removed in vacuo. Purification by silica gel column chromatography (30:70 v/v Hexane/Ethyl acetate) afforded the product 14 as an orangey/yellow solid (0.66 g, 63%). Method 1, LC/MS (3.85 min (ES$^+$) m/z (relative intensity) 952.17 ([M+H]$^+$., 100). $^1$H NMR (400 MHz, CDCl$_3$) δ 7.36 (d, 2H, J=8.4 Hz), 7.30 (s, 1H), 7.25-7.19 (m, 4H), 6.68 (s, 1H), 6.62 (d, 2H, J=8.4 Hz), 5.49 (dd, 2H, J=5.6, 10.0 Hz), 4.73 (app. t, 2H, J=10.8 Hz), 4.54 (dd, 1H, J=3.2, 10.4 Hz), 4.40 (dd, 1H, J=3.2, 10.4 Hz), 4.29-4.23 (m, 4H), 3.91-3.85 (m, 7H), 3.80-3.71 (m, 2H), 3.70-3.61 (m, 2H), 3.38-3.32

(m, 1H), 3.12-3.01 (m, 1H), 2.50-2.69 (m, 1H), 2.40 (q, 2H, J=5.6 Hz), 1.50-1.43 (m, 1H), 0.99-0.71 (m, 6H), 0.54-0.59 (m, 2H), 0.00 (s, 18H) ppm.

(c) (S)-2-(4-Aminophenyl)-8-(3-(((S)-2-cyclopropyl-7-methoxy-5-oxo-5,11a-dihydro-1H-benzo[e]pyrrolo[1,2-a][1,4]diazepin-8-yl)oxy)propoxy)-7-methoxy-1H-benzo[e]pyrrolo[1,2-a][1,4]diazepin-5(11aH)-one (15)

SEM dilactam 14 (0.66 g, 0.69 mmol) was dissolved in THF (23 mL) and cooled to −78° C. under an argon atmosphere. Super-Hydride® solution (1.7 mL, 1 M in THF) was added drop wise over 5 minutes while monitoring the temperature. After 20 minutes a small sample was taken and washed with water for LC/MS analysis. Water (50 mL) was added and the cold bath was removed. The organic layer was extracted and washed with brine (60 mL). The combined aqueous layers were washed with $CH_2Cl_2$/MeOH (90/10 v/v) (2×50 mL). The combined organic layers were dried with $MgSO_4$, filtered and the solvent removed in vacuo. The crude product was dissolved in MeOH (48 mL), $CH_2Cl_2$ (18 mL) and water (6 mL) and sufficient silica gel was added to afford a thick suspension. After 5 days stirring, the suspension was filtered through a sintered funnel and washed with $CH_2Cl_2$/MeOH (9:1) (~200 mL) until product ceased to be eluted. The organic layer was washed with brine (2×70 mL), dried with $MgSO_4$, filtered and the solvent removed in vacuo. Purification by silica gel column chromatography (100% $CHCl_3$ to 96/4 v/v $CHCl_3$/MeOH) afforded the product 15 as a yellow solid (302 mg, 66%). Method 1, LC/MS (2.42 min (ES+) m/z (relative intensity) 660.74 ([M+H]+., 30). $^1$H NMR (400 MHz, $CDCl_3$) δ 7.86 (d, 1H, J=3.6 Hz), 7.78 (d, 1H, J=3.6 Hz), 7.58-7.44 (m, 3H), 7.34-7.20 (m, 3H), 6.88-6.66 (m, 4H), 4.35-4.15 (m, 6H), 3.95-3.75 (m, 7H), 3.39-3.22 (m, 1H), 3.14-3.04 (m, 1H), 2.93-2.85 (m, 1H), 2.46-2.36 (m, 2H), 1.49-1.41 (m, 1H), 0.80-0.72 (m, 2H), 0.58-0.51 (app. s, 2H) ppm.

(d) Allyl ((2S)-1-(((2S)-1-((4-(8-(3-((2-cyclopropyl-7-methoxy-5-oxo-5,11a-dihydro-1H-benzo[e]pyrrolo[1,2-a][1,4]oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)carbamate (16)

In a degassed round bottom flask filled with argon, HO-Ala-Val-alloc (149.6 mg, 0.549 mmol) and EEDQ (135.8 mg, 0.549 mmol) were dissolved in a 9:1 mixture of dry $CH_2Cl_2$/MeOH (5 mL). The flask was wrapped in aluminium foil and the reaction mixture was allowed to stir at room temperature for 1 hour before starting material 15 (302 mg, 0.457 mmol) was added. The reaction mixture was left to stir for a further 40 hours at room temperature before the volatiles were removed by rotary evaporation under reduced pressure (the reaction was followed by LC/MS, RT starting material 2.32 min, (ES+ 660.29 ([M+H]+., 100)). The crude product was directly purified by silica gel chromatography column (100% $CHCl_3$ to 90/10 v/v $CHCl_3$/MeOH) to afford the pure product (16) in 42% yield (174 mg). Method 2 LC/MS (2.70 min (ES+) m/z (relative intensity) 914.73 ([M+H]+., 60), 660.43 (60), 184.31 (100)).

(e) (2S)-2-amino-N-((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)-3-methylbutanamide (17)

The starting material 16 (170 mg, 0.185 mmol) was dissolved in dry $CH_2Cl_2$ (5 mL) in a round bottom flask filled with argon, before pyrrolidine (41 μL, 0.21 mmol) was added. The flask was purged/refilled three times with argon before Pd(PPh$_3$)$_4$ (14 mg, 0.084 mmol) was added and the flushing operation repeated. After 1 hour, complete consumption of starting material was observed (the reaction was followed by LC/MS) and Et$_2$O (50 mL) was added to the reaction mixture which was allowed to stir until all the product had crashed out of solution. The solid was filtered through a sintered funnel and washed twice with Et$_2$O (2×25 mL). The collecting flask was replaced and the isolated solid was dissolved in CHCl$_3$ (100 mL or until all the product had passed through the sintered funnel). The volatiles were then removed by rotary evaporation under reduced pressure to afford the crude product 17 which was used directly in the next step (168 mg). LC/MS method 2 (2.70 min (ES+) m/z (relative intensity) 830.27 ([M+H]+., 50), 660.13 (80), 171.15 (100)).

(f) N—((R)-1-(((S)-1-((4-((S)-8-(3-(((S)-2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-1-(3-(2, 5-dioxo-2,5-dihydro-1H-pyrrol-1-yl)propanamido)-3,6,9,12,15,18,21,24-octaoxaheptacosan-27-amide (18)

Starting material 17 (154 mg, 0.185 mmol) and EDCl.HCl (110 mg, 0.185 mmol) were solubilised in dry $CH_2Cl_2$ (5 mL) in a round bottom flask purged and filled with argon. The mixture was left to stir at room temperature for 1 hour before PEG$_8$-maleimide (35.6 mg, 0.185 mmol) was added and the reaction mixture stirred for a further 16 hours (or until the reaction is complete, monitored by LC/MS). The reaction solution was diluted with $CH_2Cl_2$ (50 mL) and the organics were washed with H$_2$O (50 mL) and brine (50 mL) before being dried with MgSO$_4$, filtered and the solvent removed by rotary evaporation under reduced pressure to afford the crude product. Purification on silica gel column chromatography (100% CHCl$_3$ to 85/15 v/v CHCl$_3$/MeOH) gave the desired product (135 mg), however remaining traces of unreacted PEG$_8$-maleimide were observed (by LC/MS, 2.21 min, method 2). Automated reverse phase silica gel chromatography (H$_2$O/CH$_3$CN) (see general information for conditions) successfully removed the impurity affording pure final product (18, 37 mg of pure product starting from 110 mg, 33%). Overall yield=17%. Method 2 LC/MS (2.58 min (ES+) m/z (relative intensity) 1404.03 ([M+H]+., 20), 702.63 (100)). $^1$H NMR (400 MHz, CDCl$_3$) δ 7.91 (t, J=3.5 Hz, 1H), 7.80 (d, J=4.0 Hz, 1H), 7.75 (d, J=8.8 Hz, 1H), 7.69 (d, J=8.7 Hz, 1H), 7.54-7.50 (m, 2H), 7.45 (s, 1H), 7.39-7.31 (m, 2H), 6.87 (d, J=10.5 Hz, 2H), 6.76 (s, 1H), 6.72-6.68 (m, 2H), 4.74-4.62 (m, 1H), 4.45-4.17 (m, 7H), 3.95 (s, 3H), 3.94 (s, 3H), 3.67-3.58 (m, 34H), 3.54 (m, 2H), 3.42 (dd, J=10.2, 5.2 Hz, 2H), 3.16-3.07 (m, 1H), 2.92 (dd, J=16.1, 4.1 Hz, 1H), 2.62-2.49 (m, 4H), 2.48-2.39 (m, 2H), 2.37-2.25 (m, 1H), 1.92 (s, 1H), 1.52-1.44 (m, 3H), 1.10-0.93 (m, 6H), 0.79 (dd, J=9.2, 5.3 Hz, 2H), 0.57 (dd, J=9.2, 5.3 Hz, 2H), NH were not observed.

Example 2
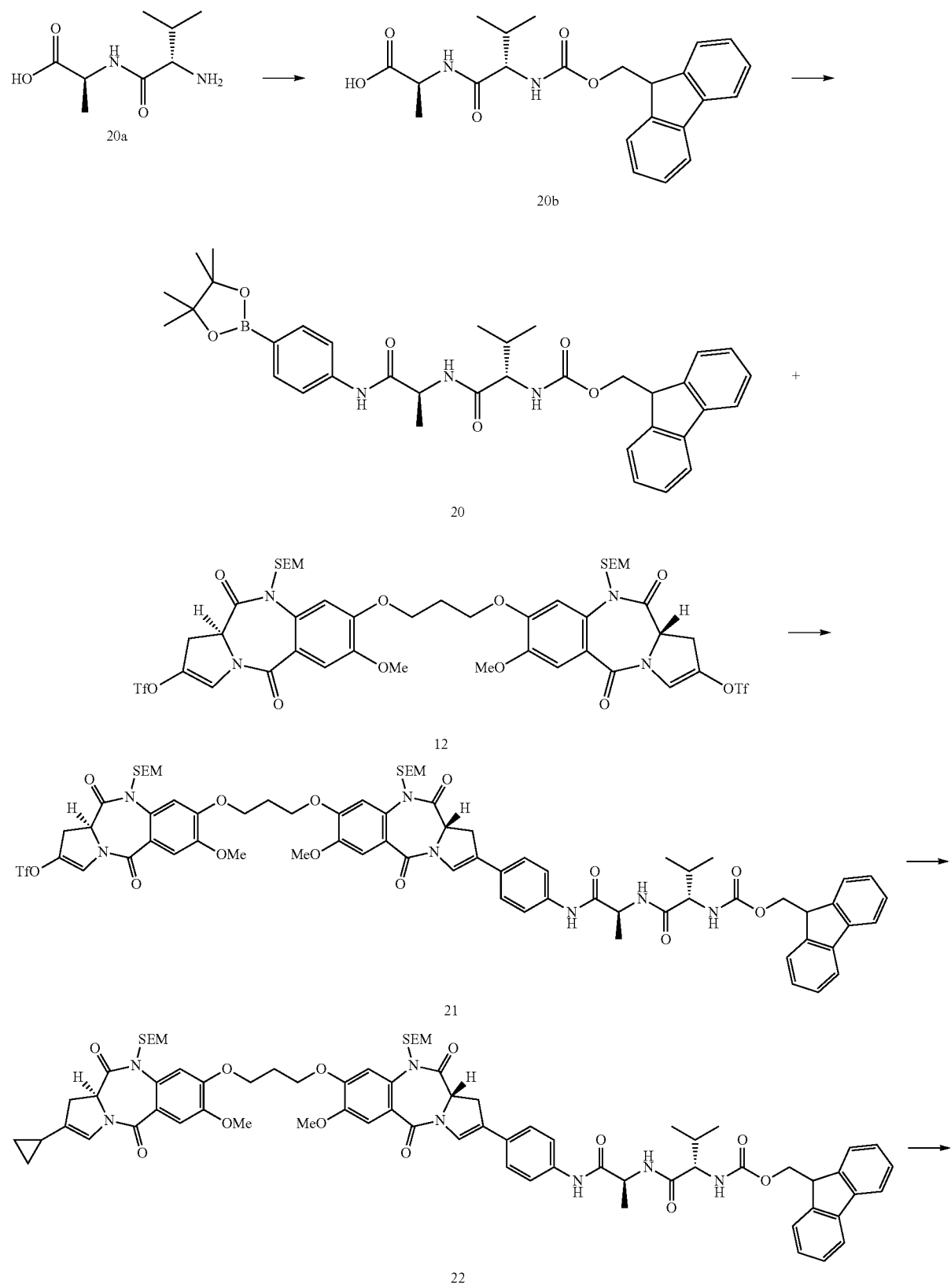

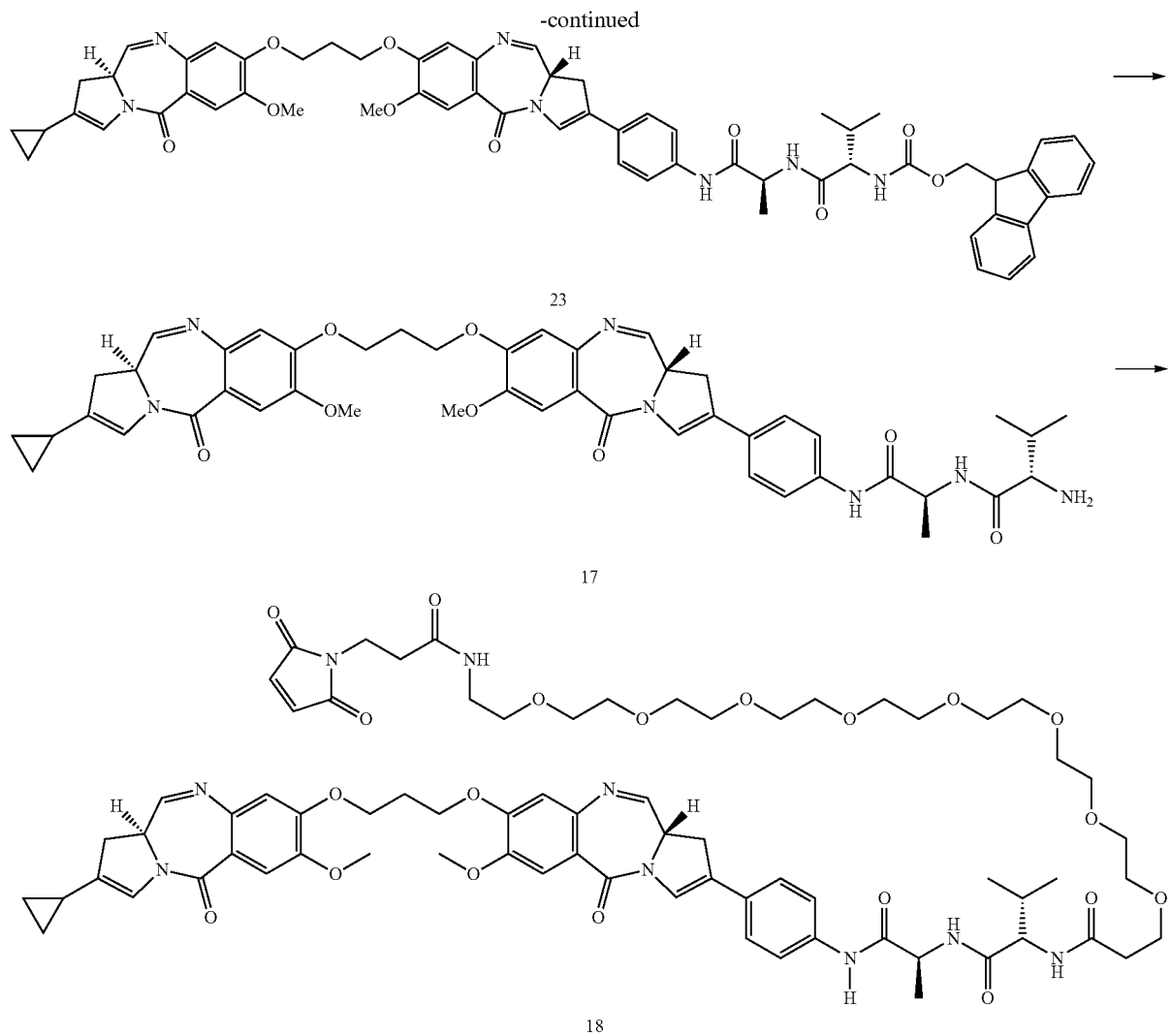

(a) (R)-2-((R)-2-(((((9H-fluoren-9-yl)methoxy)carbonyl)amino)-3-methylbutanamido) propanoic acid (20b)

HO-Ala-Val-H 20a (350 mg, 1.86 mmol) and $Na_2CO_3$ (493 mg, 4.65 mmol) were dissolved in distilled $H_2O$ (15 mL) and the mixture was cooled to 0° C. before dioxane (15 mL) was added (partial precipitation of the amino acid salt occurred). A solution of Fmoc-Cl (504 mg, 1.95 mmol) in dioxane (15 mL) was added dropwise with vigorous stirring over 10 minutes. The resulting mixture was stirred at 0° C. for 2 hours before the ice bath was removed and stirring was maintained for 16 hours. The solvent was removed by rotary evaporation under reduced pressure and the residue dissolved in water (150 mL). The pH was adjusted from 9 to 2 with 1N HCl and the aqueous layer was subsequently extracted with EtOAc (3×100 mL). The combined organics were washed with brine (100 mL), dried with $MgSO_4$, filtered and the volatiles removed by rotary evaporation under reduced pressure to afford pure HO-Ala-Val-Fmoc 20b (746 mg, 97% yield). LC/MS 2.85 min (ES+) m/z (relative intensity) 410.60; $^1$H-NMR (400 MHz, $CDCl_3$) δ 7.79 (d, J=7.77 Hz, 2H), 7.60 (d, J=7.77 Hz, 2H), 7.43 (d, J=7.5 Hz, 2H), 7.34 (d, J=7.5 Hz, 2H), 6.30 (bs, 1H), 5.30 (bs, 1H), 4.71-7.56 (m, 1H), 4.54-4.36 (m, 2H), 4.08-3.91 (m, 1H), 2.21-2.07 (m, 1H), 1.50 (d, J=7.1 Hz, 3H), 1.06-0.90 (m, 6H).

(b) (9H-fluoren-9-yl)methyl ((S)-3-methyl-1-oxo-1-(((S)-1-oxo-1-((4-(4,4,5,5-tetramethyl-1,3, 2-dioxaborolan-2-yl)phenyl)amino)propan-2-yl)amino)butan-2-yl) carbamate (20)

4-Aminophenylboronic acid pinacol ester was added (146.9 mg, 0.67 mmol) was added to a solution of HO-Ala-Val-Fmoc 20b (330 mg, 0.8 mmol), DCC (166 mg, 0.8 mmol) and DMAP (5 mg, cat.) in dry DCM (8 mL) previously stirred for 30 minutes at room temperature in a flask flushed with argon. The reaction mixture was then allowed to stir at room temperature overnight. The reaction was followed by LCMS and TLC. The reaction mixture was diluted with $CH_2Cl_2$ and the organics were washed with $H_2O$ and brine before being dried with $MgSO_4$, filtered and the solvent removed by rotary evaporation under reduced pressure. The crude product was dryloaded on a silicagel chromatography column (Hexane/EtOAc, 6:4) and pure product 20 was isolated as a white solid in 88% yield (360 mg).

(c) 8-(3-((2-(4-((S)-2-((S)-2-((((9H-fluoren-9-yl) methoxy)carbonyl)amino)-3-methylbutanamido) propanamido)phenyl)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (21)

Bis-triflate 12 (2.03 g, 1.81 mmol), boronic pinacol ester (1 g, 1.63 mmol) and $Na_2CO_3$ (881 mg, 8.31 mmol) were dissolved in a mixture of toluene/MeOH/$H_2O$, 2:1:1 (40 mL). The reaction flask was purged and filled with argon three times before tetrakis(triphenylphosphine)palladium(0) (41 mg, 0.035 mmol) was added and the reaction mixture heated to 30° C. overnight. The solvents were removed under reduce pressure and the residue was taken up in $H_2O$ (100 mL) and extracted with EtOAc (3×100 mL). The combined organics were washed with brine (100 mL), dried with $MgSO_4$, filtered and the volatiles removed by rotary evaporation under reduced pressure. The crude product was purified by silica gel chromatography column (Hexane/EtOAc, 8:2 to 25:75) to afford pure 21 in 33% yield (885 mg). LC/MS 3.85 min (ES+) m/z (relative intensity) 1452.90; $^1$H NMR (400 MHz, $CDCl_3$) δ 7.78-7.16 (m, 17H), 7.13 (s, 1H), 6.51-6.24 (m, 1H), 5.51 (dd, J=10.0, 5.1 Hz, 2H), 5.36-5.11 (m, 1H), 4.74 (dd, J=10.1, 4.4 Hz, 2H), 4.70-4.53 (m, 2H), 4.47 (d, J=6.4 Hz, 1H), 4.37 (d, J=7.2 Hz, 1H), 4.27 (m, 4H), 4.20-4.14 (m, 1H), 3.90 (s, 3H), 3.89 (s, 3H), 3.77 (ddd, J=16.7, 9.0, 6.4 Hz, 3H), 3.71-3.61 (m, 2H), 3.24-2.91 (m, 3H), 2.55-2.33 (m, 2H), 2.22-2.07 (m, 1H), 1.52-1.37 (m, 3H), 1.04-0.86 (m, 10H), 0.00 (s, 18H).

(d) (9H-fluoren-9-yl)methyl((2S)-1-(((2S)-1-((4-(8-(3-((2-cyclopropyl-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-8-yl)oxy)propoxy)-7-methoxy-5,11-dioxo-10-((2-(trimethylsilyl)ethoxy)methyl)-5,10,11,11a-tetrahydro-1H-benzo[e]pyrrolo[1,2-a][1,4]diazepin-2-yl)phenyl)amino)-1-oxopropan-2-yl)amino)-3-methyl-1-oxobutan-2-yl) carbamate (22)

Triphenylarsine (42 mg, 0.137 mmol) was added to a mixture of PBD-triflate 21 (250 mg, 0.172 mmol), cyclopropylboronic acid (73.9 mg, 0.86 mmol), silver oxide (159 mg, 0.688 mmol) and potassium phosphate tribasic (438 mg, 2.06 mmol) in dry dioxane (10 mL) under an argon atmosphere. The reaction was flushed with argon 3 times and bis(benzonitrile)palladium(II) chloride (13.2 mg, 0.034 mmol) was added. The reaction was flushed with Argon 3 more times before being warmed to 75° C. and stirred for 10 minutes. The reaction mixture was filtered through a pad of celite which was subsequently rinsed with ethyl acetate. The solvent was removed by rotary evaporation under reduced pressure. The resulting residue was subjected to flash column chromatography (silica gel; 1% methanol/chloroform). Pure fractions were collected and combined, and excess eluent was removed by rotary evaporation under reduced pressure to afford the desired product 22 (132 mg, 50% yield). LC/MS 3.83 min (ES+) m/z (relative intensity) 1345.91; $^1$H NMR (400 MHz, $CDCl_3$) δ 7.88-7.14 (m, 17H), 6.69 (s, 1H), 6.45-6.25 (m, 1H), 5.57-5.41 (m, 2H), 5.34-5.14 (m, 1H), 4.78-4.67 (m, 2H), 4.62-4.55 (m, 1H), 4.50-4.45 (m, 2H), 4.51-4.44 (m, 1H), 4.31-4.21 (m, 4H), 4.16 (m, 1H), 3.92 (s, 3H), 3.86 (s, 3H), 3.82-3.71 (m, 2H), 3.66 (m, 3H), 3.40-3.28 (m, 1H), 3.07 (m, 1H), 2.70-2.57 (m, 1H), 2.47-2.36 (m, 2H), 2.15 (m, 1H), 1.51-1.40 (m, 3H), 1.03-0.87 (m, 11H), 0.77-0.71 (m, 2H), 0.60-0.54 (m, 2H), 0.00 (t, J=3.0 Hz, 18H).

(e) (9H-fluoren-9-yl)methyl((2S)-1-(((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl) carbamate (23)

A solution of Super-Hydride® (0.5 mL, 1M in THF) was added dropwise to a solution of SEM dilactam 22 (265 mg g, 0.19 mmol) in THF (10 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with $MgSO_4$, filtered and the solvent removed by rotary evaporation under reduced pressure. The crude product was dissolved in MeOH (12 mL), $CH_2Cl_2$ (6 mL), water (2 mL) and enough silica gel to form a thick stirring suspension. After 5 days, the suspension was filtered through a sintered funnel and washed with $CH_2Cl_2$/MeOH (9:1) (200 mL) until the elution of the product was complete. The organic layer was washed with brine (2×70 mL), dried with $MgSO_4$, filtered and the solvent removed by rotary evaporation under reduced pressure. Purification by silica gel column chromatography (100% $CHCl_3$ to 96% $CHCl_3$/4% MeOH) afforded the product 23 as a yellow solid (162 mg, 78%). LC/MS 3.02 min (ES+) m/z (relative intensity) 1052.37.

(f) (2S)-2-amino-N-((2S)-1-((4-(8-(3-((2-cyclopropyl-7-methoxy-5-oxo-5,11α-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)-3-methylbutanamide (17)

Excess piperidine was added (0.2 mL, 2 mmol) to a solution of SEM-dilactam 23 (76 mg, 0.073 mmol) in DMF (1 mL). The mixture was allowed to stir at room temperature for 20 min, at which point the reaction had gone to completion (as monitored by LC/MS). The reaction mixture was diluted with $CH_2Cl_2$ (75 mL) and the organic phase was washed with $H_2O$ (3×75 mL) until complete piperidine removal. The organic phase was dried over $MgSO_4$, filtered and excess solvent removed by rotary evaporation under reduced pressure to afford crude product 17 which was used as such in the next step. LC/MS 2.32 min (ES+) m/z (relative intensity) 830.00.

(g) N-((2S)-1-(((2S)-1-((4-(8-(3-((2-cyclopropyl-7-methoxy-5-oxo-5,11a-dihydro-1H-benzo[e]pyrrolo[1,2-a][1,4]diazepin-8-yl)oxy)propoxy)-7-methoxy-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-1-(3-(2, 5-dioxo-2,5-dihydro-1H-pyrrol-1-yl)propanamido)-3,6,9,12,15,18,21,24-octaoxaheptacosan-27-amide (18)

EDCl hydrochloride (14 mg, 0.0732 mmol) was added to a suspension of Maleimide-$PEG_8$-acid (43.4 mg, 0.0732 mmol) in dry CH$_2$Cl$_2$ (5 mL) under argon atmosphere. The mixture was stirred for 1 hour at room temperature before PBD 17 (60.7 mg, 0.0732 mmol) was added. Stirring was maintained until the reaction was complete (usually 5 hours). The reaction was diluted with CH$_2$Cl$_2$ and the organic phase was washed with H$_2$O and brine before being dried over MgSO$_4$, filtered and excess solvent removed by rotary evaporation under reduced pressure by rotary evaporation under reduced pressure. The product was purified by careful silica gel chromatography (slow elution starting with 100% CHCl$_3$ up to 9:1 CHCl$_3$/MeOH) followed by reverse phase chromatography to remove unreacted maleimide-PEG$_8$-acid. The product 18 was isolated in 17.6% (21.8 mg). LC/MS 2.57 min (ES+) m/z (relative intensity) 1405.30; $^1$H NMR (400 MHz, CDCl$_3$) δ 7.91 (t, J=3.5 Hz, 1H), 7.80 (d, J=4.0 Hz, 1H), 7.75 (d, J=8.8 Hz, 1H), 7.69 (d, J=8.7 Hz, 1H), 7.54-7.50 (m, 2H), 7.45 (s, 1H), 7.39-7.31 (m, 2H), 6.87 (d, J=10.5 Hz, 2H), 6.76 (s, 1H), 6.72-6.68 (m, 2H), 4.74-4.62 (m, 1H), 4.45-4.17 (m, 7H), 3.95 (s, 3H), 3.94 (s, 3H), 3.67-3.58 (m, 34H), 3.54 (m, 2H), 3.42 (dd, J=10.2, 5.2 Hz, 2H), 3.16-3.07 (m, 1H), 2.92 (dd, J=16.1, 4.1 Hz, 1H), 2.62-2.49 (m, 4H), 2.48-2.39 (m, 2H), 2.37-2.25 (m, 1H), 1.92 (s, 1H), 1.52-1.44 (m, 3H), 1.10-0.93 (m, 6H), 0.79 (dd, J=9.2, 5.3 Hz, 2H), 0.57 (dd, J=9.2, 5.3 Hz, 2H), NH were not observed.

Example 3

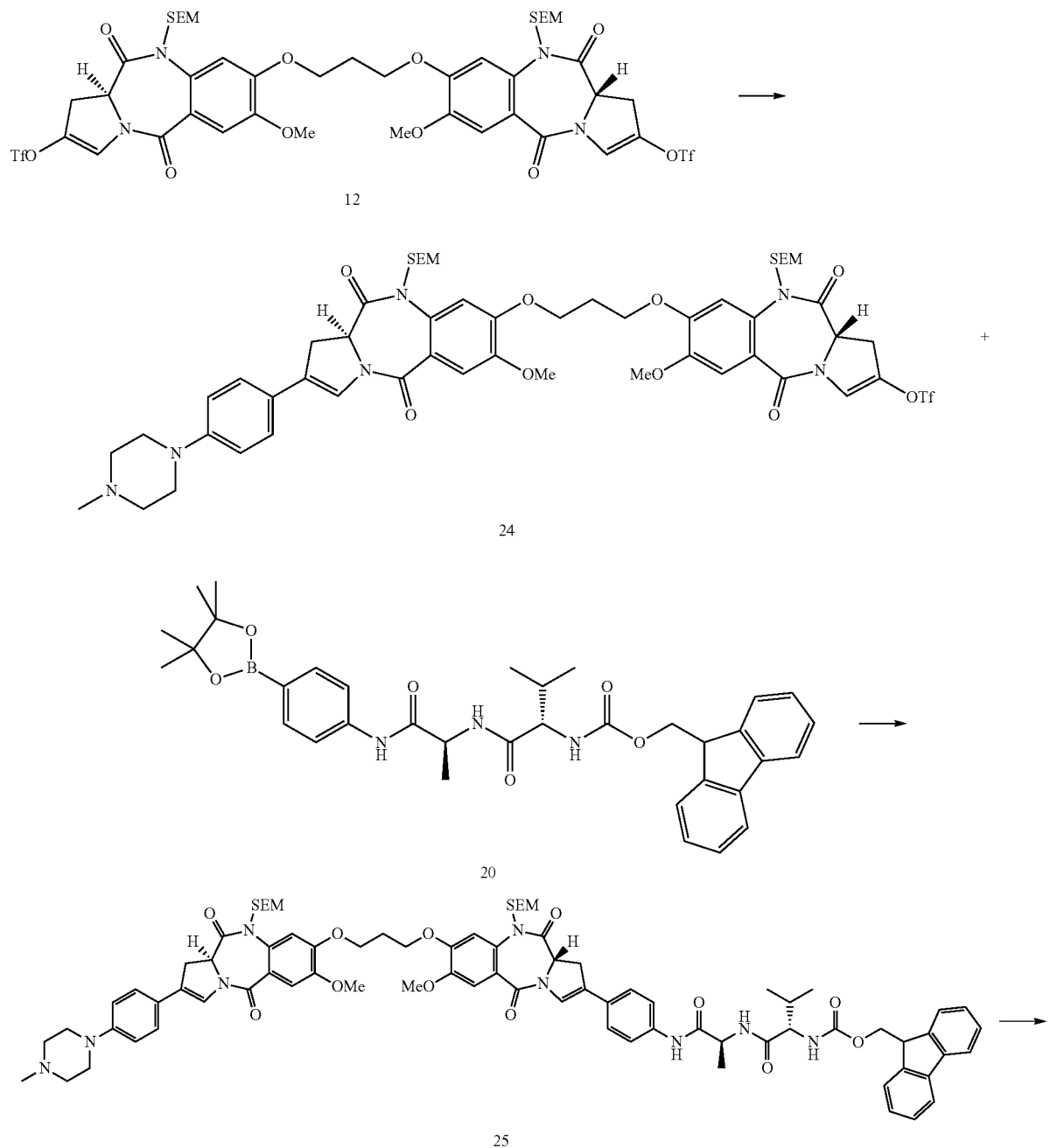

-continued

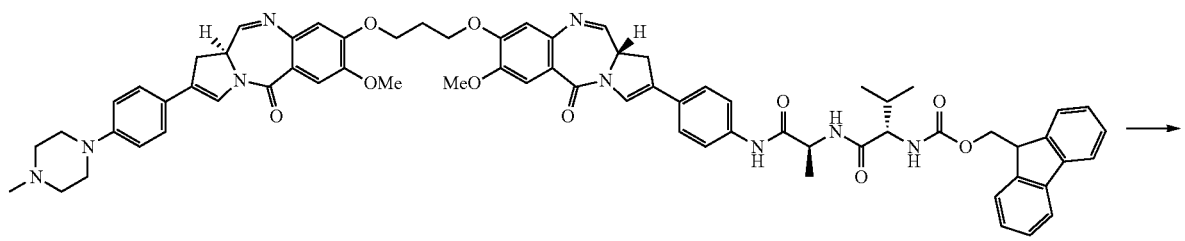

26

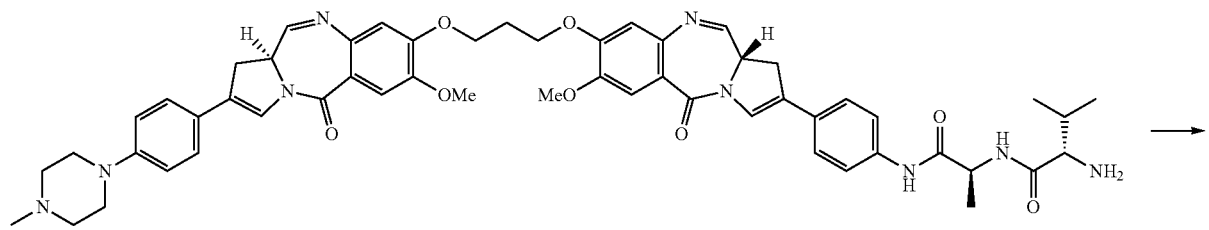

27

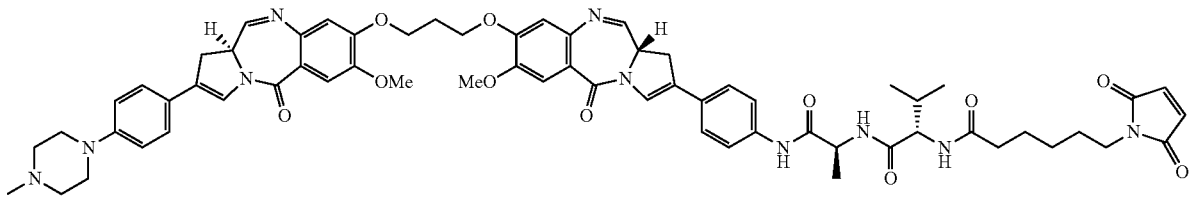

28

(a) (S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl trifluoromethanesulfonate (24)

Pd(PPh$_3$)$_4$ (20.6 mg, 0.018 mmol) was added to a stirred mixture of the bis-enol triflate 12 (500 mg, 0.44 mmol), N-methyl piperazine boronic ester (100 mg, 0.4 mmol), Na$_2$CO$_3$ (218 mg, 2.05 mmol), MeOH (2.5 mL), toluene (5 mL) and water (2.5 mL). The reaction mixture was allowed to stir at 30° C. under a nitrogen atmosphere for 24 hours after which time all the boronic ester has consumed. The reaction mixture was then evaporated to dryness before the residue was taken up in EtOAc (100 mL) and washed with H$_2$O (2×50 mL), brine (50 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 24 as a yellowish foam (122.6 mg, 25%). LC/MS 3.15 min (ES+) m/z (relative intensity) 1144 ([M+H]$^+$., 20%).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (25)

PBD-triflate 24 (359 mg, 0.314 mmol), boronic pinacol ester 20 (250 mg, 0.408 mmol) and triethylamine (0.35 mL, 2.51 mmol) were dissolved in a mixture of toluene/MeOH/H$_2$O, 2:1:1 (3 mL). The microwave vessel was purged and filled with argon three times before tetrakis(triphenylphosphine)palladium(0) (21.7 mg, 0.018 mmol) was added and the reaction mixture placed in the microwave at 80° C. for 10 minutes. Subsequently, CH$_2$Cl$_2$ (100 mL) was added and the organics were washed with water (2×50 mL) and brine (50 mL) before being dried with MgSO$_4$, filtered and the volatiles removed by rotary evaporation under reduced pressure. The crude product was purified by silica gel chromatography column (CHCl$_3$/MeOH, 100% to 9:1) to afford pure 25 (200 mg, 43% yield). LC/MS 3.27 min (ES+) m/z (relative intensity) 1478 ([M+H]$^+$., 100%).

(c) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (26)

A solution of Super-Hydride® (0.34 mL, 1M in THF) was added dropwise to a solution of SEM-dilactam 25 (200 mg, 0.135 mmol) in THF (5 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with MgSO₄, filtered and the solvent removed by rotary evaporation under reduced pressure. The crude product was dissolved in MeOH (6 mL), CH₂Cl₂ (3 mL), water (1 mL) and enough silica gel to form a thick stirring suspension. After 5 days, the suspension was filtered through a sintered funnel and washed with CH₂Cl₂/MeOH (9:1) (100 mL) until the elution of the product was complete. The organic layer was washed with brine (2×50 mL), dried with MgSO₄, filtered and the solvent removed by rotary evaporation under reduced pressure. Purification by silica gel column chromatography (100% CHCl₃ to 96% CHCl₃/4% MeOH) afforded the product 26 as a yellow solid (100 mg, 63%). LC/MS 2.67 min (ES+) m/z (relative intensity) 1186 ([M+H]⁺., 5%).

(d) (S)-2-amino-N—((S)-1-((4-((R)-7-methoxy-8-(3-(((R)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (27)

Excess piperidine was added (0.1 mL, 1 mmol) to a solution of PBD 26 (36.4 mg, 0.03 mmol) in DMF (0.9 mL). The mixture was allowed to stir at room temperature for 20 min, at which point the reaction had gone to completion (as monitored by LC/MS). The reaction mixture was diluted with CH₂Cl₂ (50 mL) and the organic phase was washed with H₂O (3×50 mL) until complete piperidine removal. The organic phase was dried over MgSO₄, filtered and excess solvent removed by rotary evaporation under reduced pressure to afford crude product 27 which was used as such in the next step. LC/MS 2.20 min (ES+) m/z (relative intensity) 964 ([M+H]⁺., 5%).

(e) 6-(2,5-dioxo-2,5-dihydro-1H-pyrrol-1-yl)-N—((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)hexanamide (28)

EDCl hydrochloride (4.7 mg, 0.03 mmol) was added to a suspension of 6-maleimidohexanoic acid (6.5 mg, 0.03 mmol) in dry CH₂Cl₂ (3 mL) under argon atmosphere. The mixture was stirred for 1 hour at room temperature before PBD 27 (34 mg, crude) was added. Stirring was maintained until the reaction was complete (6 hours). The reaction was diluted with CH₂Cl₂ and the organic phase was washed with H₂O and brine before being dried over MgSO₄, filtered and excess solvent removed by rotary evaporation under reduced pressure by rotary evaporation under reduced pressure. The product was purified by careful silica gel chromatography (slow elution starting with 100% CHCl₃ up to 9:1 CHCl₃/MeOH) followed by reverse phase chromatography to remove unreacted maleimide-PEG₈-acid. The product 28 was isolated in 41% over two steps (14.6 mg). LC/MS 2.40 min (ES+) m/z (relative intensity) 1157 ([M+H]⁺., 5%)

Example 4—Alternative Synthesis of Compound 25

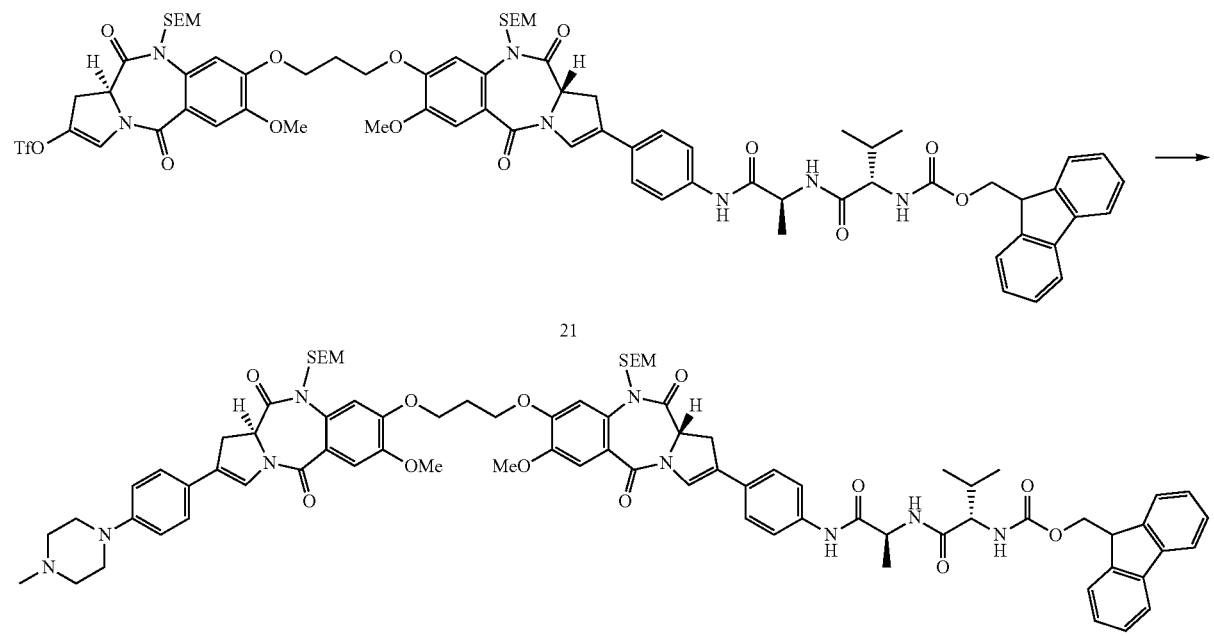

PBD-triflate 21 (469 mg, 0.323 mmol), boronic pinacol ester (146.5 mg, 0.484 mmol) and Na$_2$CO$_3$ (157 mg, 1.48 mmol) were dissolved in a mixture of toluene/MeOH/H$_2$O, 2:1:1 (10 mL). The reaction flask was purged with argon three times before tetrakis(triphenylphosphine)palladium(0) (7.41 mg, 0.0064 mmol) was added and the reaction mixture heated to 30° C. overnight. The solvents were removed under reduced pressure and the residue was taken up in H$_2$O (50 mL) and extracted with EtOAc (3×50 mL). The combined organics were washed with brine (100 mL), dried with MgSO$_4$, filtered and the volatiles removed by rotary evaporation under reduced pressure. The crude product was purified by silica gel column chromatography (CHCl$_3$ 100% to CHCl$_3$/MeOH 95%:5%) to afford pure 25 in 33% yield (885 mg). LC/MS 3.27 min (ES+) m/z (relative intensity) 1478 ([M+H]$^+$., 100%).

Example 5

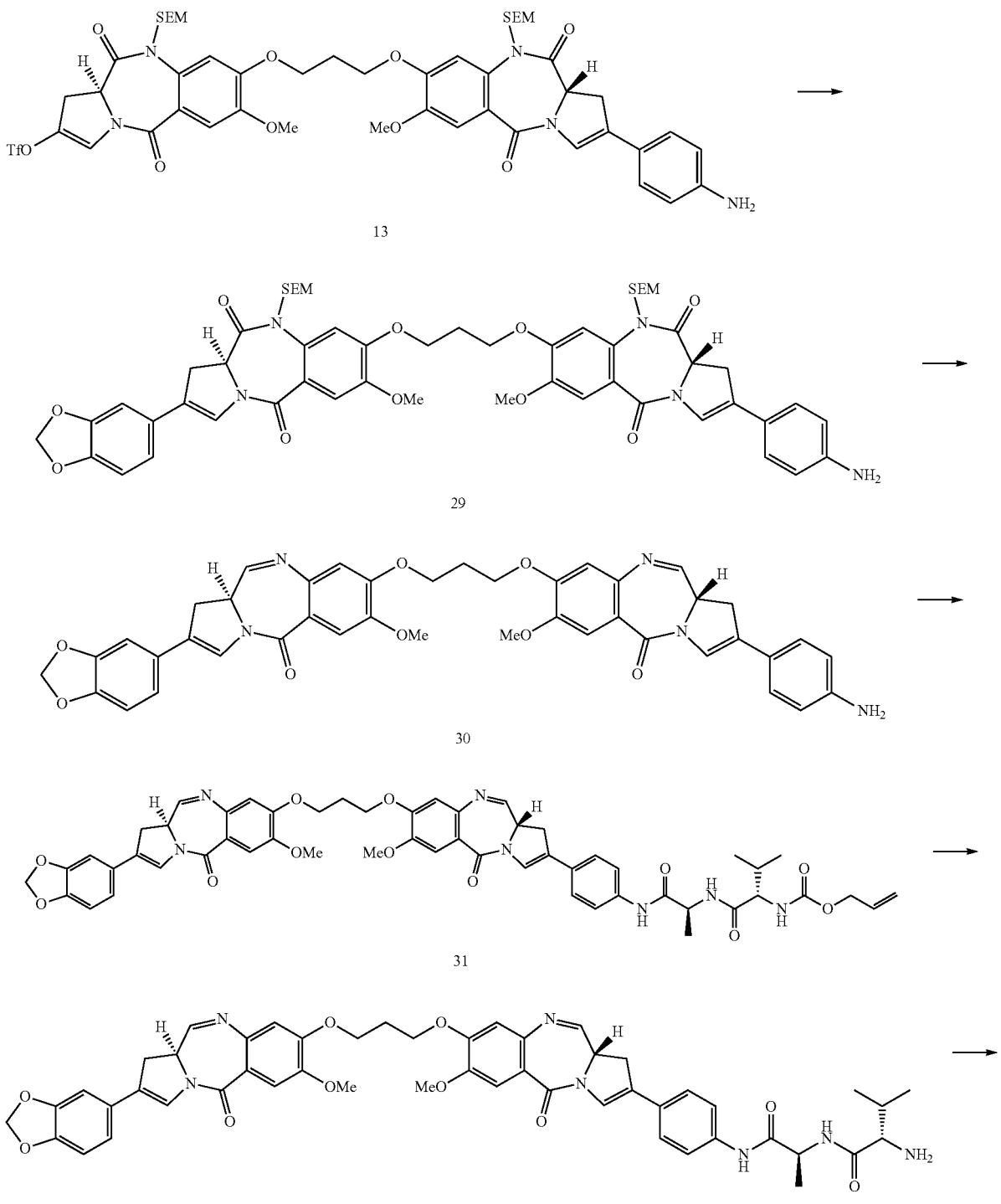

-continued

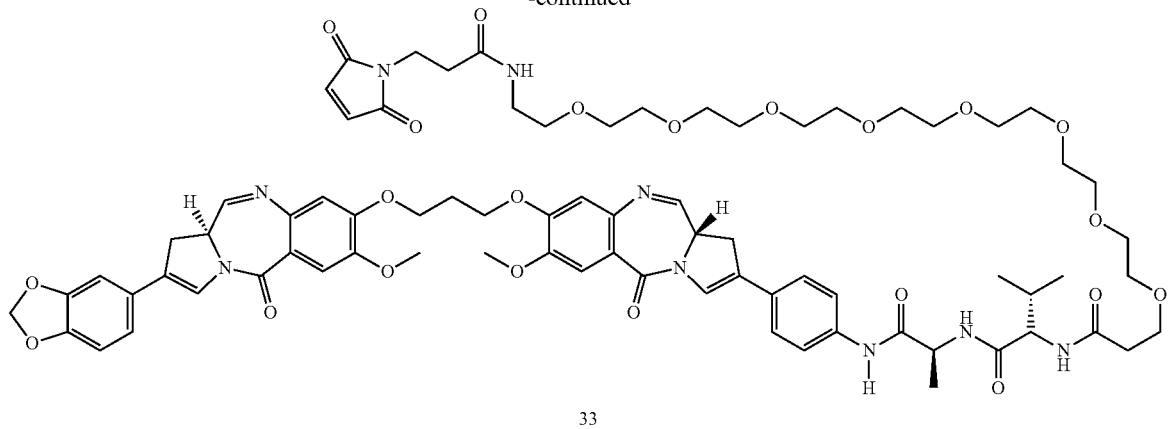

33

(a) (S)-2-(4-Aminophenyl)-8-(3-(((S)-2-(benzo[d][1,3]dioxol-5-yl)-7-methoxy-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-7-methoxy-10-((2-(trimethylsilyl)ethoxy)methyl)-1H-pyrrolo[2,1-c][1,4]benzodiazepine-5,11(10H,11aH)-dione (29)

3,4-(Methylenedioxy)phenyl boronic acid (356 mg, 2.1 mmol, 1.3 equiv.), TEA (1.8 mL, 12.9 mmol, 8 equiv.) and triflate/aniline 13 (1.75 g, 1.7 mmol, 1 equiv.) were dissolved in a mixture of ethanol (7 mL), toluene (13 mL) and water (2 mL) under an Ar atmosphere. The reaction mixture was evacuated and flushed with Ar 3 times, before addition of tetrakis(triphenylphosphine)palladium(0) (114 mg, 0.1 mmol, 0.06 equiv.). The flask was again evacuated and flushed with Ar 3 times and heated in a microwave at 80° C. for 8 minutes with 30 seconds pre-stirring time. Analysis by TLC (80:20 v/v ethyl acetate/hexane) indicated complete consumption of starting material. The reaction mixture was diluted with dichloromethane (50 mL) and washed with water (50 mL). The organic layer was dried with $MgSO_4$, filtered and the solvent removed in vacuo. Purification by silica gel column chromatography (60:40 to 20:80 v/v hexane/ethyl acetate) afforded the product 29 as a yellow solid (1.21 g, 71%). LC/MS (3.92 min (ES$^+$) m/z (relative intensity) 1032.44 ([M+H]$^+$., 100).

(b) (S)-2-(4-Aminophenyl)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-1H-pyrrolo[2,1-c][1,4]benzodiazepin-5(11aH)-one (30)

SEM dilactam 29 (0.25 g, 0.24 mmol, 1 equiv.) was dissolved in THF (8 mL) and cooled to −78° C. under an Ar atmosphere. Super-Hydride® (0.6 mL, 1 M in THF, 2.5 equiv.) was added drop wise over 5 minutes while monitoring the temperature. After 20 minutes a small sample was taken and worked-up for LCMS analysis. Water (50 mL) was added, the cold bath was removed and the solution washed with ethyl acetate (50 mL). The organic layer was extracted and washed with brine (60 mL), dried with $MgSO_4$, filtered and the solvent removed in vacuo. The crude product was dissolved in EtOH (15 mL), $CH_2Cl_2$ (7.5 mL) and water (2.5 mL) and enough silica gel was added until it was a thick suspension. After 5 days stirring, it was filtered through a sintered funnel and washed with $CH_2Cl_2$/MeOH (9:1) (100 mL) until product ceased to be eluted. The organic layer was washed with brine (2×50 mL), dried with $MgSO_4$, filtered and the solvent removed in vacuo. Purification by silica gel column chromatography (CHCl$_3$ with 1% to 4% MeOH gradient) afforded the product 30 as a yellow solid (94 mg, 53%). LC/MS (2.53 min (ES$^+$) m/z (relative intensity) 739.64 ([M]$^+$., 70).

(c) Allyl ((S)-1-(((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (31)

Under an Ar atmosphere, Alanine-Valine-Alloc (180 mg, 0.66 mmol, 1.2 equiv.) was stirred with EEDQ (163 mg, 0.66 mmol, 1.2 equiv.) in anhydrous $CH_2Cl_2$ (21 mL) and methanol (1 mL) for 1 hour. The PBD 30 (407 mg, 0.55 mmol, 1 equiv.) was dissolved in anhydrous $CH_2Cl_2$ (21 mL) and methanol (1 mL) and added to the reaction. LC/MS after 5 days stirring at room temperature showed majority product formation. The solvent was removed in vacuo before purification by column chromatography ($CH_2Cl_2$ with 1% to 6% MeOH gradient) to yield the product 31 as a yellow solid (184 mg, 34%). LC/MS (2.95 min (ES$^+$) m/z (relative intensity) 994.95 ([M+H]$^+$., 60).

(d) (S)-2-Amino-N—((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)-3-methylbutanamide (32)

The imine 31 (100 mg, 0.1 mmol, 1 equiv.) was dissolved in anhydrous DCM (10 mL) (with the aid of one drop of methanol to aid dissolution) under an Ar atmosphere. Pyrrolidine (30 µL, 0.15 mmol, 1.5 equiv.) was added drop wise before the flask was evacuated and flushed with Ar three times. Pd(PPh$_3$)$_4$ (7 mg, 6 µmol, 0.06 equiv.) was added and the flask was evacuated and flushed with Ar three times. LC/MS analysis after 1 hour indicated product formation and complete loss of starting material. Et$_2$O (60 mL) was added to the reaction mixture and it was left to stir until all the product had crashed out of solution. The precipitate was filtered through a sintered funnel and washed twice with Et$_2$O (2×20 mL). The collection flask was replaced and the isolated solid was dissolved and washed through the sinter with CHCl$_3$ (100 mL). The solvent was removed in vacuo to afford the crude product 32 as a yellow solid which was used directly in the next step. LC/MS (1.14 min (ES⁺) m/z (relative intensity) 910.40 ([M+H]⁺., 67).

(e) N—((S)-1-(((S)-1-((4-((S)-8-(3-(((S)-2-(Benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)-1-(3-(2, 5-dioxo-2,5-dihydro-1H-pyrrol-1-yl)propanamido)-3,6,9,12,15,18,21,24-octaoxaheptacosan-27-amide (33)

The imine 32 (92 mg, 0.1 mmol, 1.1 equiv.) was dissolved in CHCl₃ (6 mL) with one drop of anhydrous MeOH to aid dissolution. Maleimide-PEG₈-acid (53 mg, 0.09 mmol, 1 equiv.) was added followed by EEDQ (33 mg, 0.14 mmol, 1.5 equiv.). This was left to stir vigorously at room temperature under Ar for 4 days until LC/MS analysis showed majority product formation. The solvent was removed in vacuo and the crude product was partially purified by silica gel column chromatography (CHCl3 with 1% to 10% MeOH gradient) yielding 33 (81 mg). The material was purified further by preparative HPLC to give 33 as a yellow solid (26.3 mg, 18%). Fast Formic run: LC/MS (1.39 min (ES+) m/z (relative intensity) 1485.00 ([M+H]+., 64).

Example 6

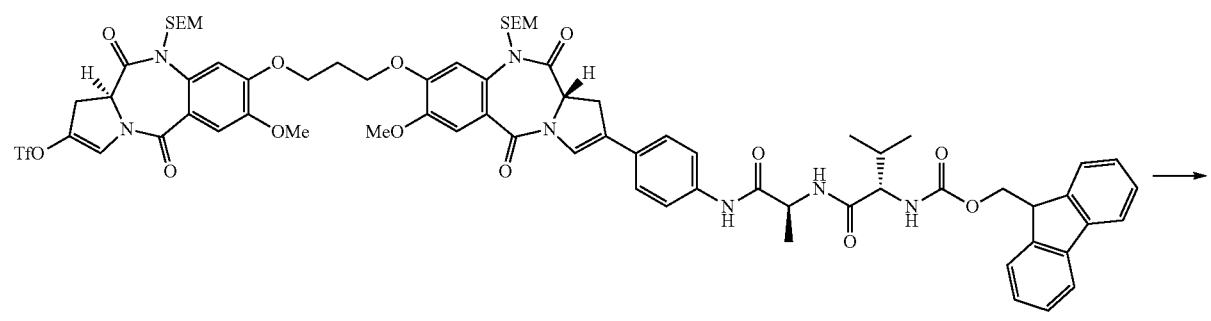

21

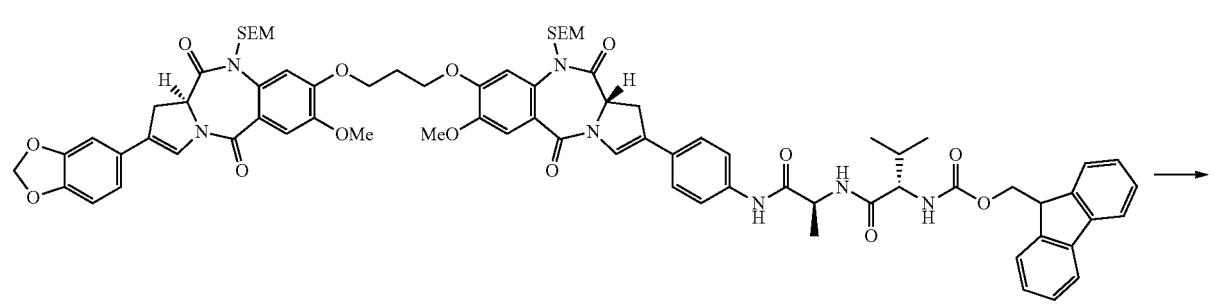

34

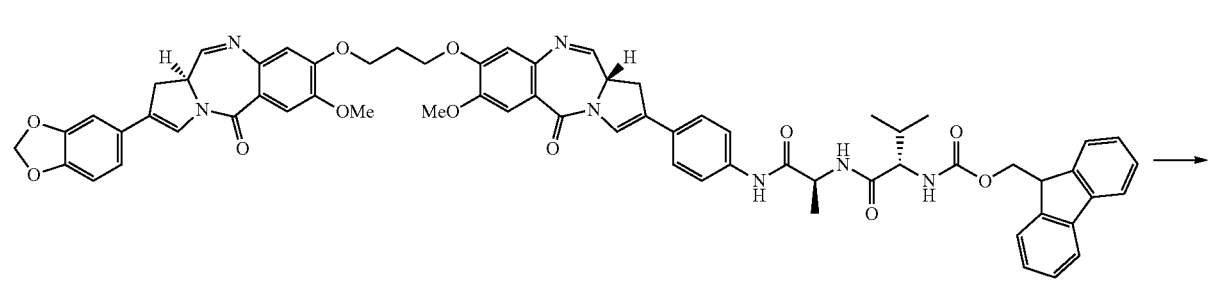

35

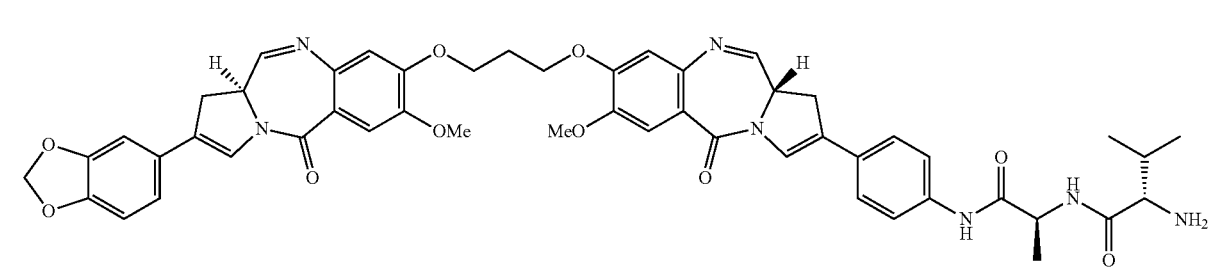

32

(a) 9H-Flouren-9-yl)methyl ((S)-1-((S)-1-((4-((S)-8-(3-(((S)-2-(benzo[d][1,3]dioxol-5-yl)-7-methoxy-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-7-methoxy-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (34)

The triflate 21 (0.5 g, 0.35 mmol, 1 equiv.), 3, 4-(methylenedioxy)phenyl boronic acid (75 mg, 0.45 mmol, 1.3 equiv.) and Na$_2$CO$_3$ (0.17 g, 1.6 mmol, 4.5 equiv.) were dissolved in toluene (11 mL), EtOH (5.5 mL) and water (5.5 mL) under an Ar atmosphere. The flask was evacuated and flushed with Ar three times. Pd(PPh$_3$)$_4$ (24 mg, 0.02 mmol, 0.06 equiv.) was added and again the flask was evacuated and flushed with Ar three times. This was heated to 30° C. and left stirring overnight. Analysis by LC/MS showed complete loss of starting material. The solvent was removed in vacuo and the residue dissolved in water (60 mL) before washing with ethyl acetate (60 mL×3). The combined organic layers were washed with brine (50 mL), dried with MgSO$_4$, filtered and the solvent removed in vacuo. Purification by column chromatography (50:50 to 25:75 v/v hexane/ethyl acetate) afforded the product 34 as a yellow solid (310 mg, 64%). LC/MS (1.44 min (ES$^-$) m/z (relative intensity) 1423.35 ([M–H]$^-$., 79).

(b) (9H-Fluoren-9-yl)methyl ((S)-1-(((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (35)

SEM dilactam 34 (0.31 g, 0.22 mmol, 1 equiv.) was dissolved in THF (10 mL) and cooled to −78° C. under an Ar atmosphere. Super-Hydride® (0.5 mL, 1 M in THF, 2.5 equiv.) was added drop wise over 5 minutes while monitoring the temperature. After 30 minutes a small sample was taken and worked-up for LC/MS analysis. Water (50 mL) was added, the cold bath was removed and the solution washed with ethyl acetate (50 mL). The organic layer was extracted and washed with brine (60 mL), dried with MgSO$_4$, filtered and the solvent removed in vacuo. The crude product was dissolved in EtOH (13.2 mL), CH$_2$Cl$_2$ (6.6 mL) and water (2.2 mL) and enough silica gel was added until it was a thick suspension. After 5 days stirring, it was filtered through a sintered funnel and washed with CH$_2$Cl$_2$/MeOH (9:1) (100 mL) until product ceased to be eluted. The organic layer was washed with brine (2×50 mL), dried with MgSO$_4$, filtered and the solvent removed in vacuo. Purification by silica gel column chromatography (CHCl$_3$ with 1% to 4% MeOH gradient) afforded the pure product 35 as a yellow solid (185 mg, 75%). LC/MS (1.70 min (ES$^+$) m/z (relative intensity) 1132.85 ([M+H]$^+$., 60).

(c) (S)-2-Amino-N—((S)-1-((4-((S)-8-(3-(((S)-2-(benzo[d][1,3]dioxol-5-yl)-7-methoxy-5-oxo-5,11a-dihydro-1H-pyrrolo[2,1-c][1,4]benzodiazepin-8-yl)oxy)propoxy)-7-methoxy-5-oxo-5,11a-dihydro-1H-pyrrolo[2,1-c][1,4]benzodiazepin-2-yl)phenyl)amino)-1-oxopropan-2-yl)-3-methylbutanamide (32)

The imine 35 (82 mg, 0.07 mmol, 1 equiv.) was dissolved in DMF (1 mL) before piperidine (0.2 mL, 2 mmol, excess) was added slowly. This solution was left to stir at room temperature for 20 minutes until LC/MS analysis showed complete consumption of starting material. The reaction mixture was diluted with CH$_2$Cl$_2$ (50 mL), washed with water (50 mL×4), dried with MgSO$_4$, filtered and the solvent removed in vacuo. The product 33 was used without further purification in the next step. LC/MS (1.15 min (ES$^+$) m/z (relative intensity) 910.60 ([M+H]$^+$., 58).

Example 7

(i) (S)-(2-amino-5-methoxy-4-((triisopropylsilyl)oxy)phenyl)(2-(((tert-butyldimethylsilyl)oxy)methyl)-4-methyl-2,3-dihydro-1H-pyrrol-1-yl)methanone (49)

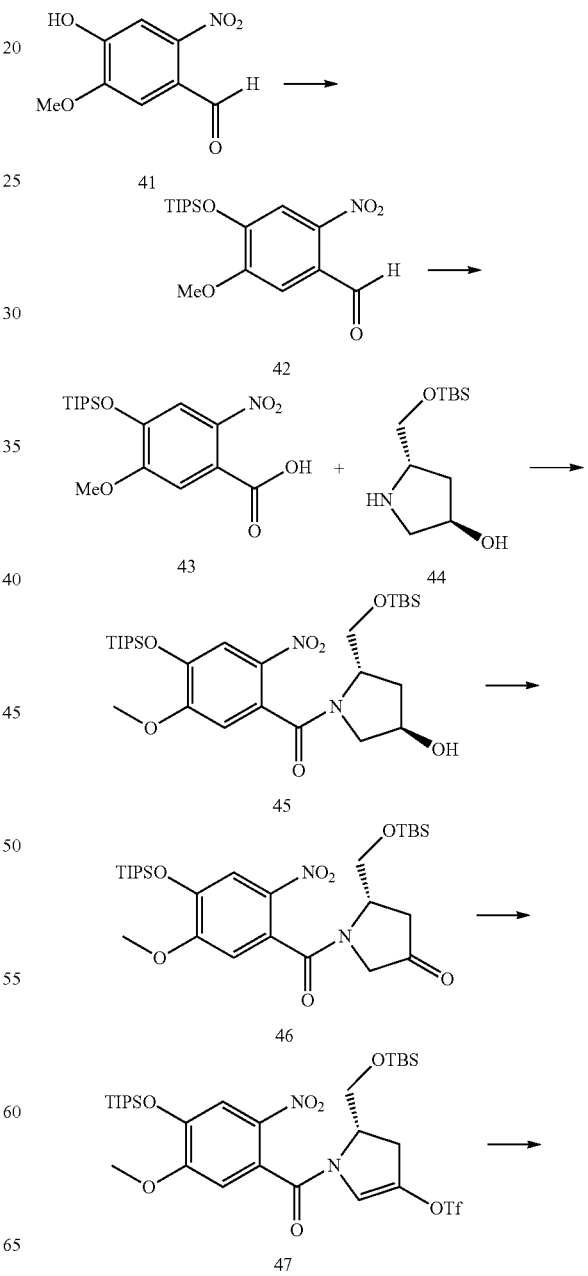

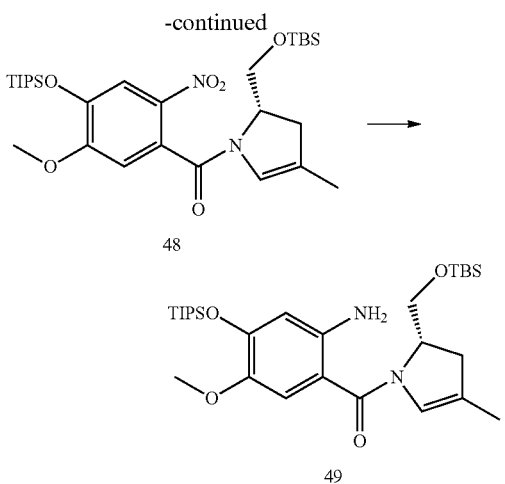

(a) 5-methoxy-2-nitro-4-((triisopropylsilyl)oxy)benzaldehyde (42)

Neat triisopropylsilylchloride (56.4 mL, 262 mmol) was added to a mixture of imidazole (48.7 g, 715.23 mmol) and 4-hydroxy-5-methoxy-2-nitrobenzaldehyde 41 (47 g, 238 mmol) (ground together). The mixture was heated until the phenol and imidazole melted and went into solution (100° C.). The reaction mixture was allowed to stir for 15 minutes and was then allowed to cool, whereupon a solid was observed to form at the bottom of the flask (imidazole chloride). The reaction mixture was diluted with 5% EtOAc/hexanes and loaded directly onto silica gel and the pad was eluted with 5% EtOAc/hexanes, followed by 10% EtOAc/hexanes (due to the low excess, very little unreacted TIPSCl was found in the product). The desired product was eluted with 5% ethyl acetate in hexane. Excess eluent was removed by rotary evaporation under reduced pressure, followed by drying under high vacuum to afford a crystalline light sensitive solid (74.4 g, 88%). Purity satisfactory by LC/MS (4.22 min (ES+) m/z (relative intensity) 353.88 ([M+H]+., 100)); $^1$H NMR (400 MHz, CDCl$_3$) δ 10.43 (s, 1H), 7.60 (s, 1H), 7.40 (s, 1H), 3.96 (s, 3H), 1.35-1.24 (m, 3H), 1.10 (m, 18H).

(b) 5-methoxy-2-nitro-4-((triisopropylsilyl)oxy)benzoic acid (43)

A solution of sodium chlorite (47.3 g, 523 mmol, 80% technical grade) and sodium dihydrogenphosphate monobasic (35.2 g, 293 mmol) (NaH$_2$PO$_4$) in water (800 mL) was added to a solution of compound 2 (74 g, 209 mmol) in tetrahydrofuran (500 mL) at room temperature. Hydrogen peroxide (60% w/w, 140 mL, 2.93 mol) was immediately added to the vigorously stirred biphasic mixture. The reaction mixture evolved gas (oxygen), the starting material dissolved and the temperature of the reaction mixture rose to 45° C. After 30 minutes LC/MS revealed that the reaction was complete. The reaction mixture was cooled in an ice bath and hydrochloric acid (1 M) was added to lower the pH to 3 (this step was found unnecessary in many instances, as the pH at the end of the reaction is already acidic; please check the pH before extraction). The reaction mixture was then extracted with ethyl acetate (1 L) and the organic phases washed with brine (2×100 mL) and dried over magnesium sulphate. The organic phase was filtered and excess solvent removed by rotary evaporation under reduced pressure to afford the product 43 in quantitative yield as a yellow solid. LC/MS (3.93 min (ES−) m/z (relative intensity) 367.74 ([M−H]−., 100)); $^1$H NMR (400 MHz, CDCl$_3$) δ 7.36 (s, 1H), 7.24 (s, 1H), 3.93 (s, 3H), 1.34-1.22 (m, 3H), 1.10 (m, 18H).

(c) ((2S,4R)-2-(((tert-butyldimethylsilyl)oxy)methyl)-4-hydroxypyrrolidin-1-yl) (5-methoxy-2-nitro-4-((triisopropylsilyl)oxy)phenyl)methanone (45)

DCC (29.2 g, 141 mmol, 1.2 eq) was added to a solution of acid 3 (43.5 g, 117.8 mmol, 1 eq), and hydroxybenzotriazole hydrate (19.8 g, 129.6 mmol, 1.1 eq) in dichloromethane (200 mL) at 0° C. The cold bath was removed and the reaction was allowed to proceed for 30 mins at room temperature, at which time a solution of (2S,4R)-2-t-butyldimethylsilyloxymethyl-4-hydroxypyrrolidine 44 (30 g, 129.6 mmol, 1.1 eq) and triethylamine (24.66 mL, 176 mmol, 1.5 eq) in dichloromethane (100 mL) was added rapidly at −10° C. under argon (on large scale, the addition time could be shortened by cooling the reaction mixture even further. The reaction mixture was allowed to stir at room temperature for 40 minutes to 1 hour and monitored by LC/MS and TLC (EtOAc). The solids were removed by filtration over celite and the organic phase was washed with cold aqueous 0.1 M HCl until the pH was measured at 4 or 5. The organic phase was then washed with water, followed by saturated aqueous sodium bicarbonate and brine. The organic layer was dried over magnesium sulphate, filtered and excess solvent removed by rotary evaporation under reduced pressure. The residue was subjected to column flash chromatography (silica gel; gradient 40/60 ethyl acetate/hexane to 80/20 ethyl acetate/hexane). Excess solvent was removed by rotary evaporation under reduced pressure afforded the pure product 45, (45.5 g of pure product 66%, and 17 g of slightly impure product, 90% in total). LC/MS 4.43 min (ES+) m/z (relative intensity) 582.92 ([M+H]+., 100); $^1$H NMR (400 MHz, CDCl$_3$) δ 7.66 (s, 1H), 6.74 (s, 1H), 4.54 (s, 1H), 4.40 (s, 1H), 4.13 (s, 1H), 3.86 (s, 3H), 3.77 (d, J=9.2 Hz, 1H), 3.36 (dd, J=11.3, 4.5 Hz, 1H), 3.14-3.02 (m, 1H), 2.38-2.28 (m, 1H), 2.10 (ddd, J=13.3, 8.4, 2.2 Hz, 1H), 1.36-1.19 (m, 3H), 1.15-1.05 (m, 18H), 0.91 (s, 9H), 0.17-0.05 (m, 6H), (presence of rotamers).

(d) (S)-5-(((tert-butyldimethylsilyl)oxy)methyl)-1-(5-methoxy-2-nitro-4-((triisopropylsilyl)oxy)benzoyl)pyrrolidin-3-one (46)

TCCA (8.82 g, 40 mmol, 0.7 eq) was added to a stirred solution of 45 (31.7 g, 54 mmol, 1 eq) and TEMPO (0.85 g, 5.4 mmol, 0.1 eq) in dry dichloromethane (250 mL) at 0° C. The reaction mixture was vigorously stirred for 20 minutes, at which point TLC (50/50 ethyl acetate/hexane) revealed complete consumption of the starting material. The reaction mixture was filtered through celite and the filtrate washed with aqueous saturated sodium bicarbonate (100 mL), sodium thiosulphate (9 g in 300 mL), brine (100 mL) and dried over magnesium sulphate. Rotary evaporation under reduced pressure afforded product 46 in quantitative yield. LC/MS 4.52 min (ES+) m/z (relative intensity) 581.08 ([M+H]+., 100); $^1$H NMR (400 MHz, CDCl$_3$) δ 7.78-7.60 (m, 1H), 6.85-6.62 (m, 1H), 4.94 (dd, J=30.8, 7.8 Hz, 1H), 4.50-4.16 (m, 1H), 3.99-3.82 (m, 3H), 3.80-3.34 (m, 3H), 2.92-2.17 (m, 2H), 1.40-1.18 (m, 3H), 1.11 (t, J=6.2 Hz, 18H), 0.97-0.75 (m, 9H), 0.15--0.06 (m, 6H), (presence of rotamers).

(e) (S)-5-(((tert-butyldimethylsilyl)oxy)methyl)-1-(5-methoxy-2-nitro-4-((triisopropylsilyl)oxy)benzoyl)-4,5-dihydro-1H-pyrrol-3-yl trifluoromethanesulfonate (47)

Triflic anhydride (27.7 mL, 46.4 g, 165 mmol, 3 eq) was injected (temperature controlled) to a vigorously stirred suspension of ketone 46 (31.9 g, 55 mmol, 1 eq) in dry dichloromethane (900 mL) in the presence of 2,6-lutidine (25.6 mL, 23.5 g, 220 mmol, 4 eq, dried over sieves) at −50° C. (acetone/dry ice bath). The reaction mixture was allowed to stir for 1.5 hours when LC/MS, following a mini work-up (water/dichloromethane), revealed the reaction to be complete. Water was added to the still cold reaction mixture and the organic layer was separated and washed with saturated sodium bicarbonate, brine and magnesium sulphate. The organic phase was filtered and excess solvent was removed by rotary evaporation under reduced pressure. The residue was subjected to column flash chromatography (silica gel; 10/90 v/v ethyl acetate/hexane), removal of excess eluent afforded the product 47 (37.6 g, 96%) LC/MS, method 2, 4.32 min (ES+) m/z (relative intensity) 712.89 ([M+H]+., 100); $^1$H NMR (400 MHz, CDCl$_3$) δ 7.71 (s, 1H), 6.75 (s, 1H), 6.05 (d, J=1.8 Hz, 1H), 4.78 (dd, J=9.8, 5.5 Hz, 1H), 4.15-3.75 (m, 5H), 3.17 (ddd, J=16.2, 10.4, 2.3 Hz, 1H), 2.99 (ddd, J=16.3, 4.0, 1.6 Hz, 1H), 1.45-1.19 (m, 3H), 1.15-1.08 (m, 18H), 1.05 (s, 6H), 0.95-0.87 (m, 9H), 0.15-0.08 (m, 6H).

(f) (S)-(2-(((tert-butyldimethylsilyl)oxy)methyl)-4-methyl-2, 3-dihydro-1H-pyrrol-1-yl) (5-methoxy-2-nitro-4-((triisopropylsilyl)oxy)phenyl)methanone (48)

Triphenylarsine (1.71 g, 5.60 mmol, 0.4 eq) was added to a mixture of triflate 47 (10.00 g, 14 mmol, 1 eq), methylboronic acid (2.94 g, 49.1 mmol, 3.5 eq), silver oxide (13 g, 56 mmol, 4 eq) and potassium phosphate tribasic (17.8 g, 84 mmol, 6 eq) in dry dioxane (80 mL) under an argon atmosphere. The reaction was flushed with argon 3 times and bis(benzonitrile)palladium(II) chloride (540 mg, 1.40 mmol, 0.1 eq) was added. The reaction was flushed with argon 3 more times before being warmed instantaneously to 110° C. (the drysyn heating block was previously warmed to 110° C. prior addition of the flask). After 10 mins the reaction was cooled to room temperature and filtered through a pad celite. The solvent was removed by rotary evaporation under reduced pressure. The resulting residue was subjected to column flash chromatography (silica gel; 10% ethyl acetate/ hexane). Pure fractions were collected and combined, and excess eluent was removed by rotary evaporation under reduced pressure afforded the product 48 (4.5 g, 55%). LC/MS, 4.27 min (ES+) m/z (relative intensity) 579.18 ([M+H]+., 100); $^1$H NMR (400 MHz, CDCl$_3$) δ 7.70 (s, 1H), 6.77 (s, 1H), 5.51 (d, J=1.7 Hz, 1H), 4.77-4.59 (m, 1H), 3.89 (s, 3H), 2.92-2.65 (m, 1H), 2.55 (d, J=14.8 Hz, 1H), 1.62 (d, J=1.1 Hz, 3H), 1.40-1.18 (m, 3H), 1.11 (s, 9H), 1.10 (s, 9H), 0.90 (s, 9H), 0.11 (d, J=2.3 Hz, 6H).

(g) (S)-(2-amino-5-methoxy-4-((triisopropylsilyl)oxy)phenyl) (2-(((tert-butyldimethylsilyl)oxy)methyl)-4-methyl-2, 3-dihydro-1H-pyrrol-1-yl)methanone (49)

Zinc powder (28 g, 430 mmol, 37 eq) was added to a solution of compound 48 (6.7 g, 11.58 mmol) in 5% formic acid in ethanol v/v (70 mL) at around 15° C. The resulting exotherm was controlled using an ice bath to maintain the temperature of the reaction mixture below 30° C. After 30 minutes the reaction mixture was filtered through a pad of celite. The filtrate was diluted with ethyl acetate and the organic phase was washed with water, saturated aqueous sodium bicarbonate and brine. The organic phase was dried over magnesium sulphate, filtered and excess solvent removed by rotary evaporation under reduced pressure. The resulting residue was subjected to flash column chromatography (silica gel; 10% ethyl acetate in hexane). The pure fractions were collected and combined and excess solvent was removed by rotary evaporation under reduced pressure to afford the product 49 (5.1 g, 80%). LC/MS, 4.23 min (ES+) m/z (relative intensity) 550.21 ([M+H]+., 100); $^1$H NMR (400 MHz, CDCl$_3$) δ 7.28 (s, 1H), 6.67 (s, 1H), 6.19 (s, 1H), 4.64-4.53 (m, J=4.1 Hz, 1H), 4.17 (s, 1H), 3.87 (s, 1H), 3.77-3.69 (m, 1H), 3.66 (s, 3H), 2.71-2.60 (m, 1H), 2.53-2.43 (m, 1H), 2.04-1.97 (m, J=11.9 Hz, 1H), 1.62 (s, 3H), 1.26-1.13 (m, 3H), 1.08-0.99 (m, 18H), 0.82 (s, 9H), 0.03--0.03 (m, J=6.2 Hz, 6H).

(ii) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate

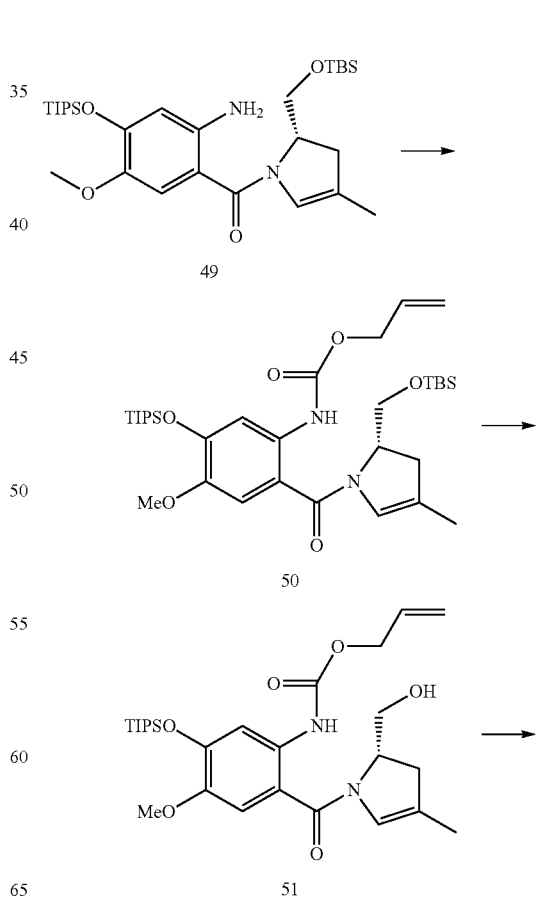

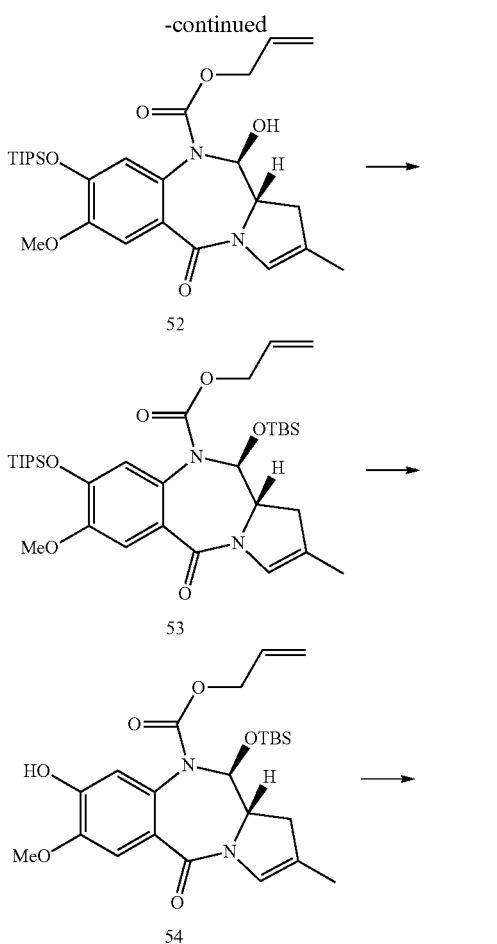

(a) (S)-allyl (2-(2-(((tert-butyldimethylsilyl)oxy)methyl)-4-methyl-2, 3-dihydro-1H-pyrrole-1-carbonyl)-4-methoxy-5-((triisopropylsilyl)oxy)phenyl) carbamate (50)

Allyl chloroformate (0.30 mL, 3.00 mmol, 1.1 eq) was added to a solution of amine 49 (1.5 g, 2.73 mmol) in the presence of dry pyridine (0.48 mL, 6.00 mmol, 2.2 eq) in dry dichloromethane (20 mL) at −78° C. (acetone/dry ice bath). After 30 minutes, the bath was removed and the reaction mixture was allowed to warm to room temperature. The reaction mixture was diluted with dichloromethane and saturated aqueous copper sulphate was added. The organic layer was then washed sequentially with saturated aqueous sodium bicarbonate and brine. The organic phase was dried over magnesium sulphate, filtered and excess solvent removed by rotary evaporation under reduced pressure to afford the product 50 which was used directly in the next reaction. LC/MS, 4.45 min (ES+) m/z (relative intensity) 632.91 ([M+H]+., 100)

(b) (S)-allyl (2-(2-(hydroxymethyl)-4-methyl-2, 3-dihydro-1H-pyrrole-1-carbonyl)-4-methoxy-5-((triisopropylsilyl)oxy)phenyl) carbamate (51)

The crude 50 was dissolved in a 7:1:1:2 mixture of acetic acid/methanol/tetrahydrofuran/water (28:4:4:8 mL) and allowed to stir at room temperature. After 3 hours, complete disappearance of starting material was observed by LC/MS. The reaction mixture was diluted with ethyl acetate and washed sequentially with water (2×500 mL), saturated aqueous sodium bicarbonate (200 mL) and brine. The organic phase was dried over magnesium sulphate filtered and excess ethyl acetate removed by rotary evaporation under reduced pressure. The resulting residue was subjected to flash column chromatography (silica gel, 25% ethyl acetate in hexane). Pure fractions were collected and combined and excess eluent was removed by rotary evaporation under reduced pressure to afford the desired product 51 (1 g, 71%). LC/MS, 3.70 min (ES+) m/z (relative intensity) 519.13 ([M+H]+., 95); $^1$H NMR (400 MHz, CDCl$_3$) δ 8.34 (s, 1H), 7.69 (s, 1H), 6.78 (s, 1H), 6.15 (s, 1H), 5.95 (ddt, J=17.2, 10.5, 5.7 Hz, 1H), 5.33 (dq, J=17.2, 1.5 Hz, 1H), 5.23 (ddd, J=10.4, 2.6, 1.3 Hz, 1H), 4.73 (tt, J=7.8, 4.8 Hz, 1H), 4.63 (dt, J=5.7, 1.4 Hz, 2H), 4.54 (s, 1H), 3.89-3.70 (m, 5H), 2.87 (dd, J=16.5, 10.5 Hz, 1H), 2.19 (dd, J=16.8, 4.6 Hz, 1H), 1.70 (d, J=1.3 Hz, 3H), 1.38-1.23 (m, 3H), 1.12 (s, 10H), 1.10 (s, 8H).

(c) (11S,11aS)-allyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10 (5H)-carboxylate (52)

Dimethyl sulphoxide (0.35 mL, 4.83 mmol, 2.5 eq) was added dropwise to a solution of oxalyl chloride (0.2 mL, 2.32 mmol, 1.2 eq) in dry dichloromethane (10 mL) at −78° C. (dry ice/acetone bath) under an atmosphere of argon. After 10 minutes a solution of 51 (1 g, 1.93 mmol) in dry dichloromethane (8 mL) was added slowly with the temperature still at −78° C. After 15 min triethylamine (1.35 mL, dried over 4 Å molecular sieves, 9.65 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure to afford product 52 (658 mg, 66%). LC/MS, 3.52 min (ES+) m/z (relative intensity) 517.14 ([M+H]+., 100); $^1$H NMR (400 MHz, CDCl$_3$) δ 7.20 (s, 1H), 6.75-6.63 (m, J=8.8, 4.0 Hz, 2H), 5.89-5.64 (m, J=9.6, 4.1 Hz, 2H), 5.23-5.03 (m, 2H), 4.68-4.38 (m, 2H), 3.84 (s, 3H), 3.83-3.77 (m, 1H), 3.40 (s, 1H), 3.05-2.83 (m, 1H), 2.59 (d, J=17.1 Hz, 1H), 1.78 (d, J=1.3 Hz, 3H), 1.33-1.16 (m, 3H), 1.09 (d, J=2.2 Hz, 9H), 1.07 (d, J=2.1 Hz, 9H).

(d) (11S,11aS)-allyl 11-((tert-butyldimethylsilyl)oxy)-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (53)

Tert-butyldimethylsilyltriflate (0.70 mL, 3.00 mmol, 3 eq) was added to a solution of compound 52 (520 mg, 1.00 mmol) and 2,6-lutidine (0.46 mL, 4.00 mmol, 4 eq) in dry dichloromethane (40 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess was removed by rotary evaporation under reduced pressure. The resulting residue was subjected to flash column chromatography (silica gel; gradient, 10% ethyl acetate in hexane to 20% ethyl acetate in hexane). Pure fractions were collected and combined and excess eluent was removed by rotary evaporation under reduced pressure to give the product 53 (540 mg, 85%). LC/MS, 4.42 min (ES+) m/z (relative intensity) 653.14 ([M+Na]$^+$., 100); $^1$H NMR (400 MHz, CDCl$_3$) δ 7.20 (s, 1H), 6.71-6.64 (m, J=5.5 Hz, 2H), 5.83 (d, J=9.0 Hz, 1H), 5.80-5.68 (m, J=5.9 Hz, 1H), 5.14-5.06 (m, 2H), 4.58 (dd, J=13.2, 5.2 Hz, 1H), 4.36 (dd, J=13.3, 5.5 Hz, 1H), 3.84 (s, 3H), 3.71 (td, J=10.1, 3.8 Hz, 1H), 2.91 (dd, J=16.9, 10.3 Hz, 1H), 2.36 (d, J=16.8 Hz, 1H), 1.75 (s, 3H), 1.31-1.16 (m, 3H), 1.12-1.01 (m, J=7.4, 2.1 Hz, 18H), 0.89-0.81 (m, 9H), 0.25 (s, 3H), 0.19 (s, 3H).

(e) (11S,11aS)-allyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (54)

Lithium acetate (87 mg, 0.85 mmol) was added to a solution of compound 53 (540 mg, 0.85 mmol) in wet dimethylformamide (6 mL, 50:1 DMF/water). After 4 hours, the reaction was complete and the reaction mixture was diluted with ethyl acetate (25 mL) and washed with aqueous citric acid solution (pH~3), water and brine. The organic layer was dried over magnesium sulphate filtered and excess ethyl acetate was removed by rotary evaporation under reduced pressure. The resulting residue was subjected to flash column chromatography (silica gel; gradient, 25% to 75% ethyl acetate in hexane). Pure fractions were collected and combined and excess eluent was removed by rotary evaporation under reduced pressure to give the product 54 (400 mg, quantitative). LC/MS, (3.33 min (ES+) m/z (relative intensity) 475.26 ([M+H]$^+$, 100).

(f) (11S,11aS)-allyl 11-((tert-butyldimethylsilyl)oxy)-8-((5-iodopentyl)oxy)-7-methoxy-2-methyl-5-oxo-11,11a-dihydro-1H-benzo[e]pyrrolo[1,2-a][1,4]diazepine-10(5H)-carboxylate (55)

Diiodopentane (0.63 mL, 4.21 mmol, 5 eq) and potassium carbonate (116 mg, 0.84 mmol, 1 eq) were added to a solution of phenol 54 (400 mg, 0.84 mmol) in acetone (4 mL, dried over molecular sieves). The reaction mixture was then warmed to 60° C. and stirred for 6 hours. Acetone was removed by rotary evaporation under reduced pressure. The resulting residue was subjected to flash column chromatography (silica gel; 50/50, v/v, hexane/ethyl acetate,). Pure fractions were collected and combined and excess eluent was removed to provide 55 in 90% yield. LC/MS, 3.90 min (ES+) m/z (relative intensity) 670.91 ([M]+, 100). $^1$H NMR (400 MHz, CDCl$_3$) δ 7.23 (s, 1H), 6.69 (s, 1H), 6.60 (s, 1H), 5.87 (d, J=8.8 Hz, 1H), 5.83-5.68 (m, J=5.6 Hz, 1H), 5.15-5.01 (m, 2H), 4.67-4.58 (m, 1H), 4.45-4.35 (m, 1H), 4.04-3.93 (m, 2H), 3.91 (s, 3H), 3.73 (td, J=10.0, 3.8 Hz, 1H), 3.25-3.14 (m, J=8.5, 7.0 Hz, 2H), 2.92 (dd, J=16.8, 10.3 Hz, 1H), 2.38 (d, J=16.8 Hz, 1H), 1.95-1.81 (m, 4H), 1.77 (s, 3H), 1.64-1.49 (m, 2H), 0.88 (s, 9H), 0.25 (s, 3H), 0.23 (s, 3H).

(iii) (11S,11aS)-4-(2-(1-((1-(allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (70)

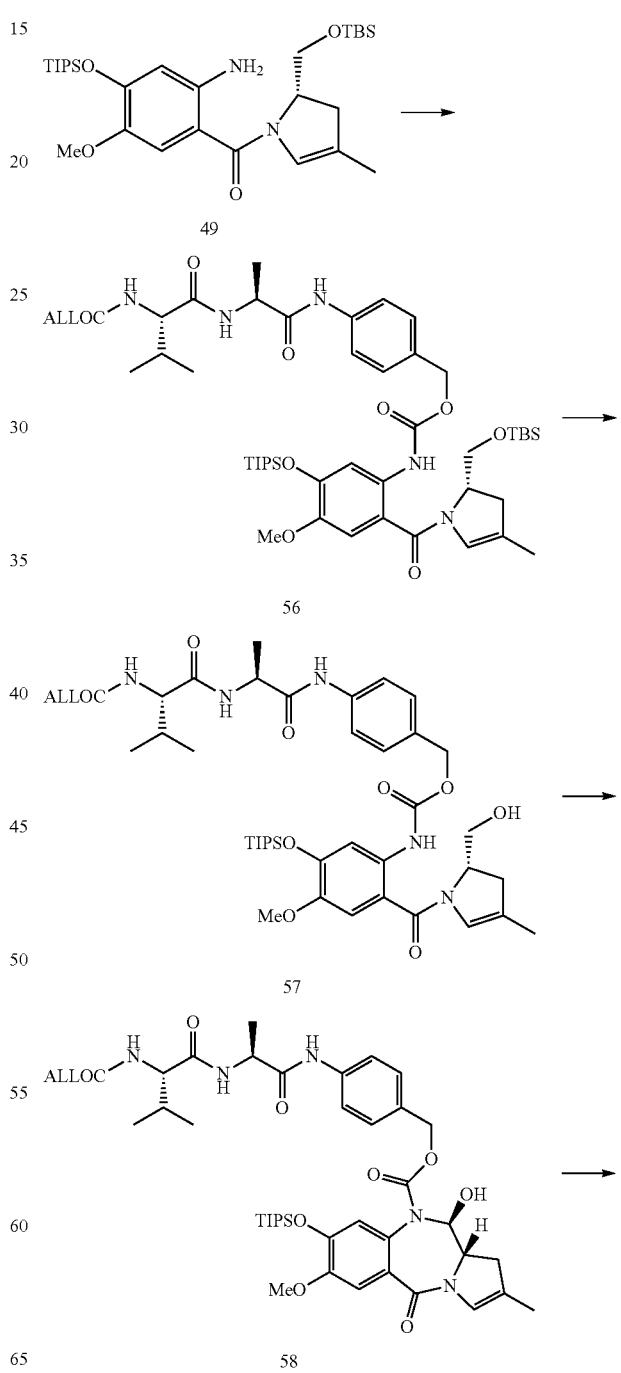

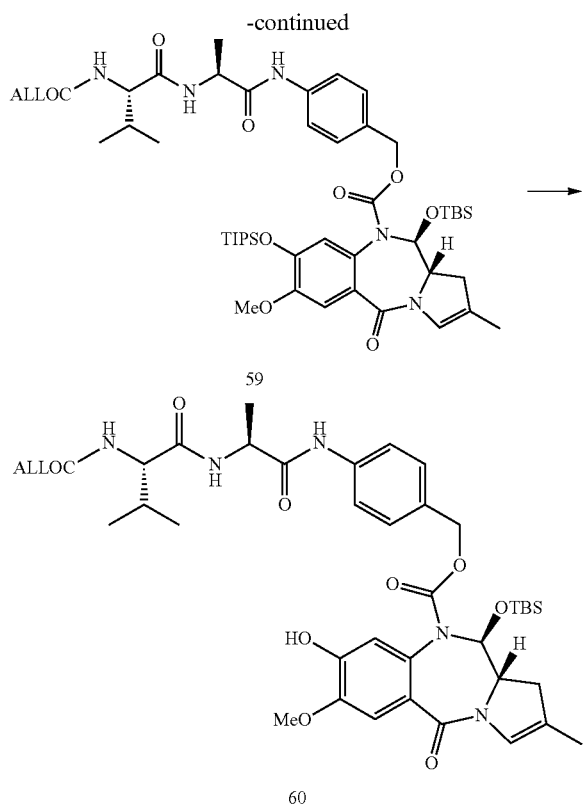

(a) Allyl 3-(2-(2-(4-(((((2-((S)-2-(((tert-butydim-ethysilyl)oxy)methyl)-4-methyl-2, 3-dihydro-1H-pyrrole-1-carbonyl)-4-methoxy-5-((triisopropylsilyl)oxy)phenyl) carbamoyl)oxy)methyl)phenyl) hydrazinyl) propanamido)-4-methyl-2-oxopentanoate (56)

Triethylamine (2.23 mL, 18.04 mmol, 2.2 eq) was added to a stirred solution of the amine 49 (4 g, 8.20 mmol) and triphosgene (778 mg, 2.95 mmol, 0.36 eq) in dry tetrahydrofuran (40 mL) at 5° C. (ice bath). The progress of the isocyanate reaction was monitored by periodically removing aliquots from the reaction mixture and quenching with methanol and performing LC/MS analysis. Once the isocyanate formation was complete a solution of the alloc-Val-Ala-PABOH (4.12 g, 12.30 mmol, 1.5 eq) and triethylamine (1.52 mL, 12.30 mmol, 1.5 eq) in dry tetrahydrofuran (40 mL) was rapidly added by injection to the freshly prepared isocyanate. The reaction mixture was allowed to stir at 40° C. for 4 hours. Excess solvent was removed by rotary evaporation under reduced pressure. The resulting residue was subjected to flash column chromatography (silica gel; gradient, 1% methanol to 5% methanol in dichloromethane). (Alternative chromatography conditions using EtOAc and Hexane have also been successful). Pure fractions were collected and combined and excess eluent was removed by rotary evaporation under reduced pressure to give the product 56 (3.9 g, 50%). LC/MS, 4.23 min (ES+) m/z (relative intensity) 952.36 ([M+H]+., 100); $^1$H NMR (400 MHz, CDCl$_3$) δ 8.62 (br s, 1H), 8.46 (s, 1H), 7.77 (br s, 1H), 7.53 (d, J=8.4 Hz, 2H), 7.32 (d, J=8.5 Hz, 2H), 6.76 (s, 1H), 6.57 (d, J=7.6 Hz, 1H), 6.17 (s, 1H), 6.03-5.83 (m, 1H), 5.26 (dd, J=33.8, 13.5 Hz, 3H), 5.10 (s, 2H), 4.70-4.60 (m, 2H), 4.58 (dd, J=5.7, 1.3 Hz, 2H), 4.06-3.99 (m, 1H), 3.92 (s, 1H), 3.82-3.71 (m, 1H), 3.75 (s, 3H), 2.79-2.64 (m, 1H), 2.54 (d, J=12.9 Hz, 1H), 2.16 (dq, J=13.5, 6.7 Hz, 1H), 1.67 (s, 3H), 1.46 (d, J=7.0 Hz, 3H), 1.35-1.24 (m, 3H), 1.12 (s, 9H), 1.10 (s, 9H), 0.97 (d, J=6.8 Hz, 3H), 0.94 (d, J=6.8 Hz, 3H), 0.87 (s, 9H), 0.07--0.02 (m, 6H).

(b) Allyl 3-(2-(2-(4-((((2-((S)-2-(hydroxymethyl)-4-methyl-2, 3-dihydro-1H-pyrrole-1-carbonyl)-4-methoxy-5-((triisopropylsilyl)oxy)phenyl) carbamoyl)oxy)methyl)phenyl) hydrazinyl) propanamido)-4-methyl-2-oxopentanoate (57)

The TBS ether 56 (1.32 g, 1.38 mmol) was dissolved in a 7:1:1:2 mixture of acetic acid/methanol/tetrahydrofuran/water (14:2:2:4 mL) and allowed to stir at room temperature. After 3 hours no more starting material was observed by LC/MS. The reaction mixture was diluted with ethyl acetate (25 mL) and washed sequentially with water, saturated aqueous sodium bicarbonate and brine. The organic phase was dried over magnesium sulphate filtered and excess ethyl acetate removed by rotary evaporation under reduced pressure. The resulting residue was subjected to flash column chromatography (silica gel, 2% methanol in dichloromethane). Pure fractions were collected and combined and excess eluent was removed by rotary evaporation under reduced pressure to afford the desired product 57 (920 mg, 80%). LC/MS, 3.60 min (ES+) m/z (relative intensity) 838.18 ([M+H]+., 100). $^1$H NMR (400 MHz, CDCl$_3$) δ 8.55 (s, 1H), 8.35 (s, 1H), 7.68 (s, 1H), 7.52 (d, J=8.1 Hz, 2H), 7.31 (d, J=8.4 Hz, 2H), 6.77 (s, 1H), 6.71 (d, J=7.5 Hz, 1H), 6.13 (s, 1H), 5.97-5.82 (m, J=5.7 Hz, 1H), 5.41-5.15 (m, 3H), 5.10 (d, J=3.5 Hz, 2H), 4.76-4.42 (m, 5H), 4.03 (t, J=6.6 Hz, 1H), 3.77 (s, 5H), 2.84 (dd, J=16.7, 10.4 Hz, 1H), 2.26-2.08 (m, 2H), 1.68 (s, 3H), 1.44 (d, J=7.0 Hz, 3H), 1.30 (dt, J=14.7, 7.4 Hz, 3H), 1.12 (s, 9H), 1.10 (s, 9H), 0.96 (d, J=6.8 Hz, 3H), 0.93 (d, J=6.8 Hz, 3H).

(c) (11S,11aS)-4-(2-(1-((1-(allyloxy)-4-methyl-1,2-dioxopentan-3-yl)amino)-1-oxopropan-2-yl)hydrazinyl)benzyl 11-hydroxy-7-methoxy-2-methyl-5-oxo-8-((triisopropylsilyl)oxy)-11,11a-dihydro-1H-benzo[e]pyrrolo[1,2-a][1,4]diazepine-10(5H)-carboxylate (58)

Dimethyl sulphoxide (0.2 mL, 2.75 mmol, 2.5 eq) was added dropwise to a solution of oxalyl chloride (0.11 mL, 1.32 mmol, 1.2 eq) in dry dichloromethane (7 mL) at −78° C. (dry ice/acetone bath) under an atmosphere of argon. After 10 minutes a solution of 57 (920 mg, 1.10 mmol) in dry dichloromethane (5 mL) was added slowly with the temperature still at −78° C. After 15 min triethylamine (0.77 mL, dried over 4 Å molecular sieves, 5.50 mmol, 5 eq) was added dropwise and the dry ice/acetone bath was removed. The reaction mixture was allowed to reach room temperature and was extracted with cold hydrochloric acid (0.1 M), saturated aqueous sodium bicarbonate and brine. The organic phase was dried over magnesium sulphate, filtered and excess dichloromethane was removed by rotary evaporation under reduced pressure. The resulting residue was subjected to column flash chromatography (silica gel; gradient 2% methanol to 5% methanol in dichloromethane). Pure fractions were collected and combined and removal of excess eluent by rotary evaporation under reduced pressure afforded the product 58 (550 mg, 60%). LC/MS, 3.43 min (ES+) m/z (relative intensity) 836.01 ([M]+., 100). $^1$H NMR (400 MHz, CDCl$_3$) δ 8.39 (s, 1H), 7.52-7.40 (m, 2H), 7.21-7.08 (m, J=11.5 Hz, 2H), 6.67 (s, 1H), 6.60-6.47 (m, J=7.4 Hz, 1H), 5.97-5.83 (m, 1H), 5.79-5.66 (m, 1H), 5.38-4.90 (m, 6H), 4.68-4.52 (m, J=18.4, 5.5 Hz, 4H), 4.04-3.94 (m, J=6.5 Hz, 1H), 3.87-3.76 (m, 5H), 3.00-2.88 (m, 1H), 2.66-2.49 (m, 2H), 2.21-2.08 (m, 2H), 1.76 (s, 3H), 1.45 (d, J=7.0 Hz, 3H), 1.09-0.98 (m, J=8.9 Hz, 18H), 0.96 (d, J=6.7 Hz, 3H), 0.93 (d, J=6.9 Hz, 3H).

(d) (11S,11aS)-4-(2-(1-((1-(Allyloxy)-4-methyl-1,2-dioxopentan-3-yl)amino)-1-oxopropan-2-yl) hydrazinyl)benzyl 11-((tert-butyldimethylsilyl)oxy)-7-methoxy-2-methyl-5-oxo-8-((triisopropylsilyl) oxy)-11,11a-dihydro-1H-benzo[e]pyrrolo[1,2-a][1,4] diazepine-10(5H)-carboxylate (59)

Tert-butyldimethylsilyltriflate (0.38 mL, 1.62 mmol, 3 eq) was added to a solution of compound 58 (450 mg, 0.54 mmol) and 2,6-lutidine (0.25 mL, 2.16 mmol, 4 eq) in dry dichloromethane (5 mL) at 0° C. under argon. After 10 min, the cold bath was removed and the reaction mixture was stirred at room temperature for 1 hour. The reaction mixture was extracted with water, saturated aqueous sodium bicarbonate and brine. The organic phase was dried over magnesium sulphate, filtered and excess solvent was removed by rotary evaporation under reduced pressure. The resulting residue was subjected to column flash chromatography (silica gel; 50/50 v/v hexane/ethyl acetate). Pure fractions were collected and combined and excess eluent was removed by rotary evaporation under reduced pressure to give the product 59 (334 mg, 65%). LC/MS, 4.18 min (ES+) m/z (relative intensity) 950.50 ([M]$^+$., 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(e) (11S,11aS)-4-(2-(1-((1-(Allyloxy)-4-methyl-1,2-dioxopentan-3-yl)amino)-1-oxopropan-2-yl)hydrazinyl)benzyl 11-((tert-butyldimethylsilyl)oxy)-8-hydroxy-7-methoxy-2-methyl-5-oxo-11,11a-dihydro-1H-benzo[e]pyrrolo[1,2-a][1,4]diazepine-10(5H)-carboxylate (60)

Lithium acetate (50 mg, 0.49 mmol) was added to a solution of compound 59 (470 mg, 0.49 mmol) in wet dimethylformamide (4 mL, 50:1 DMF/water). After 4 hours, the reaction was complete and the reaction mixture was diluted with ethyl acetate and washed with citric acid (pH~3), water and brine. The organic layer was dried over magnesium sulphate filtered and excess ethyl acetate was removed by rotary evaporation under reduced pressure. The resulting residue was subjected to column flash chromatography (silica gel; gradient, 50/50 to 25/75 v/v hexane/ethyl acetate). Pure fractions were collected and combined and excess eluent was removed by rotary evaporation under reduced pressure to give the product 60 (400 mg, quantitative). LC/MS, 3.32 min (ES+) m/z (relative intensity) 794.18 ([M+H]$^+$., 100). $^1$H NMR (400 MHz, CDCl$_3$) δ 8.53 (s, 1H), 8.02 (s, 1H), 7.44 (d, J=7.6 Hz, 2H), 7.21 (s, 1H), 7.08 (d, J=8.2 Hz, 2H), 6.72-6.61 (m, J=8.9 Hz, 2H), 6.16 (s, 1H), 5.97-5.79 (m, J=24.4, 7.5 Hz, 2H), 5.41-5.08 (m, 5H), 4.86 (d, J=12.5 Hz, 1H), 4.69-4.60 (m, 1H), 4.57 (s, 1H), 4.03 (t, J=6.7 Hz, 1H), 3.87 (s, 3H), 3.74 (td, J=9.6, 3.6 Hz, 1H), 2.43-2.09 (m, J=34.8, 19.4, 11.7 Hz, 3H), 1.76 (s, 3H), 1.43 (d, J=6.9 Hz, 3H), 1.30-1.21 (m, 3H), 0.97 (d, J=6.7 Hz, 3H), 0.92 (t, J=8.4 Hz, 3H), 0.84 (s, 9H), 0.23 (s, 3H), 0.12 (s, 3H).

(iv) (11S,11aS)-4-((2S,5S)-37-(2,5-dioxo-2,5-dihydro-1H-pyrrol-1-yl)-5-isopropyl-2-methyl-4,7,35-trioxo-10,13,16,19,22,25,28,31-octaoxa-3,6,34-triazaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (64)

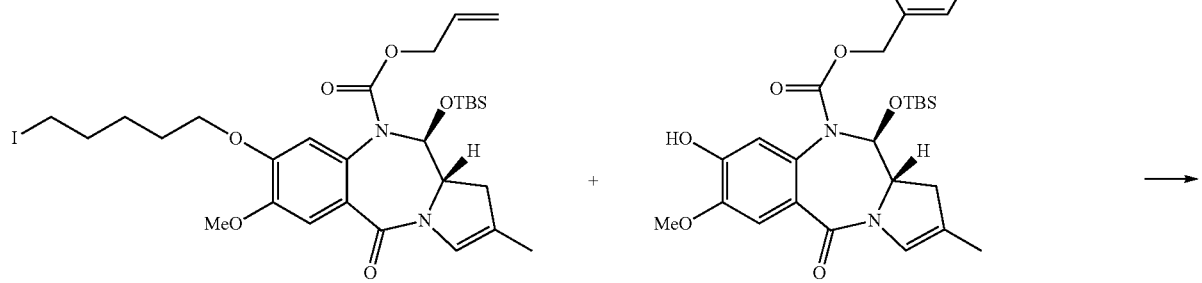

-continued
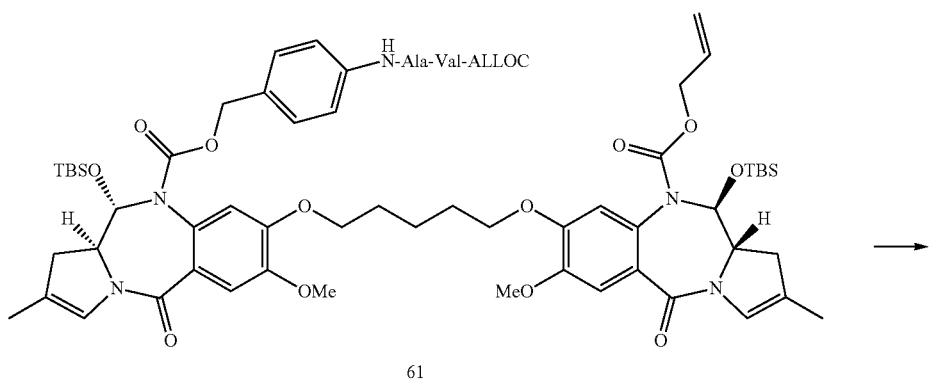
61
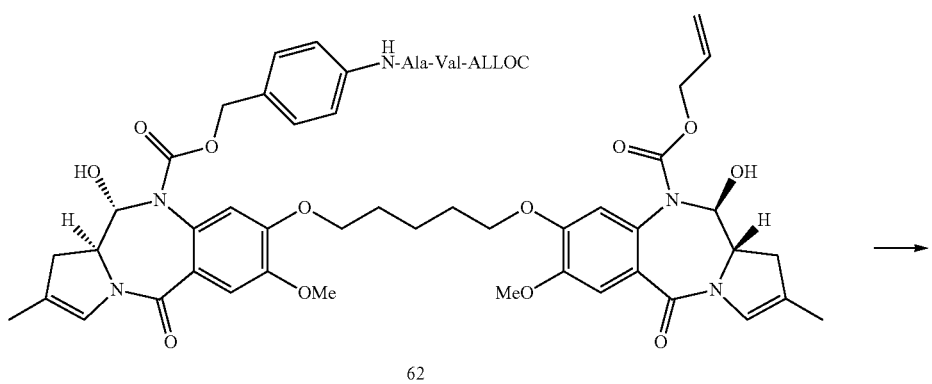
62
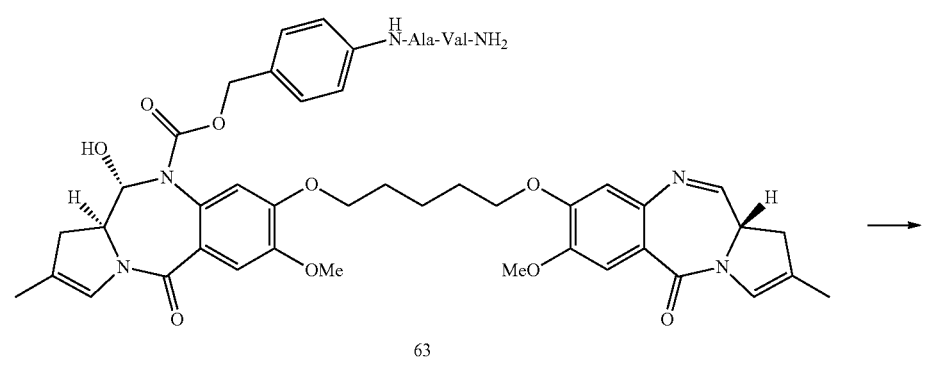
63
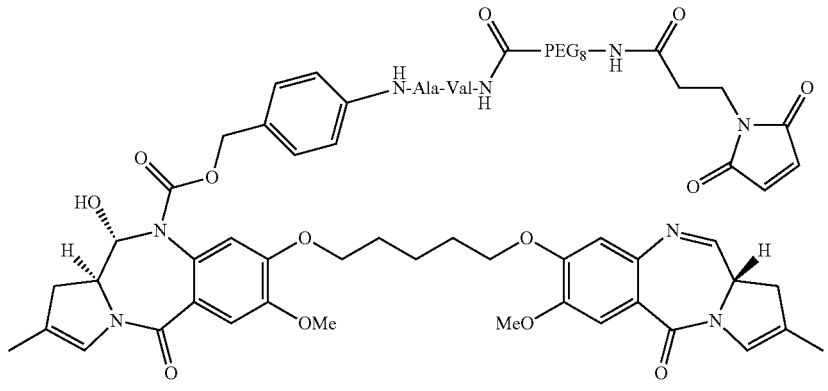
64

(a) (11S)-allyl 8-((5-(((11S)-10-(((4-(2-(1-((1-(allyloxy)-4-methyl-1,2-dioxopentan-3-yl)amino)-1-oxopropan-2-yl) hydrazinyl)benzyl)oxy)carbonyl)-11-((tert-butyldimethylsilyl)oxy)-7-methoxy-2-methyl-5-oxo-5,10,11,11a-tetrahydro-1H-benzo[e]pyrrolo[1,2-a][1,4]diazepin-8-yl)oxy)pentyl)oxy)-11-((tert-butyldimethylsilyl)oxy)-7-methoxy-2-methyl-5-oxo-11,11a-dihydro-1H-benzo[e]pyrrolo[1,2-a][1,4]diazepine-10(5H)-carboxylate (61)

Potassium carbonate (70 mg, 0.504 mmol, 1 eq) was added to a solution of 55 (370 mg, 0.552 mmol, 1.2 eq) and phenol 60 (400 mg, 0.504 mmol) in dry acetone (25 mL). The reaction was stirred 8 hours at 70° C. The LC/MS showed that all the starting material was not consumed, so the reaction was allowed to stir overnight at room temperature and stirred for an additional 2 hours the next day. Acetone was removed by rotary evaporation under reduced pressure. The resulting residue was subjected to flash column chromatography (silica gel; 80% ethyl acetate in hexane to 100% ethyl acetate). Pure fractions were collected and combined and excess eluent was removed by rotary evaporation under reduced pressure to give the product 61 (385 mg, 57%). LC/MS, 4.07 min (ES+) m/z (relative intensity) 1336.55 ([M+H]$^+$., 50).

(b) (11S)-allyl 8-((5-(((11S)-10-(((4-(2-(1-((1-(allyloxy)-4-methyl-1,2-dioxopentan-3-yl)amino)-1-oxopropan-2-yl) hydrazinyl)benzyl)oxy)carbonyl)-11-hydroxy-7-methoxy-2-methyl-5-oxo-5,10,11,11a-tetrahydro-1H-benzo[e]pyrrolo[1,2-a][1,4]diazepin-8-yl)oxy)pentyl)oxy)-11-hydroxy-7-methoxy-2-methyl-5-oxo-11,11a-dihydro-1H-benzo[e]pyrrolo[1,2-a][1,4]diazepine-10(5H)-carboxylate (62)

Tetra-n-butylammonium fluoride (1M, 0.34 mL, 0.34 mmol, 2 eq) was added to a solution of 61 (230 mg, 0.172 mmol) in dry tetrahydrofuran (3 mL). The starting material was totally consumed after 10 minutes. The reaction mixture was diluted with ethyl acetate (30 mL) and washed sequentially with water and brine. The organic phase was dried over magnesium sulphate filtered and excess ethyl acetate removed by rotary evaporation under reduced pressure. The resulting residue 62 was used as a crude mixture for the next reaction. LC/MS, 2.87 min (ES+) m/z (relative intensity) 1108.11 ([M+H]$^+$., 100).

(c) (11S)-4-(2-(1-((1-amino-3-methyl-1-oxobutan-2-yl)amino)-1-oxopropan-2-yl)hydrazinyl)benzyl 11-hydroxy-7-methoxy-8-((5-((7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (63)

Tetrakis(triphenylphosphine)palladium(0) (12 mg, 0.01 mmol, 0.06 eq) was added to a solution of crude 62 (0.172 mmol) and pyrrolidine (36 µL, 0.43 mmol, 2.5 eq) in dry dichloromethane (10 mL). The reaction mixture was stirred 20 minutes and diluted with dichloromethane and washed sequentially with saturated aqueous ammonium chloride and brine. The organic phase was dried over magnesium sulphate filtered and excess dichloromethane removed by rotary evaporation under reduced pressure. The resulting residue 63 was used as a crude mixture for the next reaction. LC/MS, 2.38 min (ES+) m/z (relative intensity) 922.16 ([M+H]$^+$., 40).

(d) (11S,11aS)-4-((2S,5S)-37-(2, 5-dioxo-2,5-dihydro-1H-pyrrol-1-yl)-5-isopropyl-2-methyl-4, 7,35-trioxo-10, 13,16, 19,22,25,28,31-octaoxa-3,6,34-triazaheptatriacontanamido)benzyl 11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-5-oxo-11,11a-dihydro-1H-benzo[e]pyrrolo[1,2-a][1,4]diazepine-10(5H)-carboxylate (64)

1-ethyl-3-(3'-dimethylaminopropyl)carbodiimide (EDCl, 33 mg, 0.172 mmol) was added to a solution of crude 63 (0.172 mmol) and Mal-(PEG)$_8$-acid (100 mg, 0.172 mmol) in dry dichloromethane (10 mL). The reaction was stirred for 2 hours and the presence of starting material was no longer observed by LC/MS. The reaction was diluted with dichloromethane and washed sequentially with water and brine. The organic phase was dried over magnesium sulphate filtered and excess dichloromethane removed by rotary evaporation under reduced pressure. The resulting residue was subjected to flash column chromatography (silica gel; 100% chloroform to 10% methanol in chloroform). Pure fractions were collected and combined and excess eluent was removed by rotary evaporation under reduced pressure to give 64 (E) (60 mg, 25% over 3 steps).

Example 8

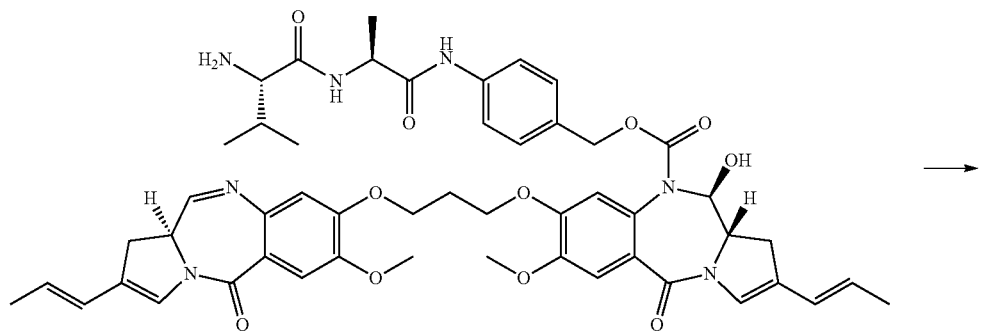

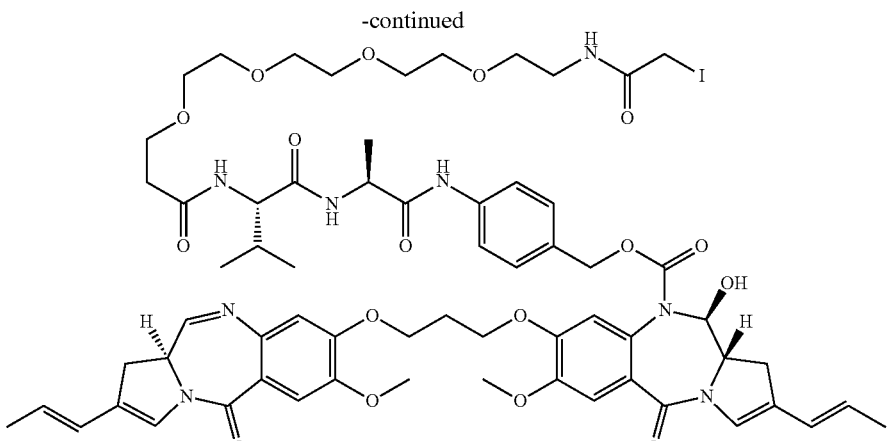

66

Compound 65 is compound 79 of WO 2011/130598

(11S)-4-(1-iodo-20-isopropyl-23-methyl-2,18,21-trioxo-6,9,12,15-tetraoxa-3,19,22-triazatetracosanamido)benzyl 11-hydroxy-7-methoxy-8-(3-((7-methoxy-5-oxo-2-((E)-prop-1-en-1-yl)-5,11a-dihydro-1H-benzo[e]pyrrolo[1,2-a][1,4]diazepin-8-yl)oxy)propoxy)-5-oxo-2-((E)-prop-1-en-1-yl)-11,11a-dihydro-1H-benzo[e]pyrrolo[1,2-a][1,4] diazepine-10(5H)-carboxylate (66)

N,N'-diisopropylcarbodiimide (DIC, 4.71 µL, 0.0304 mmol) was added to a solution of amine 65 (0.0276 mmol) and Iodo-(PEG)$_4$-acid (13.1 mg, 0.0304 mmol) in dry dichloromethane (0.8 mL). The reaction was stirred for 3 hours and the presence of starting material was no longer observed by LC/MS. The reaction mixture was directly loaded onto a thin-layer chromatography (TLC) plate and purified by prep-TLC (10% methanol in chloroform). Pure bands were scraped off the TLC plate, taken up in 10% methanol in chloroform, filtered and excess eluent removed by rotary evaporation under reduced pressure to give 66 (D) (20.9 mg, 56%). LC/MS, method 2, 3.08 min (ES+) m/z (relative intensity) 1361.16 ([M+H]$^+$, 100).

General Experimental Methods for Example 9

LCMS data were obtained using an Agilent 1200 series LC/MS with an Agilent 6110 quadrupole MS, with Electrospray ionisation. Mobile phase A—0.1% Acetic acid in water. Mobile Phase B—0.1% in acetonitrile. Flow rate of 1.00 ml/min. Gradient from 5% B rising up to 95% B over 3 minutes, remaining at 95% B for 1 minute and then back down to 5% B over 6 seconds. The total run time is 5 minutes. Column: Phenomenex Gemini-NX 3 µm C18, 30×2.00 mm. Chromatograms based on UV detection at 254 nm. Mass Spectra were achieved using the MS in positive mode. Proton NMR chemical shift values were measured on the delta scale at 400 MHz using a Bruker AV400. The following abbreviations have been used: s, singlet; d, doublet; t, triplet; q, quartet; m, multiplet; br, broad. Coupling constants are reported in Hz. Unless otherwise stated, column chromatography (by the flash procedure) were performed on Merck Kieselgel silica (Art. 9385). Mass spectroscopy (MS) data were collected using a Waters Micromass LCT instrument coupled to a Waters 2795 HPLC separations module. Thin Layer Chromatography (TLC) was performed on silica gel aluminium plates (Merck 60, F$_{254}$). All other chemicals and solvents were purchased from Sigma-Aldrich or Fisher Scientific and were used as supplied without further purification.

Optical rotations were measured on an ADP 220 polarimeter (Bellingham Stanley Ltd.) and concentrations (c) are given in g/100 mL. Melting points were measured using a digital melting point apparatus (Electrothermal). IR spectra were recorded on a Perkin-Elmer Spectrum 1000 FT IR Spectrometer. $^1$H and $^{13}$C NMR spectra were acquired at 300 K using a Bruker Avance NMR spectrometer at 400 and 100 MHz, respectively. Chemical shifts are reported relative to TMS ($\delta$=0.0 ppm), and signals are designated as s (singlet), d (doublet), t (triplet), dt (double triplet), dd (doublet of doublets), ddd (double doublet of doublets) or m (multiplet), with coupling constants given in Hertz (Hz). Mass spectroscopy (MS) data were collected using a Waters Micromass ZQ instrument coupled to a Waters 2695 HPLC with a Waters 2996 PDA. Waters Micromass ZQ parameters used were: Capillary (kV), 3.38; Cone (V), 35; Extractor (V), 3.0; Source temperature (° C.), 100; Desolvation Temperature (° C.), 200; Cone flow rate (L/h), 50; De-solvation flow rate (L/h), 250. High-resolution mass spectroscopy (HRMS) data were recorded on a Waters Micromass QTOF Global in positive W-mode using metal-coated borosilicate glass tips to introduce the samples into the instrument. Thin Layer Chromatography (TLC) was performed on silica gel aluminium plates (Merck 60, F$_{254}$), and flash chromatography utilised silica gel (Merck 60, 230-400 mesh ASTM). Except for the HOBt (NovaBiochem) and solid-supported reagents (Argonaut), all other chemicals and solvents were purchased from Sigma-Aldrich and were used as supplied without further purification. Anhydrous solvents were prepared by distillation under a dry nitrogen atmosphere in the presence of an appropriate drying agent, and were stored over 4 Å molecular sieves or sodium wire. Petroleum ether refers to the fraction boiling at 40-60° C.

General LC/MS conditions: The HPLC (Waters Alliance 2695) was run using a mobile phase of water (A) (formic acid 0.1%) and acetonitrile (B) (formic acid 0.1%). Gradient: initial composition 5% B over 1.0 min then 5% B to 95% B within 3 min. The composition was held for 0.5 min at 95% B, and then returned to 5% B in 0.3 minutes. Total gradient run time equals 5 min. Flow rate 3.0 mL/min, 400 µL was split via a zero dead volume tee piece which passes into the mass spectrometer. Wavelength detection range: 220

Example 9

(i) Key Intermediates

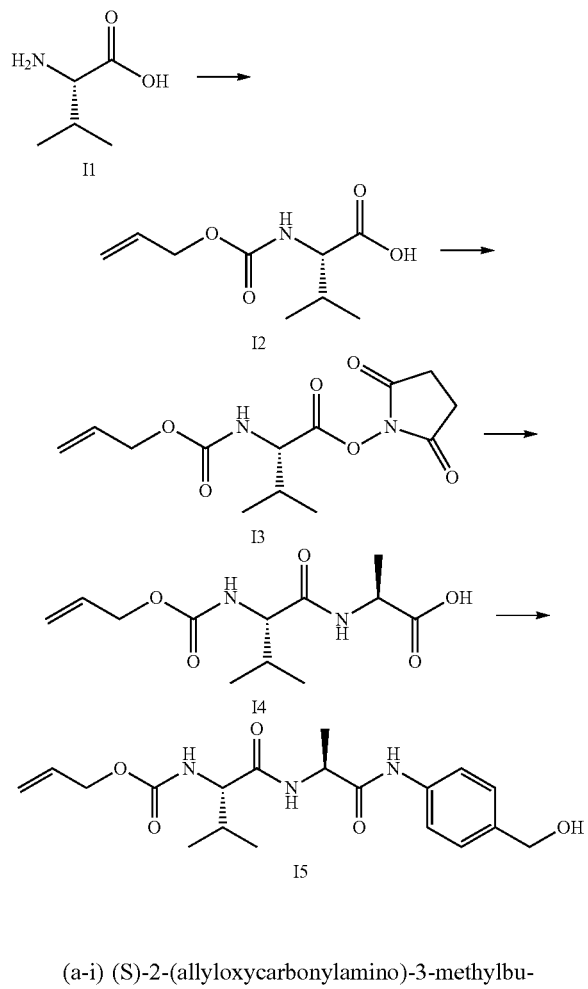

(a-i) (S)-2-(allyloxycarbonylamino)-3-methylbutanoic acid (I2)

Allyl chloroformate (36.2 ml, 340.59 mmol, 1.2 eq) was added dropwise to a stirred solution of L-valine (I1)(33.25 g, 283.82 mmol, 1.0 eq) and potassium carbonate (59.27 g, 425.74 mmol, 1.5 eq) in water (650 mL) and THF (650 mL). The reaction mixture was stirred at room temperature for 18 hours, then the solvent was concentrated under reduced pressure and the remaining solution extracted with diethyl ether (3×100 mL). The aqueous portion was acidified to pH 2 with conc. HCl and extracted with DCM (3×100 mL). The combined organics were washed with brine, dried over MgSO$_4$, filtered and concentrated under reduced pressure to afford the product as a colourless oil (57.1 g, assumed 100% yield). LC/MS (1.966 min (ES$^+$)), m/z: 202.1 [M+H]$^+$. $^1$H NMR (400 MHz, DMSO-d$_6$) δ 12.57 (br s, 1H), 7.43 (d, 1H, J=8.6 Hz), 5.96-5.86 (m, 1H), 5.30 (ddd, 1H, J=17.2, 3.4, 1.7 Hz), 5.18 (ddd, 1H, J=10.4, 2.9, 1.6 Hz), 4.48 (dt, 2H, J=5.3, 1.5 Hz), 3.85 (dd, 1H, J=8.6, 6.0 Hz), 2.03 (oct, 1H, J=6.6 Hz), 0.89 (d, 3H, J=6.4 Hz), 0.87 (d, 3H, J=6.5 Hz).

(a-ii) (S)-2,5-dioxopyrrolidin-1-yl 2-(allyloxycarbonylamino)-3-methylbutanoate (I3)

To a stirred solution of the protected acid 12 (60.6 g, 301.16 mmol, 1.0 eq) and N-hydroxysuccinimide (34.66 g, 301.16 mmol, 1.0 eq) in dry THF (800 mL) was added dicyclohexylcarbodiimide (62.14 g, 301.16 mmol, 1 eq). The reaction was stirred for 18 hours at room temperature. The reaction mixture was then filtered, the solid washed with THF and the combined filtrate was concentrated under reduced pressure. The residue was re-dissolved in DCM and left to stand at 0° C. for 30 minutes. The suspension was filtered and washed with cold DCM. Concentration of the filtrate under reduced pressure afforded the product as a viscous colourless oil (84.7 g, assumed 100% yield) which was used in the next step without further purification. LC/MS (2.194 min (ES$^+$)), m/z: 321.0 [M+Na]$^+$. $^1$H NMR (400 MHz, DMSO-d$_6$) δ 8.0 (d, 1H, J=8.3 Hz), 5.97-5.87 (m, 1H), 5.30 (ddd, 1H, J=17.2, 3.0, 1.7 Hz), 5.19 (ddd, 1H, J=10.4, 2.7, 1.4 Hz), 4.52 (dt, 2H, J=5.3, 1.4 Hz), 4.32 (dd, 1H, J=8.3, 6.6 Hz), 2.81 (m, 4H), 2.18 (oct, 1H, J=6.7 Hz), 1.00 (d, 6H, J=6.8 Hz),

(a-iii) (S)-2-((S)-2-(allyloxycarbonylamino)-3-methylbutanamido)propanoic acid (14)

A solution of succinimide ester 13(12.99 g, 43.55 mmol, 1.0 eq) in THF (50 mL) was added to a solution of L-alanine (4.07 g, 45.73 mmol, 1.05 eq) and NaHCO$_3$ (4.02 g, 47.90 mmol, 1.1 eq) in THF (100 mL) and H$_2$O (100 mL). The mixture was stirred at room temperature for 72 hours when the THF was removed under reduced pressure. The pH was adjusted to 3-4 with citric acid to precipitate a white gum. After extraction with ethyl acetate (6×150 mL), the combined organics were washed with H$_2$O (200 mL), dried over MgSO$_4$, filtered and concentrated under reduced pressure. Trituration with diethyl ether afforded the product as a white powder which was collected by filtration and washed with diethyl ether (5.78 g, 49%). LC/MS (1.925 min (ES$^+$)), m/z: 273.1 [M+H]$^+$. $^1$H NMR (400 MHz, DMSO-d$_6$) δ 12.47 (br s, 1H), 8.17 (d, 1H, J=6.8 Hz), 7.16 (d, 1H, J=9.0 Hz), 5.95-5.85 (m, 1H), 5.29 (dd, 1H, J=17.2, 1.7 Hz), 5.17 (dd, 1H, J=10.4, 1.5 Hz), 4.46 (m, 2H), 4.18 (quin, 1H, J=7.2 Hz), 3.87 (dd, 1H, J=9.0, 7.1 Hz), 1.95 (oct, 1H, J=6.8 Hz), 1.26 (d, 3H, J=7.3 Hz), 0.88 (d, 3H, J=6.8 Hz), 0.83 (d, 3H, J=6.8 Hz).

(a-iv) Allyl (S)-1-((S)-1-(4-(hydroxymethyl)phenylamino)-1-oxopropan-2-ylamino)-3-methyl-1-oxobutan-2-ylcarbamate (15)

EEDQ (5.51 g, 22.29 mmol, 1.05 eq) was added to a solution of p-aminobenzyl alcohol (2.74 g, 22.29 mmol, 1.05 eq) and acid 14 (5.78 g, 21.23 mmol, 1 eq) in dry THF (100 mL). and stirred at room temperature for 72 hours. The reaction mixture was then concentrated under reduced pressure and the resulting brown solid was triturated with diethyl ether and filtered with subsequent washing with an excess of diethyl ether to afford the product as an off-white solid (7.1 g, 88%). LC/MS (1.980 min (ES$^+$)), m/z: 378.0 [M+H]$^+$. $^1$H NMR (400 MHz, DMSO-d$_6$) δ 9.89 (br s, 1H), 8.13 (d, 1H, J=7.0 Hz), 7.52 (d, 2H, J=8.5 Hz), 7.26 (m, 1H), 7.23 (d, 2H, J=8.5 Hz), 5.91 (m, 1H), 5.30 (m, 1H), 5.17 (m, 1H), 4.46 (m, 2H), 5.09 (t, 1H, J=5.6 Hz), 4.48 (m, 2H), 4.42 (m, 3H), 3.89 (dd, 1H, J=8.6, 6.8 Hz), 1.97 (m, 1H), 1.30 (d, 3H, J=7.1 Hz), 0.88 (d, 3H, J=6.8 Hz), 0.83 (d, 3H, J=6.7 Hz).

(b)

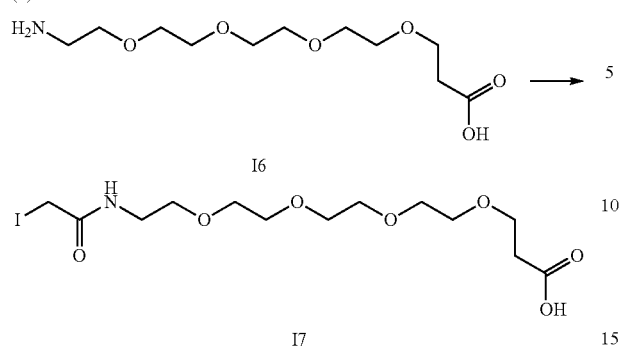

1-iodo-2-oxo-6,9,12,15-tetraoxa-3-azaoctadecan-18-oic acid (I7)

A solution of iodoacetic anhydride (0.250 g, 0.706 mmol, 1.1 eq) in dry DCM (1 mL) was added to amino-PEG$_{(4)}$-acid I6 (0.170 g, 0.642 mmol, 1.0 eq) in DCM (1 mL). The mixture was stirred in the dark at room temperature overnight. The reaction mixture was washed with 0.1 M HCl, water, dried over MgSO$_4$, filtered and concentrated under reduced pressure. The residue was purified by flash chromatography (silica gel, 3% MeOH and 0.1% formic acid in chloroform to 10% MeOH and 0.1% formic acid in chloroform) to afford the product as an orange oil (0.118 g, 42%). LC/MS (1.623 min (ES$^+$)), m/z: 433.98 [M+H]$^+$. $^1$H NMR (400 MHz, CDCl$_3$) δ 8.069 (s, 1H), 7.22 (br s, 1H), 3.79 (t, 2H, J=5.8 Hz), 3.74 (s, 2H), 3.72-3.58 (m, 14H), 3.50-3.46 (m, 2H), 2.62 (t, 2H, J=5.8 Hz).

(ii) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (74)

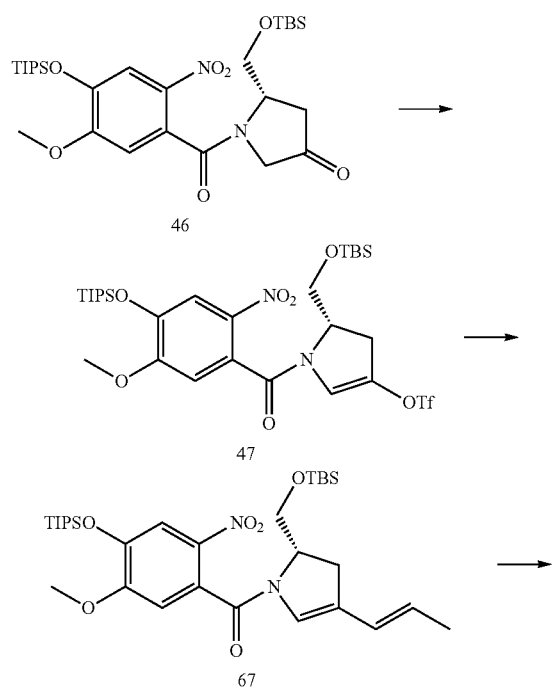

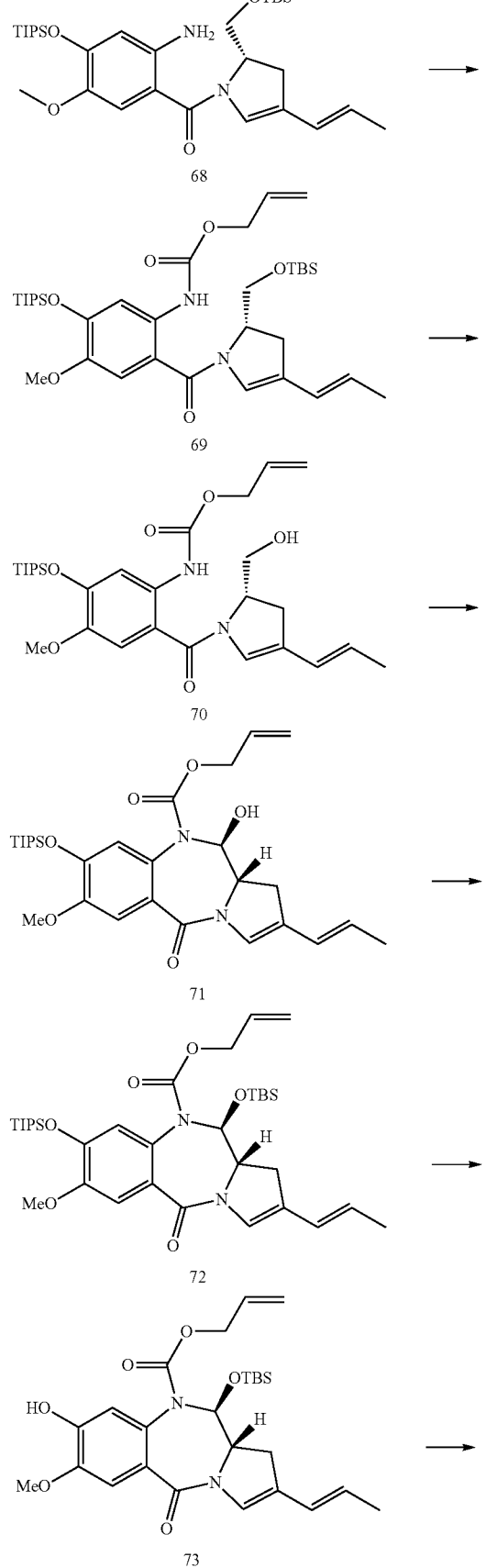

-continued

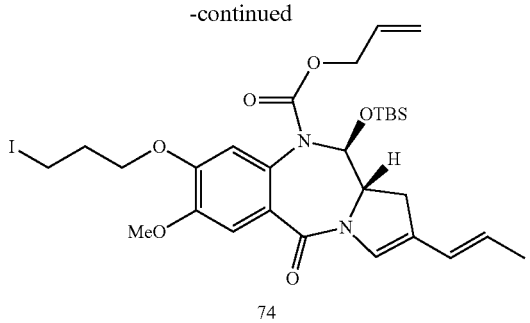

74

(a) (S)-5-((tert-butyldimethylsilyloxy)methyl)-1-(5-methoxy-2-nitro-4-(triisopropylsilyloxy)benzoyl)-4,5-dihydro-1H-pyrrol-3-yl trifluoromethanesulfonate (47)

Triflic anhydride (28.4 g, 100.0 mmol, 3.0 eq) was added dropwise, over 25 mins, to a vigorously stirred solution of the ketone 46 (19.5 g, 30.0 mmol, 1.0 eq) in DCM (550 mL) containing 2,6-lutidine (14.4 g, 130.0 mmol, 4.0 eq) at −50° C. The reaction mixture was stirred for 1.5 hours when LC/MS indicated complete reaction. The organic phase was washed successively with water (100 mL), saturated sodium bicarbonate (150 mL), brine (50 mL), and the organic phase was dried over MgSO$_4$, filtered and concentrated under reduced pressure. The residue was purified by flash chromatography (silica gel, 90/10 v/v n-hexane/EtOAc) to afford the product as a pale yellow oil (19.5 g, 82%). LC/MS (4.391 min (ES$^+$)), m/z: 713.25 [M+H]$^+$. $^1$H NMR (400 MHz, CDCl$_3$) δ 7.68 (s, 1H), 6.72 (s, 1H), 6.02 (t, 1H, J=1.9 Hz), 4.75 (m, 1H), 4.05 (m, 2H), 3.87 (s, 3H), 3.15 (ddd, 1H, J=16.2, 10.3, 2.3 Hz), 2.96 (ddd, 1H, J=16.2, 4.0, 1.6 Hz), 1.28-1.21 (m, 3H), 1.07 (d, 18H, J=7.2 Hz), 0.88 (s, 9H), 0.09 (s, 3H), 0.08 (s, 3H).

(b) (S,E)-(2-((tert-butyldimethylsilyloxy)methyl)-4-(prop-1-enyl)-2,3-dihydro-1H-pyrrol-1-yl)(5-methoxy-2-nitro-4-(triisopropylsilyloxy)phenyl)methanone (67)

Tetrakis(triphenylphosphine)palladium(0) (0.41 g, 0.35 mmol, 0.03 eq) was added to a mixture of the triflate 47 (8.4 g, 11.8 mmol, 1.0 eq), E-1-propene-1-ylboronic acid (1.42 g, 16.5 mmol, 1.4 eq) and potassium phosphate (5.0 g, 23.6 mmol, 2.0 eq) in dry dioxane (60 mL) under a nitrogen atmosphere. The mixture was stirred at 25° C. for 120 mins when LC/MS indicated complete reaction. Ethyl acetate (120 mL) and water (120 mL) were added, the organic phase was removed, washed with brine (20 mL), dried over MgSO$_4$, filtered and concentrated under reduced pressure. The residue was purified by flash chromatography (silica gel, 95/5 v/v n-hexane/EtOAc to 90/10 v/v n-hexane/EtOAc) to afford the product as a yellow foam (4.96 g, 70%). LC/MS (4.477 min (ES$^+$)), m/z: 605.0 [M+H]$^+$. $^1$H NMR (400 MHz, CDCl$_3$) δ 7.67 (s, 1H), 6.74 (s, 1H), 5.93 (d, 1H, J=15.4 Hz), 5.67 (s, 1H), 4.65 (m, 1H), 4.04 (m, 2H), 3.86 (s, 3H), 2.85 (m, 1H), 2.71 (m, 1H), 1.72 (dd, 3H, J=6.8, 1.0 Hz), 1.30-1.22 (m, 3H), 1.07 (d, 18H, J=7.2 Hz), 0.87 (s, 9H), 0.08 (s, 3H), 0.07 (s, 3H).

(c) (S,E)-(2-amino-5-methoxy-4-(triisopropylsilyloxy)phenyl) (2-((tert-butyldimethylsilyloxy)methyl)-4-(prop-1-enyl)-2,3-dihydro-1H-pyrrol-1-yl) methanone (68)

Zinc dust (22.0 g, 0.33 mol, 37 eq) was added, in portions over 20 mins, to a solution of the propenyl intermediate 67 (5.5 g, 9.1 mmol, 1.0 eq) in 5% v/v formic acid/ethanol (55 mL), using an ice bath to maintain the temperature between 25-30° C. After 30 mins, the reaction mixture was filtered through a short bed of Celite®. The Celite® was washed with ethyl acetate (65 mL) and the combined organics were washed successively with water (35 mL), saturated sodium bicarbonate (35 mL) and brine (10 mL). The organic phase was dried over MgSO$_4$, filtered and concentrated under reduced pressure. The residue was purified by flash chromatography (silica gel, 90/10 v/v n-hexane/EtOAc) to afford the product as a pale yellow oil (3.6 g, 69.0%). LC/MS (4.439 min (ES$^+$)), m/z: 575.2 [M+H]$^+$. $^1$H NMR (400 MHz, CDCl$_3$) b 6.75 (m, 1H), 6.40 (br s, 1H), 6.28 (m, 1H), 6.11 (d, 1H, J=15.4 Hz), 5.53 (m, 1H), 4.67 (m, 1H), 4.36 (m, 2H), 3.93 (br s, 1H), 3.84 (br s, 1H), 3.73 (s, 3H), 2.86 (dd, 1H, J=15.7, 10.4 Hz), 2.73 (dd, 1H, J=15.9, 4.5 Hz), 1.80 (dd, 3H, J=6.8, 1.3 Hz), 1.35-1.23 (m, 3H), 1.12 (d, 18H, J=7.3 Hz), 0.89 (s, 9H), 0.08 (s, 3H), 0.07 (s, 3H).

(d) (S,E)-allyl 2-(2-((tert-butyldimethylsilyloxy)methyl)-4-(prop-1-enyl)-2,3-dihydro-1H-pyrrole-1-carbonyl)-4-methoxy-5-(triisopropylsilyloxy)phenylcarbamate (69)

Allyl chloroformate (0.83 g, 6.88 mmol, 1.1 eq) was added to a solution of the amine 68 (3.6 g, 6.26 mmol, 1.0 eq) in dry DCM (80 mL) containing dry pyridine (1.09 g, 13.77 mmol, 2.2 eq) at −78° C. The dry ice was removed and the reaction mixture allowed to warm to room temperature. After stirring for a further 15 minutes, LC/MS indicated complete reaction. The organic phase was washed successively with 0.01N HCl (50 mL), saturated sodium bicarbonate (50 mL), brine (10 mL), dried over MgSO$_4$, filtered and concentrated under reduced pressure to leave a pale yellow oil which was used in the next step without further purification (4.12 g, assumed 100% yield). LC/MS (4.862 min (ES$^+$)), m/z: 659.2 [M+H]$^+$.

(e) (S,E)-allyl 2-(2-(hydroxymethyl)-4-(prop-1-enyl)-2,3-dihydro-1H-pyrrole-1-carbonyl)-4-methoxy-5-(triisopropylsilyloxy)phenylcarbamate (70)

The crude intermediate 69 (assumed 100% yield, 4.12 g, 6.25 mmol, 1.0 eq) was dissolved in a mixture of acetic acid (70 mL), methanol (10 mL), THF (10 mL) and water (20 mL) and allowed to stir at room temperature. After 6 hours the reaction mixture was diluted with ethyl acetate (500 mL) and washed successively with water (2×500 mL), saturated sodium bicarbonate (300 mL) and brine (50 mL). The organic phase was dried over MgSO$_4$, filtered and concentrated under reduced pressure. The residue was purified by flash chromatography (silica gel, 1/99 v/v methanol/DCM to 5/95 v/v methanol/DCM) to afford the product as a yellow oil and a further 1 g of unreacted starting material was recovered. This material was subjected to the same reaction conditions as above, but was left stirring for 16 h. After work up and purification, additional product was isolated (2.7 g, 79%, 2 steps) LC/MS (3.742 min (ES+)), m/z: 545.2 [M+H]$^+$. $^1$H NMR (400 MHz, CDCl$_3$) δ 8.38 (m, 1H), 7.72 (m, 1H), 6.81 (s, 1H), 6.37 (m, 1H), 6.10 (d, 1H, J=15.8 Hz), 5.97 (m, 1H), 5.53 (m, 1H), 5.36 (ddd, 1H, J=17.2, 3.1, 1.5 Hz), 5.25 (ddd, 1H, J=10.4, 2.5, 1.3 Hz), 4.78 (m, 1H), 4.65 (dt, 2H, J=5.7, 1.3 Hz), 3.84 (m, 3H), 3.79 (s, 3H), 3.04 (dd, 1H, J=16.7, 10.5 Hz), 2.40 (dd, 1H, J=16.0, 4.5 Hz), 1.82 (dd, 3H, J=6.8, 1.0 Hz), 1.36-1.26 (m, 3H), 1.14 (d, 18H, J=7.3 Hz).

(f) (11S,11aS)-allyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (71)

Dry dimethyl sulfoxide (1.16 g, 14.87 mmol, 3.0 eq) was added dropwise to a solution of oxalyl chloride (0.94 g, 7.43 mmol, 1.5 eq) in DCM (25 mL) at −78° C. under an atmosphere of nitrogen. Maintaining the temperature at −78° C., after 10 mins a solution of the primary alcohol 70 (2.7 g, 4.96 mmol, 1.0 eq) in DCM (20 mL) was added dropwise. After a further 15 mins, dry triethylamine (2.5 g, 24.78 mmol, 5.0 eq) was added, and the reaction mixture allowed to warm to room temperature. The reaction mixture was washed successively with cold 0.1N HCl (50 mL), saturated sodium hydrogen carbonate (50 mL) and brine (10 mL) and the organic layer was dried over MgSO$_4$, filtered and concentrated under reduced pressure to afford the product as a yellow oil which was used in the next step without further purification (2.68 g, assumed 100% yield). LC/MS (3.548 min (ES+)), m/z: 543.2 [M+H]$^+$.

(g) (11S,11aS)-ally 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (72)

Tert-butyldimethylsilyltrifluoromethane sulfonate (3.93 g, 14.87 mmol, 3.0 eq) was added to a solution of the carbinolamine 71 (assumed 100% yield, 2.68 g, 4.96 mmol, 1.0 eq) and 2,6-lutidine (2.12 g, 19.83 mmol, 4.0 eq) in dry DCM (40 mL) at 0° C. under an atmosphere of nitrogen. After 10 minutes, the reaction mixture was allowed to warm to room temperature and stirred for a further 60 minutes. The organic phase was washed successively with water (10 mL), saturated sodium bicarbonate (10 mL) and brine (5 mL), dried over MgSO$_4$, filtered and concentrated under reduced pressure. The residue was purified by flash chromatography (silica gel, chloroform to 2/98 v/v Methanol/chloroform) to afford the product as a yellow oil (2.0 g, 63%, 2 steps). LC/MS (4.748 min (ES$^+$)), m/z: 657.2 [M+H]$^+$. $^1$H NMR (400 MHz, CDCl$_3$) δ 7.19 (s, 1H), 6.86 (m, 1H), 6.66 (s, 1H), 6.22 (d, 1H, J=15.4 Hz), 5.81 (d, 1H, J=8.8 Hz), 5.78 (m, 1H), 5.48 (m, 1H), 5.11 (d, 1H, J=5.0 Hz), 5.08 (m, 1H), 4.58 (dd, 1H, J=13.4, 5.4 Hz), 4.35 (dd, 1H, J=13.2, 5.7 Hz), 3.83 (s, 3H), 3.76 (s, 1H), 3.00 (dd, 1H, J=15.6, 11.0 Hz), 2.53 (m, 1H), 1.81 (dd, 3H, J=6.8, 0.9 Hz), 1.30-1.18 (m, 3H), 1.08 (d, 9H, J=2.3 Hz), 1.06 (d, 9H, J=2.3 Hz), 0.86 (s, 9H), 0.25 (s, 3H), 0.18 (s, 3H).

(h) (11S,11aS)-allyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (73)

Lithium acetate dihydrate (0.31 g, 3.04 mmol, 1.0 eq) was added to a solution of the diazepine 72 (2.0 g, 3.04 mmol, 1.0 eq) in wet DMF (20 mL) at 25° C. and stirred for 4 hours. The reaction mixture was diluted with ethyl acetate (200 mL) and washed successively with 0.1M citric acid (50 mL, pH 3), water (50 mL) and brine (10 mL), dried over MgSO$_4$, filtered and concentrated under reduced pressure. The residue was purified by flash chromatography (silica gel, 50/50 v/v n-hexane/EtOAc to 25/75 v/v n-hexane/EtOAc) to afford the product as a pale yellow solid (0.68 g, 45%). LC/MS (3.352 min (ES$^+$)), m/z: 501.1 [M+H]$^+$. $^1$H NMR (400 MHz, CDCl$_3$) δ 7.02 (s, 1H), 6.66 (m, 1H), 6.53 (s, 1H), 6.03 (d, 1H, J=15.5 Hz), 5.80 (s, 1H), 5.63 (d, 1H, J=8.9 Hz), 5.55 (m, 1H), 5.29 (m, 1H), 4.87 (m, 2H), 4.39 (dd, 1H, J=13.5, 4.2 Hz), 4.20 (dd, 1H, J=13.2, 5.7 Hz), 3.73 (s, 3H), 3.59 (m, 1H), 2.81 (dd, 1H, J=16.1, 10.5 Hz), 2.35 (d, 1H, J=15.7 Hz), 1.61 (d, 3H, J=6.4 Hz), 0.67 (s, 9H), 0.05 (s, 3H), 0.00 (s, 3H).

(i) (11S,11aS)-allyl 11-(tert-butyldimethylsilyloxy)-8-(3-iodopropoxy)-7-methoxy-5-oxo-2-((E)-prop-1-enyl)-11,11a-dihydro-1H-benzo[e]pyrrolo[1,2-a][1,4]diazepine-10(5H)-carboxylate (74)

Diiodopropane (0.295 g, 1.00 mmol, 5.0 eq) and potassium carbonate (0.028 g, 0.20 mmol, 1.0 eq) were added to a solution of the phenol 33 (0.100 g, 0.020 mmol, 1.0 eq) in dry acetone (5 mL). The reaction mixture was heated at 60° C. for 6 hours when LC/MS showed complete reaction. The reaction mixture was concentrated to dryness under reduced pressure and the residue was purified by flash chromatography (silica gel, 75/25 v/v n-hexane/EtOAc to 50/50 v/v n-hexane/EtOAc) to afford the product as a colourless oil (0.074 g, 56%). LC/MS (3.853 min (ES$^+$)), m/z: 669.0 [M+H]$^+$. $^1$H NMR (400 MHz, CDCl$_3$) δ 7.26 (s, 1H), 6.90 (s, 1H), 6.68 (s, 1H), 6.24 (d, 1H, J=15.3 Hz), 5.87 (d, 1H, J=8.9 Hz), 5.78 (m, 1H), 5.53 (m, 1H), 5.12 (m, 2H), 4.65 (m, 2H), 4.41 (m, 1H), 4.11 (m, 1H), 3.93 (s, 3H), 3.81 (m, 1H), 3.40 (t, 2H, J=6.7 Hz), 3.05 (dd, 1H, J=16.3, 10.1 Hz), 2.57 (m, 1H), 2.34 (m, 2H), 1.84 (d, 3H, J=6.6 Hz), 0.92 (s, 9H), 0.28 (s, 3H), 0.26 (s, 3H).

(iii) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate 79)

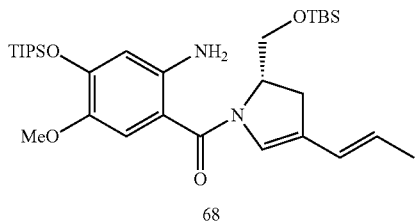

68

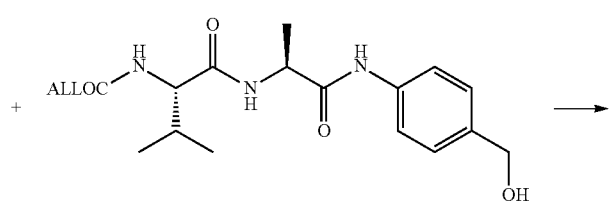

I5

-continued
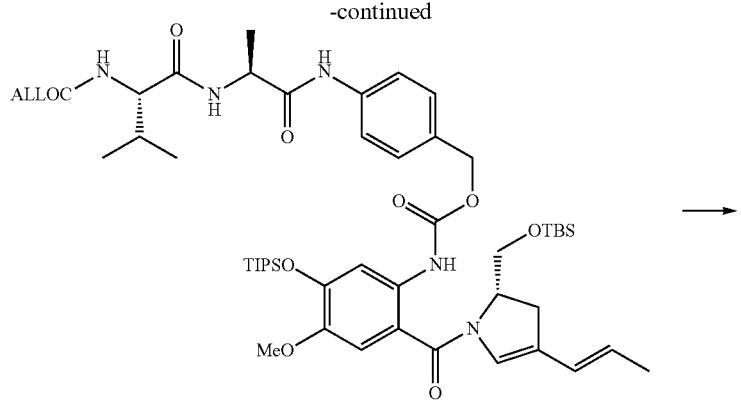
75
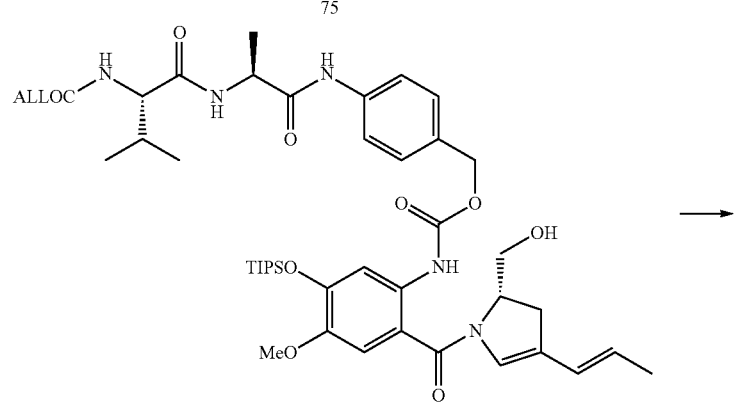
76
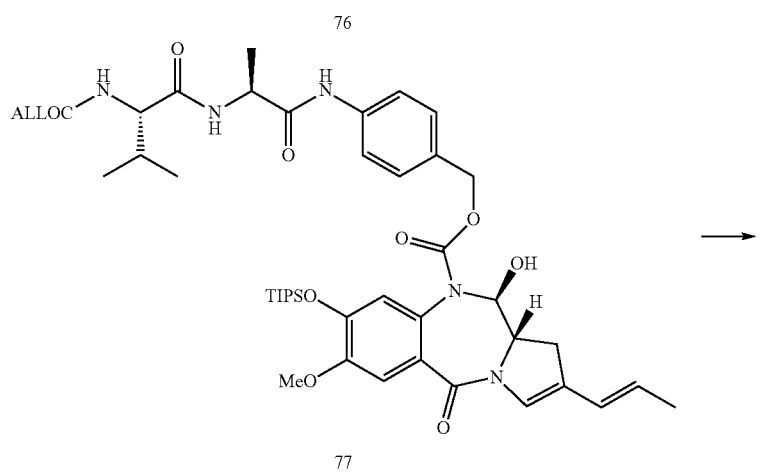
77
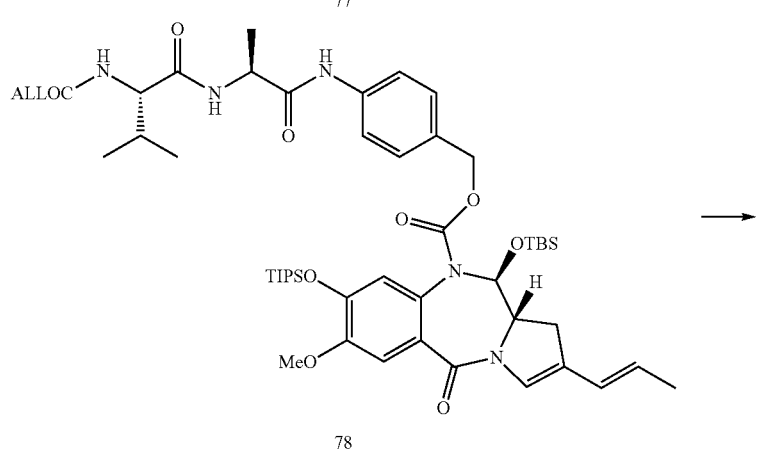
78

-continued

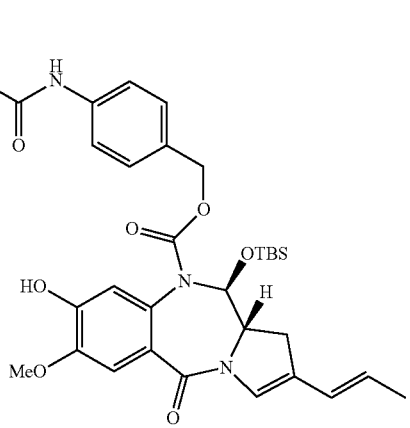

79

(a) Allyl ((S)-1-(((S)-1-((4-(((((2-((S)-2-(((tert-bu-tyldimethylsilyl)oxy)methyl)-4-((E)-prop-1-en-1-yl)-2,3-dihydro-1H-pyrrole-1-carbonyl)-4-methoxy-5-((triisopropylsilyl)oxy)phenyl) carbamoyl)oxy)methyl)phenyl)amino)-1-oxopropan-2-yl)amino)-3-methyl-1-oxobutan-2-yl)carbamate (75)

Triethylamine (0.256 mL, 1.84 mmol, 2.2 eq) was added to a stirred solution of the amine 68 (0.480 g, 0.835 mmol, 1.0 eq) and triphosgene (0.089 g, 0.301 mmol, 0.36 eq) in dry THF (15 mL) at 5° C. (ice bath). The progress of the isocyanate reaction was monitored by periodically removing aliquots from the reaction mixture and quenching with methanol and performing LCMS analysis. Once the isocyanate reaction was complete a solution of Alloc-Val-Ala-PABOH 15 (0.473 g, 1.25 mmol, 1.5 eq) and triethylamine (0.174 mL, 1.25 mmol, 1.5 eq) in dry THF (10 mL) was rapidly added by injection to the freshly prepared isocyanate. The reaction was allowed to stir at 40° C. for 4 hours followed by stirring at room temperature overnight. The mixture was concentrated under reduced pressure, and purified by flash chromatography (silica gel, 20/80 v/v n-hexane/EtOAc to 50/50 v/v n-hexane/EtOAc, then 1/99 v/v DCM/MeOH to 5/95 v/v DCM/MeOH) to afford the product as a yellow solid (0.579 g, 71%). LC/MS (4.468 min (ES$^+$)), m/z: 978.55 [M+H]$^+$. $^1$H NMR (400 MHz, CDCl$_3$) δ 8.63 (br s, 1H), 8.42 (s, 1H), 7.78 (br s, 1H), 7.53 (d, 2H, J=8.1 Hz), 7.31 (d, 2H, J=8.6 Hz), 6.76 (s, 1H), 6.59 (d, 1H, J=7.6 Hz), 6.36 (br s, 1H), 6.04 (d, 1H, J=15.9 Hz), 5.90 (m, 1H), 5.55 (m, 1H), 5.33-5.21 (m, 3H), 5.10 (s, 2H), 4.66 (m, 2H), 4.57 (dd, 2H, J=5.6, 1.0 Hz), 3.98 (dd, 1H, J=7.3, 6.8 Hz), 3.90 (m, 1H), 3.81 (m, 1H), 3.78 (s, 3H), 2.82 (dd, 1H, J=15.4, 9.6 Hz), 2.72 (dd, 1H, J=15.9, 3.5 Hz), 2.17 (m, 1H), 1.78 (dd, 3H, J=6.5, 0.8 Hz), 1.46 (d, 3H, J=7.1 Hz), 1.29 (m, 3H), 1.11 (d, 18H, J=7.1 Hz), 0.97 (d, 3H, J=6.8 Hz), 0.92 (d, 3H, J=6.8 Hz), 0.83 (s, 9H), 0.04 (s, 3H), 0.01 (s, 3H).

(b) Allyl ((S)-1-(((S)-1-((4-((((2-((S)-2-(hydroxymethyl)-4-((E)-prop-1-en-1-yl)-2,3-dihydro-1H-pyrrole-1-carbonyl)-4-methoxy-5-((triisopropylsilyl)oxy)phenyl) carbamoyl)oxy)methyl)phenyl)amino)-1-oxopropan-2-yl)amino)-3-methyl-1-oxobutan-2-yl)carbamate (76)

The silyl ether 75 (1.49 g, 1.52 mmol, 1.0 eq) was dissolved in a 7:1:1:2 mixture of acetic acid/methanol/tetrahydrofuran/water (14:2:2:4 mL) and allowed to stir at room temperature. After 2 hours the reaction was diluted with EtOAc (100 mL), washed sequentially with water, aq. sodium bicarbonate then brine. The organic phase was then dried over MgSO$_4$, filtered and concentrated under reduced pressure. The residue was purified by flash chromatography (silica gel, 100/0 then 99/1 to 92/8 v/v DCM/MeOH) to afford the product as an orange solid (1.2 g, 92%). LC/MS (3.649 min (ES$^+$)), m/z: 865.44 [M+H]$^+$. $^1$H NMR (400 MHz, CDCl$_3$) δ 8.44 (s, 1H), 8.35 (s, 1H), 7.69 (br s, 1H), 7.53 (d, 2H, J=8.7 Hz), 7.32 (d, 2H, J=8.3 Hz), 6.78 (s, 1H), 6.56 (m, 2H), 6.32 (br s, 1H), 6.05 (d, 1H, J=14.9 Hz), 5.90 (m, 1H), 5.56 (m, 1H), 5.30 (m, 2H), 5.22 (m, 1H), 5.10 (d, 2H, J=3.1 Hz), 4.73 (m, 1H), 4.64 (m, 1H), 4.57 (d, 2H, J=5.8 Hz), 4.01 (m, 1H), 3.79 (m, 2H), 3.76 (s, 3H), 2.98 (dd, 1H, J=16.3, 10.2 Hz), 2.38 (dd, 1H, J=16.6, 4.1 Hz), 2.16 (m, 1H), 1.78 (dd, 3H, J=6.8, 0.9 Hz), 1.46 (d, 3H, J=7.1 Hz), 1.29 (m, 3H), 1.11 (d, 18H, J=7.4 Hz), 0.97 (d, 3H, J=6.7 Hz), 0.92 (d, 3H, J=6.8 Hz).

(c) (11S,11aS)-4-((S)-2-((S)-2-(allyloxycarbonylamino)-3-methylbutanamido) propanamido)benzyl 11-hydroxy-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (77)

Dry dimethyl sulfoxide (0.180 g, 2.3 mmol, 3.0 eq) was added dropwise to a solution of oxalyl chloride (0.147 g, 1.1 mmol, 1.5 eq) in DCM (10 mL) at −78° C. under an atmosphere of nitrogen. Maintaining the temperature at −78° C., after 20 minutes, a solution of the primary alcohol 76 (0.666 g, 0.77 mmol, 1.0 eq) in DCM (10 mL) was added dropwise. After a further 15 minutes, dry triethylamine (0.390 g, 3.85 mmol, 5.0 eq) was added, and the reaction mixture allowed to warm to room temperature. The reaction mixture was washed successively with cold 0.1N HCl (10 mL), saturated sodium hydrogen carbonate (10 mL) and brine (5 mL). The organic layer was then dried over MgSO$_4$, filtered and concentrated under reduced pressure. The residue was then purified by flash chromatography (silica gel, 50/50 v/v n-hexane/EtOAc to 25/75 v/v n-hexane/EtOAc) to afford the product as a white solid (0.356 g, 54%). LC/MS (3.487 min (ES$^+$)), m/z: 862.2 [M+H]$^+$. $^1$H NMR (400 MHz, CDCl$_3$) δ 8.34 (br s, 1H), 7.47 (d, 2H, J=7.6 Hz), 7.17 (s, 1H), 7.14 (d, 2H, J=7.5 Hz), 6.86 (br s, 1H), 6.65 (br s, 1H), 6.42 (d, 1H, J=7.6 Hz), 6.22 (d, 1H, J=14.4 Hz), 5.80 (m, 1H), 5.40 (m, 1H), 5.53 (m, 1H), 5.32 (m, 1H), 5.21 (d, 2H, J=9.6 Hz), 5.06 (d, 1H, J=12.3 Hz), 4.90 (m, 1H), 4.58 (m, 3H), 3.98 (m, 1H), 3.84 (m, 1H), 3.81 (s, 3H), 3.50 (m, 1H), 3.05 (dd, 1H, J=16.0, 10.3 Hz), 2.76 (m, 1H), 2.15 (m, 1H), 1.80 (dd, 3H, J=6.7, 0.8 Hz), 1.44 (d, 3H, J=7.1 Hz), 1.16 (m, 3H), 1.01 (d, 18H, J=6.6 Hz), 0.96 (d, 3H, J=6.8 Hz), 0.92 (d, 3H, J=6.8 Hz).

(d) (11S,11aS)-4-((S)-2-((S)-2-(allyloxycarbonylamino)-3-methylbutanamido)propanamido)benzyl 11-(tert-butyldimethylsilyloxy)-7-methoxy-5-oxo-2-((E)-prop-1-enyl)-8-(triisopropylsilyloxy)-11,11a-dihydro-1H-benzo[e]pyrrolo[1,2-a][1,4]diazepine-10(5H)-carboxylate (78)

Tert-butyldimethylsilyltrifluoromethane sulfonate (0.46 g, 1.74 mmol, 3.0 eq) was added to a solution of secondary alcohol 77 (0.5 g, 0.58 mmol, 1.0 eq) and 2,6-lutidine (0.25 g, 2.32 mmol, 4.0 eq) in dry DCM (10 mL) at 0° C. under an atmosphere of nitrogen. After 10 minutes, the reaction mixture was allowed to warm to room temperature and stirred for a further 120 mins. The organic phase was then washed successively with water (10 mL), saturated sodium bicarbonate (10 mL) and brine (5 mL), dried over $MgSO_4$, filtered and concentrated under reduced pressure. The residue was purified by flash chromatography (silica gel, 50/50 v/v n-hexane/EtOAc) to afford the product as a white solid (0.320 g, 57%). LC/MS (4.415 min (ES$^+$)), m/z: 976.52 [M+H]$^+$. $^1$H NMR (400 MHz, CDCl$_3$) δ 8.31 (br s, 1H), 7.48 (d, 2H, J=8.0 Hz), 7.21 (s, 1H), 7.14 (d, 2H, J=8.3 Hz), 6.89 (s, 1H), 6.65 (s, 1H), 6.38 (d, 1H, J=7.3 Hz), 6.25 (d, 1H, J=14.6 Hz), 5.93 (m, 1H), 5.85 (d, 1H, J=8.8 Hz), 5.50 (m, 1H), 5.34 (m, 1H), 5.24 (m, 2H), 5.15 (d, 1H, J=12.5 Hz), 4.86 (d, 1H, J=12.2 Hz), 4.62 (m, 3H), 4.01 (m, 1H), 3.86 (s, 3H), 3.78 (m, 1H), 3.04 (m, 1H), 2.56 (m, 1H), 2.20 (m, 1H), 1.84 (dd, 3H, J=6.6, 0.7 Hz), 1.48 (d, 3H, J=6.8 Hz), 1.20 (m, 3H), 1.05 (d, 9H, J=2.9 Hz), 1.03 (d, 9H, J=2.9 Hz), 0.99 (d, 3H, J=6.8 Hz), 0.95 (d, 3H, J=6.8 Hz), 0.88 (s, 9H), 0.27 (s, 3H), 0.14 (s, 3H).

(e) (11S,11aS)-4-((S)-2-((S)-2-(allyloxycarbonylamino)-3-methylbutanamido)propanamido)benzyl 11-(tert-butyldimethylsilyloxy)-8-hydroxy-7-methoxy-5-oxo-2-((E)-prop-1-enyl)-11,11a-dihydro-1H-benzo[e]pyrrolo[1,2-a][1,4]diazepine-10(5H)-carboxylate (79)

Lithium acetate dihydrate (0.010 g, 0.10 mmol, 1.0 eq) was added to a solution of the silyl ether 78 (0.100 g, 0.10 mmol, 1.0 eq) in wet DMF (2 mL) at 25° C. for 3 hours. The reaction mixture was then diluted with ethyl acetate (20 mL) and washed successively with 0.1M citric acid (20 mL, pH 3), water (20 mL) and brine (5 mL), dried over $MgSO_4$, filtered and concentrated under reduced pressure. The residue was purified by flash chromatography (silica gel, 5/95 v/v methanol/DCM) to afford the product as a pale yellow oil (0.070 g, 83%). LC/MS (3.362 min (ES$^+$)), m/z: 820.2 [M+H]$^+$. $^1$H NMR (400 MHz, CDCl$_3$) δ 8.39 (s, 1H), 7.48 (d, 2H, J=8.2 Hz), 7.25 (s, 1H), 7.12 (d, 2H, J=8.1 Hz), 6.88 (s, 1H), 6.68 (s, 1H), 6.47 (d, 1H, J=7.6 Hz), 6.24 (d, 1H, J=15.2 Hz), 6.03 (s, 1H), 5.92 (m, 1H), 5.84 (d, 1H, J=8.9 Hz), 5.50 (m, 1H), 5.34 (m, 1H), 5.26 (m, 2H), 5.18 (d, 1H, J=12.3 Hz), 4.80 (d, 1H, J=12.4 Hz), 4.66-4.60 (m, 3H), 4.02 (m, 1H), 3.95 (s, 3H), 3.81 (m, 1H), 3.03 (m, 1H), 2.57 (m, 1H), 2.19 (m, 1H), 1.84 (dd, 3H, J=6.8, 0.8 Hz), 1.48 (d, 3H, J=7.1 Hz), 1.00 (d, 3H, J=6.8 Hz), 0.95 (d, 3H, J=6.8 Hz), 0.87 (s, 9H), 0.26 (s, 3H), 0.12 (s, 3H).

(iv) (11S,11aS)-4-((20S,23S)-1-iodo-20-isopropyl-23-methyl-2,18,21-trioxo-6,9,12,15-tetraoxa-3,19,22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-Prop-1-enyl)-11,11a-dihydro-1H-benzo[e]pyrrolo[1,2-a][1,4]diazepine-10(5H)-carboxylate (66, D)

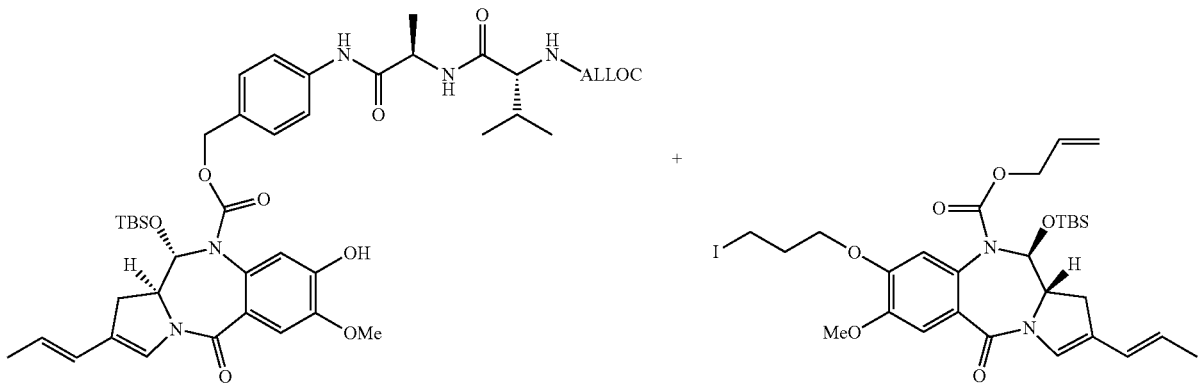

79

74

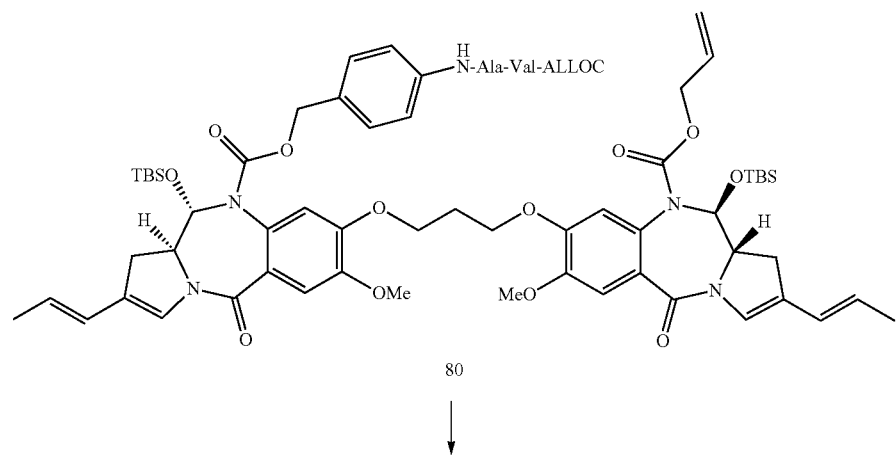
80
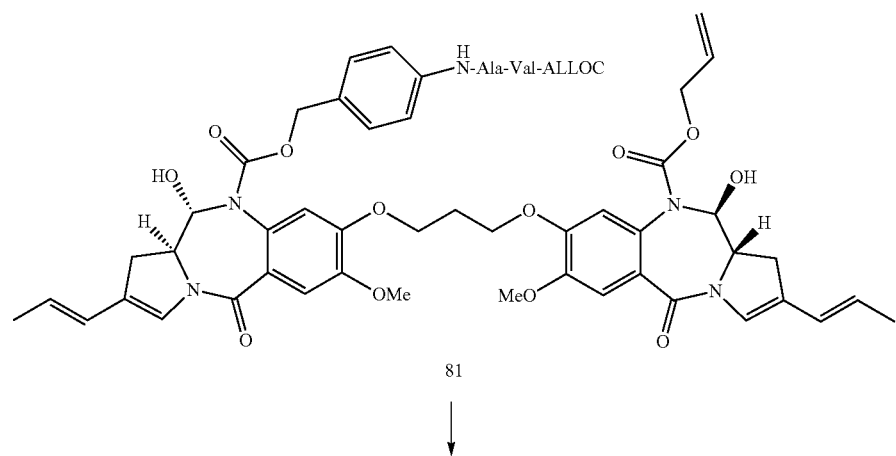
81
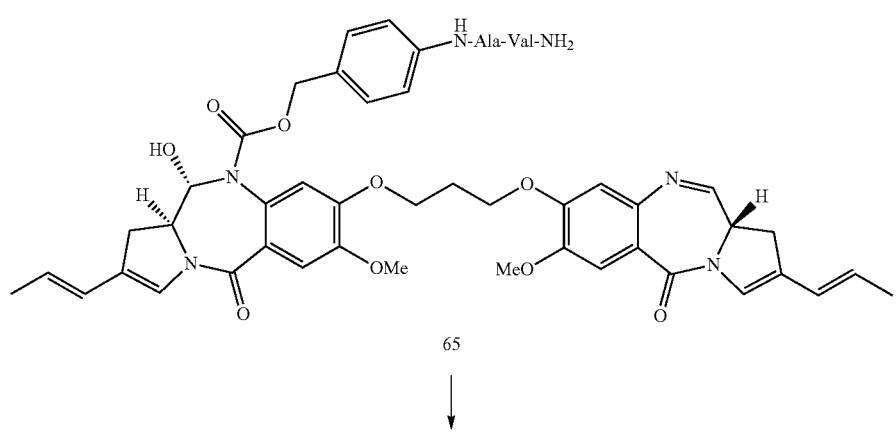
65

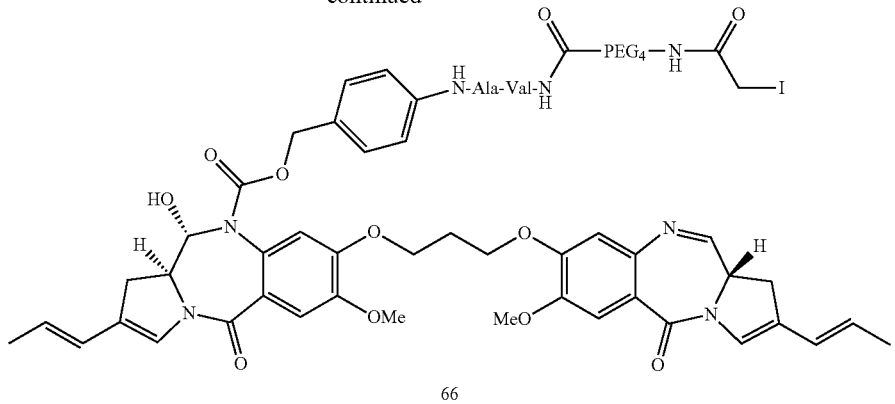

66

(a) (11S,11aS)-allyl 8-(3-((11S,11aS)-10-((4-((R)-2-((R)-2-(allyloxycarbonylamino)-3-methylbutanamido) propanamido)benzyloxy)carbonyl)-11-(tert-butyldimethylsilyloxy)-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-(tert-butyldimethylsilyloxy)-7-methoxy-5-oxo-2-((E)-prop-1-enyl)-11,11a-dihydro-1H-benzo[e]pyrrolo[1,2-a][1,4]diazepine-10(5H)-carboxylate (80)

Potassium carbonate (0.030 g, 0.21 mmol, 1.0 eq) was added to a solution of the phenol 79 (0.175 g, 0.21 mmol, 1.0 eq) and the iodo linker 74 (0.214 g, 0.32 mmol, 1.5 eq) in acetone (10 mL). The reaction mixture was heated under a nitrogen atmosphere at 75° C. in a sealed flask for 17 hours. The reaction mixture was concentrated to dryness under reduced pressure and purified by flash chromatography (silica gel, 2/98 v/v methanol/DCM to 5/95 v/v methanol/DCM) to afford the product as a pale yellow solid (0.100 g, 35%). LC/MS (4.293 min (ES$^+$)), m/z: 1359.13 [M]$^+$.

(b) (11S,11aS)-allyl 8-(3-((11S,11aS)-10-((4-((R)-2-((R)-2-(allyloxycarbonylamino)-3-methylbutanamido) propanamido)benzyloxy)carbonyl)-11-hydroxy-7-methoxy-5-oxo-2-((E)-prop-1-enyl)-5,10,11,11a-tetrahydro-1H-benzo[e]pyrrolo[1,2-a][1,4]diazepin-8-yloxy)propoxy)-11-hydroxy-7-methoxy-5-oxo-2-((E)-prop-1-enyl)-11,11a-dihydro-1H-benzo[e]pyrrolo[1,2-a][1,4]diazepine-10(5H)-carboxylate (81)

Tetra-n-butylammonium fluoride (1M, 0.22 mL, 0.22 mmol, 2.0 eq) was added to a solution of silyl ether 80 (0.150 g, 0.11 mmol, 1.0 eq) in dry THF (2 mL). The reaction mixture was stirred at room temperature for 20 minutes, after which LC/MS indicated complete reaction. The reaction mixture was diluted with ethyl acetate (10 mL) and washed sequentially with water (5 mL) and brine (5 mL). The organic phase was dried over MgSO$_4$, filtered and concentrated under reduced pressure to leave a yellow solid. Purification by flash chromatography (silica gel, 6/94 v/v methanol/DCM to 10/90 v/v methanol/DCM) afforded the product as a pale yellow solid (0.090 g, 73%). LC/MS (2.947 min (ES$^+$)), m/z: 1154.0 [M+Na]$^+$. $^1$H NMR (400 MHz, CDCl$_3$) δ 8.39 (br s, 1H), 7.39 (d, 2H, J=7.6 Hz), 7.18 (d, 2H, J=10.6 Hz), 7.10 (m, 3H), 6.86 (d, 2H, J=10.0 Hz), 6.74 (s, 1H), 6.55 (s, 1H), 6.22 (dd, 2H, J=15.3, 6.6 Hz), 5.85 (m, 2H), 5.74 (m, 3H), 5.52 (m, 2H), 5.22 (m, 1H), 5.00 (m, 2H), 4.57 (m, 6H), 4.41 (m, 2H), 4.09 (m, 4H), 3.85 (m, 11H), 3.06 (m, 2H), 2.76 (m, 2H), 2.20 (m, 2H), 2.08 (m, 1H), 1.79 (d, 6H, J=6.4 Hz), 1.40 (d, 3H, J=6.1 Hz), 0.90 (m, 6H).

(c) (11S,11aS)-4-((R)-2-((R)-2-amino-3-methylbutanamido)propanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (65)

Tetrakis(triphenylphospene)palladium(0) (0.005 g, 0.005 mmol, 0.06 eq) was added to a solution of the bis-carbinolamine 81 (0.090 g, 0.08 mmol, 1.0 eq) and pyrrolidine (16 μL, 0.20 mmol, 2.5 eq) in dry DCM (5 mL). After 20 minutes, the reaction mixture was diluted with DCM (10 mL) and washed sequentially with saturated ammonium chloride (5 mL) and brine (5 mL), dried over MgSO$_4$, filtered and the solvent was removed under reduced pressure to leave the crude product as a pale yellow solid which was used in the next step without further purification (0.075 g, assumed 100% yield). LC/MS (2.060 min (ES$^+$)), m/z: 947.2 [M+H]$^+$.

(d) (11S,11aS)-4-((20S,23S)-1-iodo-20-isopropyl-23-methyl-2,18,21-trioxo-6,9, 12, 15-tetraoxa-3, 19, 22-triazatetracosanamido)benzyl 11-hydroxy-7-methoxy-8-(3-((S)-7-methoxy-5-oxo-2-((E)-prop-1-enyl)-5,11a-dihydro-1H-benzo[e]pyrrolo[1,2-a][1,4]diazepin-8-yloxy)propoxy)-5-oxo-2-((E)-prop-1-enyl)-11,11a-dihydro-1H-benzo[e]pyrrolo[1,2-a][1,4]diazepine-10(5H)-carboxylate (66, D)

EDCl (0.015 g, 0.08 mmol, 1.0 eq) was added to a solution of amine 65 (assumed 100% yield 0.075 g, 0.08 mmol, 1.0 eq) and iodoacetamide-PEG$_4$-acid 17 (0.034 g, 0.08 mmol, 1.0 eq) in dry dichloromethane (5 mL) and the reaction was stirred in the dark. After 50 minutes, a further amount of iodoacetamide-PEG$_4$-acid 17 (0.007 g, 0.016 mmol, 0.2 eq) was added along with a further amount of EDCl (0.003 g, 0.016 mmol, 0.2 eq). After a total of 2.5 hours, the reaction mixture was diluted with dichloromethane (15 mL) and washed sequentially with water (10 mL) and brine (10 mL). The organic phase was dried over MgSO$_4$, filtered and concentrated under reduced pressure.

The resulting residue was purified by flash chromatography (silica gel, Chloroform 100% to 90:10 v/v Chloroform:Methanol). Pure fractions were combined to afford the product (0.0254 g, 23%, 2 steps). The crude fractions were collected and purified by preparative TLC (silica gel, 90:10 v/v Chloroform:Methanol) to afford a second batch of product (0.0036 g, 3%, 2 steps). LC/MS (2.689 min (ES$^+$)), m/z: 681.0 1/2 [M+2H]$^+$.
Example 10
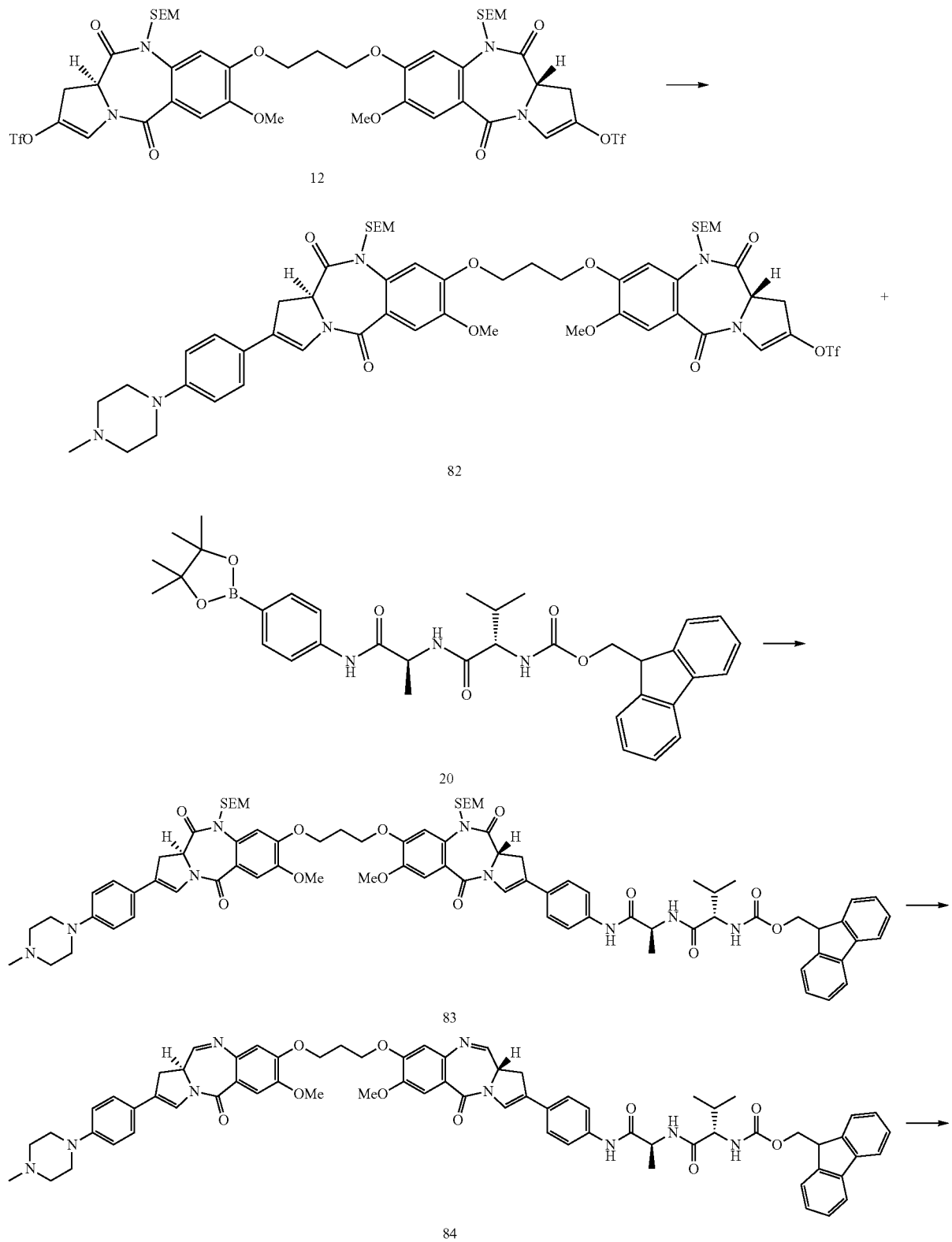

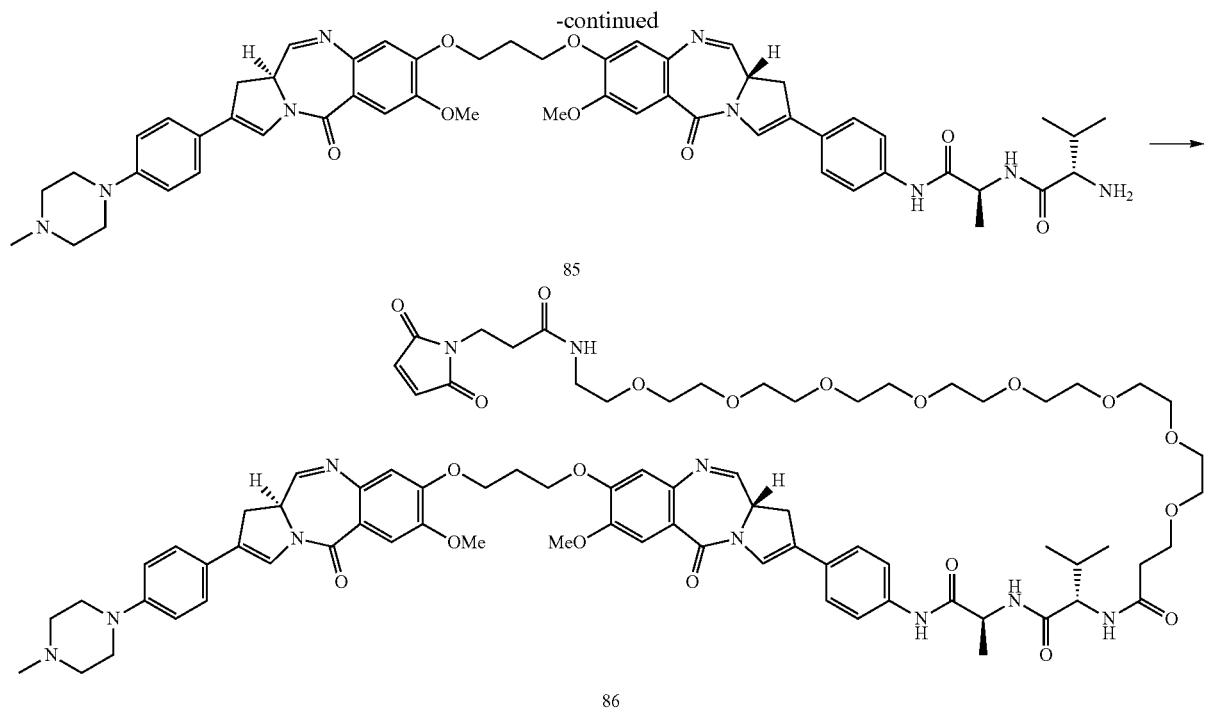

(a) (S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl trifluoromethanesulfonate (82)

Pd(PPh$_3$)$_4$ (20.6 mg, 0.018 mmol) was added to a stirred mixture of the bis-enol triflate 12 (500 mg, 0.44 mmol), N-methyl piperazine boronic ester (100 mg, 0.4 mmol), Na$_2$CO$_3$ (218 mg, 2.05 mmol), MeOH (2.5 mL), toluene (5 mL) and water (2.5 mL). The reaction mixture was allowed to stir at 30° C. under a nitrogen atmosphere for 24 hours after which time all the boronic ester has consumed. The reaction mixture was then evaporated to dryness before the residue was taken up in EtOAc (100 mL) and washed with H$_2$O (2×50 mL), brine (50 mL), dried (MgSO$_4$), filtered and evaporated under reduced pressure to provide the crude product. Purification by flash chromatography (gradient elution: 80:20 v/v Hexane/EtOAc to 60:40 v/v Hexane/EtOAc) afforded product 82 as a yellowish foam (122.6 mg, 25%). LC/MS 3.15 min (ES+) m/z (relative intensity) 1144 ([M+H]$^+$., 20%).

(b) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (83)

PBD-triflate 82 (359 mg, 0.314 mmol), boronic pinacol ester 20 (250 mg, 0.408 mmol) and triethylamine (0.35 mL, 2.51 mmol) were dissolved in a mixture of toluene/MeOH/H$_2$O, 2:1:1 (3 mL). The microwave vessel was purged and filled with argon three times before tetrakis(triphenylphosphine)palladium(0) (21.7 mg, 0.018 mmol) was added and the reaction mixture placed in the microwave at 80° C. for 10 minutes. Subsequently, CH$_2$Cl$_2$ (100 mL) was added and the organics were washed with water (2×50 mL) and brine (50 mL) before being dried with MgSO$_4$, filtered and the volatiles removed by rotary evaporation under reduced pressure. The crude product was purified by silica gel chromatography column (CHCl$_3$/MeOH, 100% to 9:1) to afford pure 83 (200 mg, 43% yield). LC/MS 3.27 min (ES+) m/z (relative intensity) 1478 ([M+H]$^+$., 100%).

(c) (9H-fluoren-9-yl)methyl ((S)-1-(((S)-1-((4-((S)-7-methoxy-8-(3-(((S)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)amino)-3-methyl-1-oxobutan-2-yl)carbamate (84)

A solution of Super-Hydride® (0.34 mL, 1M in THF) was added dropwise to a solution of SEM-dilactam 83 (200 mg, 0.135 mmol) in THF (5 mL) at −78° C. under an argon atmosphere. The addition was completed over 5 minutes in order to maintain the internal temperature of the reaction mixture constant. After 20 minutes, an aliquot was quenched with water for LC/MS analysis, which revealed that the reaction was complete. Water (20 mL) was added to the reaction mixture and the cold bath was removed. The organic layer was extracted with EtOAc (3×30 mL) and the combined organics were washed with brine (50 mL), dried with MgSO₄, filtered and the solvent removed by rotary evaporation under reduced pressure. The crude product was dissolved in MeOH (6 mL), CH₂Cl₂ (3 mL), water (1 mL) and enough silica gel to form a thick stirring suspension. After 5 days, the suspension was filtered through a sintered funnel and washed with CH₂Cl₂/MeOH (9:1) (100 mL) until the elution of the product was complete. The organic layer was washed with brine (2×50 mL), dried with MgSO₄, filtered and the solvent removed by rotary evaporation under reduced pressure. Purification by silica gel column chromatography (100% CHCl₃ to 96% CHCl₃/4% MeOH) afforded the product 84 as a yellow solid (100 mg, 63%). LC/MS 2.67 min (ES+) m/z (relative intensity) 1186 ([M+H]⁺., 5%).

(d) (S)-2-amino-N—((S)-1-((4-((R)-7-methoxy-8-(3-(((R)-7-methoxy-2-(4-(4-methylpiperazin-1-yl)phenyl)-5-oxo-5,11a-dihydro-1H-pyrrolo[2,1-c][1,4]benzodiazepin-8-yl)oxy)propoxy)-5-oxo-5,11a-dihydro-1H-pyrrolo[2,1-c][1,4]benzodiazepin-2-yl)phenyl)amino)-1-oxopropan-2-yl)-3-methylbutanamide (85)

Excess piperidine was added (0.1 mL, 1 mmol) to a solution of PBD 84 (36.4 mg, 0.03 mmol) in DMF (0.9 mL). The mixture was allowed to stir at room temperature for 20 min, at which point the reaction had gone to completion (as monitored by LC/MS). The reaction mixture was diluted with CH₂Cl₂ (50 mL) and the organic phase was washed with H₂O (3×50 mL) until complete piperidine removal. The organic phase was dried over MgSO₄, filtered and excess solvent removed by rotary evaporation under reduced pressure to afford crude product 85 which was used as such in the next step. LC/MS 2.20 min (ES+) m/z (relative intensity) 964 ([M+H]⁺., 5%).

(e) 1-(3-(2, 5-dioxo-2,5-dihydro-1H-pyrrol-1-yl)propanamido)-N-((2S)-1-(((2S)-1-((4-(7-methoxy-8-(3-((7-methoxy-2-(4-(4-methylpiperazin-1-yl)phenyl)-5-oxo-5,11a-dihydro-1H-benzo[e]pyrrolo[1,2-a][1,4]diazepin-8-yl)oxy)propoxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-3,6,9,12,15,18,21,24-octaoxaheptacosan-27-amide (86)

EDCl hydrochloride (8 mg, 0.042 mmol) was added to a suspension of Maleimide-PEG₈-acid (25 mg, 0.042 mmol) in dry CH₂Cl₂ (4 mL) under argon atmosphere. PBD 85 (42 mg, crude) was added straight away and stirring was maintained until the reaction was complete (3 hours). The reaction was diluted with CH₂Cl₂ and the organic phase was washed with H₂O and brine before being dried over MgSO₄, filtered and excess solvent removed by rotary evaporation under reduced pressure by rotary evaporation under reduced pressure. The product was purified by careful silica gel chromatography (slow elution starting with 100% CHCl₃ up to 9:1 CHCl₃/MeOH) followed by reverse phase HPLC to remove unreacted maleimide-PEG₈-acid. The product 86 was isolated in 10% over two steps (6.6 mg). LC/MS 1.16 min (ES+) m/z (relative intensity) 770.20 ([M+2H]⁺., 40%).

Example 11—Alternative Synthesis of Compound 83

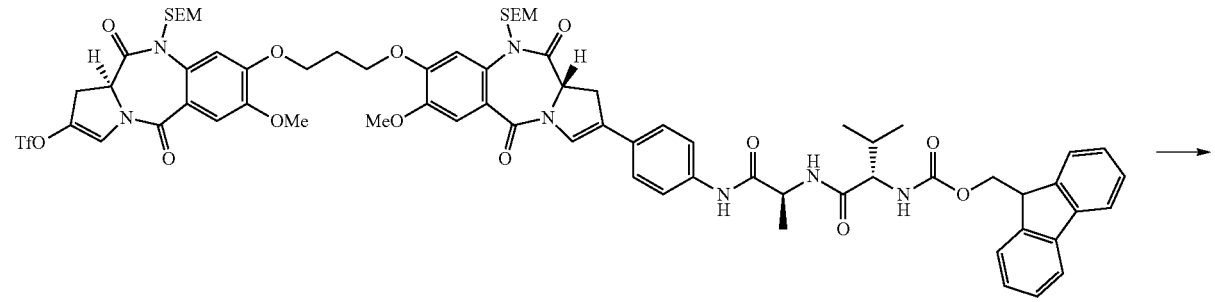

21

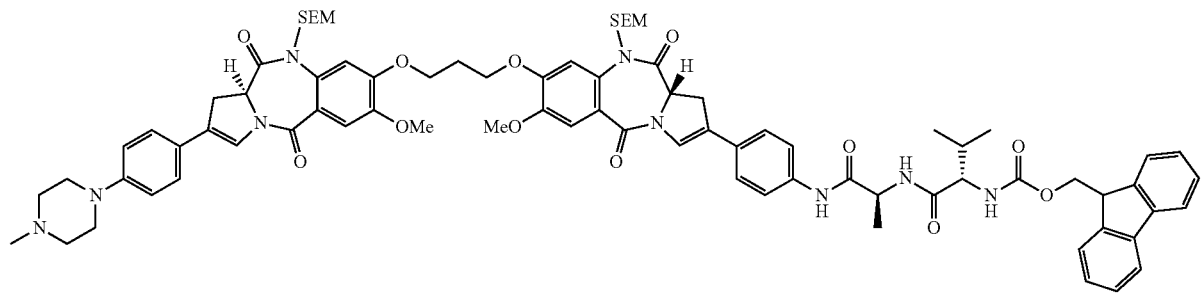

83

(9H-fluoren-9-yl)methyl ((S)-1-(((S)-1-((4-((S)-7-methoxy-8-(3-(((S)-7-methoxy-2-(4-(4-methylpiperazin-1-yl)phenyl)-5,11-dioxo-10-((2-(trimethylsilyl)ethoxy)methyl)-5,10,11,11a-tetrahydro-1H-pyrrolo[2,1-c][1,4]benzodiazepin-8-yl)oxy)propoxy)-5,11-dioxo-10-((2-(trimethylsilyl)ethoxy)methyl)-5,10,11,11a-tetrahydro-1H-pyrrolo[2,1-c][1,4]benzodiazepin-2-yl)phenyl)amino)-1-oxopropan-2-yl)amino)-3-methyl-1-oxobutan-2-yl) carbamate (83)

PBD-triflate 21 (469 mg, 0.323 mmol), boronic pinacol ester (146.5 mg, 0.484 mmol) and Na₂CO₃ (157 mg, 1.48 mmol) were dissolved in a mixture of toluene/MeOH/H₂O, 2:1:1 (10 mL). The reaction flask was purged with argon three times before tetrakis(triphenylphosphine)palladium(0) (7.41 mg, 0.0064 mmol) was added and the reaction mixture heated to 30° C. overnight. The solvents were removed under reduced pressure and the residue was taken up in H₂O (50 mL) and extracted with EtOAc (3×50 mL). The combined organics were washed with brine (100 mL), dried with MgSO₄, filtered and the volatiles removed by rotary evaporation under reduced pressure. The crude product was purified by silica gel column chromatography (CHCl₃ 100% to CHCl₃/MeOH 95%:5%) to afford pure 83 in 33% yield (885 mg). LC/MS 3.27 min (ES+) m/z (relative intensity) 1478 ([M+H]⁺., 100%).

Example 12

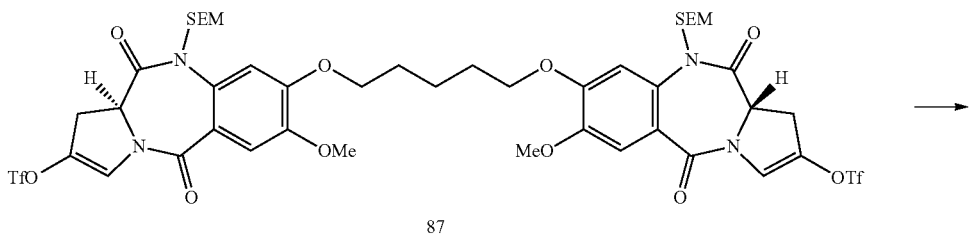

87

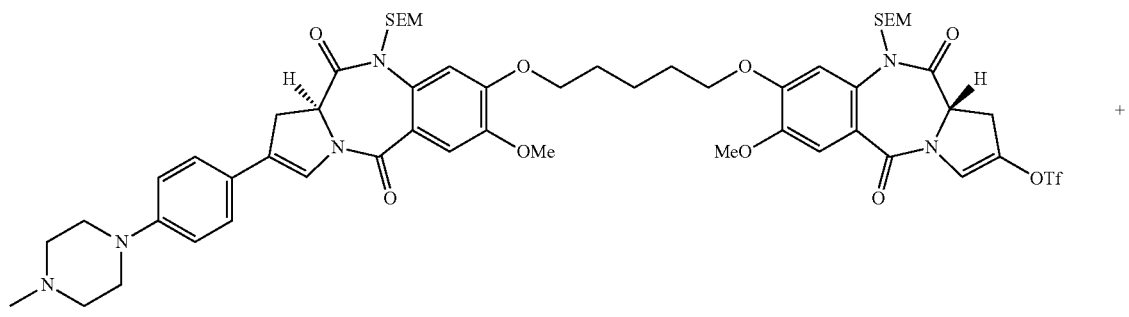

88

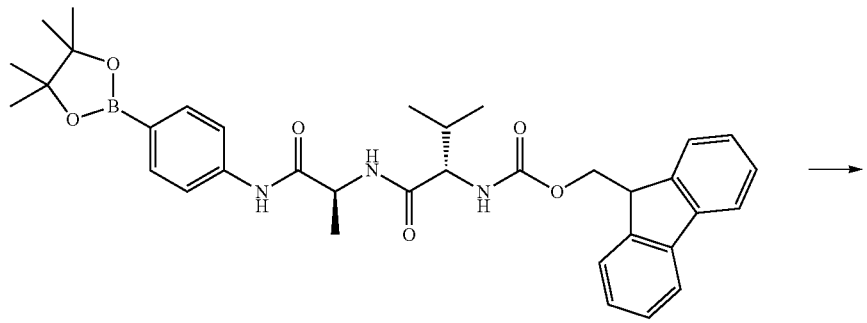

20

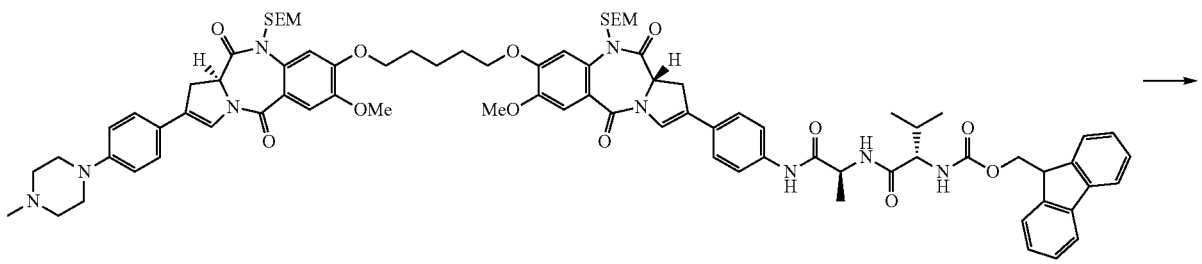

89

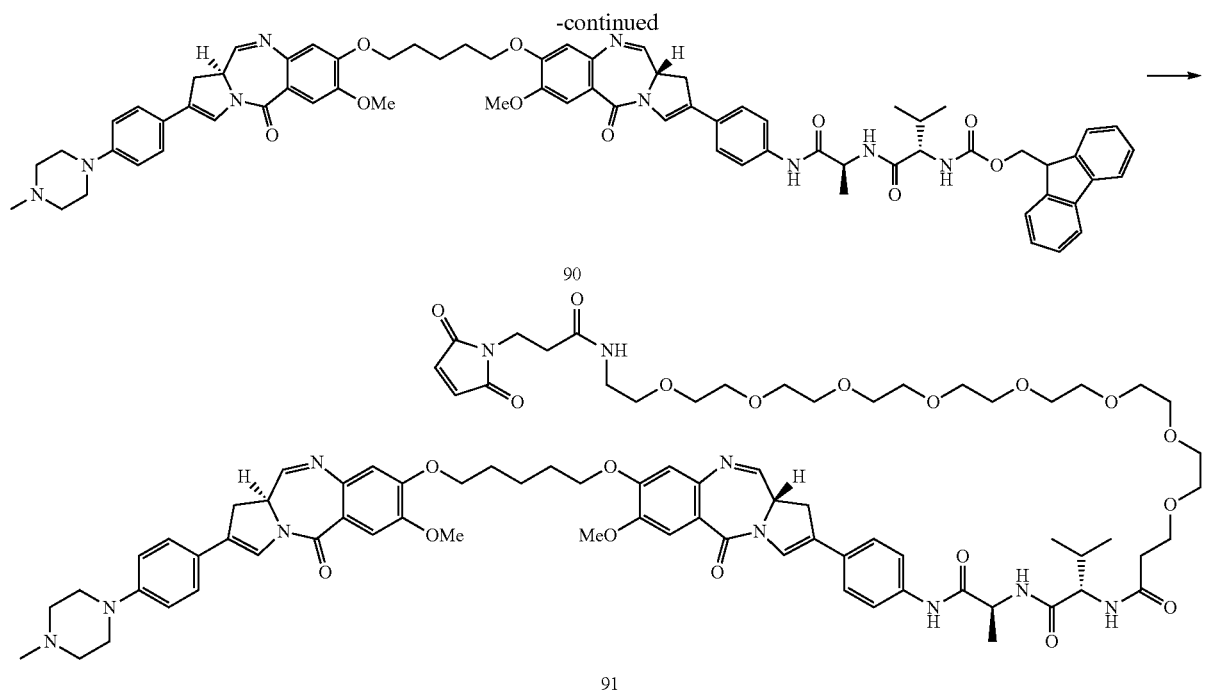

(a) (S)-7-methoxy-8-((5-(((S)-7-methoxy-2-(4-(4-methypiperazin-1-yl)phenyl)-5,11-dioxo-10-((2-(triethysilyl)ethoxy)methy)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl trifluoromethanesulfonate (88)

Pd(PPh$_3$)$_4$ (30 mg, 26 mol) was added to a stirred mixture of the bis-enol triflate 87 (1 g, 0.87 mmol), 4-(4-methylpiperazin-1-yl)phenylboronic acid, pinacol ester (264 mg, 0.87 reaction mixture was allowed to stir under a nitrogen atmosphere overnight at room temperature after which time the complete consumption of starting material was observed by TLC (EtOAc) and LC/MS (1.52 min (ES+) m/z (relative intensity) 1171.40 ([M+H]$^+$., 100)). The reaction mixture was diluted with EtOAc (400 mL) and washed with H$_2$O (2×300 mL), brine (200 mL), dried (MgSO$_4$), filtered and evaporated under reduced pressure to provide the crude product. Purification by flash chromatography (gradient elution: 100:0 v/v EtOAc/MeOH to 85:15 v/v EtOAc/MeOH) afforded the asymmetrical triflate 88 (285 mg, 28%). $^1$H NMR (400 MHz, CDCl$_3$) δ 7.39 (s, 1H), 7.37-7.29 (m, 4H), 7.23 (d, J=2.8 Hz, 2H), 7.14 (t, J=2.0 Hz, 1H), 6.89 (d, J=9.0 Hz, 2H), 5.54 (d, J=10.0 Hz, 2H), 4.71 (dd, J=10.0, 2.6 Hz, 2H), 4.62 (td, J=10.7, 3.5 Hz, 2H), 4.13-4.01 (m, 4H), 3.97-3.87 (m, 8H), 3.85-3.75 (m, 2H), 3.74-3.63 (m, 2H), 3.31-3.22 (m, 4H), 3.14 (tdd, J=16.2, 10.8, 2.2 Hz, 2H), 2.73-2.56 (m, 4H), 2.38 (d, J=2.4 Hz, 3H), 2.02-1.92 (m, 4H), 1.73 (dd, J=9.4, 6.0 Hz, 2H), 1.04-0.90 (m, 4H), 0.05--0.00 (m, 18H). MS (ES+) m/z (relative intensity) 1171.40 ([M+H]$^+$., 100).

(b) (9H-fluoren-9-yl)methyl ((S)-1-(((S)-1-((4-((S)-7-methoxy-8-((5-(((S)-7-methoxy-2-(4-(4-methyl-piperazin-1-yl)phenyl)-5,11-dioxo-10-((2-(trimethyl-silyl)ethoxy)methyl)-5,10,11,11a-tetrahydro-1H-benzo[e]pyrrolo[1,2-a][1,4]diazepin-8-yl)oxy)pentyl)oxy)-5,11-dioxo-10-((2-(trimethylsilyl)ethoxy)methyl)-5,10,11,11a-tetrahydro-1H-benzo[e]pyrrolo[1,2-a][1,4]diazepin-2-yl)phenyl)amino)-1-oxopropan-2-yl)amino)-3-methyl-1-oxobutan-2-yl)carbamate (89)

Pd(PPh$_3$)$_4$(8 mg, 7 μmol) was added to a stirred mixture of the asymmetrical triflate 88 (269 mg, 0.23 mmol), Fmoc-Val-Ala-4-aminophenylboronic acid, pinacol ester 20 (210 mg, 0.34 mmol), Na$_2$CO$_3$ (36.5 mg, 0.34 mmol), EtOH (5 mL), toluene (10 mL), THF (1 mL), and water (5 mL). The reaction mixture was allowed to stir under a nitrogen atmosphere at 35° C. for 2 hours after which time the complete consumption of starting material was observed by TLC (80:20 v/v EtOAc/MeOH) and LC/MS (1.68 min (ES+) m/z (relative intensity) 1508.10 ([M+H]$^+$., 100)). The reaction mixture was diluted with EtOAc (100 mL) and washed with H$_2$O (1×100 mL), brine (200 mL), dried (MgSO$_4$), filtered and evaporated under reduced pressure to provide the crude product. Purification by flash chromatography (gradient elution: 100:0 v/v EtOAc/MeOH to 80:20 v/v EtOAc/MeOH) afforded the SEM protected dimer 89 (240 mg, 69%). $^1$H NMR (400 MHz, CDCl$_3$) δ 8.42 (s, 1H), 7.76 (d, J=7.5 Hz, 2H), 7.63-7.49 (m, 4H), 7.45-7.28 (m, 9H), 7.25 (d, J=2.9 Hz, 1H), 6.87 (t, J=14.0 Hz, 2H), 6.41 (s, 1H), 5.63-5.49 (m, 2H), 5.25 (s, 1H), 4.71 (d, J=10.1 Hz, 2H), 4.68-4.57 (m, 2H), 4.49 (d, J=6.7 Hz, 2H), 4.20 (s, 1H), 4.16-4.02 (m, 4H), 4.00-3.87 (m, 7H), 3.86-3.61 (m, 7H), 3.30-3.21 (m, 4H), 3.19-3.05 (m, 2H), 2.69-2.54 (m, 4H), 2.37 (s, 3H), 2.04-1.92 (m, 4H), 1.91-1.79 (m, 4H), 1.72 (s, 2H), 1.46 (d, J=6.9 Hz, 3H), 1.04-0.82 (m, 8H), 0.04--0.02 (m, 18H). MS (ES+) m/z (relative intensity) 1508.10 ([M+H]$^+$., 100).

203

(c) (9H-fluoren-9-yl)methyl ((S)-1-(((S)-1-((4-((S)-7-methoxy-8-((5-(((S)-7-methoxy-2-(4-(4-methyl-piperazin-1-yl)phenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl) carbamate (90)

Super hydride (0.358 mL, 0.358 mmol, 1.0 M in THF) was added dropwise to a stirred solution of the SEM-tetralactam 89 (216 mg, 0.143 mmol) in anhydrous THF (10 mL) at −78° C. The reaction mixture was allowed to stir for 3 hours after which time the complete conversion of starting material directly was observed by LC/MS (1.37 min (ES+) m/z (relative intensity) 608.15 (([M+2H]$^{2+}$)/2,100)). The reaction mixture was carefully diluted with H$_2$O (100 mL) and extracted with DCM (100 mL). The organic layers was washed with brine (100 mL), dried over MgSO$_4$, filtered and evaporated under reduced pressure to provide the intermediate SEM-carbinolamine. The white solids were immediately dissolved in MeOH (100 mL), DCM (10 mL) and H$_2$O (20 mL) and treated with flash silica gel (50 g). The thick suspension was allowed to stir at room temperature for 4 days after which time the formation of a significant quantity of desired product was observed by TLC (90:10 v/v CHCl$_3$/MeOH). The reaction mixture was filtered through a porosity 3 sinter funnel and the pad rinsed slowly and thoroughly with 90:10 v/v CHCl$_3$/MeOH until no further product eluted (checked by TLC). The filtrate was washed with brine (100 mL), dried (MgSO$_4$), filtered and evaporated in vacuo, followed by high vacuum drying, to provide the crude product. Purification by flash chromatography (gradient elution: HPLC grade 98:2 v/v CHCl$_3$/MeOH to 88:12 v/v CHCl$_3$/MeOH) gave 90 as a mixture of carbinolamine ethers and imine (80 mg, 46%). $^1$H NMR (400 MHz, CDCl$_3$) δ 8.52 (s, 1H), 7.87 (d, J=3.9 Hz, 2H), 7.75 (d, J=7.5 Hz, 2H), 7.66-7.26 (m, 12H), 6.90 (d, J=8.8 Hz, 2H), 6.81 (s, 1H), 6.64 (d, J=6.0 Hz, 1H), 5.37 (d, J=5.7 Hz, 1H), 4.74-4.58 (m, 2H), 4.54-4.31 (m, 4H), 4.26-3.98 (m, 6H), 3.94 (s, 2H), 3.86 (dd, J=13.6, 6.6 Hz, 1H), 3.63-3.48 (m, 2H), 3.37 (dd, J=16.5, 5.6 Hz, 2H), 3.31-3.17 (m, 4H), 2.66-2.51 (m, 4H), 2.36 (s, 3H), 2.16 (d, J=5.1 Hz, 1H), 2.06-1.88 (m, 4H), 1.78-1.55 (m, 6H), 1.46 (d, J=6.8 Hz, 3H), 0.94 (d, J=6.8 Hz, 6H). MS (ES+) m/z (relative intensity) 608.15 ((([M+2H]$^{2+}$)/2,100).

204

(d) 1-(3-(2, 5-dioxo-2,5-dihydro-1H-pyrrol-1-yl)propanamido)-N—((S)-1-(((S)-1-((4-((S)-7-methoxy-8-((5-(((S)-7-methoxy-2-(4-(4-methylpiperazin-1-yl)phenyl)-5-oxo-5,11a-dihydro-1H-benzo[e]pyrrolo[1,2-a][1,4]diazepin-8-yl)oxy)pentyl)oxy)-5-oxo-5,11a-dihydro-1H-benzo[e]pyrrolo[1,2-a][1,4]diazepin-2-yl)phenyl)amino)-1-oxopropan-2-yl)amino)-3-methyl-1-oxobutan-2-yl)-3, 6,9,12,15, 18, 21, 24-octaoxaheptacosan-27-amide (91)

Piperidine (0.2 mL) was added to a solution of 90 (77 mg, 63.4 μmol) in DMF (1 mL). The reaction mixture was allowed to stir for 20 minutes. The reaction mixture was carefully diluted with DCM (50 mL) and washed with water (50 mL). The organic layers was washed with brine (100 mL), dried over MgSO$_4$, filtered and evaporated under reduced pressure to provide the unprotected valine intermediate. The crude residue was immediately redissolved in chloroform (5 mL). Mal(Peg)$_8$-acid (56 mg, 95 μmol) and EDCl (18 mg, 95 μmol) were added, followed by methanol (0.1 mL). The reaction was allowed to stir for 3 hours at room temperature at which point completion was observed by TLC and LC/MS (1.19 min (ES+) m/z (relative intensity) 784.25 ((([M+2H]$^{2+}$)/2,100)). The reaction mixture was diluted with chloroform (50 mL), washed with water (100 mL), dried (MgSO$_4$), filtered and evaporated in vacuo, followed by high vacuum drying, to provide the crude product. Purification by flash chromatography (gradient elution: HPLC grade 96:4 v/v CHCl$_3$/MeOH to 90:10 v/v CHCl$_3$/MeOH) gave 91 as a yellow solid (43 mg, 43%). $^1$H NMR (400 MHz, CDCl$_3$) b 8.73 (s, 1H), 7.88 (dd, J=7.6, 3.9 Hz, 2H), 7.75 (d, J=8.6 Hz, 2H), 7.52 (d, J=2.0 Hz, 2H), 7.44 (s, 1H), 7.40-7.28 (m, 4H), 6.91 (d, J=8.8 Hz, 2H), 6.81 (s, 2H), 6.69 (s, 2H), 6.48 (s, 1H), 4.72-4.63 (m, 1H), 4.46-4.34 (m, 2H), 4.25-4.03 (m, 6H), 3.95 (s, 4H), 3.84 (dd, J=17.2, 10.1 Hz, 4H), 3.72-3.46 (m, 30H), 3.44-3.32 (m, 4H), 3.30-3.20 (m, 4H), 2.75-2.63 (m, 1H), 2.59 (s, 4H), 2.55-2.43 (m, 3H), 2.37 (s, 3H), 2.29 (dd, J=12.7, 6.7 Hz, 1H), 2.03-1.89 (m, 4H), 1.72 (d, J=22.7 Hz, 8H), 1.46 (d, J=7.2 Hz, 3H), 1.01 (dd, J=11.5, 6.9 Hz, 6H). MS (ES$^+$) m/z (relative intensity) 784.25 ((([M+2H]$^{2+}$)/2,100).

Example 13

(i) (S)-((pentane-1,5-diylbis(oxy))bis(2-amino-5-methoxy-4, 1-phenylene))bis(((S)-2-(((tert-butyldimethylsilyl)oxy)methyl)-4-methyl-23-dihydro-1H-pyrrol-1-yl)methanone) (98)

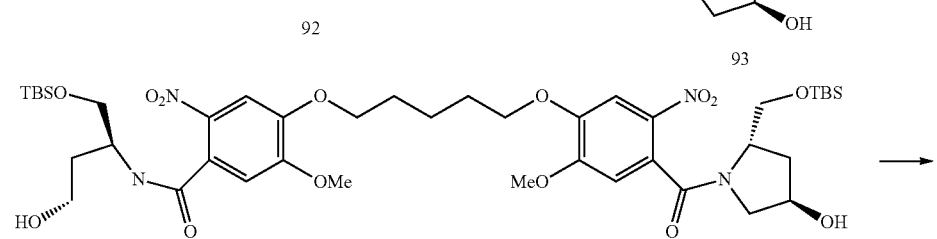

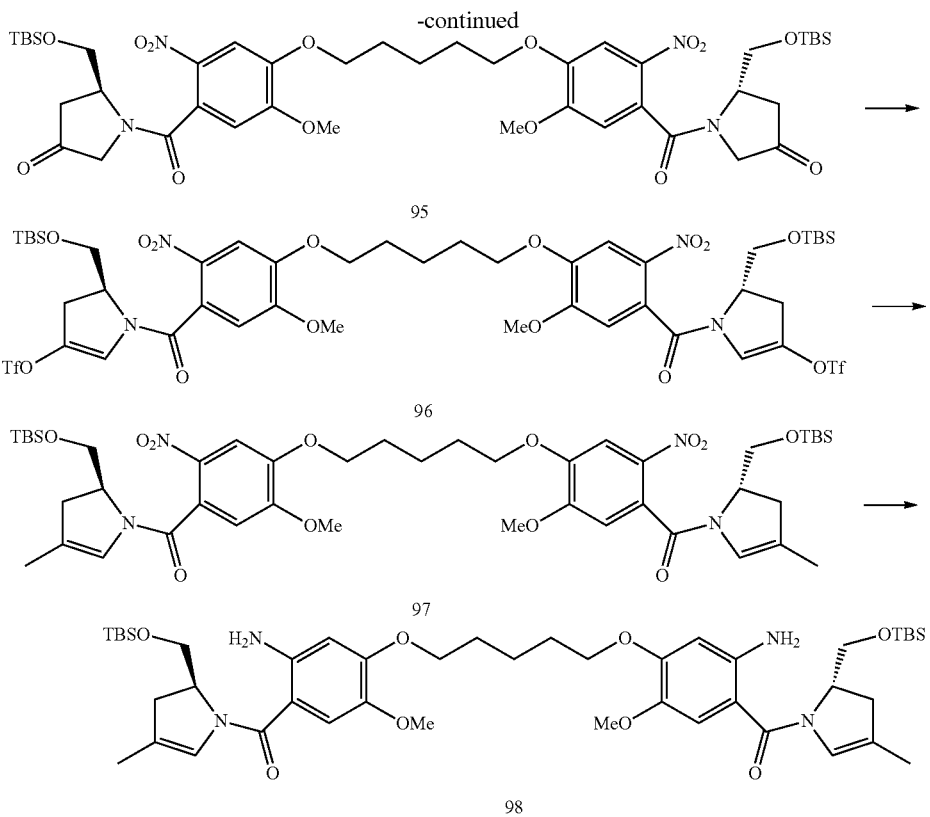

(a) (S,R)-((pentane-1,5-diylbis(oxy))bis(5-methoxy-2-nitro-4,1-phenylene))bis(((2S,4R)-2-(((tert-butyldimethylsilyl)oxy)methyl)-4-hydroxypyrrolidin-1-yl)methanone) (94)

Anhydrous DMF (approx. 0.5 mL) was added dropwise to a stirred suspension of 4,4'-(pentane-1,5-diylbis(oxy))bis(5-methoxy-2-nitrobenzoic acid) (92) (36.64 g, 74.0 mmol) and oxalyl chloride (18.79 mL, 0.222 mol, 3.0 eq.) in anhydrous DCM (450 mL) until vigorous effervescence occurred and the reaction mixture was left to stir overnight. The reaction mixture was evaporated to dryness, and triturated with diethyl ether. The resulting yellow precipitate was filtered from solution, washed with diethyl ether (100 mL) and immediately added to a solution of (3R,5S)-5-((tert-butyldimethylsilyloxy)methyl) pyrrolidin-3-ol (93) (39.40 g, 0.170 mol, 2.3 eq.) and anhydrous triethylamine (82.63 mL, 0.592 mol, 8 eq.) in anhydrous DCM (400 mL) at −40° C. The reaction mixture was allowed to slowly warm to room temperature (over 2.5 hours) after which, LCMS analysis indicated complete reaction. DCM (250 mL) was added and the mixture was transferred into a separating funnel. The organic layer was washed successively with 0.1M HCl (2×800 mL), saturated NaHCO$_3$ (500 mL) and brine (300 mL). After drying over MgSO$_4$ and filtration, evaporation of the solvent left the product as a yellow foam (62.8 g, 92%). LC/MS: RT 1.96 min; MS (ES+) m/z (relative intensity) 921.45 ([M+H]$^+$, 100).

(b) (5S,5'S)-1,1'-(4, 4'-(pentane-1,5-diylbis(oxy))bis(5-methoxy-2-nitrobenzoyl))bis(5-(((tert-butyldimethylsilyl)oxy)methyl)pyrrolidin-3-one) (95)

Trichloroisocyanuric acid (21.86 g, 94.07 mmol, 1.4 eq) was added in one portion to a solution of diol 94 (61.90 g, 67.20 mmol) and TEMPO (2.10 g, 13.44 mmol, 0.2 eq) in anhydrous DCM (500 mL) under an atmosphere of argon at 00° C. The reaction mixture was stirred at 0° C. for 20 minutes after which, LCMS analysis of the reaction mixture showed complete reaction. The reaction mixture was diluted with DCM (400 mL) and washed with saturated sodium bicarbonate (500 mL), 0.2 M sodium thiosulfate solution (600 mL), brine (400 mL) and dried (MgSO$_4$). Evaporation of the solvent gave the crude product. Flash chromatography [gradient elution 80% n-hexane/20% ethyl acetate to 100% ethyl acetate] gave pure 95 as yellow solid (49.30 g, 80%). LC/MS: RT 2.03 min; MS (ES+) m/z (relative intensity) 917.55 ([M+H]$^+$, 100).

(c) (5S,5'S)-1,1'-(4, 4'-(pentane-1,5-diylbis(oxy))bis(5-methoxy-2-nitrobenzoyl))bis(5-(((tert-butyldimethylsilyl)oxy)methyl)-4,5-dihydro-1H-pyrrole-3,1-diyl)bis(trifluoromethanesulfonate), (96)

Triflic anhydride (24.19 mL, 0.144 mol, 6.0 eq) was added dropwise to a vigorously stirred solution of bis-ketone 95 (21.98 g, 23.96 mmol) in anhydrous DCM (400 mL) containing 2,6-lutidine (22.33 mL, 0.192 mol, 8.0 eq) at −40° C. The reaction mixture was stirred at −40° C. for 30 min after which, LCMS analysis indicated complete reaction. Reaction mixture was rapidly diluted with DCM (500 mL) and washed with ice-cold water (600 mL), ice-cold saturated sodium bicarbonate (400 mL) and brine (500 mL), dried over MgSO$_4$, filtered and evaporated to leave a crude brown oil. Flash chromatography [gradient elution 80% n-hexane/20% ethyl acetate to 66% n-hexane/33% ethyl acetate] gave pure 96 as a brown foam (16.40 g, 58%). LC/MS: RT 2.28 min; MS (ES+) m/z (relative intensity) no data.

(d) (S)-((pentane-1,5-diylbis(oxy))bis(5-methoxy-2-nitro-4, 1-phenylene))bis(((S)-2-(((tert-butyldimethylsilyl)oxy)methyl)-4-methyl-2, 3-dihydro-1H-pyrrol-1-yl) methanone) (97)

Triflate 96 (5.06 g, 4.29 mmol), methyl boronic acid (1.80 g, 30.00 mmol, 7 eq) and triphenylarsine (1.05 g, 3.43 mmol, 0.8 eq) were dissolved in anhydrous dioxane and stirred under argon. Pd (II) bisbenzonitrile chloride was then added and the reaction mixture heated rapidly to 80° C. for 20 min. Reaction mixture cooled, filtered through Celite (washed through with ethyl acetate), filtrate washed with water (500 mL), brine (500 mL), dried over MgSO$_4$, filtered and evaporated. Flash chromatography [gradient elution 50% n-hexane/50% ethyl acetate] gave pure 97 as a brown foam (4.31 g, 59%). LC/MS: RT 2.23 min; MS (ES+) m/z (relative intensity) 913.50 ([M+H]$^+$, 100).

(e) (S)-((pentane-1,5-diylbis(oxy))bis(2-amino-5-methoxy-4, 1-phenylene))bis(((S)-2-(((tert-butyldimethylsilyl)oxy)methyl)-4-methyl-2, 3-dihydro-1H-pyrrol-1-yl) methanone) (98)

Zinc dust (26.48 g, 0.405 mol, 36.0 eq) was added in one portion to a solution of bis-nitro compound 97 (10.26 g, 11.24 mmol) in 5% formic acid/methanol (200 mL) keeping the temperature between 25-30° C. with the aid of a cold water bath. The reaction was stirred at 30° C. for 20 minutes after which, LCMS showed complete reaction. The reaction mixture was filtered through Celite to remove the excess zinc, which was washed with ethyl acetate (600 mL). The organic fractions were washed with water (500 mL), saturated sodium bicarbonate (500 mL) and brine (400 mL), dried over MgSO$_4$ and evaporated. Flash chromatography [gradient elution 100% chloroform to 99% chloroform/1% methanol] gave pure 98 as an orange foam (6.22 g, 65%). LC/MS: RT 2.20 min; MS (ES+) m/z (relative intensity) 853.50 ([M+H]$^+$, 100).

(ii) 4-((R)-2-((R)-2-(((allyloxy)carbonyl)amino)-3-methylbutanamido)propanamido)benzyl 4-((10R, 13R)-10-isopropyl-13-methyl-8,11-dioxo-2,5-dioxa-9,12-diazatetradecanamido)benzyl ((S)-(pentane-1, 5-diylbis(oxy))bis(2-((S)-2-(hydroxymethyl)-4-methyl-2,3-dihydro-1H-pyrrole-1-carbonyl)-4-methoxy-5,1-phenylene))dicarbamate (103)

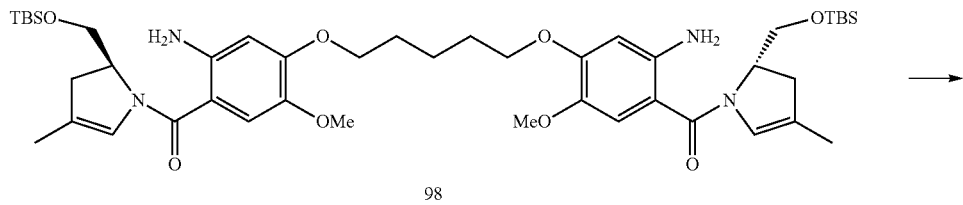

98

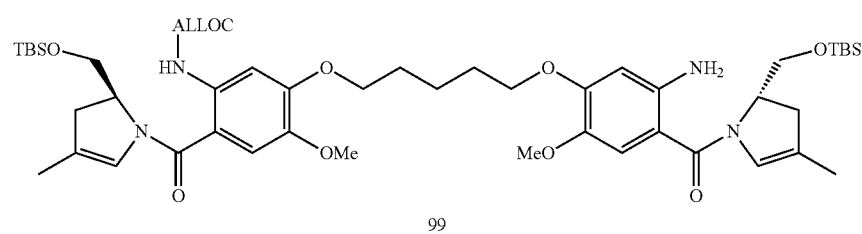

99

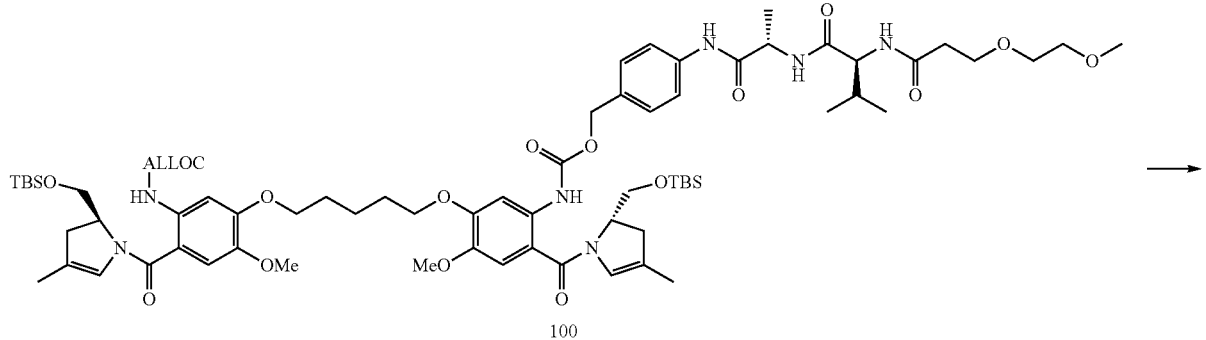

100

-continued

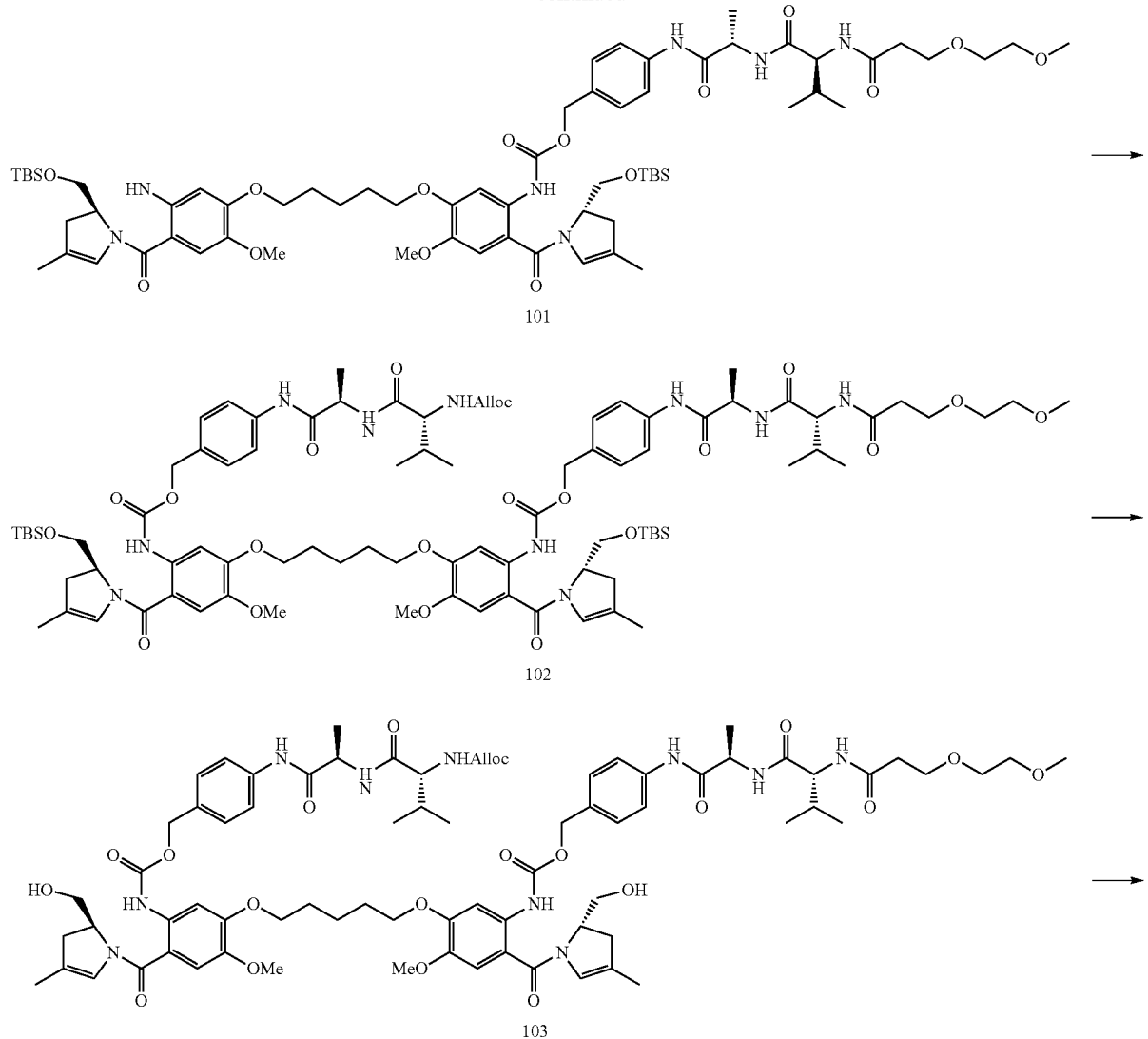

101

102

103

(a) Allyl (5-((5-(5-amino-4-((S)-2-(((tert-butyldimethylsilyl)oxy)methyl)-4-methyl-2,3-dihydro-1H-pyrrole-1-carbonyl)-2-methoxyphenoxy)pentyl)oxy)-2-((S)-2-(((tert-butyldimethylsilyl)oxy)methyl)-4-methyl-2, 3-dihydro-1H-pyrrole-1-carbonyl)-4-methoxyphenyl)carbamate (99)

Pyridine (1.156 mL, 14.30 mmol, 1.5 eq) was added to a solution of the bis-aniline 98 (8.14 g, 9.54 mmol) in anhydrous DCM (350 mL) at −78° C. under an atmosphere of argon. After 5 minutes, allyl chloroformate (0.911 mL, 8.58 mmol, 0.9 eq) was added and the reaction mixture allowed to warm to room temperature. The reaction mixture was diluted with DCM (250 mL), washed with saturated $CuSO_4$ solution (400 mL), saturated sodium bicarbonate (400 mL) and brine (400 mL), dried over $MgSO_4$. Flash chromatography [gradient elution 66% n-hexane/33% ethyl acetate to 33% n-hexane/66% ethyl acetate] gave pure 99 as an orange foam (3.88 g, 43%). LC/MS: RT 2.27 min; MS (ES+) m/z (relative intensity) 937.55 ([M+H]+, 100).

(b) Allyl 4-((10S,13S)-10-isopropyl-13-methyl-8,11-dioxo-2,5-dioxa-9,12-diazatetradecanamido)benzyl ((S)-(pentane-1,5-diylbis(oxy))bis(2-((S)-2-(((tert-butyldimethylsilyl)oxy)methyl)-4-methyl-2, 3-dihydro-1H-pyrrole-1-carbonyl)-4-methoxy-5, 1-phenylene))dicarbamate (100)

Triethylamine (0.854 mL, 6.14 mmol, 2.2 eq) was added to a stirred solution of the aniline 99 (2.62 g, 2.79 mmol) and triphosgene (0.30 g, 1.00 mmol, 0.36 eq) in anhydrous THF (50 mL) under argon 0° C. The reaction mixture was stirred at room temperature for 5 minutes. LCMS analysis of an aliquot quenched with methanol, showed formation of the isocyanate. A solution of mPEG$_2$-Val-Ala-PAB-OH (1.54 g, 3.63 mmol, 1.3 eq) and triethylamine (0.583 mL, 4.19 mmol, 1.5 eq) in dry THF (50 mL) was added in one portion and the resulting mixture was stirred overnight at 40° C. The solvent of the reaction mixture was evaporated leaving a crude product. Flash chromatography [gradient elution 100% chloroform to 98% chloroform/2% methanol] gave pure 100 as a light orange solid (2.38 g, 62%). LC/MS: RT 2.29 min; MS (ES+) m/z (relative intensity) no data.

(c) 4-((10S,13S)-10-isopropyl-13-methyl-8,11-di-oxo-2,5-dioxa-9,12-diazatetradecanamido)benzyl (5-((5-(5-amino-4-((S)-2-(((tert-butyldimethylsilyl)oxy)methyl)-4-methyl-2, 3-dihydro-1H-pyrrole-1-carbonyl)-2-methoxyphenoxy)pentyl)oxy)-2-((S)-2-(((tert-butyldimethylsilyl)oxy)methyl)-4-methyl-2, 3-dihydro-1H-pyrrole-1-carbonyl)-4-methoxyphenyl)carbamate (101)

Tetrakis(triphenylphosphine)palladium (39 mg, 0.034 mmol, 0.02 eq) was added to a stirred solution of 100 (2.35 g, 1.69 mmol) and pyrrolidine (0.35 mL, 4.24 mmol, 2.5 eq) in anhydrous DCM (25 mL) under argon at room temperature. Reaction mixture allowed to stir for 45 min then diluted with DCM (100 mL), washed with saturated ammonium chloride solution (100 mL), brine (100 mL), dried over MgSO$_4$, filtered and evaporated. Flash chromatography [gradient elution 100% chloroform to 95% chloroform/5% methanol] gave pure 101 as a yellow solid (1.81 g, 82%). LC/MS: RT 2.21 min; MS (ES+) m/z (relative intensity) 1303.65 ([M+H]$^+$, 100).

(d) 4-((R)-2-((R)-2-(((allyloxy)carbonyl)amino)-3-methylbutanamido)propanamido)benzyl 4-((10R, 13R)-10-isopropyl-13-methyl-8,11-dioxo-2,5-dioxa-9,12-diazatetradecanamido)benzyl ((S)-(pentane-1, 5-diylbis(oxy))bis(2-((S)-2-(((tert-butyldimethylsilyl)oxy)methyl)-4-methyl-2, 3-dihydro-1H-pyrrole-1-carbonyl)-4-methoxy-5, 1-phenylene))dicarbamate (102)

Triethylamine (0.419 mL, 3.01 mmol, 2.2 eq) was added to a stirred solution of the aniline 101 (1.78 g, 1.37 mmol) and triphosgene (0.15 g, 0.49 mmol, 0.36 eq) in anhydrous THF (50 mL) under argon 0° C. The reaction mixture was stirred at room temperature for 5 min. LCMS analysis of an aliquot quenched with methanol, showed formation of the isocyanate. A solution of Alloc-Val-Ala-PAB-OH (0.67 g, 1.78 mmol, 1.3 eq) and triethylamine (0.29 mL, 2.05 mmol, 1.5 eq) in dry THF (45 mL) was added in one portion and the resulting mixture was stirred overnight at 40° C. The solvent of the reaction mixture was evaporated leaving a crude product. Flash chromatography [gradient elution 100% ethyl acetate to 97% ethyl acetate/3% methanol] gave pure 102 as a pale yellow solid (1.33 g, 57%). LC/MS: RT 2.21 min; MS (ES+) m/z (relative intensity) no data.

(e) 4-((R)-2-(R)-2-(((allyloxy)carbonyl)amino)-3-methylbutanamido)propanamido)benzyl 4-((10R, 13R)-10-isopropyl-13-methyl-8,11-dioxo-2,5-dioxa-9,12-diazatetradecanamido)benzyl ((S)-(pentane-1, 5-diylbis(oxy))bis(2-((S)-2-(hydroxymethyl)-4-methyl-2, 3-dihydro-1H-pyrrole-1-carbonyl)-4-methoxy-5, 1-phenylene))dicarbamate (103)

Tetra-n-butylammonium fluoride (1 M, 1.52 mL, 1.52 mmol, 2.0 eq) was added to a solution of the TBS protected compound 102 (1.30 g, 0.76 mmol) in anhydrous THF (15 mL). The reaction mixture was stirred at room temperature for 4 hours. The reaction mixture was diluted with chloroform (100 mL) and washed sequentially with water (40 mL) and brine (40 mL). The organic phase was dried over MgSO$_4$ and evaporated to leave a yellow solid. Flash chromatography [gradient elution 95% ethyl acetate/5% methanol to 90% ethyl acetate/10% methanol] gave pure 103 as a pale yellow solid (1.00 g, 89%). LC/MS: RT 1.60 min; MS (ES+) m/z (relative intensity) 1478.45 (100).

(iii) (11S,11aS)-4-((2R,5R)-37-(2,5-dioxo-2,5-di-hydro-1H-pyrrol-1-yl)-5-isopropyl-2-methyl-4,7,35-trioxo-10,13,16,19,22,25,28,31-octaoxa-3,6,34-tri-azaheptatriacontanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (106)

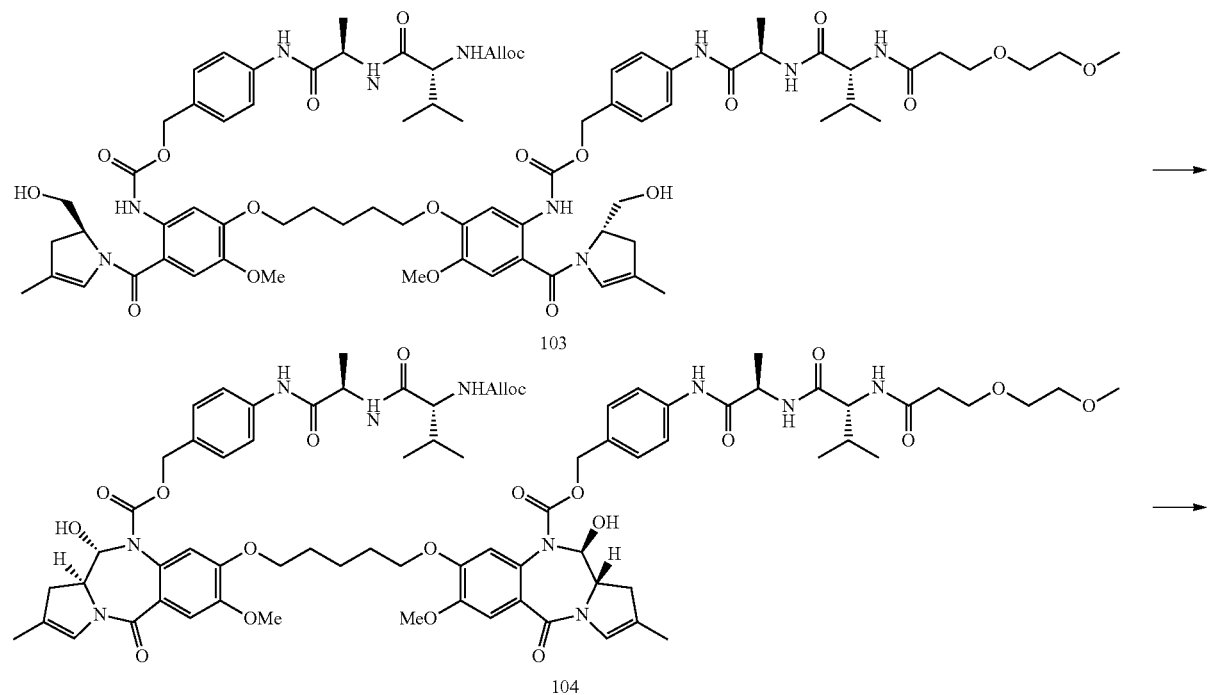

-continued

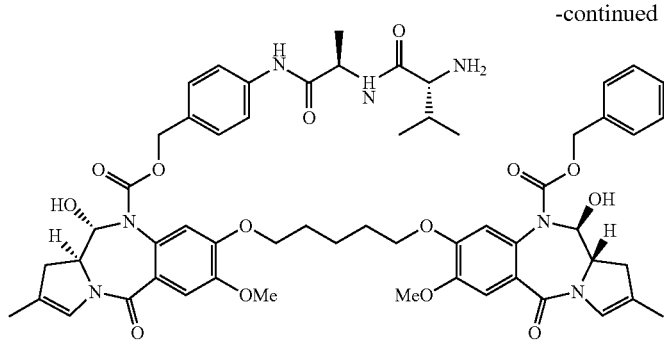

105

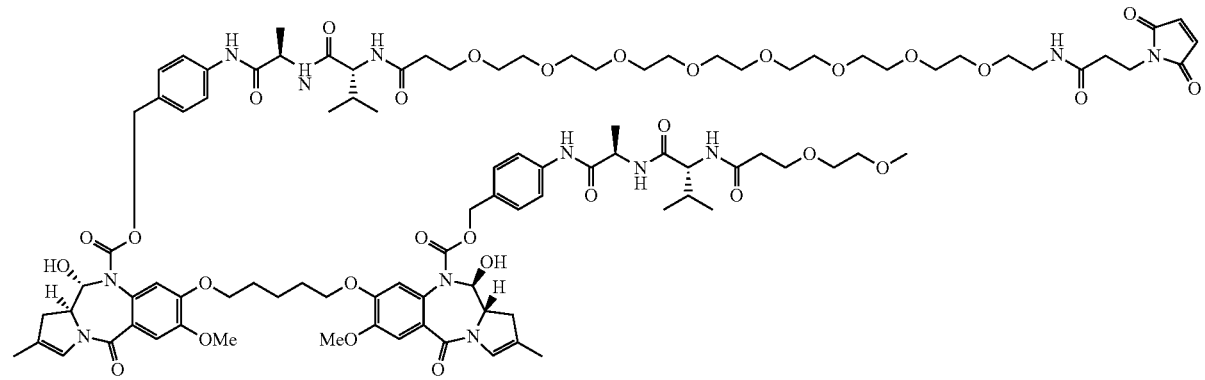

106

(a) (11S,11aS)-4-((R)-2-((R)-2-(((allyloxy)carbonyl)amino)-3-methylbutanamido)propanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (104)

Dess-Martin periodinane (0.59 g, 1.38 mmol, 2.1 eq) was added to a stirred solution of 103 (0.97 g, 0.66 mmol) in anhydrous DCM under argon at room temperature. The reaction mixture was allowed to stir for 4 hours. Reaction mixture diluted with DCM (100 mL), washed with saturated sodium bicarbonate solution (3×100 mL), water (100 mL), brine (100 mL), dried over MgSO₄, filtered and evaporated. Flash chromatography [gradient elution 100% chloroform to 95% chloroform/5% methanol] gave pure 104 as a pale yellow solid (0.88 g, 90%). LC/MS: RT 1.57 min; MS (ES+) m/z (relative intensity) 1473.35 (100).

(b) (11S,11aS)-4-((R)-2-((R)-2-amino-3-methylbutanamido)propanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (105)

Tetrakis(triphenylphosphine)palladium (5 mg, 0.004 mmol, 0.06 eq) was added to a solution of 104 (105 mg, 0.071 mmol) and pyrrolidine (7 µL, 0.086 mmol, 1.2 eq) in anhydrous DCM (5 mL). The reaction mixture was stirred 15 minutes then diluted with chloroform (50 mL) and washed sequentially with saturated aqueous ammonium chloride (30 mL) and brine (30 mL). The organic phase was dried over magnesium sulphate, filtered and evaporated. Flash chromatography [gradient elution 100% chloroform to 90% chloroform/10% methanol] gave pure 105 as a pale yellow solid (54 mg, 55%). LC/MS: RT 1.21 min; MS (ES+) m/z (relative intensity) 1389.50 (100).

(c) (11S,11aS)-4-((2R,5R)-37-(2, 5-dioxo-2,5-dihydro-1H-pyrrol-1-yl)-5-isopropyl-2-methyl-4, 7,35-trioxo-10, 13, 16, 19,22,25,28,31-octaoxa-3,6,34-triazaheptatriacontanamido)benzyl 11-hydroxy-8-((5-(((11S,11aS)-11-hydroxy-10-(((4-((10R,13R)-10-isopropyl-13-methyl-8,11-dioxo-2,5-dioxa-9,12-diazatetradecanamido)benzyl)oxy)carbonyl)-7-methoxy-2-methyl-5-oxo-5,10,11,11a-tetrahydro-1H-pyrrolo[2,1-c][1,4]benzodiazepin-8-yl)oxy)pentyl)oxy)-7-methoxy-2-methyl-5-oxo-11,11a-dihydro-1H-pyrrolo[2,1-c][1,4]benzodiazepine-10(5H)-carboxylate (106)

N-(3-Dimethylaminopropyl)-N'-ethylcarbodiimide (28 mg, 0.146 mmol, 1 eq) was added to a solution of 105 (203 mg, 0.146 mmol) and maleimide-PEG₈ acid (87 mg, 0.146 mmol) in chloroform (5 mL). The reaction was stirred for 1.5 h then diluted with chloroform (50 mL), washed with water (50 mL), brine (30 mL), dried over magnesium sulphate, filtered and evaporated. Flash chromatography [gradient elution 100% DCM to 90% DCM/10% methanol] gave 106 as a pale yellow solid (205 mg, 72%). LC/MS: RT 5.75 min; MS (ES+) m/z (relative intensity) 982.90 (100), 1963.70 (5).

Example 14: Activity of Released Compounds

K562 Assay

K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour or 96 hours at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 µL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 µL per well. DMSO (200 µL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

Compound RelC has an $IC_{50}$ of less than 0.1 pM in this assay.

Compound RelE has an $IC_{50}$ of 0.425 nM in this assay.

Example 15: Formation of Conjugates

General Antibody Conjugation Procedure

Antibodies between 1-10 mg/ml in 30 mM Histidine, 200 mM sorbitol, pH 6 is increased in pH from 6 to 7.5 by the addition of a volume of 0.5 M Tris, 25 mM EDTA, pH 8.5, equivalent to 6.7% of the mAb volume. DTT reductant is added to the batch as a 20-fold molar excess with respect to antibody and the reduction reaction is allowed to proceed overnight at room temperature (no agitation). Post reduction the antibody is desalted into 0.1 M sodium phosphate pH 7.5. Reduced antibody is reoxidised by the addition of 25 mM DHAA as a 20 fold molar excess with respect to antibody and the reoxidation reaction is allowed to proceed for a total of 2 hours at 20° C. Conjugation is initiated by the addition of DMA and 10 mM drug-linker is added in that order to achieve a 5% v/v final and 3 fold excess relative to the antibody, respectively. The conjugation reaction is incubated for 60 min. Post conjugation the reaction is quenched with a 3 fold molar excess of N-acetyl cysteine and incubated for an additional 30 mins. The final products can be analysed by SEC, HIC, PLRP and non-reducing gel electrophoresis.

Corresponding antibody-drug conjugates can be determined by analysis by High-Performance Liquid Chromatography (HPLC) or Ultra-High-Performance Liquid Chromatography (UHPLC) to assess drug-per-antibody ratio (DAR) using reverse-phase chromatography (RP) or Hydrophobic-Interaction Chromatography (HIC), coupled with UV-Visible, Fluorescence or Mass-Spectrometer detection; aggregate level and monomer purity can be analysed by HPLC or UHPLC using size-exclusion chromatography coupled with UV-Visible, Fluorescence or Mass-Spectrometer detection. Final conjugate concentration is determined by a combination of spectroscopic (absorbance at 280, 214 and 330 nm) and biochemical assay (bicinchonic acid assay BCA; Smith, P. K., et al. (1985) Anal. Biochem. 150 (1): 76-85; using a known-concentration IgG antibody as reference). Antibody-drug conjugates are generally sterile filtered using 0.2 µm filters under aseptic conditions, and stored at +4° C., −20° C. or −80° C.

DAR Determination

Antibody or ADC (ca. 35 µg in 35 µL) was reduced by addition of 10 µL borate buffer (100 mM, pH~8.4) and 5 µL DTT (0.5 M in water), and heated at 37° C. for 15 minutes. The sample was diluted with 1 volume of acetonitrile: water: formic acid (49%: 49%: 2% v/v), and injected onto a Widepore 3.6µ XB-C18 150×2.1 mm (P/N 00F-4482-AN) column (Phenomenex Aeris) at 80° C., in a UPLC system (Shimadzu Nexera) with a flow rate of 1 ml/min equilibrated in 75% Buffer A (Water, Trifluoroacetic acid (0.1% v/v) (TFA), 25% buffer B (Acetonitrile: water: TFA 90%: 10%: 0.1% v/v). Bound material was eluted using a gradient from 25% to 55% buffer B in 10 min. Peaks of UV absorption at 214 nm were integrated. The following peaks were identified for each ADC or antibody: native antibody light chain (L0), native antibody heavy chain (H0), and each of these chains with added drug-linkers (labelled L1 for light chain with one drug and H1, H2, H3 for heavy chain with 1, 2 or 3 attached drug-linkers). The UV chromatogram at 330 nm was used for identification of fragments containing drug-linkers (i.e., L1, H1, H2, H3).

A PBD/protein molar ratio was calculated for both light chains and heavy chains:

$$\frac{\text{Drug}}{\text{Protein}} \text{ ratio on light chain} = \frac{\% \text{ Area at 214 nm for } L1}{\% \text{ Area at 214 nm for } L0 \text{ and } L1}$$

$$\frac{\text{Drug}}{\text{Protein}} \text{ ratio on heavy chain} = \frac{\sum_{n=0}^{3} n \times (\% \text{ area at 214 for } Hn)}{\sum_{n=0}^{3} \% \text{ area at 214 for } Hn}$$

Final DAR is calculated as:

$$DAR = 2 \times \left(\frac{\text{Drug}}{\text{Protein}} \text{ ratio on light chain} + \frac{\text{Drug}}{\text{Protein}} \text{ ratio on heavy chain}\right)$$

DAR measurement is carried out at 214 nm because it minimises interference from drug-linker absorbance.

Generation of ADCs

Mouse 5E5 is an anti-Tn MUC 1 antibody comprising a VH domain having the sequence according to SEQ ID NO. 1 and a VL domain having the sequence according to SEQ ID NO. 30.

Ab1 is an anti-Tn MUC 1 antibody comprising a VH domain having the sequence according to SEQ ID NO. 9 and a VL domain having the sequence according to SEQ ID NO. 31.

Ab2 is an anti-Tn MUC 1 antibody comprising a VH domain having the sequence according to SEQ ID NO. 19 and a VL domain having the sequence according to SEQ ID NO. 31.

Ab3 is an anti-Tn MUC 1 antibody comprising a VH domain having the sequence according to SEQ ID NO. 28 and a VL domain having the sequence according to SEQ ID NO. 31.

Ab4 is an anti-Tn MUC 1 antibody comprising a VH domain having the sequence according to SEQ ID NO. 9 and a VL domain having the sequence according to SEQ ID NO. 33.

Ab5 is an anti-Tn MUC 1 antibody comprising a VH domain having the sequence according to SEQ ID NO. 19 and a VL domain having the sequence according to SEQ ID NO. 33.

Ab6 is an anti-Tn MUC 1 antibody comprising a VH domain having the sequence according to SEQ ID NO. 28 and a VL domain having the sequence according to SEQ ID NO. 33.

ADCs targeted to TnMUC1 were generated by conjugating the above antibodies to warhead-linker ConjE as described above. The resulting ADCs are listed in the table below. B12 anti-HIV gp120 antibody was used to generate control non-TnMUC1 targeted ADCs.

| ADC | DAR | Concentration [mg/ml] |
|---|---|---|
| Mouse 5E5-ConjE | 2.76 | 1.78 |
| Ab1-ConjE | 2.32 | 2.57 |
| Ab4-ConjE | 2.77 | 2.70 |
| Ab2-ConjE | 3.45 | 1.68 |
| B12-ConjE | 2.5 | 0.53 |

Example 12: Development of 5E5 Constructs

Design

Three heavy chain constructs were designed by CDR grafting from mouse 5E5 VH into the FWs of AB066839, AY392978.1 and AF455547.1 respectively. DNA sequences were optimised for expression by GeneArt. Variants were made by back-mutating mismatches at vernier and 5 Å CDR envelope residues or back-mutating mismatched vernier residues only.

Two light chain constructs 5E5RKA and 5E5RKB were designed by grafting CDRs from 5E5VK into the acceptor framework (FW) of DQ172590 and DQ841010. Sequence optimised variant light chain constructs 5E5RKA1 and 5E5RKB1 were created by back-mutating mismatches at vernier and 5 Å CDR FW envelope residues.

All sequences are set out in the "sequences section".

Expression and Testing of Initial VH Constructs

The DNA sequences of all constructs were optimised for expression and synthesised by GeneArt. GeneArt plasmids were subcloned into pfuse expression vectors (protocol 1). Pairs of humanised VH and chimeric VK constructs or chimeric VH and humanised VK constructs were used to transiently transfect HEK293T cells using protocol 2. IgG in conditioned medium harvested from these transfected cell cultures was measured using protocol 3 and its Tn-MUC1 binding was measured using protocol 4.

Expression and Testing of Further Constructs

Further V region versions were generated so as to identify residues which are critical to maintaining Tn-MUC1 binding potency. All sequences are set out in the "Sequences section".

Final Construct Design and Generation

In each V region construct, it was found that some back mutations were critical to binding potency, whereas other back mutations were unnecessary. The final VH and VK designs incorporate these necessary back-mutations and are shown, as protein sequences, in the "Sequences section".

Example 13: In Vitro Testing of Final Constructs

Expression levels of the constructs were tested as per protocols 2 and 3. Most final constructs expressed well, particularly Ab1, Ab4, and Ab2. In contrast, Ab6 expression is low (see Table 2 below).

The expression of the Ab1 and Ab2 antibodies was up to 6× and up to 4× better than the mouse antibody expressed in static transfected HEK293T or shaken HEK293F cells respectively (Table 2).

Figure 2:
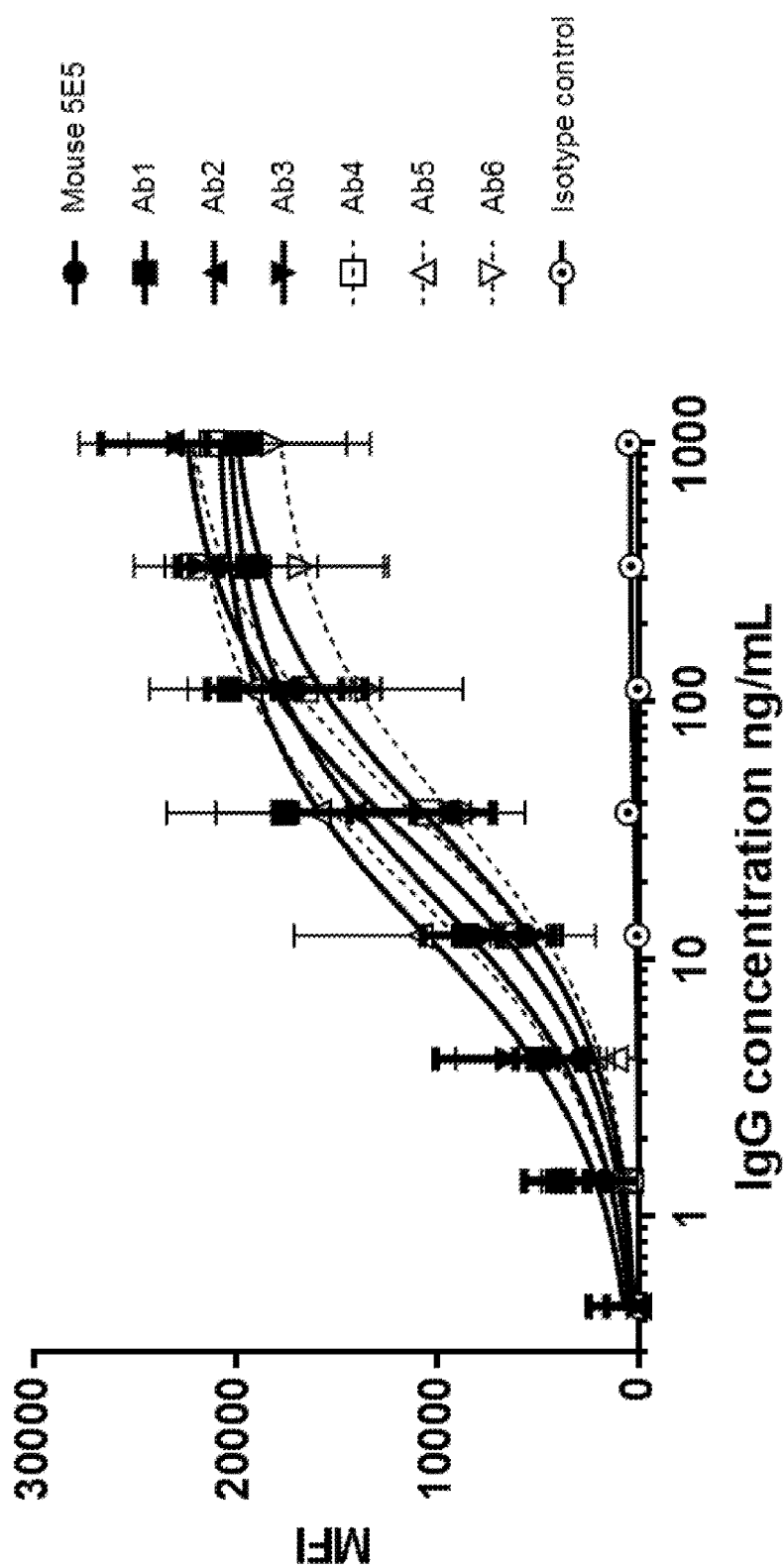
FIG. 2: Thermal denaturation of humanised 5E5 antibodies: unpurified antibodies FIG. 3 Thermal denaturation of humanised 5E5 antibodies: purified antibodies
Figure 3:

IgG binding potency to Tn-MUC1 was measured as per protocol 4 and binding to the ZR-75-1 cell line, which expresses Tn-MUC1, was measured as per protocol 6. The Tn-MUC1 binding assay data show that the TnMUC1 binding potency of Ab6 is substantially improved over the mouse 5E5 in the (see Table 2 below, along with FIG. 1). The flow cytometry $EC_{50}$ data show that the ZR-75-1 binding potency of Ab1, Ab2 and Ab5 is substantially improved over the mouse 5E5 (see Table 2 below, along with FIG. 2).

A thermal denaturation assay was performed according to protocol 5 in order to investigate molecular stability. The most heat-stable humanised 5E5 versions are Ab1 and Ab2.

TABLE 2

| | Tn-MUC1 binding $EC_{50}$ ng/ml | ZR-75-1 cell binding $EC_{50}$ ng/ml | Static HEK293T transient IgG μg/ml | Shaken HEK293F transient IgG μg/ml | $T_m$ ° C. |
|---|---|---|---|---|---|
| Mouse 5E5 | 31.10 | 28.34 | 4.0 | 18.9 | 69.97 |
| Ab1 | 24.57 | 9.86 | 23.1 | 63.2 | 69.37 |
| Ab2 | 34.46 | 16.83 | 24.9 | 27.2 | 68.32 |
| Ab3 | 61.48 | 26.78 | 3.0 | 7.0 | 65.32 |
| Ab4 | 75.49 | 42.29 | 10.9 | 18.9 | 65.23 |
| Ab5 | 26.87 | 18.42 | 3.3 | 17.2 | 62.58 |
| Ab6 | 19.80 | 41.30 | 0.18 | 1.0 | n.d. |

Example 14: In Vivo Testing of Final Constructs

The Tn-MUC1(+ve) cell line ZR75-1 was used in a mouse xenograft model to test the in vivo efficacy of ADCs comprising the humanised 5E5 constructs. The anti-HIV gp120 antibody, B12, linked to ConjE was used as a null-binder isotype control in the same model.

Study Design

Drugs and Treatment:

| Group No | Animals per group | ADC | Dose level (mg/kg) | Dose volume (mg/kg) |
|---|---|---|---|---|
| 1 | 15 | [vehicle only] | — | — |
| 2 | 15 | Mouse 5E5-ConjE | 0.3 Qwkx3 | 10 |
| 3 | 15 | Mouse 5E5-ConjE | 1.0 Qwkx3 | 10 |
| 4 | 15 | Ab1-ConjE | 0.3 Qwkx3 | 10 |
| 5 | 15 | Ab1-ConjE | 1.0 Qwkx3 | 10 |
| 6 | 15 | Ab4-ConjE | 0.3 Qwkx3 | 10 |
| 7 | 15 | Ab4-ConjE | 1.0 Qwkx3 | 10 |
| 8 | 15 | Ab2-ConjE | 0.3 Qwkx3 | 10 |
| 9 | 15 | Ab2-ConjE | 1.0 Qwkx3 | 10 |
| 10 | 15 | isotype control-ConjE | 1.0 Qwkx3 | 10 |

Procedures:

Set up CR female CB.17 SCID mice with $1\times10^7$ ZR-75-1 tumor cells in 50% Matrigel sc in flank. Cell Injection Volume is 0.1 mL/mouse. Age at Start Date: 8 to 12 weeks.

Perform a pair match when tumors reach an average size of 100-150 mm³, and begin treatment. Body Weight: qdx5 then biwk to end. Caliper Measurement: biweekly to end. Implant estradiol pellets, s.c. between the scapulae, 3-7 days prior to cell implantation.

Report any adverse reactions or death immediately. Any individual animal with a single observation of > than 30% body weight loss or three consecutive measurements of >25% body weight loss will be euthanized. Any group with two measurements of mean body weight loss of >20% or >10% mortality will stop dosing. The group is not euthanized and recovery is allowed. Within a group with >20% weight loss, individuals hitting the individual body weight loss endpoint will be euthanized. If the group treatment related body weight loss is recovered to within 10% of the original weights, dosing may resume at a lower dose or less frequent dosing schedule. Exceptions to non-treatment body weight % recovery may be allowed on a case-by-case basis.

Endpoint TGD. Animals are to be monitored individually. The endpoint of the experiment is a tumor volume of 1000 mm³ or 45 days, whichever comes first. Responders can be followed longer. When the endpoint is reached, the animals are to be euthanized.

General Methodological Approach

For the calculation of group mean tumor volumes the following rule was applied: when an animal exited the study due to tumor size, the final tumor volume recorded for the animal was included with the data used to calculate the mean volume at subsequent time points. Error bars indicate standard error of the mean (SEM). Tumor volumes values were not used to calculate group mean tumor volumes when fewer than 50% of the animals in a group remained in the study. Prism (GraphPad, San Diego, Calif.) was used for graphical presentations and statistical analyses.

Results

Figure 4:
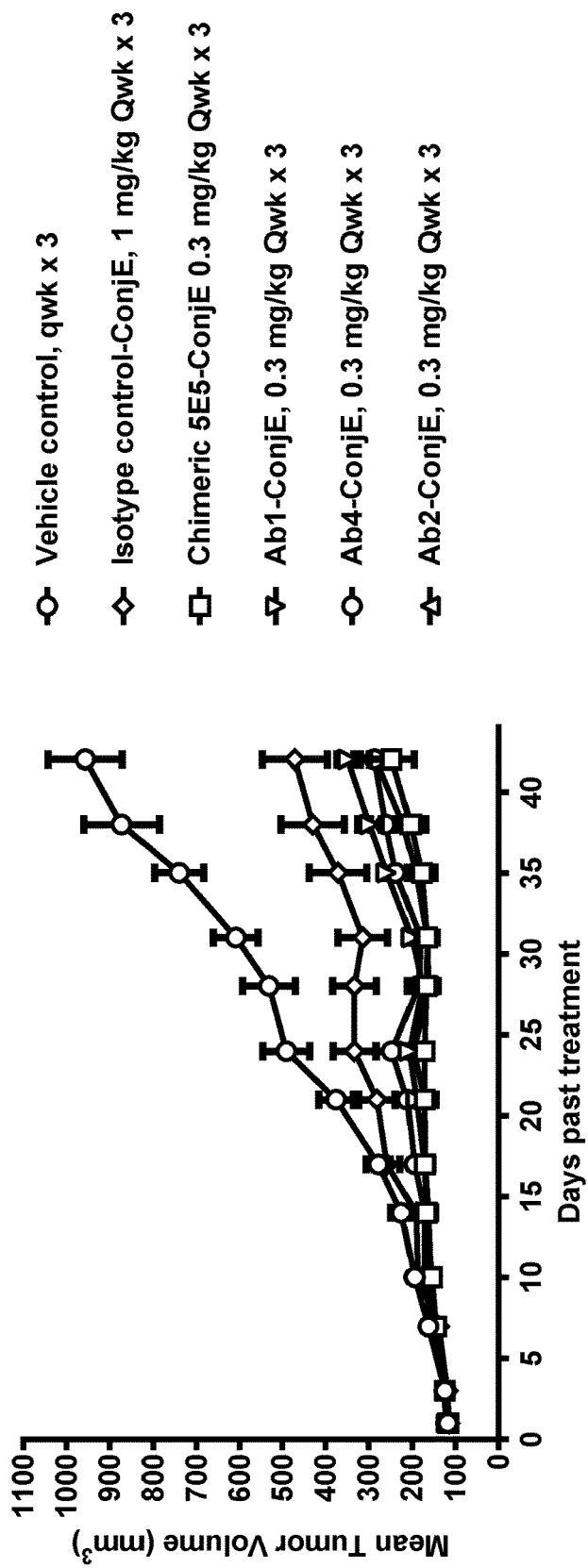
FIG. 4: In-vivo cytotoxicity of humanised 5E5 antibodies at 0.3 mg/kg
Figure 5:
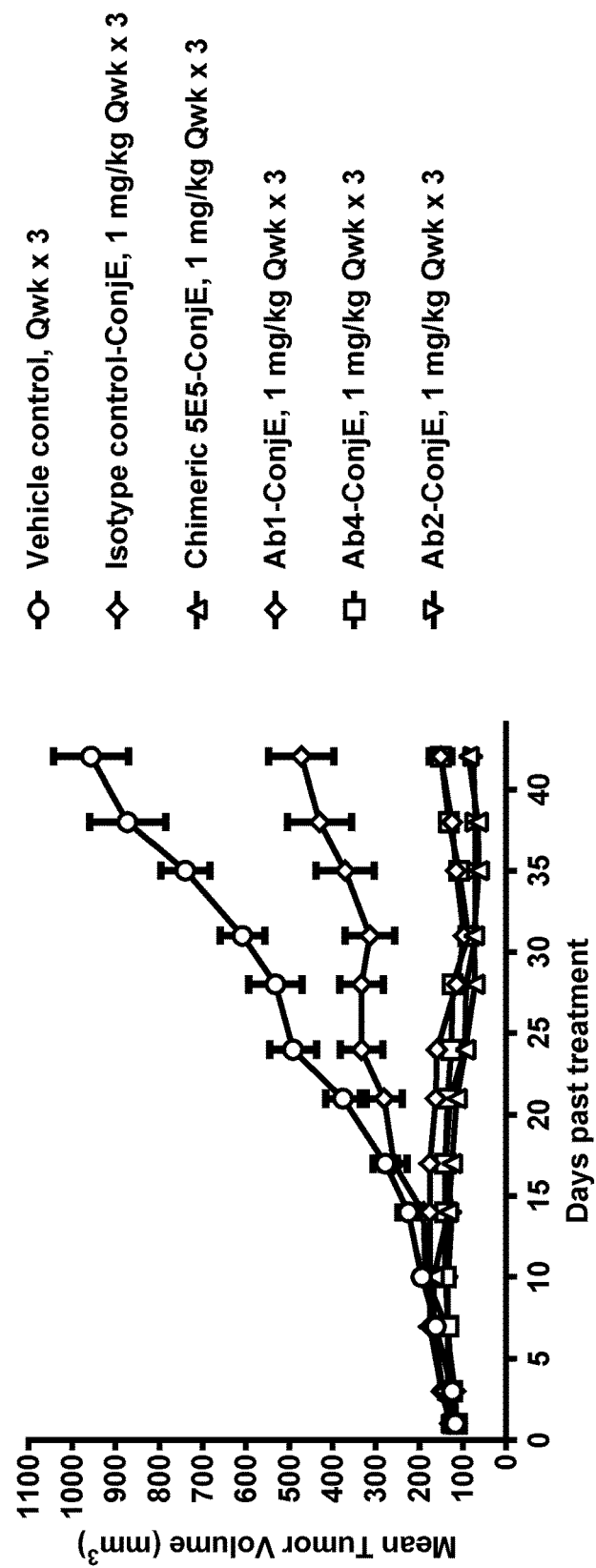
FIG. 5: In-vivo cytotoxicity of humanised 5E5 antibodies at 1.0 mg/kg

FIGS. 4 and 5 shows ADCs comprising the humanised 5E5 in a ZR-75-1 xenograft model. Mice were dosed when the mean tumor volume per experimental group reached 0.1 cm³ and they were treated with 3× weekly doses of the ADC at 0.3 or 1 mg/kg (for 5E5 ADCs) and 1 mg/kg (for B12 ADC) via the tail vein. Data represent the mean tumour volume (+/−SEM) in each group of fifteen mice.

The ADCs dosed at 1.0 mg/kg uniformly exhibited more potent anti-tumor activity than those dosed at 0.3 mg/kg. In addition, all of the 5E5 ADCs exhibited significantly higher anti-tumour activity than the isotype control ADC, even when the 5E5 ADC was dosed at 0.3 mg/kg compared to the B12 ADC's 1.0 mg/kg. The anti-tumor activity of the 5E5 ADCs was broadly comparable to that of mouse 5E5.

Example 15: Further In Vivo Testing of Final Constructs

Female SWISS nude mice were subcutaneously implanted with ODS-BRE-407 (human primary breast tumor) fragments, into the right flank, on day 0.

On day 33, when the tumors reached a mean volume of 124±52 mm3, treatments were started. ADC were administered i.v., weekly for 3 consecutive weeks (q7d×3).

The group receiving Ab1-ConjE; 0.3 mg/kg, q7d×3, was re-challenged with a single dose of Ab1-ConjE, 1 mg/kg on day 76.

Tumor volumes were measured and recorded twice a week and the study was terminated on day 112.

Figure 6:
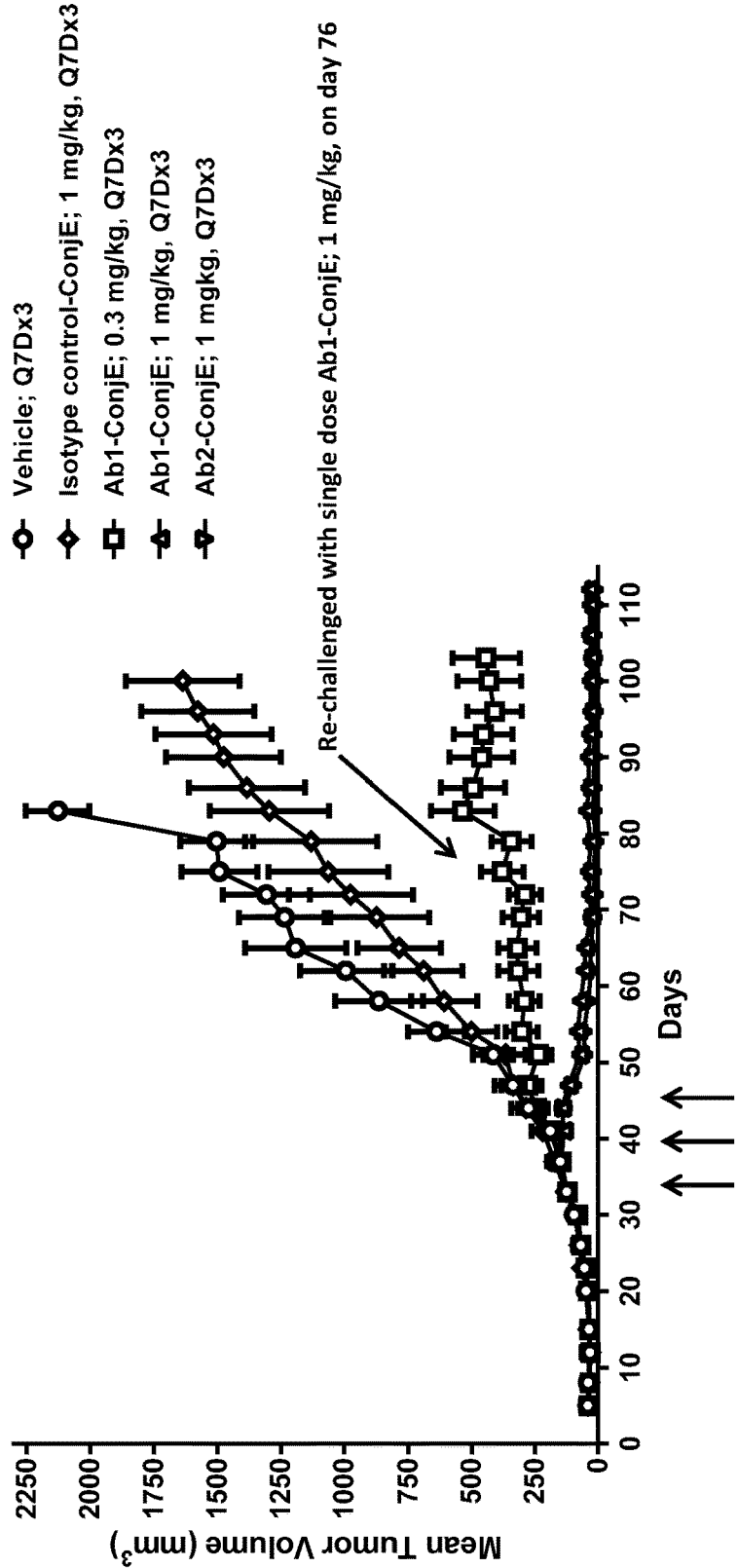
FIG. 6: In-vivo anti-tumour activity of humanised 5E5 antibodies at 0.3 mg/kg and 1.0 mg/kg. Arrows below x-axis indicate day of treatment (day 33, day 40, and day 47).

FIG. 6 shows that, as for the data in Example 14, the ADCs dosed at 1.0 mg/kg uniformly exhibited more potent anti-tumor activity than the ADC dosed at 0.3 mg/kg. In addition, all of the 5E5 ADCs exhibited significantly higher anti-tumour activity than the isotype control ADC.

Abbreviations

5E5 VH VH of mouse 5E5 antibody
5E5 VK VK of mouse 5E5 antibody
5E5RHA1 Humanised versionA1, of 5E5 VH
5E5RKA1 Humanised version, A1, of 5E5 VK
A Adenine
Å Angstrom
Ac acetyl
Acm acetamidomethyl
Alloc allyloxycarbonyl
B7 The anti-LPA antibody product of mouse hybridoma clone B7
Boc di-tert-butyl dicarbonate
bp base pairs
Bzl benzyl, where Bzl-OMe is methoxybenzyl and Bzl-Me is methylbenzene
C Cytosine
Cbz or Z benzyloxy-carbonyl, where Z—Cl and Z—Br are chloro- and bromobenzyloxy carbonyl respectively
CDR Complementarity determining region in the immunoglobulin variable regions, defined using the Kabat numbering system
D-gene Diversity gene
DMF N,N-dimethylformamide
DNA Deoxyribonucleic acid
Dnp dinitrophenyl
DTT dithiothreitol
Fmoc 9H-fluoren-9-ylmethoxycarbonyl
FW Framework region: the immunoglobulin variable regions excluding the CDR regions
G Guanine
IgG Immunoglobulin G
imp N-10 imine protecting group: 3-(2-methoxyethoxy) propanoate-Val-Ala-PAB
MC-OSu maleimidocaproyl-O—N-succinimide
J-gene Joining gene
Kabat an immunoglobulin alignment and numbering system pioneered by Elvin A Kabat
mAb monoclonal antibody
Moc methoxycarbonyl
MP maleimidopropanamide
Mtr 4-methoxy-2,3,6-trimethtylbenzenesulfonyl
PAB para-aminobenzyloxycarbonyl
PEG ethyleneoxy
PNZ p-nitrobenzyl carbamate
Psec 2-(phenylsulfonyl)ethoxycarbonyl
T Thymine
TBDMS tert-butyldimethylsilyl
TBDPS tert-butyldiphenylsilyl
t-Bu tert-butyl
Teoc 2-(trimethylsilyl)ethoxycarbonyl
Tos tosyl
Troc 2,2,2-trichlorethoxycarbonyl chloride
Trt trityl
V region The segment of IgG chains which is variable in sequence between different antibodies. It extends to Kabat residue 109 in the light chain and 113 in the heavy chain.
VCl Framework residue classified as vernier or canonical or VH-VL interface
V-gene The gene segment that is rearranged, together with a J (and D for VH) gene, to generate a complete VK (or VH)
VH Immunoglobulin heavy chain variable region VK Immunoglobulin kappa light chain variable region
Xan xanthyl

REFERENCES

[1] C. Chothia, et al., "Domain association in immunoglobulin molecules. The packing of variable domains," J Mol. Biol. 186(3), 651 (1985).
[2] J. Foote and G. Winter, "Antibody framework residues affecting the conformation of the hypervariable loops," J Mol. Biol. 224(2), 487 (1992).
[3] E. A Kabat, et al., sequences of proteins of immunological interest, 5 ed. (NIH National Technical Information Service, 1991).
[4] V. Morea, A. M. Lesk, and A. Tramontano, "Antibody modeling: implications for engineering and design," Methods 20(3), 267 (2000).

STATEMENTS OF DISCLOSURE

1. An isolated humanized antibody that binds to Tn-MUC1, wherein the isolated humanized antibody comprises a heavy chain variable region having the amino acid sequence of SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, or 29, a light chain variable region having the amino acid sequence of SEQ ID NO: 31, 32, 33, or 34, and optionally comprises a constant region derived from one or more human antibodies.

2. The isolated humanized antibody according to statement 1, wherein the isolated humanized antibody comprises:
(i) a heavy chain variable region having the amino acid sequence of SEQ ID NO: 2 and a light chain variable region having the amino acid sequence of SEQ ID NO: 30;
(ii) a heavy chain variable region having the amino acid sequence of SEQ ID NO: 3 and a light chain variable region having the amino acid sequence of SEQ ID NO: 30;
(iii) a heavy chain variable region having the amino acid sequence of SEQ ID NO: 4 and a light chain variable region having the amino acid sequence of SEQ ID NO: 30;
(iv) a heavy chain variable region having the amino acid sequence of SEQ ID NO: 5 and a light chain variable region having the amino acid sequence of SEQ ID NO: 30;
(v) a heavy chain variable region having the amino acid sequence of SEQ ID NO: 6 and a light chain variable region having the amino acid sequence of SEQ ID NO: 30;
(vi) a heavy chain variable region having the amino acid sequence of SEQ ID NO: 7 and a light chain variable region having the amino acid sequence of SEQ ID NO: 30;
(vii) a heavy chain variable region having the amino acid sequence of SEQ ID NO: 8 and a light chain variable region having the amino acid sequence of SEQ ID NO: 30;
(viii) a heavy chain variable region having the amino acid sequence of SEQ ID NO: 9 and a light chain variable region having the amino acid sequence of SEQ ID NO: 30;
(ix) a heavy chain variable region having the amino acid sequence of SEQ ID NO: 10 and a light chain variable region having the amino acid sequence of SEQ ID NO: 30;
(x) a heavy chain variable region having the amino acid sequence of SEQ ID NO: 11 and a light chain variable region having the amino acid sequence of SEQ ID NO: 30;
(xi) a heavy chain variable region having the amino acid sequence of SEQ ID NO: 12 and a light chain variable region having the amino acid sequence of SEQ ID NO: 30;
(xii) a heavy chain variable region having the amino acid sequence of SEQ ID NO: 13 and a light chain variable region having the amino acid sequence of SEQ ID NO: 30;
(xiii) a heavy chain variable region having the amino acid sequence of SEQ ID NO: 14 and a light chain variable region having the amino acid sequence of SEQ ID NO: 30;
(xiv) a heavy chain variable region having the amino acid sequence of SEQ ID NO: 15 and a light chain variable region having the amino acid sequence of SEQ ID NO: 30;
(xv) a heavy chain variable region having the amino acid sequence of SEQ ID NO: 16 and a light chain variable region having the amino acid sequence of SEQ ID NO: 30;
(xvi) a heavy chain variable region having the amino acid sequence of SEQ ID NO: 17 and a light chain variable region having the amino acid sequence of SEQ ID NO: 30;
(xvii) a heavy chain variable region having the amino acid sequence of SEQ ID NO: 18 and a light chain variable region having the amino acid sequence of SEQ ID NO: 30;
(xviii) a heavy chain variable region having the amino acid sequence of SEQ ID NO: 19 and a light chain variable region having the amino acid sequence of SEQ ID NO: 30;
(xix) a heavy chain variable region having the amino acid sequence of SEQ ID NO: 20 and a light chain variable region having the amino acid sequence of SEQ ID NO: 30;
(xx) a heavy chain variable region having the amino acid sequence of SEQ ID NO: 21 and a light chain variable region having the amino acid sequence of SEQ ID NO: 30;
(xxi) a heavy chain variable region having the amino acid sequence of SEQ ID NO: 22 and a light chain variable region having the amino acid sequence of SEQ ID NO: 30;
(xxii) a heavy chain variable region having the amino acid sequence of SEQ ID NO: 23 and a light chain variable region having the amino acid sequence of SEQ ID NO: 30;
(xxiii) a heavy chain variable region having the amino acid sequence of SEQ ID NO: 24 and a light chain variable region having the amino acid sequence of SEQ ID NO: 30;
(xxiv) a heavy chain variable region having the amino acid sequence of SEQ ID NO: 25 and a light chain variable region having the amino acid sequence of SEQ ID NO: 30;
(xxv) a heavy chain variable region having the amino acid sequence of SEQ ID NO: 26 and a light chain variable region having the amino acid sequence of SEQ ID NO: 30;
(xxvi) a heavy chain variable region having the amino acid sequence of SEQ ID NO: 27 and a light chain variable region having the amino acid sequence of SEQ ID NO: 30;
(xxvii) a heavy chain variable region having the amino acid sequence of SEQ ID NO: 28 and a light chain variable region having the amino acid sequence of SEQ ID NO: 30;
(xxviii) a heavy chain variable region having the amino acid sequence of SEQ ID NO: 29 and a light chain variable region having the amino acid sequence of SEQ ID NO: 30;
(xxix) a heavy chain variable region having the amino acid sequence of SEQ ID NO: 1 and a light chain variable region having the amino acid sequence of SEQ ID NO: 31;
(xxx) a heavy chain variable region having the amino acid sequence of SEQ ID NO: 2 and a light chain variable region having the amino acid sequence of SEQ ID NO: 31;
(xxxi) a heavy chain variable region having the amino acid sequence of SEQ ID NO: 3 and a light chain variable region having the amino acid sequence of SEQ ID NO: 31;
(xxxii) a heavy chain variable region having the amino acid sequence of SEQ ID NO: 4 and a light chain variable region having the amino acid sequence of SEQ ID NO: 31;
(xxxiii) a heavy chain variable region having the amino acid sequence of SEQ ID NO: 5 and a light chain variable region having the amino acid sequence of SEQ ID NO: 31;
(xxxiv) a heavy chain variable region having the amino acid sequence of SEQ ID NO: 6 and a light chain variable region having the amino acid sequence of SEQ ID NO: 31;

(xxxv) a heavy chain variable region having the amino acid sequence of SEQ ID NO: 7 and a light chain variable region having the amino acid sequence of SEQ ID NO: 31;
(xxxvi) a heavy chain variable region having the amino acid sequence of SEQ ID NO: 8 and a light chain variable region having the amino acid sequence of SEQ ID NO: 31;
(xxxvii) a heavy chain variable region having the amino acid sequence of SEQ ID NO: 9 and a light chain variable region having the amino acid sequence of SEQ ID NO: 31;
(xxxviii) a heavy chain variable region having the amino acid sequence of SEQ ID NO: 10 and a light chain variable region having the amino acid sequence of SEQ ID NO: 31;
(xxxix) a heavy chain variable region having the amino acid sequence of SEQ ID NO: 11 and a light chain variable region having the amino acid sequence of SEQ ID NO: 31;
(xl) a heavy chain variable region having the amino acid sequence of SEQ ID NO: 12 and a light chain variable region having the amino acid sequence of SEQ ID NO: 31;
(xli) a heavy chain variable region having the amino acid sequence of SEQ ID NO: 13 and a light chain variable region having the amino acid sequence of SEQ ID NO: 31;
(xlii) a heavy chain variable region having the amino acid sequence of SEQ ID NO: 14 and a light chain variable region having the amino acid sequence of SEQ ID NO: 31;
(xliii) a heavy chain variable region having the amino acid sequence of SEQ ID NO: 15 and a light chain variable region having the amino acid sequence of SEQ ID NO: 31;
(xliv) a heavy chain variable region having the amino acid sequence of SEQ ID NO: 16 and a light chain variable region having the amino acid sequence of SEQ ID NO: 31;
(xlv) a heavy chain variable region having the amino acid sequence of SEQ ID NO: 17 and a light chain variable region having the amino acid sequence of SEQ ID NO: 31;
(xlvi) a heavy chain variable region having the amino acid sequence of SEQ ID NO: 18 and a light chain variable region having the amino acid sequence of SEQ ID NO: 31;
(xlvii) a heavy chain variable region having the amino acid sequence of SEQ ID NO: 19 and a light chain variable region having the amino acid sequence of SEQ ID NO: 31;
(xlviii) a heavy chain variable region having the amino acid sequence of SEQ ID NO: 20 and a light chain variable region having the amino acid sequence of SEQ ID NO: 31;
(xlix) a heavy chain variable region having the amino acid sequence of SEQ ID NO: 21 and a light chain variable region having the amino acid sequence of SEQ ID NO: 31;
(l) a heavy chain variable region having the amino acid sequence of SEQ ID NO: 22 and a light chain variable region having the amino acid sequence of SEQ ID NO: 31;
(li) a heavy chain variable region having the amino acid sequence of SEQ ID NO: 23 and a light chain variable region having the amino acid sequence of SEQ ID NO: 31;
(lii) a heavy chain variable region having the amino acid sequence of SEQ ID NO: 24 and a light chain variable region having the amino acid sequence of SEQ ID NO: 31;
(liii) a heavy chain variable region having the amino acid sequence of SEQ ID NO: 25 and a light chain variable region having the amino acid sequence of SEQ ID NO: 31;
(liv) a heavy chain variable region having the amino acid sequence of SEQ ID NO: 26 and a light chain variable region having the amino acid sequence of SEQ ID NO: 31;
(lv) a heavy chain variable region having the amino acid sequence of SEQ ID NO: 27 and a light chain variable region having the amino acid sequence of SEQ ID NO: 31;
(lvi) a heavy chain variable region having the amino acid sequence of SEQ ID NO: 28 and a light chain variable region having the amino acid sequence of SEQ ID NO: 31;
(lvii) a heavy chain variable region having the amino acid sequence of SEQ ID NO: 29 and a light chain variable region having the amino acid sequence of SEQ ID NO: 31;
(lviii) a heavy chain variable region having the amino acid sequence of SEQ ID NO: 1 and a light chain variable region having the amino acid sequence of SEQ ID NO: 32;
(lix) a heavy chain variable region having the amino acid sequence of SEQ ID NO: 2 and a light chain variable region having the amino acid sequence of SEQ ID NO: 32;
(lx) a heavy chain variable region having the amino acid sequence of SEQ ID NO: 3 and a light chain variable region having the amino acid sequence of SEQ ID NO: 32;
(lxi) a heavy chain variable region having the amino acid sequence of SEQ ID NO: 4 and a light chain variable region having the amino acid sequence of SEQ ID NO: 32;
(lxii) a heavy chain variable region having the amino acid sequence of SEQ ID NO: 5 and a light chain variable region having the amino acid sequence of SEQ ID NO: 32;
(lxiii) a heavy chain variable region having the amino acid sequence of SEQ ID NO: 6 and a light chain variable region having the amino acid sequence of SEQ ID NO: 32;
(lxiv) a heavy chain variable region having the amino acid sequence of SEQ ID NO: 7 and a light chain variable region having the amino acid sequence of SEQ ID NO: 32;
(lxv) a heavy chain variable region having the amino acid sequence of SEQ ID NO: 8 and a light chain variable region having the amino acid sequence of SEQ ID NO: 32;
(lxvi) a heavy chain variable region having the amino acid sequence of SEQ ID NO: 9 and a light chain variable region having the amino acid sequence of SEQ ID NO: 32;
(lxvii) a heavy chain variable region having the amino acid sequence of SEQ ID NO: 10 and a light chain variable region having the amino acid sequence of SEQ ID NO: 32;
(lxviii) a heavy chain variable region having the amino acid sequence of SEQ ID NO: 11 and a light chain variable region having the amino acid sequence of SEQ ID NO: 32;
(lxix) a heavy chain variable region having the amino acid sequence of SEQ ID NO: 12 and a light chain variable region having the amino acid sequence of SEQ ID NO: 32;
(lxx) a heavy chain variable region having the amino acid sequence of SEQ ID NO: 13 and a light chain variable region having the amino acid sequence of SEQ ID NO: 32;
(lxxi) a heavy chain variable region having the amino acid sequence of SEQ ID NO: 14 and a light chain variable region having the amino acid sequence of SEQ ID NO: 32;
(lxxii) a heavy chain variable region having the amino acid sequence of SEQ ID NO: 15 and a light chain variable region having the amino acid sequence of SEQ ID NO: 32;
(lxxiii) a heavy chain variable region having the amino acid sequence of SEQ ID NO: 16 and a light chain variable region having the amino acid sequence of SEQ ID NO: 32;
(lxxiv) a heavy chain variable region having the amino acid sequence of SEQ ID NO: 17 and a light chain variable region having the amino acid sequence of SEQ ID NO: 32;
(lxxv) a heavy chain variable region having the amino acid sequence of SEQ ID NO: 18 and a light chain variable region having the amino acid sequence of SEQ ID NO: 32;
(lxxvi) a heavy chain variable region having the amino acid sequence of SEQ ID NO: 19 and a light chain variable region having the amino acid sequence of SEQ ID NO: 32;
(lxxvii) a heavy chain variable region having the amino acid sequence of SEQ ID NO: 20 and a light chain variable region having the amino acid sequence of SEQ ID NO: 32;
(lxxviii) a heavy chain variable region having the amino acid sequence of SEQ ID NO: 21 and a light chain variable region having the amino acid sequence of SEQ ID NO: 32;

(lxxix) a heavy chain variable region having the amino acid sequence of SEQ ID NO: 22 and a light chain variable region having the amino acid sequence of SEQ ID NO: 32;

(lxxx) a heavy chain variable region having the amino acid sequence of SEQ ID NO: 23 and a light chain variable region having the amino acid sequence of SEQ ID NO: 32;

(lxxxi) a heavy chain variable region having the amino acid sequence of SEQ ID NO: 24 and a light chain variable region having the amino acid sequence of SEQ ID NO: 32;

(lxxxii) a heavy chain variable region having the amino acid sequence of SEQ ID NO: 25 and a light chain variable region having the amino acid sequence of SEQ ID NO: 32;

(lxxxiii) a heavy chain variable region having the amino acid sequence of SEQ ID NO: 26 and a light chain variable region having the amino acid sequence of SEQ ID NO: 32;

(lxxxiv) a heavy chain variable region having the amino acid sequence of SEQ ID NO: 27 and a light chain variable region having the amino acid sequence of SEQ ID NO: 32;

(lxxxv) a heavy chain variable region having the amino acid sequence of SEQ ID NO: 28 and a light chain variable region having the amino acid sequence of SEQ ID NO: 32;

(lxxxvi) a heavy chain variable region having the amino acid sequence of SEQ ID NO: 29 and a light chain variable region having the amino acid sequence of SEQ ID NO: 32;

(lxxxvii) a heavy chain variable region having the amino acid sequence of SEQ ID NO: 1 and a light chain variable region having the amino acid sequence of SEQ ID NO: 33;

(lxxxviii) a heavy chain variable region having the amino acid sequence of SEQ ID NO: 2 and a light chain variable region having the amino acid sequence of SEQ ID NO: 33;

(lxxxix) a heavy chain variable region having the amino acid sequence of SEQ ID NO: 3 and a light chain variable region having the amino acid sequence of SEQ ID NO: 33;

(xc) a heavy chain variable region having the amino acid sequence of SEQ ID NO: 4 and a light chain variable region having the amino acid sequence of SEQ ID NO: 33;

(xci) a heavy chain variable region having the amino acid sequence of SEQ ID NO: 5 and a light chain variable region having the amino acid sequence of SEQ ID NO: 33;

(xcii) a heavy chain variable region having the amino acid sequence of SEQ ID NO: 6 and a light chain variable region having the amino acid sequence of SEQ ID NO: 33;

(xciii) a heavy chain variable region having the amino acid sequence of SEQ ID NO: 7 and a light chain variable region having the amino acid sequence of SEQ ID NO: 33;

(xciv) a heavy chain variable region having the amino acid sequence of SEQ ID NO: 8 and a light chain variable region having the amino acid sequence of SEQ ID NO: 33;

(xcv) a heavy chain variable region having the amino acid sequence of SEQ ID NO: 9 and a light chain variable region having the amino acid sequence of SEQ ID NO: 33;

(xcvi) a heavy chain variable region having the amino acid sequence of SEQ ID NO: 10 and a light chain variable region having the amino acid sequence of SEQ ID NO: 33;

(xcvii) a heavy chain variable region having the amino acid sequence of SEQ ID NO: 11 and a light chain variable region having the amino acid sequence of SEQ ID NO: 33;

(xciii) a heavy chain variable region having the amino acid sequence of SEQ ID NO: 12 and a light chain variable region having the amino acid sequence of SEQ ID NO: 33;

(xciv) a heavy chain variable region having the amino acid sequence of SEQ ID NO: 13 and a light chain variable region having the amino acid sequence of SEQ ID NO: 33;

(xcv) a heavy chain variable region having the amino acid sequence of SEQ ID NO: 14 and a light chain variable region having the amino acid sequence of SEQ ID NO: 33;

(xcvi) a heavy chain variable region having the amino acid sequence of SEQ ID NO: 15 and a light chain variable region having the amino acid sequence of SEQ ID NO: 33;

(xcvii) a heavy chain variable region having the amino acid sequence of SEQ ID NO: 16 and a light chain variable region having the amino acid sequence of SEQ ID NO: 33;

(xcviii) a heavy chain variable region having the amino acid sequence of SEQ ID NO: 17 and a light chain variable region having the amino acid sequence of SEQ ID NO: 33;

(xciv) a heavy chain variable region having the amino acid sequence of SEQ ID NO: 18 and a light chain variable region having the amino acid sequence of SEQ ID NO: 33;

(xcv) a heavy chain variable region having the amino acid sequence of SEQ ID NO: 19 and a light chain variable region having the amino acid sequence of SEQ ID NO: 33;

(xcvi) a heavy chain variable region having the amino acid sequence of SEQ ID NO: 20 and a light chain variable region having the amino acid sequence of SEQ ID NO: 33;

(xcvii) a heavy chain variable region having the amino acid sequence of SEQ ID NO: 21 and a light chain variable region having the amino acid sequence of SEQ ID NO: 33;

(xcviii) a heavy chain variable region having the amino acid sequence of SEQ ID NO: 22 and a light chain variable region having the amino acid sequence of SEQ ID NO: 33;

(xcix) a heavy chain variable region having the amino acid sequence of SEQ ID NO: 23 and a light chain variable region having the amino acid sequence of SEQ ID NO: 33;

(c) a heavy chain variable region having the amino acid sequence of SEQ ID NO: 24 and a light chain variable region having the amino acid sequence of SEQ ID NO: 33;

(ci) a heavy chain variable region having the amino acid sequence of SEQ ID NO: 25 and a light chain variable region having the amino acid sequence of SEQ ID NO: 33;

(cii) a heavy chain variable region having the amino acid sequence of SEQ ID NO: 26 and a light chain variable region having the amino acid sequence of SEQ ID NO: 33;

(ciii) a heavy chain variable region having the amino acid sequence of SEQ ID NO: 27 and a light chain variable region having the amino acid sequence of SEQ ID NO: 33;

(civ) a heavy chain variable region having the amino acid sequence of SEQ ID NO: 28 and a light chain variable region having the amino acid sequence of SEQ ID NO: 33;

(cv) a heavy chain variable region having the amino acid sequence of SEQ ID NO: 29 and a light chain variable region having the amino acid sequence of SEQ ID NO: 33;

(cvi) a heavy chain variable region having the amino acid sequence of SEQ ID NO: 1 and a light chain variable region having the amino acid sequence of SEQ ID NO: 34;

(cvii) a heavy chain variable region having the amino acid sequence of SEQ ID NO: 2 and a light chain variable region having the amino acid sequence of SEQ ID NO: 34;

(cviii) a heavy chain variable region having the amino acid sequence of SEQ ID NO: 3 and a light chain variable region having the amino acid sequence of SEQ ID NO: 34;

(cix) a heavy chain variable region having the amino acid sequence of SEQ ID NO: 4 and a light chain variable region having the amino acid sequence of SEQ ID NO: 34;

(cx) a heavy chain variable region having the amino acid sequence of SEQ ID NO: 5 and a light chain variable region having the amino acid sequence of SEQ ID NO: 34;

(cxi) a heavy chain variable region having the amino acid sequence of SEQ ID NO: 6 and a light chain variable region having the amino acid sequence of SEQ ID NO: 34;

(cxii) a heavy chain variable region having the amino acid sequence of SEQ ID NO: 7 and a light chain variable region having the amino acid sequence of SEQ ID NO: 34;

(cxiii) a heavy chain variable region having the amino acid sequence of SEQ ID NO: 8 and a light chain variable region having the amino acid sequence of SEQ ID NO: 34;

(cxiv) a heavy chain variable region having the amino acid sequence of SEQ ID NO: 9 and a light chain variable region having the amino acid sequence of SEQ ID NO: 34;

(cxv) a heavy chain variable region having the amino acid sequence of SEQ ID NO: 10 and a light chain variable region having the amino acid sequence of SEQ ID NO: 34;

(cxvi) a heavy chain variable region having the amino acid sequence of SEQ ID NO: 11 and a light chain variable region having the amino acid sequence of SEQ ID NO: 34;

(cxvii) a heavy chain variable region having the amino acid sequence of SEQ ID NO: 12 and a light chain variable region having the amino acid sequence of SEQ ID NO: 34;

(cxviii) a heavy chain variable region having the amino acid sequence of SEQ ID NO: 13 and a light chain variable region having the amino acid sequence of SEQ ID NO: 34;

(cxix) a heavy chain variable region having the amino acid sequence of SEQ ID NO: 14 and a light chain variable region having the amino acid sequence of SEQ ID NO: 34;

(cxx) a heavy chain variable region having the amino acid sequence of SEQ ID NO: 15 and a light chain variable region having the amino acid sequence of SEQ ID NO: 34;

(cxxi) a heavy chain variable region having the amino acid sequence of SEQ ID NO: 16 and a light chain variable region having the amino acid sequence of SEQ ID NO: 34;

(cxxii) a heavy chain variable region having the amino acid sequence of SEQ ID NO: 17 and a light chain variable region having the amino acid sequence of SEQ ID NO: 34;

(cxxiii) a heavy chain variable region having the amino acid sequence of SEQ ID NO: 18 and a light chain variable region having the amino acid sequence of SEQ ID NO: 34;

(cxxiv) a heavy chain variable region having the amino acid sequence of SEQ ID NO: 19 and a light chain variable region having the amino acid sequence of SEQ ID NO: 34;

(cxxv) a heavy chain variable region having the amino acid sequence of SEQ ID NO: 20 and a light chain variable region having the amino acid sequence of SEQ ID NO: 34;

(cxxvi) a heavy chain variable region having the amino acid sequence of SEQ ID NO: 21 and a light chain variable region having the amino acid sequence of SEQ ID NO: 34;

(cxxvii) a heavy chain variable region having the amino acid sequence of SEQ ID NO: 22 and a light chain variable region having the amino acid sequence of SEQ ID NO: 34;

(cxxviii) a heavy chain variable region having the amino acid sequence of SEQ ID NO: 23 and a light chain variable region having the amino acid sequence of SEQ ID NO: 34;

(cxxix) a heavy chain variable region having the amino acid sequence of SEQ ID NO: 24 and a light chain variable region having the amino acid sequence of SEQ ID NO: 34;

(cxxx) a heavy chain variable region having the amino acid sequence of SEQ ID NO: 25 and a light chain variable region having the amino acid sequence of SEQ ID NO: 34;

(cxxxi) a heavy chain variable region having the amino acid sequence of SEQ ID NO: 26 and a light chain variable region having the amino acid sequence of SEQ ID NO: 34;

(cxxxii) a heavy chain variable region having the amino acid sequence of SEQ ID NO: 27 and a light chain variable region having the amino acid sequence of SEQ ID NO: 34;

(cxxxiii) a heavy chain variable region having the amino acid sequence of SEQ ID NO: 28 and a light chain variable region having the amino acid sequence of SEQ ID NO: 34; or (cxxxiv) a heavy chain variable region having the amino acid sequence of SEQ ID NO: 29 and a light chain variable region having the amino acid sequence of SEQ ID NO: 34.

3. The humanized antibody according to any one of statements 1 to 2, wherein said antibody binds Tn-MUC1 with an affinity (Kd) of at least $10^{-6}$ M.

4. The humanized antibody according to statement 3, wherein said antibody binds Tn-MUC1 with an affinity (Kd) of at least $10^{-9}$ M.

5. The humanized antibody according to any one of statements 1 to 4, wherein said antibody competitively inhibits the binding to Tn-MUC1 of an antibody comprising a heavy chain variable region having the amino acid sequence of SEQ ID NO: 1 and a light chain variable region having the amino acid sequence of SEQ ID NO: 30.

6. The humanized antibody according to any one of statements 1 to 5, wherein said antibody competitively inhibits the binding to Tn-MUC1 of the mouse 5E5 antibody.

7. The humanized antibody according to any one of statements 1 to 6, wherein said antibody or antibody fragment substantially neutralizes at least one activity of at least one Tn-MUC1.

8. The humanized antibody according to any one of statements 1 to 7, wherein said antibody or antibody fragment expresses at a level of at least 10 micrograms/ml in a static HEK293T transient expression system.

9. The humanized antibody according to any one of statements 1 to 7, wherein said antibody or antibody fragment expresses at a level of at least 20 micrograms/ml in a shaken HEK293T transient expression system.

10. The humanized antibody according to any one of statements 1 to 9, wherein said antibody has a melting temperature ($T_m$) of at least 62° C.

11. The humanized antibody according to any one of statements 1 to 10, wherein said antibody or antibody fragment has a constant region of either isotype IgG1, IgG2, IgG3 or IgG4, or a mutated IgG constant region, and optionally a light chain constant region of isotype kappa or lambda.

12. The humanized antibody according to any one of statements 1 to 11, wherein the humanized antibody fragment is a scFv, Fab or F(ab')$_2$.

13. A conjugate of formula L-(D$^L$)$_p$, where DL is of formula I or II:

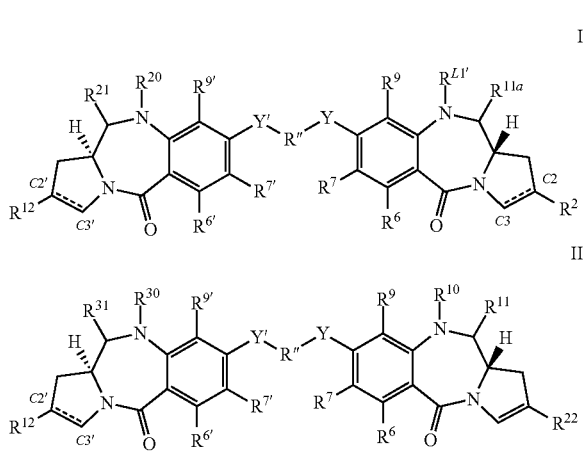

wherein:

L is an isolated humanized antibody that binds to Tn-MUC1 (Ab) according to any one of statements 1 to 12;

when there is a double bond present between C2' and C3', $R^{12}$ is selected from the group consisting of:

(ia) C-10 aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

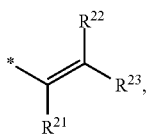

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

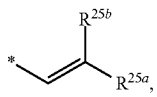

wherein one of $R^{25a}$ and $R^{25b}$ is H and the other is selected from: phenyl, which phenyl is optionally substituted by a group selected from halo, methyl, methoxy; pyridyl; and thiophenyl; and (if)

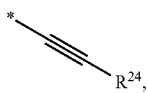

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

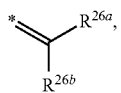

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted $C_{1-12}$ alkyl, $C_{3-20}$ heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{13}$ alkylene;

(ib) $C_{1-5}$ saturated aliphatic alkyl;

(ic) $C_{3-6}$ saturated cycloalkyl;

(id)

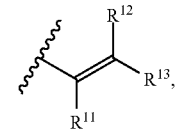

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

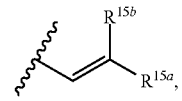

wherein one of $R^{15a}$ and $R^{15b}$ is H and the other is selected from: phenyl, which phenyl is optionally substituted by a group selected from halo, methyl, methoxy; pyridyl; and thiophenyl; and (if)

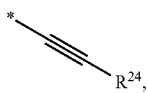

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, $R^2$ is

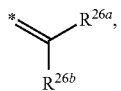

where $R^{116}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

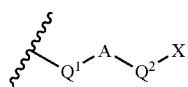

IIIa where A is a $C_{5-7}$ aryl group, and either
(i) $Q^1$ is a single bond, and $Q^2$ is selected from a single bond and —Z—$(CH_2)_n$—, where Z is selected from a single bond, O, S and NH and n is from 1 to 3; or
(ii) $Q^1$ is —CH=CH—, and $Q^2$ is a single bond;

(b)

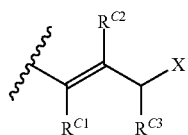

IIIb where;
$R^{C1}$, $R^{C2}$ and $R^{C3}$ are independently selected from H and unsubstituted $C_{1-2}$ alkyl;

(c)

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, CO—$R^{L2'}$, NH—C(=O)—$R^{L2'}$, NHNH—$R^{L2'}$, CONHNH—$R^{L2'}$,

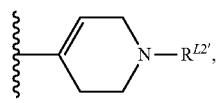 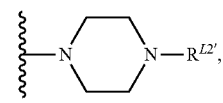

$NR^NR^{L2'}$, wherein $R^N$ is selected from the group comprising H and $C_{1-4}$ alkyl;

$R^{L2'}$ is a linker for connection to the antibody (Ab);
$R^{10}$ and $R^{11}$ either together form a double bond between the nitrogen and carbon atoms to which they are bound or;
$R^{10}$ is H and $R^{11}$ is selected from OH, $OR^A$ and $SO_zM$;
$R^{30}$ and $R^{31}$ either together form a double bond between the nitrogen and carbon atoms to which they are bound or;
$R^{30}$ is H and $R^{31}$ is selected from OH, $OR^A$ and $SO_zM$.

14. The conjugate according to statement 13, wherein $R^7$ is selected from H, OH and OR.

15. The conjugate according to statement 14, wherein $R^7$ is a $C_{1-4}$ alkyloxy group.

16. The conjugate according to any one of statements 13 to 15, wherein Y is O.

17. The conjugate according to any one of statements 13 to 16, wherein R" is $C_{3-7}$ alkylene.

18. The conjugate according to any one of statements 13 to 17, wherein $R^9$ is H.

19. The conjugate according to any one of statements 13 to 18, wherein $R^6$ is selected from H and halo.

20. The conjugate according to any one of statements 13 to 29, wherein there is a double bond between C2' and C3', and $R^{12}$ is a $C_{5-7}$ aryl group.

21. The conjugate according to statement 20, wherein $R^{12}$ is phenyl.

22. The conjugate according to any one of statements 13 to 19, wherein there is a double bond between C2' and C3', and $R^{12}$ is a $C_{8-10}$ aryl group.

23. The conjugate according to any one of statements 20 to 22, wherein $R^{12}$ bears one to three substituent groups.

24. The conjugate according to any one of statements 20 to 23, wherein the substituents are selected from methoxy, ethoxy, fluoro, chloro, cyano, bis-oxy-methylene, methyl-piperazinyl, morpholino and methyl-thiophenyl.

25. The conjugate according to any one of statements 13 to 19, wherein there is a double bond between C2' and C3', and $R^{12}$ is a $C_{1-5}$ saturated aliphatic alkyl group.

26. A compound according to statement 25, wherein $R^{12}$ is methyl, ethyl or propyl.

27. The conjugate according to any one of statements 13 to 19, wherein there is a double bond between C2' and C3', and $R^{12}$ is a $C_{3-6}$ saturated cycloalkyl group.

28. The conjugate according to statement 27, wherein $R^{12}$ is cyclopropyl.

29. The conjugate according to any one of statements 13 to 19, wherein there is a double bond between C2' and C3', and $R^{12}$ is a group of formula:

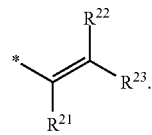

30. The conjugate according to statement 29, wherein the total number of carbon atoms in the $R^{12}$ group is no more than 4.

31. The conjugate according to statement 30, wherein the total number of carbon atoms in the $R^{12}$ group is no more than 3.

32. The conjugate according to any one of statements 29 to 31, wherein one of $R^{21}$, $R^{22}$ and $R^{23}$ is H, with the other two groups being selected from H, $C_{1-3}$ saturated alkyl, $C_{2-3}$ alkenyl, $C_{2-3}$ alkynyl and cyclopropyl.

33. The conjugate according to any one of statements 29 to 31, wherein two of $R^{21}$, $R^{22}$ and $R^{23}$ are H, with the other group being selected from H, $C_{1-3}$ saturated alkyl, $C_{2-3}$ alkenyl, $C_{2-3}$ alkynyl and cyclopropyl.

34. The conjugate according to any one of statements 13 to 19, wherein there is a double bond between C2' and C3', and $R^{12}$ is a group of formula:

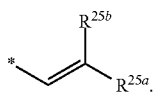

35. The conjugate according to statement 34, wherein $R^{12}$ is the group:

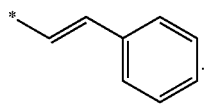

36. The conjugate according to any one of statements 13 to 19, wherein there is a double bond between C2' and C3', and $R^{12}$ is a group of formula:

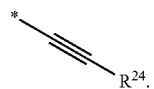

37. The conjugate according to statement 36, wherein $R^{24}$ is selected from H, methyl, ethyl, ethenyl and ethynyl.

38. The conjugate according to statement 37, wherein $R^{24}$ is selected from H and methyl.

39. The conjugate according to any one of statements 13 to 19, wherein there is a single bond between C2' and C3', $R^{12}$ is

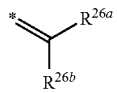

and $R^{26a}$ and $R^{26b}$ are both H.

40. The conjugate according to any one of statements 13 to 19, wherein there is a single bond between C2' and C3', $R^{12}$ is

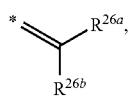

and $R^{26a}$ and $R^{26b}$ are both methyl.

41. The conjugate according to any one of statements 13 to 19, wherein there is a single bond between C2' and C3', $R^{12}$ is

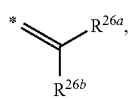

one of $R^{26a}$ and $R^{26b}$ is H, and the other is selected from $C_{1-4}$ saturated alkyl, $C_{2-3}$ alkenyl, which alkyl and alkenyl groups are optionally substituted.

[Formula I]

42. The conjugate according to any one of statements 13 to 41, wherein there is a double bond between C2 and C3, and $R^2$ is a $C_{5-7}$ aryl group.

43. The conjugate according to statement 42, wherein $R^2$ is phenyl.

44. The conjugate according to any one of statements 13 to 41, wherein there is a double bond between C2 and C3, and $R^1$ is a $C_{8-10}$ aryl group.

45. A compound according to any one of statements 42 to 44, wherein $R^2$ bears one to three substituent groups.

46. The conjugate according to any one of statements 42 to 45, wherein the substituents are selected from methoxy, ethoxy, fluoro, chloro, cyano, bis-oxy-methylene, methyl-piperazinyl, morpholino and methyl-thiophenyl.

47. The conjugate according to any one of statements 13 to 41, wherein there is a double bond between C2 and C3, and $R^2$ is a $C_{1-5}$ saturated aliphatic alkyl group.

48. The conjugate according to statement 47, wherein $R^2$ is methyl, ethyl or propyl.

49. The conjugate according to any one of statements 13 to 41, wherein there is a double bond between C2 and C3, and $R^2$ is a $C_{3-6}$ saturated cycloalkyl group.

50. The conjugate according to statement 49, wherein $R^2$ is cyclopropyl.

51. The conjugate according to any one of statements 13 to 41, wherein there is a double bond between C2 and C3, and $R^2$ is a group of formula:

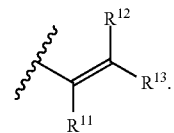

52. The conjugate according to statement 51, wherein the total number of carbon atoms in the $R^2$ group is no more than 4.

53. The conjugate according to statement 52, wherein the total number of carbon atoms in the $R^2$ group is no more than 3.

54. The conjugate according to any one of statements 51 to 53, wherein one of $R^{11}$, $R^{12}$ and $R^{13}$ is H, with the other two groups being selected from H, $C_{1-3}$ saturated alkyl, $C_{2-3}$ alkenyl, $C_{2-3}$ alkynyl and cyclopropyl.

55. The conjugate according to any one of statements 51 to 53, wherein two of $R^{11}$, $R^{12}$ and $R^{13}$ are H, with the other group being selected from H, $C_{1-3}$ saturated alkyl, $C_{2-3}$ alkenyl, $C_{2-3}$ alkynyl and cyclopropyl.

56. The conjugate according to any one of statements 13 to 41, wherein there is a double bond between C2 and C3, and $R^2$ is a group of formula:

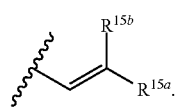

57. The conjugate according to statement 56, wherein $R^2$ is the group:

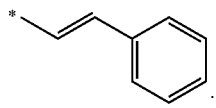

58. The conjugate according to any one of statements 13 to 41, wherein there is a double bond between C2 and C3, and $R^2$ is a group of formula:

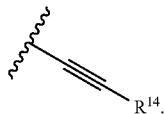

59. The conjugate according to statement 59, wherein $R^{14}$ is selected from H, methyl, ethyl, ethenyl and ethynyl.
60. The conjugate according to statement 59, wherein $R^{14}$ is selected from H and methyl.
61. The conjugate according to any one of statements 13 to 41, wherein there is a single bond between C2 and C3, $R^2$ is

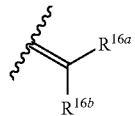

and $R^{16a}$ and $R^{16b}$ are both H.
62. The conjugate according to any one of statements 13 to 41, wherein there is a single bond between C2 and C3, $R^2$ is

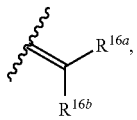

and $R^{16a}$ and $R^{16b}$ are both methyl.
63. The conjugate according to any one of statements 13 to 41, wherein there is a single bond between C2 and C3, $R^2$ is

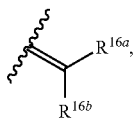

one of $R^{16a}$ and $R^{16b}$ is H, and the other is selected from $C_{1-4}$ saturated alkyl, $C_{2-3}$ alkenyl, which alkyl and alkenyl groups are optionally substituted.
64. The conjugate according to any one of statements 13 to 63, wherein $R^{11a}$ is OH.
65. The conjugate according to any one of statements 13 to 64, wherein $R^{21}$ is OH.
66. The conjugate according to any one of statements 13 to 64, wherein $R^{21}$ is OMe.
67. The conjugate according to any one of statements 13 to 66, wherein $R^{20}$ is H.
68. The conjugate according to any one of statements 13 to 66, wherein $R^{20}$ is $R^C$.
69. The conjugate according to statement 68, wherein $R^C$ is selected from the group consisting of: Alloc, Fmoc, Boc, Troc, Teoc, Psec, Cbz and PNZ.

70. The conjugate according to statement 68, wherein $R^C$ is a group:

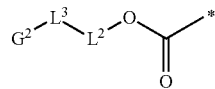

where the asterisk indicates the point of attachment to the N10 position, $G^2$ is a terminating group, $L^3$ is a covalent bond or a cleavable linker $L^1$, $L^2$ is a covalent bond or together with OC(=O) forms a self-immolative linker.

71. The conjugate according to statement 70, wherein $G^2$ is Ac or Moc or is selected from the group consisting of: Alloc, Fmoc, Boc, Troc, Teoc, Psec, Cbz and PNZ.
72. The conjugate according to any one of statements 1 to 64, wherein $R^{20}$ and $R^{21}$ together form a double bond between the nitrogen and carbon atoms to which they are bound.

[Formula II]
73. The conjugate according to any one of statements 13 to 41, wherein $R^{22}$ is of formula IIIa, and A is phenyl.
74. The conjugate according to any one of statements 13 to 41 and statement 73, wherein $R^{22}$ is of formula IIa, and $Q^1$ is a single bond.
75. The conjugate according to statement 73, wherein $Q^2$ is a single bond.
76. The conjugate according to statement 73, wherein $Q^2$ is —Z—$(CH_2)_n$—, Z is O or S and n is 1 or 2.
77. The conjugate according any one of statements 13 to 41 and statement 73, wherein $R^{22}$ is of formula IIIa, and $Q^1$ is —CH=CH—.
78. The conjugate according to any one of statements 13 to 41, wherein $R^{22}$ is of formula IIIb, and $R^{C1}$, $R^{C2}$ and $R^{C3}$ are independently selected from H and methyl.
79. The conjugate according to statement 78, wherein $R^{C1}$, $R^{C2}$ and $R^{C3}$ are all H.
80. The conjugate according to statement 78, wherein $R^{C1}$, $R^{C2}$ and $R^{C3}$ are all methyl.
81. The conjugate according to any one of statements 13 to 41 and statements 73 to 80, wherein $R^{22}$ is of formula IIIa or formula IIIb and X is selected from O—$R^{L2'}$, S—$R^{L2'}$, $CO_2$—$R^{L2'}$, —N—C(=O)—$R^{L2'}$ and NH—$R^{L2'}$.
82. The conjugate according to statement 81, wherein X is NH—$R^{L2'}$.
83. The conjugate according to any one of statements 13 to 41, wherein $R^{22}$ is of formula IIIc, and Q is $NR^N$—$R^{L2'}$.
84. The conjugate according to statement 83, wherein $R^N$ is H or methyl.
85. The conjugate according to any one of statements 13 to 41, wherein $R^{22}$ is of formula IIIc, and Q is O—$R^{L2'}$ or S—$R^{L2'}$.
86. The conjugate according to any one of statements 13 to 41 and statements 73 to 85, wherein $R^{11}$ is OH.
87. The conjugate according to any one of statements 13 to 41 and statements 73 to 85, wherein $R^{11}$ is OMe.
88. The conjugate according to any one of statements 13 to 41 and statements 73 to 85, wherein $R^{10}$ is H.
89. The conjugate according to any one of statements 13 to 41 and statements 73 to 85, wherein $R^{10}$ and $R^{11}$ together form a double bond between the nitrogen and carbon atoms to which they are bound.
90. The conjugate according to any one of statements 13 to 41 and statements 73 to 89, wherein $R^{31}$ is OH.
91. The conjugate according to any one of statements 13 to 41 and statements 73 to 89, wherein $R^{31}$ is OMe.

92. The conjugate according to any one of statements 13 to 41 and statements 73 to 91, wherein $R^{30}$ is H.

93. The conjugate according to any one of statements 13 to 41 and statements 73 to 89, wherein $R^{30}$ and $R^{31}$ together form a double bond between the nitrogen and carbon atoms to which they are bound.

94. The conjugate according to any one of statements 13 to 93, wherein $R^{6'}$, $R^{7'}$, $R^{9'}$, and Y' are the same as $R^6$, $R^7$, $R^9$, and Y.

95. The conjugate according to any one of statements 13 to 94 wherein, wherein $L$-$R^{L1'}$ or $L$-$R^{L2'}$ is a group:

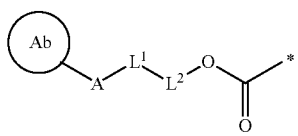

where the asterisk indicates the point of attachment to the PBD, Ab is the antibody, $L^1$ is a cleavable linker, A is a connecting group connecting $L^1$ to the antibody, $L^2$ is a covalent bond or together with —OC(=O)— forms a self-immolative linker.

96. The conjugate of statement 95, wherein $L^1$ is enzyme cleavable.

97. The conjugate of statement 95 or statement 96, wherein $L^1$ comprises a contiguous sequence of amino acids.

98. The conjugate of statement 97, wherein $L^1$ comprises a dipeptide and the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-,
-Phe-Cit-,
-Leu-Cit-,
-Ile-Cit-,
-Phe-Arg-,
-Trp-Cit-.

99. The conjugate according to statement 98, wherein the group —$X_1$—$X_2$— in dipeptide, —NH—$X_1$—$X_2$—CO—, is selected from:
-Phe-Lys-,
-Val-Ala-,
-Val-Lys-,
-Ala-Lys-,
-Val-Cit-.

100. The conjugate according to statement 99, wherein the group —$X_1$—$X_2$— in dipeptide, —NH—$X_1$—$X_2$—CO—, is -Phe-Lys-, -Val-Ala- or -Val-Cit-.

101. The conjugate according to any one of statements 98 to 100, wherein the group $X_2$—CO— is connected to $L^2$.

102. The conjugate according to any one of statements 98 to 101, wherein the group NH—$X_1$— is connected to A.

103. The conjugate according to any one of statements 98 to 102, wherein $L^2$ together with OC(=O) forms a self-immolative linker.

104. The conjugate according to statement 102, wherein C(=O)O and $L^2$ together form the group:

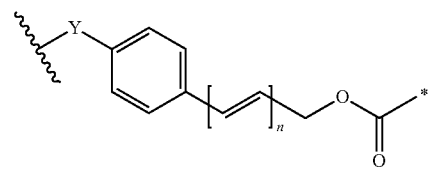

where the asterisk indicates the point of attachment to the PBD, the wavy line indicates the point of attachment to the linker $L^1$, Y is NH, O, C(=O)NH or C(=O)O, and n is 0 to 3.

105. The conjugate according to statement 104, wherein Y is NH.

106. The conjugate according to statement 104 or statement 105, wherein n is 0.

107. The conjugate according to statement 105, wherein $L^1$ and $L^2$ together with —OC(=O)— comprise a group selected from:

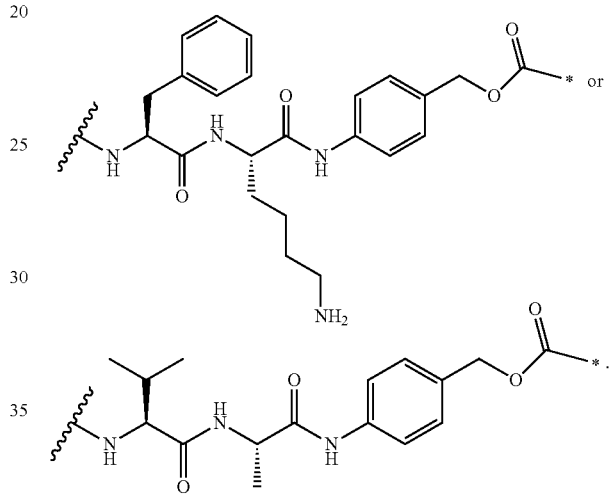

where the asterisk indicates the point of attachment to the PBD, and the wavy line indicates the point of attachment to the remaining portion of the linker $L^1$ or the point of attachment to A.

108. The conjugate according to statement 107, wherein the wavy line indicates the point of attachment to A.

109. The conjugate according to any one of statements 95 to 108, wherein A is:

(i)

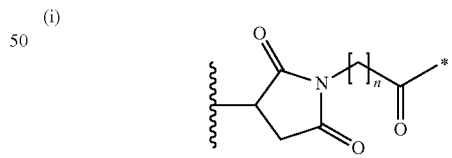

where the asterisk indicates the point of attachment to $L^1$, the wavy line indicates the point of attachment to the antibody, and n is 0 to 6; or (ii)

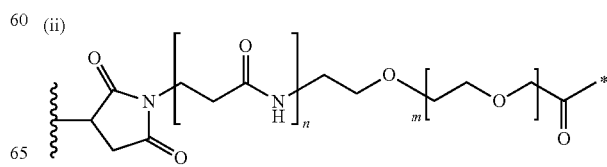

where the asterisk indicates the point of attachment to $L^1$, the wavy line indicates the point of attachment to the antibody, n is 0 or 1, and m is 0 to 30.
110. A conjugate according to statement 13 of formula
ConjA:
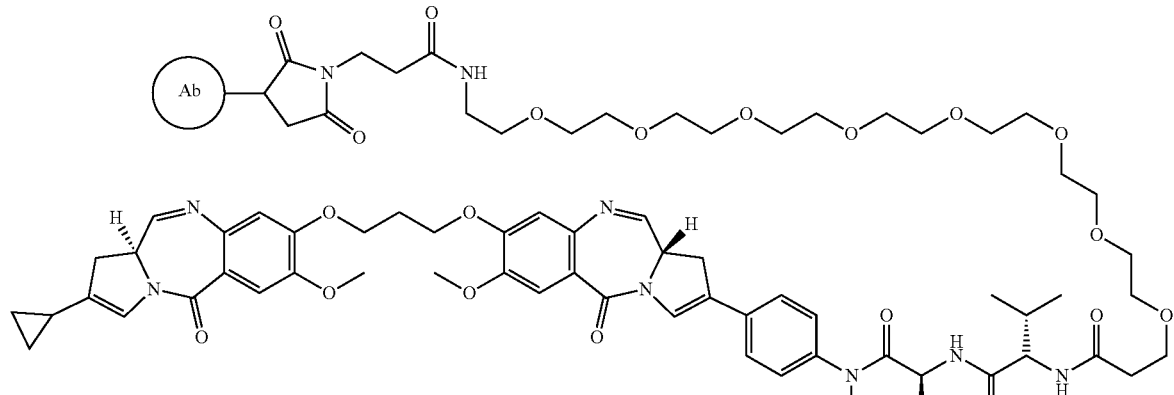
ConjA
ConjB:
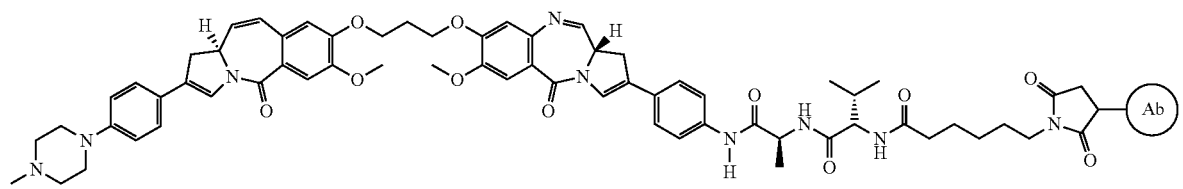
ConjB
ConjC:
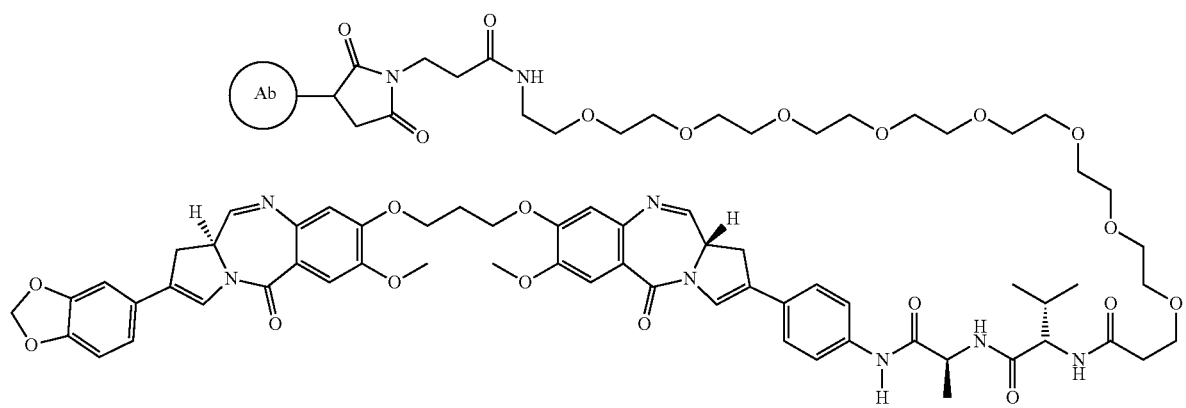
ConjC ConjD:
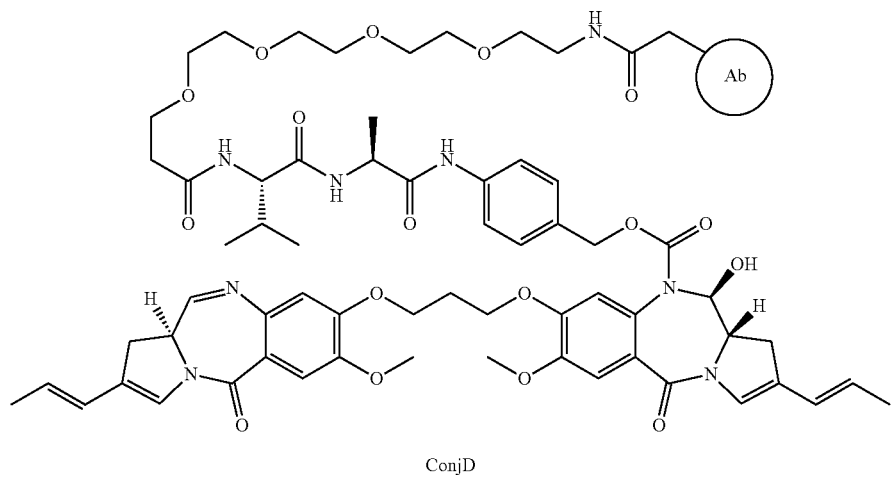
ConjD
ConjE:
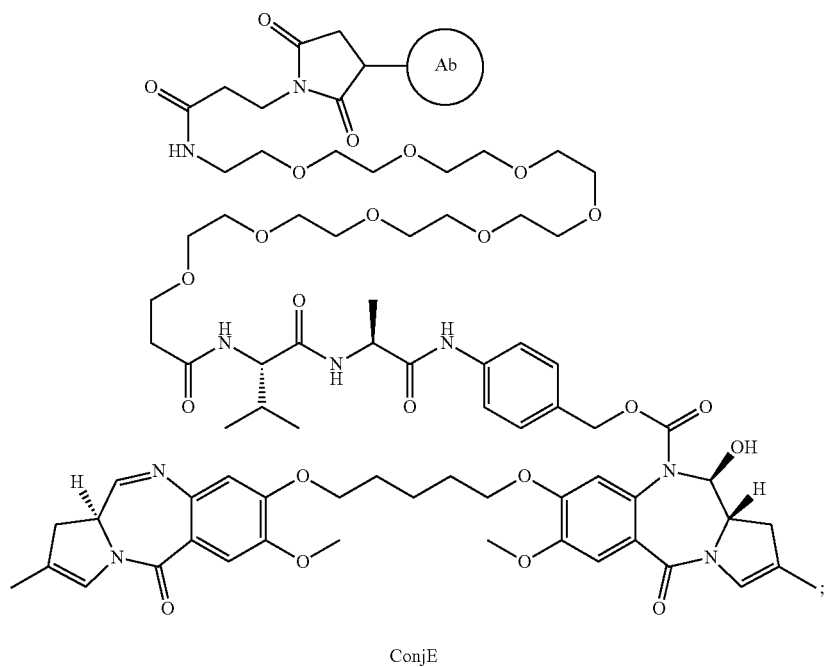
ConjE
ConjF:
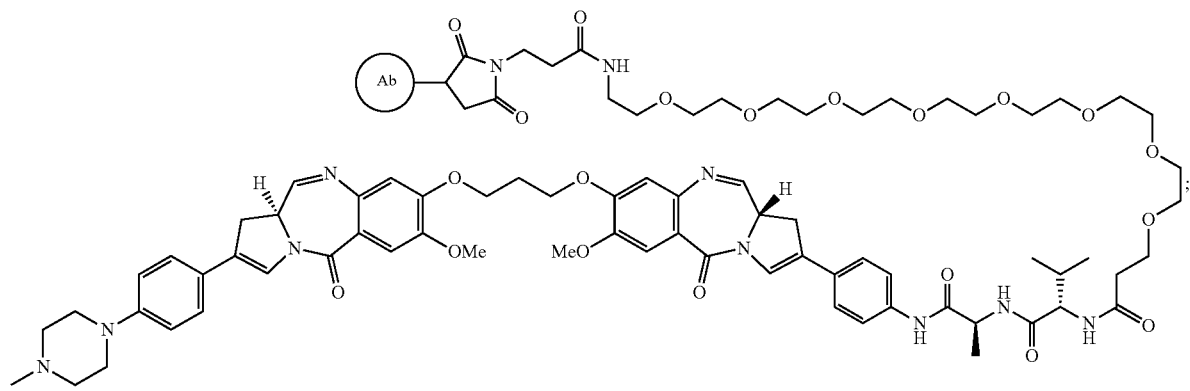
ConjF ConjG:

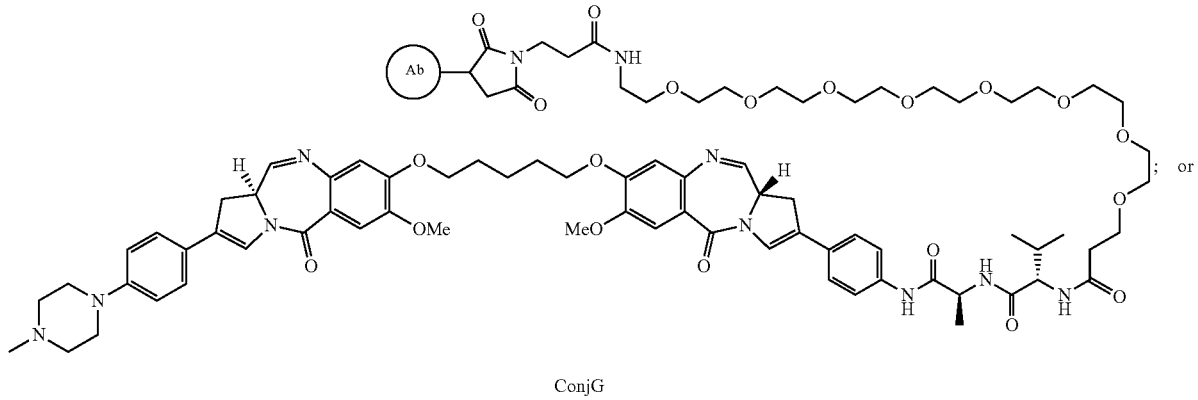

ConjG

ConjH:

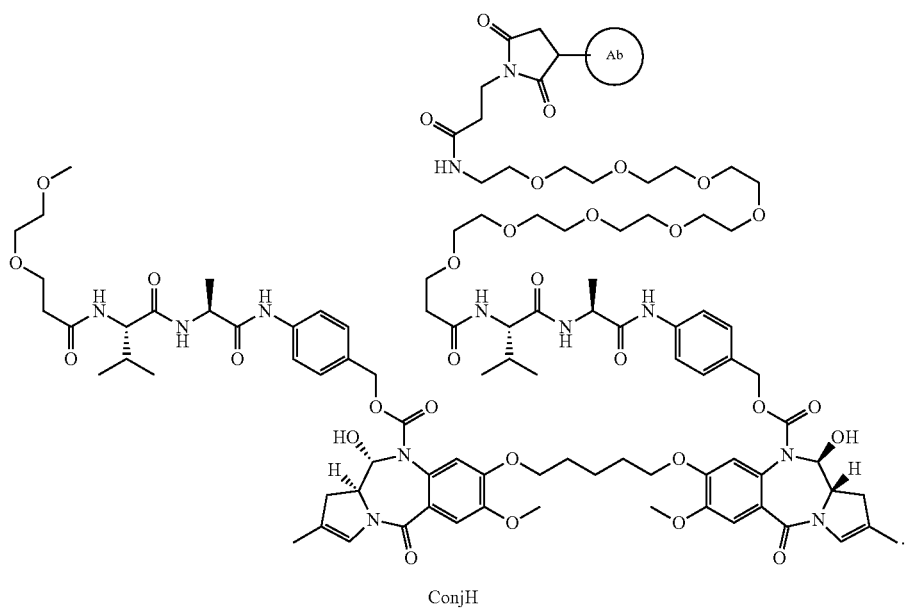

ConjH

111. The drug-conjugate according to any one of statements 13 to 110 wherein the drug loading (p) of drugs (D) to antibody (Ab) is an integer from 1 to about 8.

112. The drug-conjugate according to statement 111 wherein p is 1, 2, 3, or 4.

113. The drug-conjugate according to statement 111 comprising a mixture of the antibody-drug conjugate compounds, wherein the average drug loading per antibody in the mixture of antibody-drug conjugate compounds is about 2 to about 5.

114. The drug-conjugate according to any one of statements 13 to 113, for use in therapy.

115. The drug-conjugate according to any one of statements 13 to 113, for use in the treatment of a proliferative disease in a subject.

116. The drug-conjugate according to any one of statements 13 to 113, for use in the treatment of a proliferative disease in a subject, wherein the subject has raised levels of Tn-MUC1, CA 27.29, or CA 15-3 and wherein the method comprises identifying that the subject has raised levels of Tn-MUC1, CA 27.29, or CA 15-3 and administering the conjugate to the patient.

117. The drug-conjugate according to any one of statements 13 to 113, for use in the treatment of a proliferative disease in a subject, wherein the proliferative disease is associated with raised levels of Tn-MUC1, CA 27.29, or CA 15-3, the method comprising administering the conjugate to the patient.

118. The drug-conjugate according to any one of statements 115 to 117, wherein the disease is cancer.

119. A pharmaceutical composition comprising the drug-conjugate of any one of statements 13 to 113 and a pharmaceutically acceptable diluent, carrier or excipient.

120. The pharmaceutical composition of statement 119 further comprising a therapeutically effective amount of a chemotherapeutic agent.

121. Use of a drug-conjugate according to any one of statements 13 to 113 in the preparation of a medicament for use in the treatment of a proliferative disease in a subject.

122 A method of treating cancer comprising administering to a patient the pharmaceutical composition according to either one of statements 119 or 120.

123. The method of statement 122 wherein the patient is administered a chemotherapeutic agent, in combination with the drug-conjugate.

124. A polynucleotide encoding a humanized antibody according to any one of statements 1 to 12.

125. A vector comprising the polynucleotide of statement 124.

126. The vector of statement 125 wherein the vector is an expression vector.

127. A host cell comprising a vector according to either one of statements 125 or 126.

128. The host cell according to statement 127 wherein the host cell is prokaryotic, eukaryotic, or mammalian.

129. A conjugate comprising the humanized antibody according to any one of statements 1 to 12 coupled to a functional moiety.

130. The conjugate according to statement 129, wherein the functional moiety is selected from a drug, a reporter, a toxin, an organic moiety, and a binding member.

131. The conjugate according to statement 130 wherein the reporter is a fluorescent compound, a radionuclide, or an enzyme.

132. The conjugate according to statement 130 wherein the binding member is an antibody or antibody fragment.

133. The conjugate according to any one of statements 129 to 133, wherein the humanized antibody is covalently bonded to the functional moiety.

134. A method of selecting an individual for treatment with the drug-conjugate according to any one of statements 13 to 113, or with the pharmaceutical composition of either one of statements 119 or 120, which method comprises assessing the level of TnMUC1;
wherein individuals having TnMUC1 are selected for treatment.

135. A method of timing the application of treatment of an individual with the drug-conjugate according to any one of statements 13 to 113, or with the pharmaceutical composition of either one of statements 119 or 120, which method comprises assessing the level of TnMUC1;
wherein the treatment is applied if the individual has TnMUC1.

136. The method according to either one of statements 134 or 135, wherein the individual has cancer and treatment reduces tumour volume.

SEQUENCES

SEQ ID NO: 1 [5E5VH]
QVQLQQSDAELVKPGSSVKISCKASGYTFTDHAIHWVKQKPEQGLEWIGH
FSPGNTDIKYNDKFKGKATLTVDRSSSTAYMQLNSLTSEDSAVYFCKTST
FFFDYWGQGTTLTVSS

SEQ ID NO: 2 [5E5RHA]
QVQLVQSGAEVKKTGSSVKVSCKASGYTFTDHAIHWVRQAPGQALEVVMG
HFSPGNTDIKYNDKFKGRVTITRDRSMSTAYMELSSLRSEDTAMYYCATS
TFFFDYWGQGTMVTVSS

SEQ ID NO: 3 [5E5RHA2]
QVQLVQSGAEVKKTGSSVKVSCKASGYTFTDHAIHWVRQAPGQALEWIGH
FSPGNTDIKYNDKFKGRATLTVDRSMSTAYMELSSLRSEDTAMYYCKTST
FFFDYWGQGTMVTVSS

SEQ ID NO: 4 [5E5RHA3]
QVQLVQSGAEVKKTGSSVKVSCKASGYTFTDHAIHWVRQAPGQALEVVMG
HFSPGNTDIKYNDKFKGRATLTVDRSMSTAYMELSSLRSEDTAMYYCKTS
TFFFDYWGQGTMVTVSS

SEQ ID NO: 5 [5E5RHA4]
QVQLVQSGAEVKKTGSSVKVSCKASGYTFTDHAIHWVRQAPGQALEWIGH
FSPGNTDIKYNDKFKGRVTLTVDRSMSTAYMELSSLRSEDTAMYYCKTST
FFFDYWGQGTMVTVSS

SEQUENCES

SEQ ID NO: 6 [5E5RHA5]
QVQLVQSGAEVKKTGSSVKVSCKASGYTFTDHAIHWVRQAPGQALEWIGH
FSPGNTDIKYNDKFKGRATITVDRSMSTAYMELSSLRSEDTAMYYCKTST
FFFDYWGQGTMVTVSS

SEQ ID NO: 7 [5E5RHA6]
QVQLVQSGAEVKKTGSSVKVSCKASGYTFTDHAIHWVRQAPGQALEWIGH
FSPGNTDIKYNDKFKGRATLTRDRSMSTAYMELSSLRSEDTAMYYCKTST
FFFDYWGQGTMVTVSS

SEQ ID NO: 8 [5E5RHA7]
QVQLVQSGAEVKKTGSSVKVSCKASGYTFTDHAIHWVRQAPGQALEWIGH
FSPGNTDIKYNDKFKGRATLTVDRSMSTAYMELSSLRSEDTAMYYCATST
FFFDYWGQGTMVTVSS

SEQ ID NO: 9 [5E5RHA8]
QVQLVQSGAEVKKTGSSVKVSCKASGYTFTDHAIHWVRQAPGQALEVVMG
HFSPGNTDIKYNDKFKGRVTLTVDRSMSTAYMELSSLRSEDTAMYYCKTS
TFFFDYWGQGTMVTVSS

SEQ ID NO: 10 [5E5RHB]
EVQLVQSGAEVKKPGESLKISCKISGYIFTDHAIHWVRQMPGKGLEVVMG
HFSPGNTDIKYNDKFKGQVTFSVDRSINTAYLQWSSLKASDTAIYFCARS
TFFFDYWGQGTRVTVSS

SEQ ID NO: 11 [5E5RHB2]
EVQLVQSGAEVKKPGESLKISCKISGYIFTDHAIHWVRQMPGKGLEWIGH
FSPGNTDIKYNDKFKGQATLSVDRSINTAYLQWSSLKASDTAIYFCKTST
FFFDYWGQGTRVTVSS

SEQ ID NO: 12 [5E5RHB3]
EVQLVQSGAEVKKPGESLKISCKISGYIFTDHAIHWVRQMPGKGLEWIGH
FSPGNTDIKYNDKFKGQATLSVDRSINTAYLQWSSLKASDTAIYFCKTST
FFFDYWGQGTRVTVSS

SEQ ID NO: 13 [5E5RHB4]
EVQLVQSGAEVKKPGESLKISCKISGYIFTDHAIHWVRQMPGKGLEWMGH
FSPGNTDIKYNDKFKGQATLSVDRSINTAYLQWSSLKASDTAIYFCKTST
FFFDYWGQGTRVTVSS

SEQ ID NO: 14 [5E5RHB5]
EVQLVQSGAEVKKPGESLKISCKISGYIFTDHAIHWVRQMPGKGLEWIGH
FSPGNTDIKYNDKFKGQVTLSVDRSINTAYLQWSSLKASDTAIYFCKTST
FFFDYWGQGTRVTVSS

SEQ ID NO: 15 [5E5RHB6]
EVQLVQSGAEVKKPGESLKISCKISGYIFTDHAIHWVRQMPGKGLEWIGH
FSPGNTDIKYNDKFKGQATFSVDRSINTAYLQWSSLKASDTAIYFCKTST
FFFDYWGQGTRVTVSS

SEQ ID NO: 16 [5E5RHB7]
EVQLVQSGAEVKKPGESLKISCKISGYTFTDHAIHWVRQMPGKGLEWIGH
FSPGNTDIKYNDKFKGQATLSVDRSINTAYLQWSSLKASDTAIYFCATST
FFFDYWGQGTRVTVSS

SEQ ID NO: 17 [5E5RHB8]
EVQLVQSGAEVKKPGESLKISCKISGYTFTDHAIHWVRQMPGKGLEWIGH
FSPGNTDIKYNDKFKGQATLSVDRSINTAYLQWSSLKASDTAIYFCKRST
FFFDYWGQGTRVTVSS

SEQ ID NO: 18 [5E5RHB9]
EVQLVQSGAEVKKPGESLKISCKISGYIFTDHAIHWVRQMPGKGLEVVMG
HFSPGNTDIKYNDKFKGQATLSVDRSINTAYLQWSSLKASDTAIYFCKTS
TFFFDYWGQGTRVTVSS

SEQ ID NO: 19 [5E5RHB10]
EVQLVQSGAEVKKPGESLKISCKISGYIFTDHAIHWVRQMPGKGLEVVMG
HFSPGNTDIKYNDKFKGQVTLSVDRSINTAYLQWSSLKASDTAIYFCKTS
TFFFDYWGQGTRVTVSS

SEQ ID NO: 20 [5E5RHC]
EVQLVESGAEVKKPGASVEVSCQASGYTFTDHAIHWVRQAPGQGLEWMGH
FSPGNTDIKYNDKFKGRVTMTRDTSINTAYMELRRLRSDDTAVYYCATST
FFFDYWGQGTMVTVSS

SEQ ID NO: 21 [5E5RHC2]
EVQLVESGAEVKKPGASVEVSCQASGYTFTDHAIHWVRQAPGQGLEWIGH
FSPGNTDIKYNDKFKGRATLTVDRSINTAYMELRRLRSDDTAVYYCKTST
FFFDYWGQGTMVTVSS

SEQ ID NO: 22 [5E5RHC3]
EVQLVESGAEVKKPGASVEVSCQASGYTFTDHAIHWVRQAPGQGLEWMGH
FSPGNTDIKYNDKFKGRATLTVDRSINTAYMELRRLRSDDTAVYYCKTST
FFFDYWGQGTMVTVSS

SEQ ID NO: 23 [5E5RHC4]
EVQLVESGAEVKKPGASVEVSCQASGYTFTDHAIHWVRQAPGQGLEWIGH
FSPGNTDIKYNDKFKGRVTLTVDRSINTAYMELRRLRSDDTAVYYCKTST
FFFDYWGQGTMVTVSS

SEQ ID NO: 24 [5E5RHC5]
EVQLVESGAEVKKPGASVEVSCQASGYTFTDHAIHWVRQAPGQGLEWIGH
FSPGNTDIKYNDKFKGRATMTVDRSINTAYMELRRLRSDDTAVYYCKTST
FFFDYWGQGTMVTVSS

SEQ ID NO: 25 [5E5RHC6]
FSPGNTDIKYEVQLVESGAEVKKPGASVEVSCQASGYTFTDHAIHWVRQA
PGQGLEWIGHNDKFKGRATLTRDRSINTAYMELRRLRSDDTAVYYCKTST
FFFDYWGQGTMVTVSS

SEQ ID NO: 26 [5E5RHC7]
EVQLVESGAEVKKPGASVEVSCQASGYTFTDHAIHWVRQAPGQGLEWIGH
FSPGNTDIKYNDKFKGRATLTVDTSINTAYMELRRLRSDDTAVYYCKTST
FFFDYWGQGTMVTVSS

SEQ ID NO: 27 [5E5RHC8]
EVQLVESGAEVKKPGASVEVSCQASGYTFTDHAIHWVRQAPGQGLEWIGH
FSPGNTDIKYNDKFKGRATLTVDRSINTAYMELRRLRSDDTAVYYCATST
FFFDYWGQGTMVTVSS

SEQ ID NO: 28 [5E5RHC9]
EVQLVESGAEVKKPGASVEVSCQASGYTFTDHAIHWVRQAPGQGLEWMGH
FSPGNTDIKYNDKFKGRVTMTVDRSINTAYMELRRLRSDDTAVYYCKTST
FFFDYWGQGTMVTVSS

SEQ ID NO: 29 [5E5RHC9 + V67A]
EVQLVESGAEVKKPGASVEVSCQASGYTFTDHAIHWVRQAPGQGLEWMGH
FSPGNTDIKYNDKFKGRATMTVDRSINTAYMELRRLRSDDTAVYYCKTST
FFFDYWGQGTMVTVSS

SEQ ID NO: 30 [5E5VK]
DIVMTQSPSSLTVTAGEKVTMICKSSQSLLNSGDQKNYLTWYQQKPGQPP
KLLIFWASTRESGVPDRFTGSGSGTDFTLTISSVQAEDLAVYYCQNDYSY
PLTFGAGTKLELK

SEQ ID NO: 31 [5E5RKA]
DIVMTQSPDSLAVSLGERATINCKSSQSLLNSGDQKNYLTWYQQKPGQPP
KLLIYWASTRESGVPDRFSGSGSGTDFTLTISSLQAEDVAVYYCQNDYSY
PLTFGQGTKVEIK

SEQ ID NO: 32 [5E5RKA1]
DIVMTQSPDSLAVSLGERATIICKSSQSLLNSGDQKNYLTWYQQKPGQPP
KLLIFWASTRESGVPDRFTGSGSGTDFTLTISSLQAEDVAVYYCQNDYSY
PLTFGQGTKVEIK

SEQ ID NO: 33 [5E5RKB]
DIVMTQSPLSLPVTPGEPASISCKSSQSLLNSGDQKNYLTWYLQKPGQSP
QLLIYWASTRESGVPDRFSGSGSGTDFTLKISRVEAEDVGVYYCQNDYSY
PLTFGGGTKVEIK

SEQ ID NO: 34 [5E5RKB1]
DIVMTQSPLSLPVTPGEPASIICKSSQSLLNSGDQKNYLTWYLQKPGQSP
QLLIYWASTRESGVPDRFTGSGSGTDFTLKISRVEAEDVGVYYCQNDYSY
PLTFGGGTKVEIK

SEQ ID NO: 160 (IgG1 CH3):
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK

SEQ ID NO. 161 (IgG2 CH3):
GQPREPQVYTLPPSREEMTKNQVSLTCLVKGFYPSDISVEWESNGQPENN
YKTTPPMLDSDGSFFLYSKLTVDKSRWQQGNVFSCSVMHEALHNHYTQKS
LSLSPGK

SEQ ID NO. 162 (IgG3 CH3):
GQPREPQVYTLPPSREEMTKNQVSLTCLVKGFYPSDIAVEWESSGQPENN
YNTTPPMLDSDGSFFLYSKLTVDKSRWQQGNIFSCSVMHEALHNRFTQKS
LSLSPGK

SEQ ID NO. 163 (IgG4 CH3):
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKS
LSLSLGK

SEQ ID NO. 164 (IgG1m CH3):
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK

SEQ ID NO. 165 (IgG1m[non-1] CH3):
GQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKS
LSLSPGK SEQ ID NO. 166 (IgG1 CH3 S→C):
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LCLSPGK SEQ ID NO. 167 (IgG2 CH3 S→C):
GQPREPQVYTLPPSREEMTKNQVSLTCLVKGFYPSDISVEWESNGQPENN
YKTTPPMLDSDGSFFLYSKLTVDKSRWQQGNVFSCSVMHEALHNHYTQKS
LCLSPGK SEQ ID NO. 168 (IgG3 CH3 S→C):
GQPREPQVYTLPPSREEMTKNQVSLTCLVKGFYPSDIAVEWESSGQPENN
YNTTPPMLDSDGSFFLYSKLTVDKSRWQQGNIFSCSVMHEALHNRFTQKS
LCLSPGK SEQ ID NO. 169 (IgG4 CH3 S→C):
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKS
LCLSLGK SEQ ID NO. 170 (IgG1 m CH3 S→C):
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LCLSPGK SEQ ID NO. 171 (IgG1 m[non-1] CH3 S→C):
GQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKS
LCLSPGK SEQ ID NO. 180 (IgG1 Fc):
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK SEQ ID NO. 181 (IgG2 Fc):
KCCVECPPCPAPPVAG-PSVFLFPPKPKDTLMISRTPEVTCVVVDVSHED
PEVQFNWYVDGVEVHNAKTKPREEQFNSTFRVVSVLTVVHQDWLNGKEYK
CKVSNKGLPAPIEKTISKTKGQPREPQVYTLPPSREEMTKNQVSLTCLVK
GFYPSDISVEWESNGQPENNYKTTPPMLDSDGSFFLYSKLTVDKSRWQQG
NVFSCSVMHEALHNHYTQKSLSLSPGK SEQ ID NO. 182 (IgG3 Fc):
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLSLSPGK

SEQUENCES

SEQ ID NO. 183 (IgG4 Fc):
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK

SEQ ID NO. 184 (IgG1m Fc):
DKTHTCPPCPAPELLGGPSVFLFPPKPKDTLMISRTPEVTCVVVDVSHED
VPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

SEQ ID NO. 185 (IgG1m[non-1] Fc):
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQG
NVFSCSVMHEALHNHYTQKSLSLSPGK SEQ ID NO. 186 (IgG1 Fc S→C):
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLCLSPGK SEQ ID NO. 187 (IgG2 Fc S→C):
KCCVECPPCPAPPVAG-PSVFLFPPKPKDTLMISRTPEVTCVVVDVSHED
PEVQFNWYVDGVEVHNAKTKPREEQFNSTFRVVSVLTVVHQDWLNGKEYK
CKVSNKGLPAPIEKTISKTKGQPREPQVYTLPPSREEMTKNQVSLTCLVK
GFYPSDISVEWESNGQPENNYKTTPPMLDSDGSFFLYSKLTVDKSRWQQG
NVFSCSVMHEALHNHYTQKSLCLSPGK SEQ ID NO. 188 (IgG3 Fc S→C):
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLCLSPGK SEQ ID NO. 189 (IgG4 Fc S→C):
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLCLSLGK SEQ ID NO. 190 (IgG1m Fc S→C):
DKTHTCPPCPAPELLGGPSVFLFPPKPKDTLMISRTPEVTCVVVDVSEDP
EVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGN
VFSCSVMHEALHNHYTQKSLCLSPGK SEQ ID NO. 191 (IgG1m[non-1] Fc S→C):
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQG
NVFSCSVMHEALHNHYTQKSLCLSPGK

---

The invention claimed is:

1. An isolated humanized antibody that binds to Tn-MUC1, wherein the isolated humanized antibody comprises a heavy chain variable region having the amino acid sequence of SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, or 29, a light chain variable region having the amino acid sequence of SEQ ID NO: 31, 32, 33, or 34, and optionally comprises a constant region derived from one or more human antibodies.

2. The isolated humanized antibody according to claim 1, wherein the isolated humanized antibody comprises:

(i) a heavy chain variable region having the amino acid sequence of SEQ ID NO: 1 and a light chain variable region having the amino acid sequence of SEQ ID NO: 31;

(ii) a heavy chain variable region having the amino acid sequence of SEQ ID NO: 2 and a light chain variable region having the amino acid sequence of SEQ ID NO: 31;

(iii) a heavy chain variable region having the amino acid sequence of SEQ ID NO: 3 and a light chain variable region having the amino acid sequence of SEQ ID NO: 31;

(iv) a heavy chain variable region having the amino acid sequence of SEQ ID NO: 4 and a light chain variable region having the amino acid sequence of SEQ ID NO: 31;

(v) a heavy chain variable region having the amino acid sequence of SEQ ID NO: 5 and a light chain variable region having the amino acid sequence of SEQ ID NO: 31;

(vi) a heavy chain variable region having the amino acid sequence of SEQ ID NO: 6 and a light chain variable region having the amino acid sequence of SEQ ID NO: 31;

(vii) a heavy chain variable region having the amino acid sequence of SEQ ID NO: 7 and a light chain variable region having the amino acid sequence of SEQ ID NO: 31;

(viii) a heavy chain variable region having the amino acid sequence of SEQ ID NO: 8 and a light chain variable region having the amino acid sequence of SEQ ID NO: 31;

(ix) a heavy chain variable region having the amino acid sequence of SEQ ID NO: 9 and a light chain variable region having the amino acid sequence of SEQ ID NO: 31;

(x) a heavy chain variable region having the amino acid sequence of SEQ ID NO: 10 and a light chain variable region having the amino acid sequence of SEQ ID NO: 31;

(xi) a heavy chain variable region having the amino acid sequence of SEQ ID NO: 11 and a light chain variable region having the amino acid sequence of SEQ ID NO: 31;

(xii) a heavy chain variable region having the amino acid sequence of SEQ ID NO: 12 and a light chain variable region having the amino acid sequence of SEQ ID NO: 31;

(xiii) a heavy chain variable region having the amino acid sequence of SEQ ID NO: 13 and a light chain variable region having the amino acid sequence of SEQ ID NO: 31;

(xiv) a heavy chain variable region having the amino acid sequence of SEQ ID NO: 14 and a light chain variable region having the amino acid sequence of SEQ ID NO: 31;

(xv) a heavy chain variable region having the amino acid sequence of SEQ ID NO: 15 and a light chain variable region having the amino acid sequence of SEQ ID NO: 31;

(xvi) a heavy chain variable region having the amino acid sequence of SEQ ID NO: 16 and a light chain variable region having the amino acid sequence of SEQ ID NO: 31;

(xvii) a heavy chain variable region having the amino acid sequence of SEQ ID NO: 17 and a light chain variable region having the amino acid sequence of SEQ ID NO: 31;

(xviii) a heavy chain variable region having the amino acid sequence of SEQ ID NO: 18 and a light chain variable region having the amino acid sequence of SEQ ID NO: 31;

(xix) a heavy chain variable region having the amino acid sequence of SEQ ID NO: 19 and a light chain variable region having the amino acid sequence of SEQ ID NO: 31;

(xx) a heavy chain variable region having the amino acid sequence of SEQ ID NO: 20 and a light chain variable region having the amino acid sequence of SEQ ID NO: 31;

(xxi) a heavy chain variable region having the amino acid sequence of SEQ ID NO: 21 and a light chain variable region having the amino acid sequence of SEQ ID NO: 31;

(xxii) a heavy chain variable region having the amino acid sequence of SEQ ID NO: 22 and a light chain variable region having the amino acid sequence of SEQ ID NO: 31;

(xxiii) a heavy chain variable region having the amino acid sequence of SEQ ID NO: 23 and a light chain variable region having the amino acid sequence of SEQ ID NO: 31;

(xxiv) a heavy chain variable region having the amino acid sequence of SEQ ID NO: 24 and a light chain variable region having the amino acid sequence of SEQ ID NO: 31;

(xxv) a heavy chain variable region having the amino acid sequence of SEQ ID NO: 25 and a light chain variable region having the amino acid sequence of SEQ ID NO: 31;

(xxvi) a heavy chain variable region having the amino acid sequence of SEQ ID NO: 26 and a light chain variable region having the amino acid sequence of SEQ ID NO: 31;

(xxvii) a heavy chain variable region having the amino acid sequence of SEQ ID NO: 27 and a light chain variable region having the amino acid sequence of SEQ ID NO: 31;

(xxviii) a heavy chain variable region having the amino acid sequence of SEQ ID NO: 28 and a light chain variable region having the amino acid sequence of SEQ ID NO: 31;
(xxix) a heavy chain variable region having the amino acid sequence of SEQ ID NO: 29 and a light chain variable region having the amino acid sequence of SEQ ID NO: 31;
(xxx) a heavy chain variable region having the amino acid sequence of SEQ ID NO: 1 and a light chain variable region having the amino acid sequence of SEQ ID NO: 32;
(xxxi) a heavy chain variable region having the amino acid sequence of SEQ ID NO: 2 and a light chain variable region having the amino acid sequence of SEQ ID NO: 32;
(xxxii) a heavy chain variable region having the amino acid sequence of SEQ ID NO: 3 and a light chain variable region having the amino acid sequence of SEQ ID NO: 32;
(xxxiii) a heavy chain variable region having the amino acid sequence of SEQ ID NO: 4 and a light chain variable region having the amino acid sequence of SEQ ID NO: 32;
(xxxiv) a heavy chain variable region having the amino acid sequence of SEQ ID NO: 5 and a light chain variable region having the amino acid sequence of SEQ ID NO: 32;
(xxxv) a heavy chain variable region having the amino acid sequence of SEQ ID NO: 6 and a light chain variable region having the amino acid sequence of SEQ ID NO: 32;
(xxxvi) a heavy chain variable region having the amino acid sequence of SEQ ID NO: 7 and a light chain variable region having the amino acid sequence of SEQ ID NO: 32;
(xxxvii) a heavy chain variable region having the amino acid sequence of SEQ ID NO: 8 and a light chain variable region having the amino acid sequence of SEQ ID NO: 32;
(xxxviii) a heavy chain variable region having the amino acid sequence of SEQ ID NO: 9 and a light chain variable region having the amino acid sequence of SEQ ID NO: 32;
(xxxix) a heavy chain variable region having the amino acid sequence of SEQ ID NO: 10 and a light chain variable region having the amino acid sequence of SEQ ID NO: 32;
(xl) a heavy chain variable region having the amino acid sequence of SEQ ID NO: 11 and a light chain variable region having the amino acid sequence of SEQ ID NO: 32;
(xli) a heavy chain variable region having the amino acid sequence of SEQ ID NO: 12 and a light chain variable region having the amino acid sequence of SEQ ID NO: 32;
(xlii) a heavy chain variable region having the amino acid sequence of SEQ ID NO: 13 and a light chain variable region having the amino acid sequence of SEQ ID NO: 32;
(xliii) a heavy chain variable region having the amino acid sequence of SEQ ID NO: 14 and a light chain variable region having the amino acid sequence of SEQ ID NO: 32;
(xliv) a heavy chain variable region having the amino acid sequence of SEQ ID NO: 15 and a light chain variable region having the amino acid sequence of SEQ ID NO: 32;
(xlv) a heavy chain variable region having the amino acid sequence of SEQ ID NO: 16 and a light chain variable region having the amino acid sequence of SEQ ID NO: 32;
(xlvi) a heavy chain variable region having the amino acid sequence of SEQ ID NO: 17 and a light chain variable region having the amino acid sequence of SEQ ID NO: 32;
(xlvii) a heavy chain variable region having the amino acid sequence of SEQ ID NO: 18 and a light chain variable region having the amino acid sequence of SEQ ID NO: 32;
(xlviii) a heavy chain variable region having the amino acid sequence of SEQ ID NO: 19 and a light chain variable region having the amino acid sequence of SEQ ID NO: 32;
(xlix) a heavy chain variable region having the amino acid sequence of SEQ ID NO: 20 and a light chain variable region having the amino acid sequence of SEQ ID NO: 32;
(l) a heavy chain variable region having the amino acid sequence of SEQ ID NO: 21 and a light chain variable region having the amino acid sequence of SEQ ID NO: 32;
(li) a heavy chain variable region having the amino acid sequence of SEQ ID NO: 22 and a light chain variable region having the amino acid sequence of SEQ ID NO: 32;
(lii) a heavy chain variable region having the amino acid sequence of SEQ ID NO: 23 and a light chain variable region having the amino acid sequence of SEQ ID NO: 32;
(liii) a heavy chain variable region having the amino acid sequence of SEQ ID NO: 24 and a light chain variable region having the amino acid sequence of SEQ ID NO: 32;
(liv) a heavy chain variable region having the amino acid sequence of SEQ ID NO: 25 and a light chain variable region having the amino acid sequence of SEQ ID NO: 32;
(lv) a heavy chain variable region having the amino acid sequence of SEQ ID NO: 26 and a light chain variable region having the amino acid sequence of SEQ ID NO: 32;
(lvi) a heavy chain variable region having the amino acid sequence of SEQ ID NO: 27 and a light chain variable region having the amino acid sequence of SEQ ID NO: 32;
(lvii) a heavy chain variable region having the amino acid sequence of SEQ ID NO: 28 and a light chain variable region having the amino acid sequence of SEQ ID NO: 32;
(lviii) a heavy chain variable region having the amino acid sequence of SEQ ID NO: 29 and a light chain variable region having the amino acid sequence of SEQ ID NO: 32;
(lix) a heavy chain variable region having the amino acid sequence of SEQ ID NO: 1 and a light chain variable region having the amino acid sequence of SEQ ID NO: 33;

(lx) a heavy chain variable region having the amino acid sequence of SEQ ID NO: 2 and a light chain variable region having the amino acid sequence of SEQ ID NO: 33;

(lxi) a heavy chain variable region having the amino acid sequence of SEQ ID NO: 3 and a light chain variable region having the amino acid sequence of SEQ ID NO: 33;

(lxii) a heavy chain variable region having the amino acid sequence of SEQ ID NO: 4 and a light chain variable region having the amino acid sequence of SEQ ID NO: 33;

(lxiii) a heavy chain variable region having the amino acid sequence of SEQ ID NO: 5 and a light chain variable region having the amino acid sequence of SEQ ID NO: 33;

(lxiv) a heavy chain variable region having the amino acid sequence of SEQ ID NO: 6 and a light chain variable region having the amino acid sequence of SEQ ID NO: 33;

(lxv) a heavy chain variable region having the amino acid sequence of SEQ ID NO: 7 and a light chain variable region having the amino acid sequence of SEQ ID NO: 33;

(lxvi) a heavy chain variable region having the amino acid sequence of SEQ ID NO: 8 and a light chain variable region having the amino acid sequence of SEQ ID NO: 33;

(lxvii) a heavy chain variable region having the amino acid sequence of SEQ ID NO: 9 and a light chain variable region having the amino acid sequence of SEQ ID NO: 33;

(lxviii) a heavy chain variable region having the amino acid sequence of SEQ ID NO: 10 and a light chain variable region having the amino acid sequence of SEQ ID NO: 33;

(lxix) a heavy chain variable region having the amino acid sequence of SEQ ID NO: 11 and a light chain variable region having the amino acid sequence of SEQ ID NO: 33;

(lxx) a heavy chain variable region having the amino acid sequence of SEQ ID NO: 12 and a light chain variable region having the amino acid sequence of SEQ ID NO: 33;

(lxxi) a heavy chain variable region having the amino acid sequence of SEQ ID NO: 13 and a light chain variable region having the amino acid sequence of SEQ ID NO: 33;

(lxxii) a heavy chain variable region having the amino acid sequence of SEQ ID NO: 14 and a light chain variable region having the amino acid sequence of SEQ ID NO: 33;

(lxxiii) a heavy chain variable region having the amino acid sequence of SEQ ID NO: 15 and a light chain variable region having the amino acid sequence of SEQ ID NO: 33;

(lxxiv) a heavy chain variable region having the amino acid sequence of SEQ ID NO: 16 and a light chain variable region having the amino acid sequence of SEQ ID NO: 33;

(lxxv) a heavy chain variable region having the amino acid sequence of SEQ ID NO: 17 and a light chain variable region having the amino acid sequence of SEQ ID NO: 33;

(lxxvi) a heavy chain variable region having the amino acid sequence of SEQ ID NO: 18 and a light chain variable region having the amino acid sequence of SEQ ID NO: 33;

(lxxvii) a heavy chain variable region having the amino acid sequence of SEQ ID NO: 19 and a light chain variable region having the amino acid sequence of SEQ ID NO: 33;

(lxxviii) a heavy chain variable region having the amino acid sequence of SEQ ID NO: 20 and a light chain variable region having the amino acid sequence of SEQ ID NO: 33;

(lxxix) a heavy chain variable region having the amino acid sequence of SEQ ID NO: 21 and a light chain variable region having the amino acid sequence of SEQ ID NO: 33;

(lxxx) a heavy chain variable region having the amino acid sequence of SEQ ID NO: 22 and a light chain variable region having the amino acid sequence of SEQ ID NO: 33;

(lxxxi) a heavy chain variable region having the amino acid sequence of SEQ ID NO: 23 and a light chain variable region having the amino acid sequence of SEQ ID NO: 33;

(lxxxii) a heavy chain variable region having the amino acid sequence of SEQ ID NO: 24 and a light chain variable region having the amino acid sequence of SEQ ID NO: 33;

(lxxxiii) a heavy chain variable region having the amino acid sequence of SEQ ID NO: 25 and a light chain variable region having the amino acid sequence of SEQ ID NO: 33;

(lxxxiv) a heavy chain variable region having the amino acid sequence of SEQ ID NO: 26 and a light chain variable region having the amino acid sequence of SEQ ID NO: 33;

(lxxxv) a heavy chain variable region having the amino acid sequence of SEQ ID NO: 27 and a light chain variable region having the amino acid sequence of SEQ ID NO: 33;

(lxxxvi) a heavy chain variable region having the amino acid sequence of SEQ ID NO: 28 and a light chain variable region having the amino acid sequence of SEQ ID NO: 33;

(lxxxvii) a heavy chain variable region having the amino acid sequence of SEQ ID NO: 29 and a light chain variable region having the amino acid sequence of SEQ ID NO: 33;

(lxxxviii) a heavy chain variable region having the amino acid sequence of SEQ ID NO: 1 and a light chain variable region having the amino acid sequence of SEQ ID NO: 34;

(lxxxix) a heavy chain variable region having the amino acid sequence of SEQ ID NO: 2 and a light chain variable region having the amino acid sequence of SEQ ID NO: 34;

(xc) a heavy chain variable region having the amino acid sequence of SEQ ID NO: 3 and a light chain variable region having the amino acid sequence of SEQ ID NO: 34;

(xci) a heavy chain variable region having the amino acid sequence of SEQ ID NO: 4 and a light chain variable region having the amino acid sequence of SEQ ID NO: 34;

(xcii) a heavy chain variable region having the amino acid sequence of SEQ ID NO: 5 and a light chain variable region having the amino acid sequence of SEQ ID NO: 34;
(xciii) a heavy chain variable region having the amino acid sequence of SEQ ID NO: 6 and a light chain variable region having the amino acid sequence of SEQ ID NO: 34;
(xciv) a heavy chain variable region having the amino acid sequence of SEQ ID NO: 7 and a light chain variable region having the amino acid sequence of SEQ ID NO: 34;
(xcv) a heavy chain variable region having the amino acid sequence of SEQ ID NO: 8 and a light chain variable region having the amino acid sequence of SEQ ID NO: 34;
(xcvi) a heavy chain variable region having the amino acid sequence of SEQ ID NO: 9 and a light chain variable region having the amino acid sequence of SEQ ID NO: 34;
(xcvii) a heavy chain variable region having the amino acid sequence of SEQ ID NO: 10 and a light chain variable region having the amino acid sequence of SEQ ID NO: 34;
(xcviii) a heavy chain variable region having the amino acid sequence of SEQ ID NO: 11 and a light chain variable region having the amino acid sequence of SEQ ID NO: 34;
(xcix) a heavy chain variable region having the amino acid sequence of SEQ ID NO: 12 and a light chain variable region having the amino acid sequence of SEQ ID NO: 34;
(c) a heavy chain variable region having the amino acid sequence of SEQ ID NO: 13 and a light chain variable region having the amino acid sequence of SEQ ID NO: 34;
(ci) a heavy chain variable region having the amino acid sequence of SEQ ID NO: 14 and a light chain variable region having the amino acid sequence of SEQ ID NO: 34;
(cii) a heavy chain variable region having the amino acid sequence of SEQ ID NO: 15 and a light chain variable region having the amino acid sequence of SEQ ID NO: 34;
(ciii) a heavy chain variable region having the amino acid sequence of SEQ ID NO: 16 and a light chain variable region having the amino acid sequence of SEQ ID NO: 34;
(civ) a heavy chain variable region having the amino acid sequence of SEQ ID NO: 17 and a light chain variable region having the amino acid sequence of SEQ ID NO: 34;
(cv) a heavy chain variable region having the amino acid sequence of SEQ ID NO: 18 and a light chain variable region having the amino acid sequence of SEQ ID NO: 34;
(cvi) a heavy chain variable region having the amino acid sequence of SEQ ID NO: 19 and a light chain variable region having the amino acid sequence of SEQ ID NO: 34;
(cvii) a heavy chain variable region having the amino acid sequence of SEQ ID NO: 20 and a light chain variable region having the amino acid sequence of SEQ ID NO: 34;
(cviii) a heavy chain variable region having the amino acid sequence of SEQ ID NO: 21 and a light chain variable region having the amino acid sequence of SEQ ID NO: 34;
(cix) a heavy chain variable region having the amino acid sequence of SEQ ID NO: 22 and a light chain variable region having the amino acid sequence of SEQ ID NO: 34;
(cx) a heavy chain variable region having the amino acid sequence of SEQ ID NO: 23 and a light chain variable region having the amino acid sequence of SEQ ID NO: 34;
(cxi) a heavy chain variable region having the amino acid sequence of SEQ ID NO: 24 and a light chain variable region having the amino acid sequence of SEQ ID NO: 34;
(cxii) a heavy chain variable region having the amino acid sequence of SEQ ID NO: 25 and a light chain variable region having the amino acid sequence of SEQ ID NO: 34;
(cxiii) a heavy chain variable region having the amino acid sequence of SEQ ID NO: 26 and a light chain variable region having the amino acid sequence of SEQ ID NO: 34;
(cxiv) a heavy chain variable region having the amino acid sequence of SEQ ID NO: 27 and a light chain variable region having the amino acid sequence of SEQ ID NO: 34;
(cxv) a heavy chain variable region having the amino acid sequence of SEQ ID NO: 28 and a light chain variable region having the amino acid sequence of SEQ ID NO: 34; or
(cxvi) a heavy chain variable region having the amino acid sequence of SEQ ID NO: 29 and a light chain variable region having the amino acid sequence of SEQ ID NO: 34.

3. The humanized antibody according to claim 1, wherein said antibody binds Tn-MUC1 with an affinity (Kd) of at least $10^{-6}$ M.

4. The humanized antibody according to claim 3, wherein said antibody binds Tn-MUC1 with an affinity (Kd) of at least $10^{-9}$ M.

5. The humanized antibody according to claim 1, wherein said antibody competitively inhibits the binding to Tn-MUC1 of an antibody comprising a heavy chain variable region having the amino acid sequence of SEQ ID NO: 1 and a light chain variable region having the amino acid sequence of SEQ ID NO: 30.

6. The humanized antibody according to claim 1, wherein said antibody competitively inhibits the binding to Tn-MUC1 of the mouse 5E5 antibody.

7. The humanized antibody according to claim 1, wherein said antibody or antibody fragment substantially neutralizes at least one activity of at least one Tn-MUC1.

8. The humanized antibody according to claim 1, wherein said antibody or antibody fragment expresses at a level of at least 10 micrograms/ml in a static HEK293T transient expression system.

9. The humanized antibody according to claim 1, wherein said antibody or antibody fragment expresses at a level of at least 20 micrograms/ml in a shaken HEK293T transient expression system.

10. The humanized antibody according to claim 1, wherein said antibody has a melting temperature ($T_m$) of at least 62° C.

11. The humanized antibody according to claim 1, wherein said antibody or antibody fragment has a constant region of either isotype IgG1, IgG2, IgG3 or IgG4, or a mutated IgG constant region, and optionally a light chain constant region of isotype kappa or lambda.

12. The humanized antibody according to claim 1, wherein the humanized antibody fragment is a scFv, Fab or F(ab')$_2$.

13. A polynucleotide encoding a humanized antibody according to claim 1.

14. A conjugate comprising the humanized antibody according to claim 1 coupled to a functional moiety.

15. The conjugate according to claim 14, wherein the functional moiety is selected from a drug, a reporter, a toxin, an organic moiety, and a binding member.

16. The conjugate according to claim 15 wherein the reporter is a fluorescent compound, a radionuclide, or an enzyme.

17. The conjugate according to claim 15 wherein the binding member is an antibody or antibody fragment.

18. The conjugate according to claim 14, wherein the humanized antibody is covalently bonded to the functional moiety.

19. A pharmaceutical composition comprising the humanized antibody according to claim 1, and a pharmaceutically acceptable diluent, carrier or excipient.

20. The pharmaceutical composition of claim 19 further comprising a therapeutically effective amount of a chemotherapeutic agent.

21. A method of treating cancer comprising administering to a patient the pharmaceutical composition according to claim 19.

22. The method of claim 21 wherein the patient is administered a chemotherapeutic agent, in combination with the humanized antibody.

23. A method of treating a proliferative disease in a subject, wherein the proliferative disease is associated with raised levels of Tn-MUC1, the method comprising administering to the subject the conjugate according to claim 14.

* * * * *

SEQUENCE LISTING

<160> NUMBER OF SEQ ID NOS: 191

<210> SEQ ID NO 1
<211> LENGTH: 116
<212> TYPE: PRT
<213> ORGANISM: Artificial sequence
<220> FEATURE:
<223> OTHER INFORMATION: Synthetic sequence 5E5VH

<400> SEQUENCE: 1

```
Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Lys Ala Thr Leu Thr Val Asp Arg Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Phe Asp Tyr Trp Gly Gln Gly Thr Thr Leu
            100                 105                 110

Thr Val Ser Ser
        115
```

<210> SEQ ID NO 2
<211> LENGTH: 116
<212> TYPE: PRT

<213> ORGANISM: Artificial sequence
<220> FEATURE:
<223> OTHER INFORMATION: Synthetic sequence: Humanized antibody heavy
      chain variable region 5E5RHA

<400> SEQUENCE: 2

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Ala Leu Glu Trp Met
            35                  40                  45

Gly His Phe Ser Pro Gly Asn Thr Asp Ile Lys Tyr Asn Asp Lys Phe
        50                  55                  60

Lys Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Thr Ser Thr Phe Phe Phe Asp Tyr Trp Gly Gln Gly Thr Met Val
            100                 105                 110

Thr Val Ser Ser
        115

<210> SEQ ID NO 3
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA2

<400> SEQUENCE: 3

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Ala Leu Glu Trp Ile
            35                  40                  45

Gly His Phe Ser Pro Gly Asn Thr Asp Ile Lys Tyr Asn Asp Lys Phe
        50                  55                  60

Lys Gly Arg Ala Thr Leu Thr Val Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 4
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA3

<400> SEQUENCE: 4

Gln Val Gln Leu Val Gln Ser Gly Ala Glu Val Lys Lys Thr Gly Ser
1               5                   10                  15

```
Ser Val Lys Val Ser Cys Lys Ala Ser Gly Tyr Thr Phe Thr Asp His
            20                  25                  30

Ala Ile His Trp Val Arg Gln Ala Pro Gly Gln Ala Leu Glu Trp Met
            35                  40                  45

Gly His Phe Ser Pro Gly Asn Thr Asp Ile Lys Tyr Asn Asp Lys Phe
 50                  55                  60

Lys Gly Arg Ala Thr Leu Thr Val Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 5
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA4

<400> SEQUENCE: 5

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Ala Leu Glu Trp Ile
            35                  40                  45

Gly His Phe Ser Pro Gly Asn Thr Asp Ile Lys Tyr Asn Asp Lys Phe
 50                  55                  60

Lys Gly Arg Val Thr Leu Thr Val Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 6
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA5

<400> SEQUENCE: 6

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Ala Leu Glu Trp Ile
            35                  40                  45

Gly His Phe Ser Pro Gly Asn Thr Asp Ile Lys Tyr Asn Asp Lys Phe
 50                  55                  60
```

Lys Gly Arg Ala Thr Ile Thr Val Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 7
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA6

<400> SEQUENCE: 7

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Ala Leu Glu Trp Ile
            35                  40                  45

Gly His Phe Ser Pro Gly Asn Thr Asp Ile Lys Tyr Asn Asp Lys Phe
        50                  55                  60

Lys Gly Arg Ala Thr Leu Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 8
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA7

<400> SEQUENCE: 8

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Ala Leu Glu Trp Ile
            35                  40                  45

Gly His Phe Ser Pro Gly Asn Thr Asp Ile Lys Tyr Asn Asp Lys Phe
        50                  55                  60

Lys Gly Arg Ala Thr Leu Thr Val Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Thr Ser Thr Phe Phe Phe Asp Tyr Trp Gly Gln Gly Thr Met Val
            100                 105                 110

Thr Val Ser Ser
        115

<210> SEQ ID NO 9
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHA8

<400> SEQUENCE: 9

Gln Val Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Ala Leu Glu Trp Met
        35                  40                  45

Gly His Phe Ser Pro Gly Asn Thr Asp Ile Lys Tyr Asn Asp Lys Phe
    50                  55                  60

Lys Gly Arg Val Thr Leu Thr Val Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 10
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB

<400> SEQUENCE: 10

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Ile Phe Thr Asp His
            20                  25                  30

Ala Ile His Trp Val Arg Gln Met Pro Gly Lys Gly Leu Glu Trp Met
        35                  40                  45

Gly His Phe Ser Pro Gly Asn Thr Asp Ile Lys Tyr Asn Asp Lys Phe
    50                  55                  60

Lys Gly Gln Val Thr Phe Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Ala Arg Ser Thr Phe Phe Phe Asp Tyr Trp Gly Gln Gly Thr Arg Val
            100                 105                 110

Thr Val Ser Ser
        115

<210> SEQ ID NO 11
<211> LENGTH: 116
<212> TYPE: PRT
<213> ORGANISM: Artificial sequence

```
<220> FEATURE:
<223> OTHER INFORMATION: Synthetic sequence: Humanized antibody heavy
      chain variable region 5E5RHB2

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
        115

<210> SEQ ID NO 12
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB3

<400> SEQUENCE: 12

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Ile Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
        115

<210> SEQ ID NO 13
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB4

<400> SEQUENCE: 13

Glu Val Gln Leu Val Gln Ser Gly Ala Glu Val Lys Lys Pro Gly Glu
1               5                   10                  15
```

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Met
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
            115

<210> SEQ ID NO 14
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB5

<400> SEQUENCE: 14

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Val Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
            115

<210> SEQ ID NO 15
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB6

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Ala Thr Phe Ser Val Asp Arg Ser Ile Asn Thr Ala Tyr

```
Leu Gln Trp Ser Ser Leu Lys Ala Ser Asp Thr Ala Ile Tyr Phe Cys
                85                  90                  95

Lys Thr Ser Thr Phe Phe Asp Tyr Trp Gly Gln Gly Thr Arg Val
            100                 105                 110

Thr Val Ser Ser
        115

<210> SEQ ID NO 16
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB7

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Ala Thr Ser Thr Phe Phe Asp Tyr Trp Gly Gln Gly Thr Arg Val
            100                 105                 110

Thr Val Ser Ser
        115

<210> SEQ ID NO 17
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB8

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Thr Phe Thr Asp His
            20                  25                  30

Ala Ile His Trp Val Arg Gln Met Pro Gly Lys Gly Leu Glu Trp Ile
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Arg Ser Thr Phe Phe Asp Tyr Trp Gly Gln Gly Thr Arg Val
            100                 105                 110

Thr Val Ser Ser
```

<210> SEQ ID NO 18
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB9

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Ile Phe Thr Asp His
            20                  25                  30

Ala Ile His Trp Val Arg Gln Met Pro Gly Lys Gly Leu Glu Trp Met
        35                  40                  45

Gly His Phe Ser Pro Gly Asn Thr Asp Ile Lys Tyr Asn Asp Lys Phe
    50                  55                  60

Lys Gly Gln Ala Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
        115

<210> SEQ ID NO 19
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHB10

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Ile Ser Gly Tyr Ile Phe Thr Asp His
            20                  25                  30

Ala Ile His Trp Val Arg Gln Met Pro Gly Lys Gly Leu Glu Trp Met
        35                  40                  45

Gly His Phe Ser Pro Gly Asn Thr Asp Ile Lys Tyr Asn Asp Lys Phe
    50                  55                  60

Lys Gly Gln Val Thr Leu Ser Val Asp Arg Ser Ile Asn Thr Ala Tyr
65                  70                  75                  80

Leu Gln Trp Ser Ser Leu Lys Ala Ser Asp Thr Ala Ile Tyr Phe Cys
                85                  90                  95

Lys Thr Ser Thr Phe Phe Phe Asp Tyr Trp Gly Gln Gly Thr Arg Val
            100                 105                 110

Thr Val Ser Ser
        115

<210> SEQ ID NO 20
<211> LENGTH: 116
<212> TYPE: PRT
<213> ORGANISM: Artificial sequence
<220> FEATURE:
<223> OTHER INFORMATION: Synthetic sequence: Humanized antibody heavy chain variable region 5E5RHC

<400> SEQUENCE: 20

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly His Phe Ser Pro Gly Asn Thr Asp Ile Lys Tyr Asn Asp Lys Phe
    50                  55                  60

Lys Gly Arg Val Thr Met Thr Arg Asp Thr Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Ala Thr Ser Thr Phe Phe Phe Asp Tyr Trp Gly Gln Gly Thr Met Val
            100                 105                 110

Thr Val Ser Ser
        115

<210> SEQ ID NO 21
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC2

<400> SEQUENCE: 21

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Arg Ala Thr Leu Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 22
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC3

<400> SEQUENCE: 22

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

```
Ala Ile His Trp Val Arg Gln Ala Pro Gly Gln Gly Leu Glu Trp Met
            35                  40                  45

Gly His Phe Ser Pro Gly Asn Thr Asp Ile Lys Tyr Asn Asp Lys Phe
        50                  55                  60

Lys Gly Arg Ala Thr Leu Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
                100                 105                 110

Thr Val Ser Ser
        115

<210> SEQ ID NO 23
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC4

<400> SEQUENCE: 23

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
            35                  40                  45

Gly His Phe Ser Pro Gly Asn Thr Asp Ile Lys Tyr Asn Asp Lys Phe
        50                  55                  60

Lys Gly Arg Val Thr Leu Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
                100                 105                 110

Thr Val Ser Ser
        115

<210> SEQ ID NO 24
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC5

<400> SEQUENCE: 24

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
            35                  40                  45

Gly His Phe Ser Pro Gly Asn Thr Asp Ile Lys Tyr Asn Asp Lys Phe
        50                  55                  60

Lys Gly Arg Ala Thr Met Thr Val Asp Arg Ser Ile Asn Thr Ala Tyr
65                  70                  75                  80
```

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 25
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC6

<400> SEQUENCE: 25

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Arg Ala Thr Leu Thr Arg Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 26
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC7

<400> SEQUENCE: 26

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Arg Ala Thr Leu Thr Val Asp Thr Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 27
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC8

<400> SEQUENCE: 27

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Arg Ala Thr Leu Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Ala Thr Ser Thr Phe Phe Phe Asp Tyr Trp Gly Gln Gly Thr Met Val
            100                 105                 110

Thr Val Ser Ser
        115

<210> SEQ ID NO 28
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC9

<400> SEQUENCE: 28

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly His Phe Ser Pro Gly Asn Thr Asp Ile Lys Tyr Asn Asp Lys Phe
    50                  55                  60

Lys Gly Arg Val Thr Met Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 29
<211> LENGTH: 116
<212> TYPE: PRT
<213> ORGANISM: Artificial sequence
<220> FEATURE:
<223> OTHER INFORMATION: Synthetic sequence: Humanized antibody heavy
      chain variable region 5E5RHC9 + V67A

<400> SEQUENCE: 29

Glu Val Gln Leu Val Glu Ser Gly Ala Glu Val Lys Lys Pro Gly Ala
1               5                   10                  15

Ser Val Glu Val Ser Cys Gln Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly His Phe Ser Pro Gly Asn Thr Asp Ile Lys Tyr Asn Asp Lys Phe
    50                  55                  60

Lys Gly Arg Ala Thr Met Thr Val Asp Arg Ser Ile Asn Thr Ala Tyr
65                  70                  75                  80

Met Glu Leu Arg Arg Leu Arg Ser Asp Asp Thr Ala Val Tyr Tyr Cys
                85                  90                  95

Lys Thr Ser Thr Phe Phe Phe Asp Tyr Trp Gly Gln Gly Thr Met Val
            100                 105                 110

Thr Val Ser Ser
        115

<210> SEQ ID NO 30
<211> LENGTH: 113
<212> TYPE: PRT
<213> ORGANISM: Artificial sequence
<220> FEATURE:
<223> OTHER INFORMATION: Synthetic sequence: 5E5VK

<400> SEQUENCE: 30

Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 31
<211> LENGTH: 113
<212> TYPE: PRT
<213> ORGANISM: Artificial sequence
<220> FEATURE:
<223> OTHER INFORMATION: Synthetic sequence: Humanized antibody light
      chain variable region 5E5RKA

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Val Glu Ile
               100                 105                 110

Lys

<210> SEQ ID NO 32
<211> LENGTH: 113
<212> TYPE: PRT
<213> ORGANISM: Artificial sequence
<220> FEATURE:
<223> OTHER INFORMATION: Synthetic sequence: Humanized antibody light
      chain variable region 5E5RKA1

<400> SEQUENCE: 32

Asp Ile Val Met Thr Gln Ser Pro Asp Ser Leu Ala Val Ser Leu Gly
 1               5                  10                  15

Glu Arg Ala Thr Ile Ile Cys Lys Ser Ser Gln Ser Leu Leu Asn Ser
                20                  25                  30

Gly Asp Gln Lys Asn Tyr Leu Thr Trp Tyr Gln Lys Pro Gly Gln
            35                  40                  45

Pro Pro Lys Leu Leu Ile Phe Trp Ala Ser Thr Arg Glu Ser Gly Val
            50                  55                  60

Pro Asp Arg Phe Thr Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Asp Tyr Ser Tyr Pro Leu Thr Phe Gly Gln Gly Thr Lys Val Glu Ile
               100                 105                 110

Lys

<210> SEQ ID NO 33
<211> LENGTH: 113
<212> TYPE: PRT
<213> ORGANISM: Artificial sequence
<220> FEATURE:
<223> OTHER INFORMATION: Synthetic sequence: Humanized antibody light
      chain variable region 5E5RKB

<400> SEQUENCE: 33

Asp Ile Val Met Thr Gln Ser Pro Leu Ser Leu Pro Val Thr Pro Gly
 1               5                  10                  15

Glu Pro Ala Ser Ile Ser Cys Lys Ser Ser Gln Ser Leu Leu Asn Ser
                20                  25                  30

Gly Asp Gln Lys Asn Tyr Leu Thr Trp Tyr Leu Gln Lys Pro Gly Gln
            35                  40                  45

Ser Pro Gln Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Asn
                85                  90                  95

Asp Tyr Ser Tyr Pro Leu Thr Phe Gly Gly Gly Thr Lys Val Glu Ile

Lys

<210> SEQ ID NO 34
<211> LENGTH: 113
<212> TYPE: PRT
<213> ORGANISM: Artificial sequence
<220> FEATURE:
<223> OTHER INFORMATION: Synthetic sequence: Humanized antibody light
      chain variable region 5E5RKB1

<400> SEQUENCE: 34

Asp Ile Val Met Thr Gln Ser Pro Leu Ser Leu Pro Val Thr Pro Gly
1               5                   10                  15

Glu Pro Ala Ser Ile Ile Cys Lys Ser Ser Gln Ser Leu Leu Asn Ser
            20                  25                  30

Gly Asp Gln Lys Asn Tyr Leu Thr Trp Tyr Leu Gln Lys Pro Gly Gln
        35                  40                  45

Ser Pro Gln Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Ser Tyr Pro Leu Thr Phe Gly Gly Gly Thr Lys Val Glu Ile
            100                 105                 110

Lys

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160
<211> LENGTH: 107
<212> TYPE: PRT
<213> ORGANISM: Homo sapiens

<400> SEQUENCE: 160

```
Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 161
<211> LENGTH: 107
<212> TYPE: PRT
<213> ORGANISM: Homo sapiens

<400> SEQUENCE: 161

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ser Val Glu Trp Glu Ser Asn Gly Gln Pro Glu
        35                  40                  45

Asn Asn Tyr Lys Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 162
<211> LENGTH: 107
<212> TYPE: PRT
<213> ORGANISM: Homo sapiens

<400> SEQUENCE: 162

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
        35                  40                  45

Asn Asn Tyr Asn Thr Thr Pro Pro Met Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 163
<211> LENGTH: 107
<212> TYPE: PRT
<213> ORGANISM: Homo sapiens

<400> SEQUENCE: 163

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys 100         105

<210> SEQ ID NO 164
<211> LENGTH: 107
<212> TYPE: PRT
<213> ORGANISM: Homo sapiens

<400> SEQUENCE: 164

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 165
<211> LENGTH: 107
<212> TYPE: PRT
<213> ORGANISM: Homo sapiens

<400> SEQUENCE: 165

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 166
<211> LENGTH: 107
<212> TYPE: PRT
<213> ORGANISM: Artificial sequence
<220> FEATURE:
<223> OTHER INFORMATION: Synthetic sequence: CH3 domain IgG1 CH3 Ser/Cys

<400> SEQUENCE: 166

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

```
Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Cys Leu Ser Pro Gly Lys
            100                 105
```

<210> SEQ ID NO 167
<211> LENGTH: 107
<212> TYPE: PRT
<213> ORGANISM: Artificial sequence
<220> FEATURE:
<223> OTHER INFORMATION: Synthetic sequence: CH3 domain IgG2 CH3 Ser/Cys

<400> SEQUENCE: 167

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
             20                  25                  30

Tyr Pro Ser Asp Ile Ser Val Glu Trp Glu Ser Asn Gly Gln Pro Glu
         35                  40                  45

Asn Asn Tyr Lys Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Cys Leu Ser Pro Gly Lys
            100                 105
```

<210> SEQ ID NO 168
<211> LENGTH: 107
<212> TYPE: PRT
<213> ORGANISM: Artificial sequence
<220> FEATURE:
<223> OTHER INFORMATION: Synthetic sequence: CH3 domain IgG3 CH3 Ser/Cys

<400> SEQUENCE: 168

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
             20                  25                  30

Tyr Pro Ser Asp Ile Ala Val Glu Trp Glu Ser Ser Gly Gln Pro Glu
         35                  40                  45

Asn Asn Tyr Asn Thr Thr Pro Pro Met Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Ile Phe Ser Cys Ser Val Met His Glu Ala Leu His Asn Arg Phe
                 85                  90                  95

Thr Gln Lys Ser Leu Cys Leu Ser Pro Gly Lys
            100                 105
```

<210> SEQ ID NO 169
<211> LENGTH: 107
<212> TYPE: PRT
<213> ORGANISM: Artificial sequence
<220> FEATURE:
<223> OTHER INFORMATION: Synthetic sequence: CH3 domain IgG4 CH3 Ser/Cys

<400> SEQUENCE: 169

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Cys Leu Ser Leu Gly Lys
            100                 105

<210> SEQ ID NO 170
<211> LENGTH: 107
<212> TYPE: PRT
<213> ORGANISM: Artificial sequence
<220> FEATURE:
<223> OTHER INFORMATION: Synthetic sequence: CH3 domain IgG1 m CH3
      Ser/Cys

<400> SEQUENCE: 170

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Cys Leu Ser Pro Gly Lys
            100                 105

<210> SEQ ID NO 171
<211> LENGTH: 107
<212> TYPE: PRT
<213> ORGANISM: Artificial sequence
<220> FEATURE:
<223> OTHER INFORMATION: Synthetic sequence: CH3 domain IgG1 m(non-1)
      CH3 Ser/Cys

<400> SEQUENCE: 171

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe

```
                50              55              60
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Cys Leu Ser Pro Gly Lys
            100                 105
```

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 227
<212> TYPE: PRT
<213> ORGANISM: Homo sapiens

<400> SEQUENCE: 180

```
Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
```

```
            20                  25                  30
Ile Ser Arg Thr Pro Glu Val Thr Cys Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 181
<211> LENGTH: 226
<212> TYPE: PRT
<213> ORGANISM: Homo sapiens

<400> SEQUENCE: 181

Lys Cys Cys Val Glu Cys Pro Pro Cys Pro Ala Pro Pro Val Ala Gly
 1                   5                  10                  15

Pro Ser Val Phe Leu Phe Pro Pro Lys Pro Lys Asp Thr Leu Met Ile
                 20                  25                  30

Ser Arg Thr Pro Glu Val Thr Cys Val Val Val Asp Val Ser His Glu
            35                  40                  45

Asp Pro Glu Val Gln Phe Asn Trp Tyr Val Asp Gly Val Glu Val His
 50                  55                  60

Asn Ala Lys Thr Lys Pro Arg Glu Glu Gln Phe Asn Ser Thr Phe Arg
 65                  70                  75                  80

Val Val Ser Val Leu Thr Val Val His Gln Asp Trp Leu Asn Gly Lys
                 85                  90                  95

Glu Tyr Lys Cys Lys Val Ser Asn Lys Gly Leu Pro Ala Pro Ile Glu
            100                 105                 110

Lys Thr Ile Ser Lys Thr Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ser Val Glu Trp
145                 150                 155                 160
```

```
Glu Ser Asn Gly Gln Pro Glu Asn Asn Tyr Lys Thr Thr Pro Pro Met
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 182
<211> LENGTH: 227
<212> TYPE: PRT
<213> ORGANISM: Homo sapiens

<400> SEQUENCE: 182

Asp Thr Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Lys Trp Tyr Val Asp Gly Val Glu Val
    50                  55                  60

His Asn Ala Lys Thr Lys Pro Arg Glu Glu Gln Tyr Asn Ser Thr Phe
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Ile Phe Ser Cys Ser Val Met
        195                 200                 205

His Glu Ala Leu His Asn Arg Phe Thr Gln Lys Ser Leu Ser Leu Ser
    210                 215                 220

Pro Gly Lys
225

<210> SEQ ID NO 183
<211> LENGTH: 227
<212> TYPE: PRT
<213> ORGANISM: Homo sapiens

<400> SEQUENCE: 183

Lys Tyr Gly Pro Pro Cys Pro Ser Cys Pro Ala Pro Glu Phe Leu Gly
1               5                   10                  15
```

```
Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Gln
            35                  40                  45

Glu Asp Pro Glu Val Gln Phe Asn Trp Tyr Val Asp Gly Val Glu Val
 50                      55                  60

His Asn Ala Lys Thr Lys Pro Arg Glu Glu Gln Phe Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Gly Leu Pro Ser Ser Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Gln Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
                180                 185                 190

Asp Lys Ser Arg Trp Gln Glu Gly Asn Val Phe Ser Cys Ser Val Met
                195                 200                 205

His Glu Ala Leu His Asn His Tyr Thr Gln Lys Ser Leu Ser Leu Ser
210                 215                 220

Leu Gly Lys
225

<210> SEQ ID NO 184
<211> LENGTH: 227
<212> TYPE: PRT
<213> ORGANISM: Homo sapiens

<400> SEQUENCE: 184

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
 50                      55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 185
<211> LENGTH: 227
<212> TYPE: PRT
<213> ORGANISM: Homo sapiens

<400> SEQUENCE: 185

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 186
<211> LENGTH: 227
<212> TYPE: PRT
<213> ORGANISM: Artificial sequence
<220> FEATURE:
<223> OTHER INFORMATION: Synthetic sequence: Fc region IgG1 Fc Ser/Cys

<400> SEQUENCE: 186

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Cys Leu Ser
    210                 215                 220

Pro Gly Lys
225

<210> SEQ ID NO 187
<211> LENGTH: 226
<212> TYPE: PRT
<213> ORGANISM: Artificial sequence
<220> FEATURE:
<223> OTHER INFORMATION: Synthetic sequence: Fc region IgG2 Fc Ser/Cys

<400> SEQUENCE: 187

Lys Cys Cys Val Glu Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Gln Phe Asn Trp Tyr Val Asp Gly Val Glu Val His
50                  55                  60

Asn Ala Lys Thr Lys Pro Arg Glu Glu Gln Phe Asn Ser Thr Phe Arg
65                  70                  75                  80

Val Val Ser Val Leu Thr Val Val His Gln Asp Trp Leu Asn Gly Lys
                85                  90                  95

Glu Tyr Lys Cys Lys Val Ser Asn Lys Gly Leu Pro Ala Pro Ile Glu
            100                 105                 110

Lys Thr Ile Ser Lys Thr Lys Gly Gln Pro Arg Glu Pro Gln Val Tyr
        115                 120                 125

```
Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ser Val Glu Trp
145                 150                 155                 160

Glu Ser Asn Gly Gln Pro Glu Asn Asn Tyr Lys Thr Thr Pro Pro Met
                165                 170                 175

Leu Asp Ser Asp Gly Ser Phe Phe Leu Tyr Ser Lys Leu Thr Val Asp
                180                 185                 190

Lys Ser Arg Trp Gln Gln Gly Asn Val Phe Ser Cys Ser Val Met His
                195                 200                 205

Glu Ala Leu His Asn His Tyr Thr Gln Lys Ser Leu Cys Leu Ser Pro
    210                 215                 220

Gly Lys
225

<210> SEQ ID NO 188
<211> LENGTH: 227
<212> TYPE: PRT
<213> ORGANISM: Artificial sequence
<220> FEATURE:
<223> OTHER INFORMATION: Synthetic sequence: Fc region IgG3 Fc Ser/Cys

<400> SEQUENCE: 188

Asp Thr Pro Pro Cys Pro Arg Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Gln Phe Lys Trp Tyr Val Asp Gly Val Glu Val
    50                  55                  60

His Asn Ala Lys Thr Lys Pro Arg Glu Glu Gln Tyr Asn Ser Thr Phe
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Thr Lys Gly Gln Pro Arg Glu Pro Gln Val
            115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Ser Gly Gln Pro Glu Asn Asn Tyr Asn Thr Thr Pro Pro
                165                 170                 175

Met Leu Asp Ser Asp Gly Ser Phe Phe Leu Tyr Ser Lys Leu Thr Val
                180                 185                 190

Asp Lys Ser Arg Trp Gln Gln Gly Asn Ile Phe Ser Cys Ser Val Met
                195                 200                 205

His Glu Ala Leu His Asn Arg Phe Thr Gln Lys Ser Leu Cys Leu Ser
    210                 215                 220

Pro Gly Lys
225

<210> SEQ ID NO 189
<211> LENGTH: 227
```

```
<212> TYPE: PRT
<213> ORGANISM: Artificial sequence
<220> FEATURE:
<223> OTHER INFORMATION: Synthetic sequence: Fc region IgG4 Fc Ser/Cys

<400> SEQUENCE: 189

Lys Tyr Gly Pro Pro Cys Pro Ser Cys Pro Ala Pro Glu Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Gln
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Gly Leu Pro Ser Ser Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Gln Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
            180                 185                 190

Asp Lys Ser Arg Trp Gln Glu Gly Asn Val Phe Ser Cys Ser Val Met
        195                 200                 205

His Glu Ala Leu His Asn His Tyr Thr Gln Lys Ser Leu Cys Leu Ser
    210                 215                 220

Leu Gly Lys
225

<210> SEQ ID NO 190
<211> LENGTH: 227
<212> TYPE: PRT
<213> ORGANISM: Artificial sequence
<220> FEATURE:
<223> OTHER INFORMATION: Synthetic sequence: Fc region IgG1m Fc Ser/Cys

<400> SEQUENCE: 190

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Cys Leu Ser
    210                 215                 220

Pro Gly Lys
225

<210> SEQ ID NO 191
<211> LENGTH: 227
<212> TYPE: PRT
<213> ORGANISM: Artificial sequence
<220> FEATURE:
<223> OTHER INFORMATION: Synthetic sequence: Fc region IgG1m(non-1) Fc
      Ser/Cys

<400> SEQUENCE: 191

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Cys Leu Ser

-continued

| 210 | 215 | 220 |

Pro Gly Lys
225